United States Patent
Gellman et al.

(10) Patent No.: US 8,062,312 B2
(45) Date of Patent: *Nov. 22, 2011

(54) SYSTEMS, DEVICES, AND METHODS FOR MINIMALLY INVASIVE PELVIC SURGERY

(75) Inventors: Barry N. Gellman, Easton, MA (US);
Rodney Brenneman, San Juan Capistrano, CA (US); David Sauvageau, Methuen, MA (US); William Pintauro, Ft. Lauderdale, FL (US); Rodney Appell, Shaker Heights, OH (US); Armand A. Morin, Berkeley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/615,261

(22) Filed: Nov. 9, 2009

(65) Prior Publication Data
US 2010/0174132 A1    Jul. 8, 2010

Related U.S. Application Data

(63) Continuation of application No. 11/495,971, filed on Jul. 28, 2006, now Pat. No. 7,614,999.

(51) Int. Cl.
*A61B 17/04*    (2006.01)

(52) U.S. Cl. .................................................. 606/148
(58) Field of Classification Search ........... 600/29–32, 600/37; 128/897–899; 606/119, 148, 151–156, 606/222–225
See application file for complete search history.

(56) References Cited

U.S. PATENT DOCUMENTS

| 6,423,080 B1 * | 7/2002 | Gellman et al. | 606/148 |
| 6,752,814 B2 * | 6/2004 | Gellman et al. | 606/148 |

FOREIGN PATENT DOCUMENTS

| JP | 1211651 A | 8/1999 |
| WO | WO96/06567 | 7/1996 |

* cited by examiner

*Primary Examiner* — John Lacyk
(74) *Attorney, Agent, or Firm* — Bingham McCutchen LLP

(57) ABSTRACT

The invention, in various embodiments, provides systems, devices, and methods for treating urinary incontinence.
The invention also provides a driver and methods for advancing needles, cannulas, and other medical devices through the pubic bone. The driver may be used in connection with a driver frame assembly for proper positioning and stabilization of the driver, and with other devices for creating a cavity in the urethral floor and for positioning medical devices therein. The invention also provides simple connections for attaching a suture to a device within the cavity in the urethral floor or in the vagina, and also for attaching sutures to the pubic bone.

17 Claims, 109 Drawing Sheets

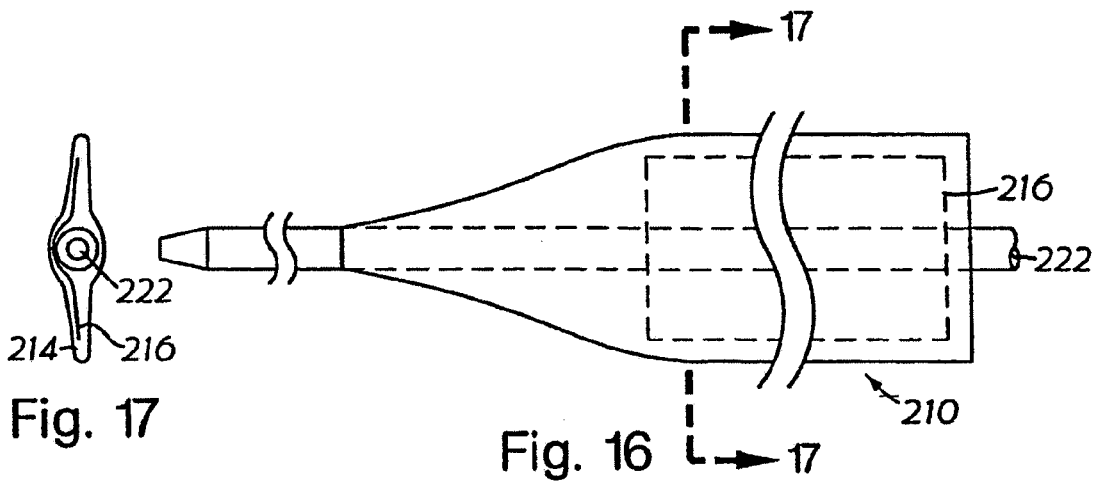
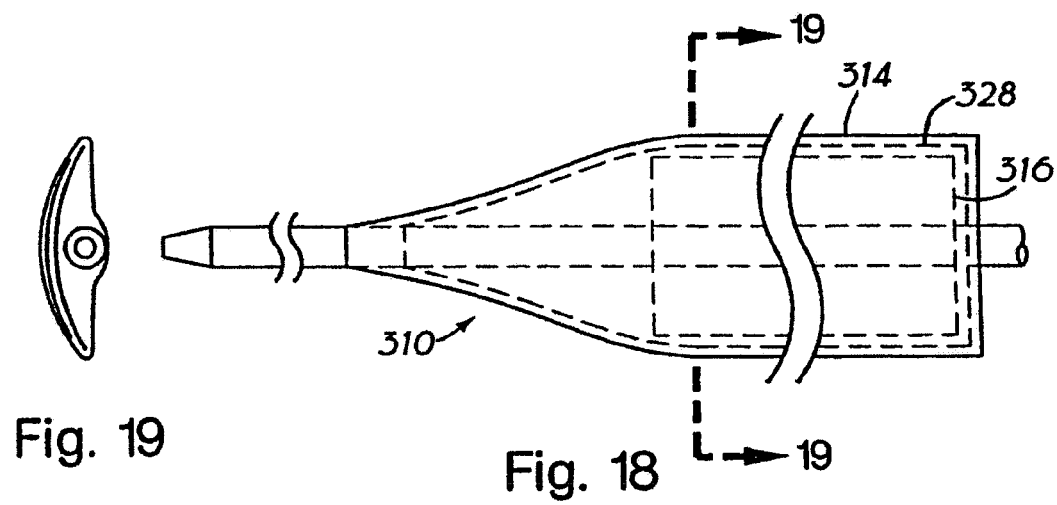
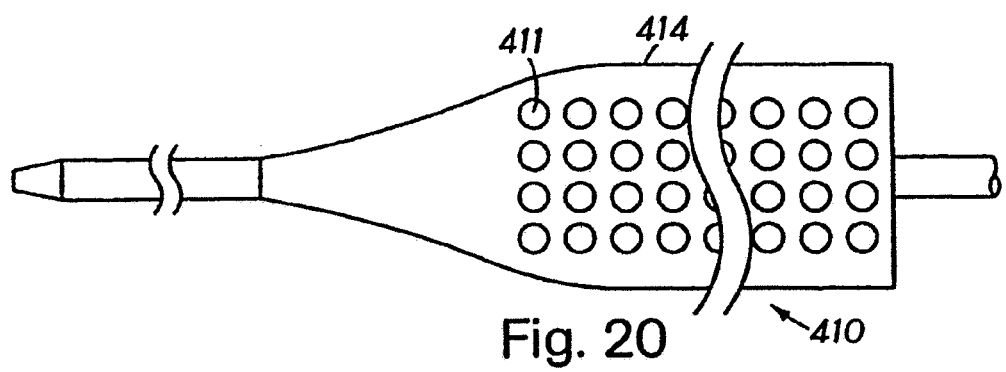

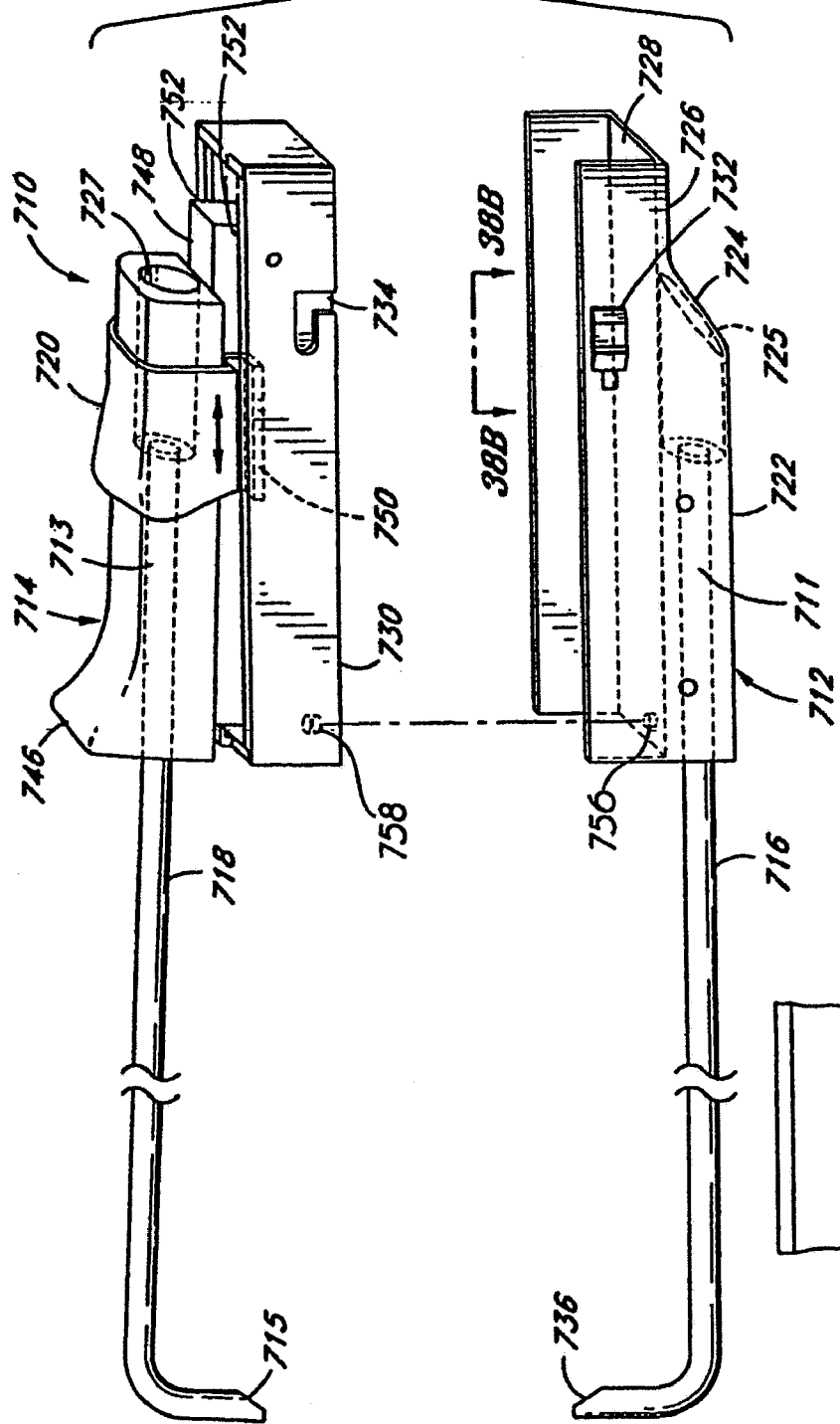
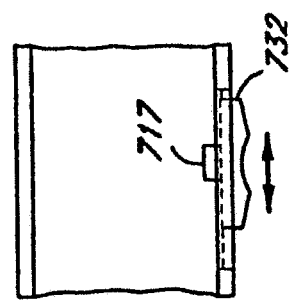

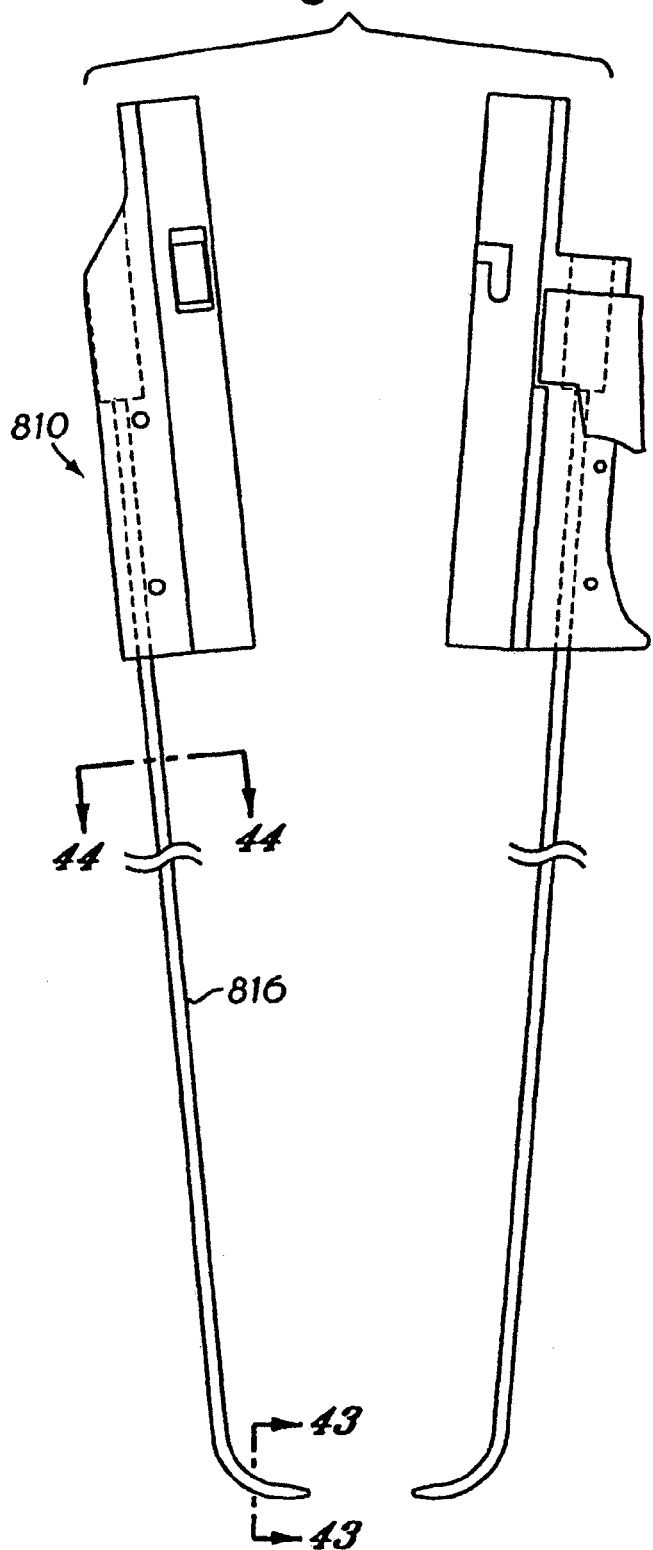
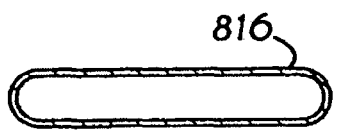
Fig. 42
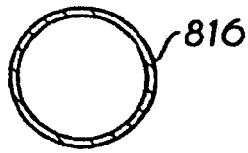
Fig. 43
Fig. 44

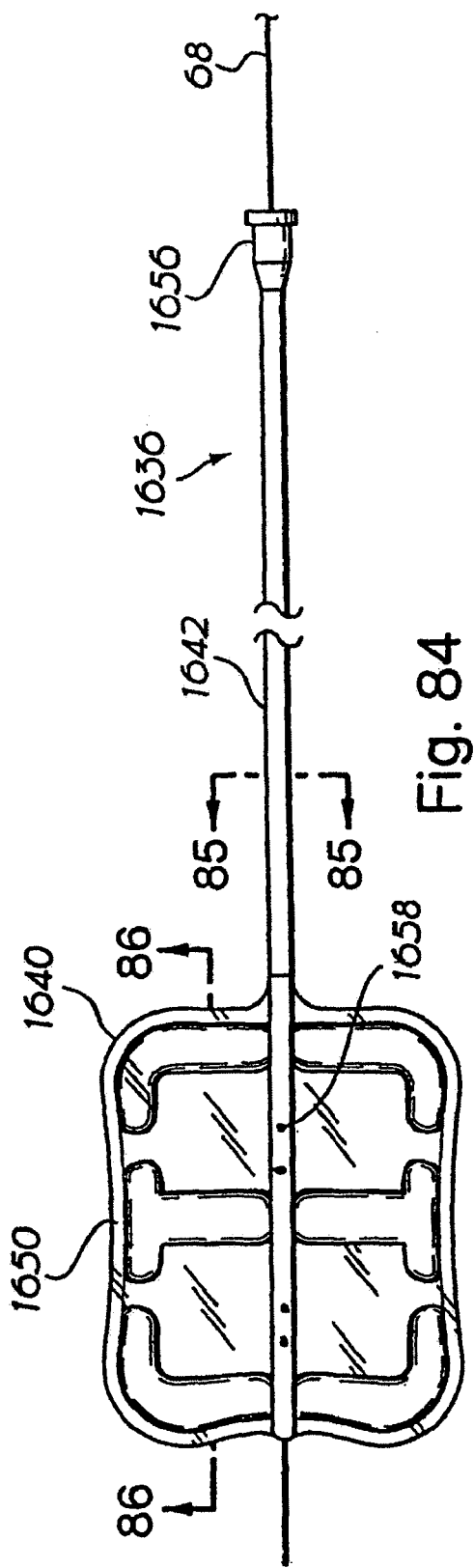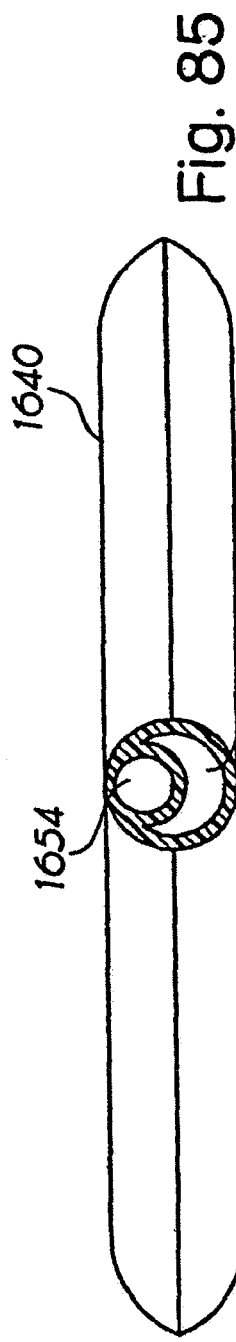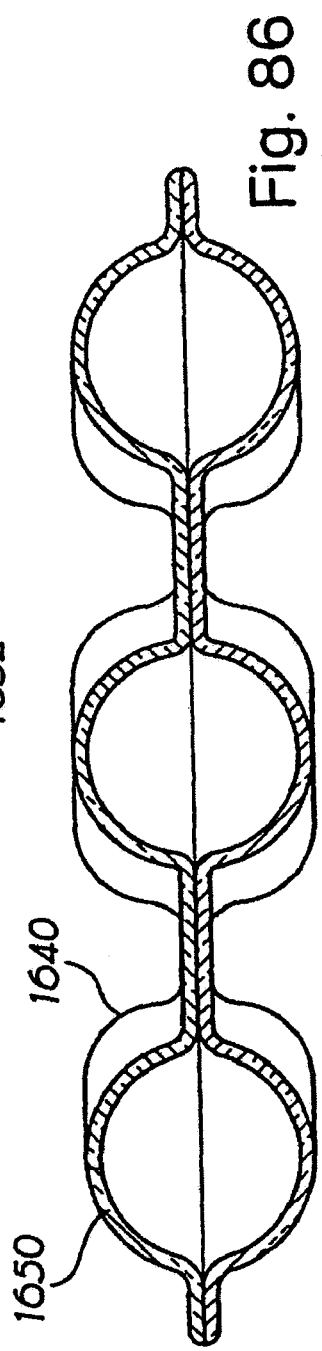

SYSTEMS, DEVICES, AND METHODS FOR MINIMALLY INVASIVE PELVIC SURGERY

RELATED APPLICATIONS

This application is a continuation of prior application Ser. No. 11/495,971, filed Jul. 28, 2006, now U.S. Pat. No. 7,614,999, which is a continuation of prior application Ser. No. 10/939,191, filed Sep. 10, 2004, now U.S. Pat. No. 7,691,052, which is a continuation of prior application Ser. No. 10/774,826, filed Feb. 9, 2004, now U.S. Pat. No. 7,691,050, and prior application Ser. No. 10/774,842, filed Feb. 9, 2004, now U.S. Pat. No. 7,413,540, both of which are continuations of application Ser. No. 10/015,114, filed Nov. 12, 2001, now U.S. Pat. No. 6,752,814, which is a continuation of application Ser. No. 09/023,965, filed Feb. 13, 1998, now U.S. Pat. No. 6,423,080, which claims the benefit of and priority to U.S. Provisional Patent Application Ser. No. 60/038,171, filed Feb. 13, 1997, all of which are hereby incorporated by reference in their entirety.

FIELD OF THE INVENTION

Part A

The present invention relates to devices and methods for treating incontinence.

Part B

The present invention relates to methods and devices for improving urinary incontinence. More particularly, the present invention relates to methods and devices for creating a cavity near the urethral floor, methods and devices for placement of a urethral sling or other device in such a cavity, and methods and devices for driving bone-piercing guides into and through the pubic bone for use in stabilizing the urethral or pelvic floor.

BACKGROUND OF THE INVENTION

Part A

Urinary incontinence is a widespread problem in the United States and throughout the world. Urinary incontinence affects people of all ages and can severely impact a patient both physiologically and psychologically.

In approximately 30% of the women suffering from urinary incontinence, incontinence is caused by intrinsic sphincter deficiency (ISD), a condition in which the valves of the urethral sphincter do not properly coapt. In approximately another 30% of incontinent women, incontinence is caused by hypermobility, a condition in which the muscles around the bladder relax, causing the bladder neck and proximal urethra to rotate and descend in response to increases in intraabdominal pressure.

Hypermobility may be the result of pregnancy or other conditions which weaken the muscles. In an additional group of women with urinary incontinence, the condition is caused by a combination of ISD and hypermobility.

In addition to the conditions described above, urinary incontinence has a number of other causes, including birth defects, disease, injury, aging, and urinary tract infection.

Numerous approaches for treating urinary incontinence are available. For example, several procedures for stabilizing and/or slightly compressing the urethra so as to prevent the leakage of urine have been developed. The stabilizing or compressive force may be applied directly by sutures passing through the soft tissue surrounding the urethra or, alternatively, may be applied by means of a sling located under the urethra and suspended by sutures. The sutures may be anchored to the pubic bone by means of bone anchors or, alternatively, the sutures may be attached to other structures such as fascia.

A device for dissecting around a tubular structure such as the urethra or the bladder neck is available from Lone Star Medical Products. The Lone Star device has two shafts which can be positioned in the tissue between the urethra and the vaginal wall using cystoscopy, vaginal or rectal examination, or an examination of the position of the instrument around the urethra with the bladder opened. The two shafts can be locked together to pinch the intervening tissue. A sharp blade is inserted into one of the shafts and advanced into the second shaft, cutting the tissue in between the two shafts. The cut in the tissue can be expanded using a right angle clamp and an artificial sphincter guided by a suture attached to the cutting blade of the device can be introduced into the expanded cut.

With the Lone Star device, the distance between the two shafts cannot be gradually adjusted. In addition, the ends of the shafts of the Lone Star device come in direct contact with the tissue or bone while being advanced towards the tissue between the urethra and the upper vaginal wall. The shafts of the Lone Star device are flat at their distal ends.

Thus, there is a need for devices which simplify treatments for urinary incontinence and increase their safety. Sling application devices for treating urinary incontinence which reduce the risk of inadvertent pinching of the urethra and undesirable scoring of tissue or bone during advancement of the device would be particularly desirable. It is also desirable to have a sling application device that does not employ a guiding suture and can create or maintain an opening in the tissue between the urethra and the upper vaginal wall without the use of a right angle clamp, thereby simplifying the procedure.

U.S. Pat. No. 5,611,515, issued Mar. 18, 1997 to Benderev et al., introduces pioneering minimally invasive percutaneous and transvaginal bladder neck stabilization approaches. The percutaneous approach of Benderev et al. involves stabilizing the bladder neck using a bone anchor which is percutaneously introduced from the abdominal side of the patient. The transvaginal approach of Benderev et al. involves stabilizing the bladder neck using a staple or bone anchor which is transvaginally placed into the pubic bone. There is also a need for further devices and methods for improving or maintaining urinary continence involving stabilization or compression of the bladder neck or urethra, particularly devices and methods of the present invention that are less invasive than many of those currently available.

Part B

The present invention relates to the treatment of stress urinary incontinence "SUI," and to improved methods and surgical devices for the surgical treatment of SUI. The devices disclosed herein are additionally useful in a wide variety of other surgical procedures.

Genuine stress incontinence is the involuntary loss of urine due to a sudden rise in intra-abdominal pressure. It has been estimated that between 40% and 50% of young, healthy nulliparous women admit to occasional mild stress incontinence; however, at least 80% of stress incontinence patients are in the perimenopausal age group and are multiparous. Raz has suggested that the female urethral continence mechanism is dependent on the interaction of four urethral factors: urethral closing pressure, urethral length, urethrotrigonal anatomy, and urethral reception of intraabdominal pressure. Raz, S., Modified bladder neck suspension for female stress incontinence, Urology, 17:82, 1981.

The urethral closing pressure is predominantly a result of the interaction of smooth and striated muscle sphincter activity, but there is also some contribution by nonmuscular urethral factors such as the submucosal vascular plexus, the elastin and collagen content of the urethral tissues, and a sphincter like effect of the mucosa. There has been considerable diversity of opinion regarding the anatomic structure and the innervation of the urethral sphincters, and a variety of views have been expressed in the literature.

Urethral length is important in the maintenance of continence. However, although it certainly interacts with other factors to contribute to continence, a short urethra alone will not produce incontinence. Urethral length varies considerably in normal women, and women with proven genuine stress urinary incontinence do not invariably have urethral shortening.

Urethrotrigonal anatomy, which can be demonstrated by lateral cystourethrography, should fulfill certain criteria. The bladder base should lie above the level of the inferior ramus of the symphysis, and with straining should not descend more than 1.5 cm. There should be a normal urethrotrigonal alignment with an angle normally less than 100 degrees, and the urethral axis should be approximately 35 degrees from the vertical. In the hypermobile situation loss of all of the normal anatomic features may occur, a radiologic finding that correlates with the clinical finding of cystourethrocele. However, clinical experience has shown that the coexistence of cystourethrocele and incontinence does not predict that the incontinence is of a genuine stress variety.

The transmission of intra-abdominal pressure to the intra-abdominal portion of the proximal urethra is also reported to be important in the maintenance of continence. This is a passive phenomenon, and is the result of the normal anatomic configuration just described. Whenever there is a rise in intra-abdominal pressure during such stresses as coughing or straining, the pressure is transmitted not only to the bladder but also to the proximal urethra, with resultant increase in the closing pressure, and prevention of leakage. If the urethral axis is altered, rotational descent will drop the proximal urethra and bladder base from its intra-abdominal location, and will obviously impair such pressure transmission.

A wide variety of operations have been used to correct this condition, generally involving the principles of elevating the bladder neck anteriorly and/or elongating and narrowing the proximal urethra. Two of the most popular operations today for stress incontinence are the Marshall-Marchetti-Krantz and Birch vesicourethropexies. The Marshall-Marchetti-Krantz technique has at least an eighty-five percent success rate, against which other operative success rates must be measured. Recently, the Pereyra operation and its modifications have enjoyed some popularity, but less than basic techniques.

Notwithstanding the foregoing, however, there remains a need for an improved treatment for SUI. Preferably, the treatment is as noninvasive as possible under the circumstances, and will eliminate or minimize hospitalization and the use of general anesthetics. In addition, there remains a need for improved medical instrumentation such as tissue cavity dilators, incision guides, bone-piercing guide drivers, and quick-connect slings and suture-securing devices for use in connection with SUI treatment and other medical procedures. U.S. patent application Ser. No. 08/042,739, entitled "Bladder Neck Suspension Procedure", filed Apr. 5, 1993 by Benderev et al., now issued U.S. Pat. No. 5,611,515, introduces pioneering minimally invasive percutaneous and transvaginal bladder neck stabilization approaches. The percutaneous approach of Benderev et al. involves stabilizing the bladder neck using a bone anchor which is percutaneously introduced from the abdominal side of the patient. The transvaginal approach of Benderev et al. involves stabilizing the bladder neck using a staple or bone anchor which is transvaginally placed into the pubic bone. The methods and devices of the present invention may be used in several urethral or bladder neck stabilization procedures that are less invasive than many of those currently available.

SUMMARY OF THE INVENTION

Part A

The present invention relates to devices and methods for use in percutaneous and hiatal approaches treatments for urinary incontinence. In particular, the present invention relates to guide member placement devices, sling application catheters, tissue dissectors/dilators, sling application devices and a sling application system, tissue expanders, grasping devices, and balloon catheters. Methods for using the preceding devices to stabilize the bladder neck or the urethral floor in order to maintain or improve urinary continence are also disclosed.

One aspect of the present invention is a guide member placement device for inserting a guide member in a body tissue. The guide member placement device comprises a shaft having a proximal end, a distal end, and a lumen extending therethrough. The lumen of the shaft is adapted for receiving a guide member. The distal end of the shaft has an engaging member for engaging another guide member placement device. In one embodiment of the guide member placement device, the device further comprises a blunt dissection tip at the distal end of the shaft and a handle with a lumen extending therethrough wherein the lumen of the shaft and the lumen of the handle are aligned. In a further embodiment, the blunt dissection tip is on a blunt dissector within the shaft and is extendable from and retractable in the shaft. In a further embodiment, the guide member placement device is adapted for use in urethral floor reconstruction procedures. In yet another embodiment, the guide member placement device is adapted for use in bladder neck stabilization procedures. In one embodiment of the guide member placement device, the engaging member comprises a male connector. In another embodiment of the guide member placement device, the engaging member comprises a female connector. In yet another embodiment of the guide member placement device, the shaft has a straight proximal section, a bent intermediate section and a distal end oriented at an angle of approximately 90 degrees relative to the proximal section. In another embodiment, the guide member placement device further comprises a guide member removably positioned in the lumen of the shaft. In one aspect of this embodiment, the guide member comprises a guide wire. In another aspect of this embodiment, the guide member comprises a suture.

Another aspect of the present invention is a method of inserting a guide member into a body tissue. A shaft of a first guide member placement device is inserted percutaneously and advanced through the body tissue to a central point through which the guide member will pass. A shaft of a second guide member placement device is inserted percutaneously and advanced through the body tissue to the central point through which the guide member will pass. An engaging member on a distal end of the shaft of the first guide member placement device is coupled to an engaging member on a distal end of a shaft of a second guide member placement device such that a lumen in the shaft of the first guide member placement device is fluid communication with a lumen in the shaft of the second guide member placement device. A guide member is passed through the lumens of the coupled shafts of the first guide member placement device and the second guide member placement device. The shaft of the first guide member placement device and the shaft of the second guide member placement device are removed from the body, thereby leaving the guide member in the body tissue. In one embodiment of the method, the first and second shafts are percutaneously inserted through first and second suprapubic incisions. In another embodiment of the method, the shafts of the first and second guide member placement devices are inserted into a pre-formed opening or pocket in the body tissue. In another embodiment of the method, the method further comprises the step of creating an opening in the body tissue by extending and retracting a blunt dissector tip from at least one of the guide member placement devices. In another embodiment of the method, the pre-formed opening or pocket is in the tissue between the urethra and the upper vaginal wall such that the guide member is left in the pre-formed opening or pocket.

Another aspect of the present invention is a sling application catheter comprising a catheter having a sling therein, wherein the sling is releasably engaged with the catheter. In one embodiment of the sling application catheter, the catheter has a pouch therein for releasably engaging the sling. The sling application catheter of claim 18, wherein said catheter is adapted to travel over a guide member. In yet another embodiment of the sling application catheter, the distal end of the catheter is tapered. In yet another embodiment of the sling application catheter, the distal end of the pouch is tapered. In one embodiment of the sling application catheter, the pouch is porous. In another embodiment of the sling application catheter, the pouch further comprises a stiffener for increasing its rigidity. The stiffener may be in the interior of the pouch or on the exterior of the pouch. In another embodiment of the sling application catheter, the stiffener is porous.

Another aspect of the present invention is a method of introducing a sling into a body tissue. The method comprises the steps of passing a sling application catheter catheter through the body tissue. The sling application catheter comprises a catheter having a sling therein which is releasably engaged to the catheter. The sling is released form the sling application catheter, thereby introducing the sling into the body tissue.

In one aspect of the method of introducing a sling into a body tissue, the method further comprises making a first incision and a second incision and the step of passing the sling application catheter through the body tissue comprises passing the sling application catheter into the first incision and out of the second incision. In one embodiment of the method of introducing a sling into a body tissue, the sling is released from the sling application catheter by withdrawing the sling from a pouch in the sling application catheter. In another embodiment, the sling application catheter is passed through the body tissue over a guide member. In yet another embodiment, the sling is introduced into the tissue between the urethra and the upper vaginal wall. In still another embodiment, the first incision and the second incision are suprapubic incisions. In another embodiment, the method further comprises the step of withdrawing the sling from the pouch by grasping an end of the sling while withdrawing the distal end of the sling application catheter out of the second suprapubic incision. In yet another embodiment, the step of withdrawing the sling from the pouch comprises withdrawing a sterile sling.

Another aspect of the present invention is a tissue dissector/dilator for creating and dilating an opening or pocket in a body tissue. The tissue dissector/dilator comprises a body, a noncompliant shaft attached to the body, a dissector carried on the shaft for creating an opening or a pocket in the body tissue, and a dilator carried on the shaft for dilating the opening or pocket in the body tissue. In one embodiment, the shaft has a lumen extending therethrough and the dissector is within the lumen in the shaft and is axially movable, such that the dissector can be extended from and retracted in the shaft. In another embodiment, the shaft has a lumen extending therethrough and the dilator is within the lumen in the shaft and is axially movable, such that the dilator can be extended from and retracted in said shaft. In another embodiment, the shaft has a lumen extending therethrough and both the dissector and the dilator are within the lumen of the shaft and are axially movable, such that the dissector and the dilator can be extended from and retracted in the shaft. In one embodiment, the axially movable dissector and the axially movable expandable dilator are integral. In another embodiment, the tissue dissector/dilator is adapted for use in bladder neck stabilization procedures.

In still another embodiment of the tissue dissector/dilator, the body of the tissue dissector/dilator further comprises a first control member for extending and retracting the axially movable integral dissector and expandable dilator between a first position in which the dissector extends from the shaft, a second position in which both the dissector and the dilator extend from the shaft, and a third position in which the dissector and the dilator are retracted inside the shaft. In this embodiment, the body of the tissue dissector/dilator also comprises a second control member for expanding the dilator in the opening or pocket in the body tissue, thereby dilating the opening or pocket and for collapsing the dilator following dilation of the opening or pocket. In another embodiment, the first control member for extending and retracting the axially movable integral dissector and expandable dilator comprises a spring return button which engages the axially movable integral dissector and expandable dilator so as to extend or retract said axially movable integral dissector and expandable dilator. In still another embodiment, the spring return button can be positioned to lock the axially movable integral dissector and expandable dilator in a fully extended position. In yet another embodiment, the spring return button provides a one to one stroke motion to the axially movable integral dissector and expandable dilator.

In a further embodiment of the tissue dissector/dilator, the axially movable integral dissector and expandable dilator is a catheter comprising an outer tube having a lumen extending therethrough and at least one expandable balloon in the lumen of the outer tube. In this embodiment, the expandable balloon has an inflation tube at its proximal end and a blunt dissector at its distal end, wherein the inflation tube is in fluid communication with the interior of the balloon. In still another embodiment, the second control member for expanding the dilator comprises a trigger on the body and a syringe in the body comprising a plunger, a reservoir, and a tip. In this embodiment, the tissue dissector/dilator also comprises a syringe locking mechanism, wherein the tip of the syringe fixedly engages the syringe locking mechanism to place the reservoir of the syringe in fluid communication with the balloon catheter, and the trigger engages the plunger of the syringe such that squeezing the trigger depresses the plunger of the syringe thereby dispensing fluid from the syringe and expanding the balloon of the catheter. In still another embodiment, the catheter further comprises a second lumen adapted for passage of a guide member. In a further embodiment, the catheter further comprises a third lumen. In another embodiment, the third lumen is adapted for receiving an ultrasound catheter. In still another embodiment, the third lumen is adapted for receiving an implant. In another embodiment, the third lumen is adapted for irrigation.

Another aspect of the present invention is a tissue dissector/dilator for creating and dilating an opening or pocket in a body tissue comprising a body, a noncompliant shaft attached to said body, a dissection means carried on the shaft for dissecting an opening or pocket in a body tissue, and a dilation means carried on the shaft for dilating the opening or pocket.

Another aspect of the present invention is a method of creating and dilating an opening or pocket in a body tissue. A noncompliant shaft of a tissue dissector/dilator is percutaneously inserted into the body tissue. The shaft is advanced through the body tissue. A dissector is extended from a distal end of the shaft to create a first opening or pocket in the body tissue and a dilator is extended from the distal end of the shaft. The dilator is expanded within the first opening or pocket to dilate the first opening or pocket. In one embodiment of the method, the tissue dissector/dilator is percutaneously inserted through a suprapubic incision. In another embodiment, the body tissue is the tissue between the urethra and the upper vaginal wall and the first opening or pocket is perpendicular to the longitudinal axis of the urethra and extends from one side of the urethra to the other. In another embodiment the method further comprises percutaneously inserting a noncompliant shaft of a second tissue dissector/dilator into the body tissue, advancing the noncompliant shaft of the second tissue dissector/dilator through the body tissue, extending a dissector from a distal end of the shaft of the second tissue dissector/dilator to create a second opening or pocket in the tissue, extending a dilator from the distal end of the shaft of the second tissue dissector/dilator and expanding said dilator within the second opening or pocket, thereby dilating the second opening or pocket and forming from the first and second openings or pockets a continuous opening or pocket in the body tissue. In a further embodiment, the second tissue dissector/dilator is percutaneously inserted through a suprapubic incision. In yet another embodiment of the method, the body tissue is the tissue between the urethra and the upper vaginal wall and the continuous opening or pocket is perpendicular to the longitudinal axis of the urethra and extends from one side of the urethra to the other.

Another aspect of the present invention is a sling application device for inserting a sling into a pocket in a body tissue. The sling application device comprises a first shaft and a second shaft. The first and second shafts have lumens extending therethrough. The lumens have dimensions adapted for receiving a sling therein. The sling application device also comprises an adjuster for incrementally adjusting the distance between said first and second shafts. In one embodiment, the lumens of the first and second shafts have dimensions adapted for receiving a sling introducer having a sling releasably engaged thereto. In another embodiment, the sling application device further comprises a first handle attached to the first shaft and a second handle attached to the second shaft. In this embodiment, the first and second handles have openings therein which are in fluid communication with the lumens in the shafts to which the handles are attached and the first and second handles are adapted to be connected to one another. In another embodiment, the adjuster engages the first and second handles.

In one embodiment of the sling application device the first and second shafts are curved. In still another embodiment, the first and second shafts have a small radius 90° curve at their distal ends, such that the first and second shafts are adapted for use in urethral stabilization procedures. In another embodiment, the first and second shafts have a side bend. In yet another embodiment, the radius of curvature at the distal ends of the first and second shafts is not planar with the axial portions of the shafts of the first and second shafts. In still another embodiment, the upper edges of the distal ends of the first and second shafts are indented relative to the lower edges. In another embodiment, the first and second handles are adapted for interlocking. In a further embodiment, the adjuster comprises an articulating lock. In still another embodiment, the first shaft and the second shaft are cylindrical. In one embodiment, the first shaft and the second shaft comprise flat tubes. In another embodiment, the portion of the first shaft and the second shaft proximal to the bend is cylindrical and the portion distal to the bend is a flat tube. In another embodiment, the proximal portions of the first and second shafts are oriented at an angle of about 90° relative to the distal portions of the first and second shafts. In another embodiment, the sling application device further comprises a blunt dissector for dissecting the body tissue without scoring or creasing tissue or bone with which it comes in contact. In this embodiment, the blunt dissector comprises a dissector shaft adapted for insertion into the first and second shafts of the sling application device. The dissector shaft has a generally rigid tip at its distal end. The rigid tip protrudes from the distal ends of the first and second shafts of the sling application device when the blunt dissector is inserted into the first and second shafts of the sling application device. In yet another embodiment, the blunt dissector comprises an obturator.

Another aspect of the present invention is a sling introducer adapted for introducing a sling attached thereto into an opening or pocket in a body tissue without the use of sutures. The sling introducer comprises a sling engager having the sling releasably engaged thereto. The sling engager is adapted for advancement through a first shaft and a second shaft of a sling application device. The length of the sling introducer is at least equal to the sum of the lengths of the first and second shafts of the sling application device. In one embodiment, the sling engager comprises a pouch for releasably engaging said sling. In another embodiment, the pouch has pores therein for permitting a solution to access said sling. In still another embodiment, the distal end of the pouch has a narrow lead. In a further embodiment, the pouch is reinforced.

Another aspect of the present invention is a tissue cutter for forming a cavity in a tissue. The tissue cutter comprises an elongated housing adapted to fit within a shaft of a sling application device and an extendable and a retractable blade within the housing. The blade is adapted to form the cavity in the tissue. In one embodiment, the blade comprises a razor. In another embodiment, the razor is sized such that the cavity formed with the razor has dimensions adapted for insertion of a sling therein.

Another aspect of the present invention is a sling application system. The sling application system includes a sling application device comprising a first shaft and a second shaft. The first and second shafts of the sling application device have lumens extending therethrough. The lumens have dimensions adapted for receiving a sling introducer therein. The sling application device also comprises an adjuster for incrementally adjusting the distance between the first and second shafts. The sling application system also includes a blunt dissector for dissecting a body tissue without scoring or creasing tissue or bone with which it comes in contact. The blunt dissector comprises a dissector shaft adapted for insertion into the first and second shafts of the sling application device. The dissector shaft has a generally rigid tip at its distal end wherein the generally rigid tip protrudes from the distal ends of the first and second shafts of the sling application device when the blunt dissector is inserted into the first and second shafts. The sling application system also comprises a sling introducer for introducing a sling attached thereto into an opening or pocket in the body tissue without the use of sutures. The sling introducer comprises a sling engager having the sling releasably engaged thereto. The sling engager is adapted for advancement through the lumens of the first and second shafts of the sling application device wherein the sling introducer has a length sufficient to extend between the first and second shafts of the sling application device. In one embodiment, the sling application system further comprises a tissue cutter for forming a cavity in the body tissue. The tissue cutter comprises an elongated housing adapted to fit within the second shaft of the sling application device and an extendable and retractable blade within the housing. The blade is adapted to form a cavity in the body tissue.

Yet another aspect of the present invention is a method for introducing a sling into a body tissue. A first blunt dissector is inserted into a first shaft of a sling application device. The first shaft having the first blunt dissector therein is inserted percutaneously and advanced through the body tissue. A second blunt dissector is inserted into a second shaft of the sling application device. The second shaft having the second blunt dissector therein is inserted percutaneously and advanced through the body tissue. The distance between the distal ends of said first and second shafts is decreased. A sling introducer having the sling releasably engaged thereto is advanced between the first and second shafts of the sling application device. The sling is released from the sling introducer. The first and second shafts are removed from the body tissue, thereby introducing the sling into the body tissue. In one embodiment, the method further comprises making a first incision and a second incision wherein the first shaft of the sling application device is inserted into the first incision prior to advancing it through the body tissue and the second shaft of the sling application device is inserted into the second incision prior to advancing it through the body tissue. In another embodiment, the sling is introduced into a pre-formed pocket in the tissue between the urethra and the vaginal wall. In a further embodiment, the first incision and the second incision are suprapubic incisions. In still another embodiment, the method further comprises inserting a tissue cutter into the first shaft of the sling application device and extending the tissue cutter into the body tissue between the distal ends of the first and second shafts, thereby dissecting the body tissue.

Another aspect of the present invention is a balloon catheter comprising an outer tube having a lumen extending therethrough and at least one expandable balloon adapted for dilating an opening or pocket in the tissue between the urethra and the upper vaginal wall. The expandable balloon has a proximal end and a distal end in the lumen of the outer tube. The expandable balloon also has an inflation tube at its proximal end. The inflation tube is in fluid communication with the interior of the balloon. In one embodiment, the expandable balloon has a blunt dissection tip at its distal end which has sufficient rigidity to allow it to create an opening or pocket in the solid body tissue. In one embodiment, the balloon catheter comprises a plurality of expandable balloons in fluid communication with the inflation tube. In another embodiment, the balloon catheter is adapted to fit in the lumen of a large bore needle. In still another embodiment, the expandable balloon has a flat profile. In another embodiment, the balloon further comprises internal non-expansive ribs. In yet another embodiment, the catheter extends into the interior of the balloon. In still another embodiment, the balloon is on the exterior surface of the catheter.

Another aspect of the present invention is a detachable member sling application device for introducing a sling having sutures attached thereto into an opening or pocket in a body tissue. The detachable member sling application device has a housing with an introduction shaft connected thereto. The introduction shaft has a lumen extending therethrough which is adapted to receive the sling having sutures attached thereto. The detachable member sling application device also has a detachable member on the distal end of the introduction shaft. The detachable member is connected to at least one of the sutures attached to the sling. In one embodiment, the detachable member sling application device further comprises an axially movable needle. In this embodiment, the needle comprises a needle shaft and a sharpened point. The needle is located inside the lumen of the introduction shaft and is extendable therefrom.

Another aspect of the present invention is a retrieval device for introducing a sling into an opening or pocket in a body tissue, comprising a shaft having an engaging member at its distal end. The engaging member is adapted to engage a detachable member connected to a suture attached to the sling.

Another aspect of the present invention is a method of stabilizing the bladder neck. A pocket or opening is formed in the tissue between the urethra and the upper vaginal wall. A sling application device is inserted into the pocket or opening. A sling is introduced into the pocket or opening with the sling application device. The sling is secured to tissue or bone to stabilize the bladder neck. In one embodiment the method further comprises providing a detachable member sling application device. The detachable member sling application device has a housing with an introduction shaft connected thereto. The introduction shaft has a lumen extending therethrough which is adapted to receive the sling having sutures attached thereto. The detachable member sling application device also has a detachable member on the distal end of the introduction shaft. The detachable member is connected to at least one of the sutures attached to the sling. In this embodiment, the step of inserting a sling application device into the pocket or opening comprises inserting the detachable member sling application device into the opening or pocket. Another step in this embodiment comprises detaching a detachable member from a distal end of the shaft of the detachable member sling application device. The detachable member is connected to the sling. Another step in this embodiment comprises introducing a shaft of a retrieval device into the opening or pocket. Yet another step in this embodiment comprises engaging the detachable member with an engaging member on the shaft of the retrieval device. Another step of this embodiment comprises withdrawing the shaft of the retrieval device from the opening or pocket, thereby introducing the sling of the detachable member sling application device into the opening or pocket. In another embodiment, the method further comprises extending an axially movable needle from a distal end of the shaft of the detachable member sling application device into the body tissue and toggling the needle to move the detachable member within the opening or pocket. In still another embodiment, the opening or pocket is in a hiatus between a urethra and an upper vaginal wall. In another embodiment, the method further comprises the step of expanding the opening or pocket in the hiatus using a balloon catheter having at least one expandable balloon with a blunt dissection tip at its distal end. In this embodiment, the blunt dissection tip has sufficient rigidity to allow it to make the opening in the body tissue when contacting the tissue.

Another aspect of the present invention is a device for expanding an opening or pocket within a body tissue. The device comprises a tube having a lumen extending therethrough, an axially movable expandable and collapsible expansion basket attached to the tube for insertion into the opening or pocket within the body tissue and expansion thereof, and an expansion and collapse control in communication with the expandable and collapsible basket for expanding and collapsing the basket. In one embodiment, the basket comprises a plurality of wires. In another embodiment, the expansion and collapse control comprises a pull wire.

Another aspect of the present invention is a grasping device adapted for insertion into a lumen of an expansion device having an expansion basket for expanding an opening or pocket within a body tissue. The grasping device comprises a catheter having a grasping member on its distal end for grasping a suture or guide member which has been advanced into the expansion basket of the expansion device. In one embodiment, the grasping member comprises a self-expanding basket. In another embodiment, the self-expanding basket is adapted to fit inside the expansion basket of the expansion device when the expansion basket of the expansion device is in an expanded configuration.

Another aspect of the present invention is a method of creating a pocket in the tissue between the urethra and the upper vaginal wall comprising hydrodissecting the tissue.

Another aspect of the present invention is a method for holding a pocket in a body tissue in an open position. A lumen is made in the body tissue. The lumen in the body tissue is expanded to create the pocket in the body tissue. An expansion device is inserted into the pocket and an expansion basket on the expansion device is expanded in the pocket, thereby holding the pocket in the open position. In one embodiment, the body tissue comprises a hiatus between a urethra and an upper vaginal wall. In another embodiment, the lumen is expanded with a balloon catheter. In another embodiment, the method further comprises inserting a suture or guide member through a suprapubic incision into the pocket, inserting a grasping device comprising a catheter having a grasping member on its distal end into a lumen of the expansion device, grasping the suture or guide member with the grasping device, and withdrawing the suture or guide member to a desired position. In one embodiment, the suture or guide member is grasped under direct vision.

Yet another aspect of the invention is a method of introducing a sling into an opening in a body tissue comprising holding a pocket or opening in a body tissue in an open position with an expansion basket as described above, grasping a suture or guide wire within the expanded opening as described above, and drawing the suture or guide wire to a desired position. The method is performed on each side of the urethra such that two sutures extend from the patient's body. The two sutures are tied together and used to guide a sling into the opening. In one embodiment, the body tissue comprises a hiatus between the urethra and the upper vaginal wail.

Yet another aspect of the invention is a method of introducing a sling into an opening in a body tissue comprising holding a pocket or opening in a body tissue in an open position with an expansion basket as described above, grasping a suture or guide wire within the expanded opening as described above, and drawing the suture or guide wire to a desired position. The method is performed on each side of the urethra such that two sutures extend from the patient's body. A sling is attached to the two sutures outside of the patient's body and introduced into the opening in the body tissue. In one embodiment, the body tissue comprises a hiatus between the urethra and the upper vaginal wall.

Part B

It is an objective of this invention to provide a means and method for relatively sterile placement of urethral slings. It is a further objective of this invention to provide an apparatus for straight line positioning for bone piercing, so as to achieve proper placement of urethral slings and to minimize difficulty in aligning a bone-piercing apparatus with the ultimate target in a tissue cavity. Another objective is to provide apparatus and a method for reconstructing and stabilizing the urethral or pelvic floor by affixing devices placed to support the urethral or pelvic floor to a fixed reference tissue such as a bone. A further objective is to provide improvements over current techniques that require drilling holes in a bone, and the placement of bone anchors therein.

This invention has the additional objective of providing rapid and simple surgical connections for connecting a suture to a medical device inside a tissue cavity or other structure in the body that may be in need of stabilization. This invention also seeks to provide alternatives to transvaginal methods of urethral and pelvic floor reconstruction and stabilization, to minimize the risk of infection, and to enable surgeons to approach the urethral or pelvic floor from different locations. Finally, it is a further objective to provide minimally invasive means and methods of securing a target tissue to an immoveable reference tissue, such as the pubic bone. One of more of these objectives is satisfied by various embodiments of the invention.

The invention provides a dilator for creating a cavity in tissue. The dilator has two functional portions: an insertion spreader and handles. The insertion spreader includes of two facing guides that may be semi-cylindrical. The spreader has open and closed positions. In the closed position the guides are close together and the dilator may have the appearance of a split tube or cylinder, while in the open position the guides are separated. In both positions the guides remain essentially parallel to each other.

The insertion spreader may be attached to the handles for manipulation of the guides. The handles can be joined together with a pivot, so that pivoting the handles translates to a movement of the guides either toward or away from one another. The dilator may also have a ratcheting lock for maintaining the insertion spreader in a fixed position. The penetrating ends of the guides also may be sharpened to facilitate penetrating the target tissue.

The dilator aspect of the invention also provides a method of creating a tissue cavity by using the dilator. With the insertion spreader in the closed position the spreader is advanced into the target tissue. When the spreader reaches the desired depth the handles are moved to separate the guides. The separation of the guides causes a tearing of the tissue, creating a cavity therein.

This method also may be employed by first advancing a needle partially into the tissue to create an insertion path. The guides of the spreader are positioned about the protruding part of the needle and inserted into the tissue along the same path created by the needle.

This method for spreading tissue with the dilator of the invention may be used to create a cavity in the vaginal hiatus. The term "vaginal hiatus" refers to the tissue between the urethra and the vagina. This term may apply to the exterior surface between the distal urethra and the vaginal orifice as well as to the deeper tissue between the urethra and the upper vaginal wall. In some cases spreading may be facilitated by performing an episiotomy of the skin of the vaginal hiatus. The method of this aspect of the invention also may be performed transvaginally to create a cavity, for example in the vaginal wall. Whatever the tissue, the method may be preceded with a fluid-dissection of the target tissue, wherein a solution is injected into the tissue to create a fluid bolus. The fluid bolus forms a pocket in the tissue, and the dilator is used to create an opening connecting the outer surface to the pocket.

The invention also provides an insert card for advancing a medical device, for example a urethral sling, into a tissue cavity. One end of the card holds the sling to be used for stabilizing tissue or internal structures of the urethral or pelvic floor. The other end of the card is fashioned to permit a physician to grasp and manipulate the card, or to align or connect the card with other external devices, such as those disclosed herein. The sides of the card may be adapted for use with the dilator mentioned above. Thus the card can be used to enhance both the sterility and the positional precision in a sling-placement procedure.

The card and the dilator may thus be used in a method of advancing a sling into a tissue cavity. The tissue cavity is created by the dilator as described above, and the spreader is locked in the open position. A sling is placed in the proper position on the card, and the card is positioned so that its lateral edges align with and slide into the spreader guides. The spreader guides provide a track for the insertion of the card to the desired depth within the cavity. This method of sling placement may be used in procedures employing a variety of techniques for securing the sling, including techniques adapted for slings that are to be secured with sutures, quick connect devices, bone anchors, staples, and the like.

Also provided in this invention is an incision guide for creating a cavity between the urethra and the vagina. The incision guide has a catheter that is inserted into the urethra. This catheter expands and straightens the urethra, essentially immobilizing the urethra in an easily identified position. Also part of the incision guide is a cutter that slides along the catheter and makes an incision into the vaginal hiatus that is a fixed distance from, and therefore parallel to, the urethra. The catheter may display graduation marks or other indicia to enable a surgeon to determine the position of the catheter or the cutter relative to the bladder neck.

The incision guide of the invention may also have a stop, such as a block or a ring, that locks in place on the catheter. The stop abuts the cutter and prevents insertion of the cutter beyond the desired depth of incision.

The cutter portion of the incision guide may be a needle, a blade, a bipolar knife, or other incision device adapted for slidably mounting to the rigid catheter. One example of such an adapted incision device is the dilator of the invention as described above.

The incision guide aspect of the present invention provides a method of creating a cavity in the vaginal hiatus. The method includes the steps of inserting the catheter into the urethra, determining the position of the bladder neck by using the catheter, and inserting the attached cutter into the vaginal hiatus. The catheter allows straight-line tracking for the cutter and indicates the depth of incision, thus avoiding injury to the bladder.

This method of creating a cavity in the vaginal hiatus may be used in concert with the method of placing a sling in a cavity by use of the card, as discussed above. The card supporting the sling may advance into the cavity having its edges in contact with the hiatal tissue along the sides of the cavity. Alternatively the dilator of the invention also may be used to serve as a guide for the card, after the cavity is made using the incision guide of the invention. When the card reaches the intended depth in the cavity, the sling is in proper position for fastening in place.

An additional aspect of the present invention provides a driver for driving a guide into or through the pubic bone. The driver has two jaws and a slide bar. The first jaw has a distal end that inserts into a tissue cavity and a proximal end that attaches to the slide bar. The second jaw slides along the slide bar toward the first jaw. The second jaw has a bone-piercing guide attached to it such that the guide moves toward the first jaw when the second jaw is advanced along the slide bar. The guide connected to the driver may be a cannula, a needle, or a like device adapted for driving through bone.

The driver provides a method of driving a guide through the pubic bone. The steps include: inserting the first jaw of the driver into a tissue cavity, locating the pubic bone, positioning the driver to align the pubic bone between the first jaw and the second jaw, and advancing the second jaw toward the first jaw to drive the guide through the pubic bone.

The invention further provides a method for passing a device through the pubic bone. The guide is driven through the pubic bone as outlined above. The guide is next retracted, leaving a path through the bone, and the device is passed through the pubic bone along the path made by the guide. The device passed by this method may be a suture, a suture passer, a quick-connect fastening device, and the like.

In an additional method of this aspect of the invention, the driver of the invention is used to advance a cannula through the pubic bone. The lumen of the cannula constitutes a channel through the pubic bone. A device may then be passed through the bone within the lumen of the cannula. Devices that may be passed by this method include a suture, a suture passer, a quick-connect fastening device, and the like.

A further method of pelvic surgery provided by the invention includes the following steps. A cannula is driven through the pubic bone with the driver of the invention. The cannula is further driven into the tissue cavity in which the first jaw of the driver is positioned. The first end of a suture is passed through the cannula and secured to a structure within the cavity. The second end of the suture is secured to the pubic bone, thereby stabilizing tissue adjacent to the cavity. According to this method, the cannula may be removed from the bone before either end of the suture is secured, or the suture within the tissue cavity may be secured before withdrawal of the cannula. The suture within the tissue cavity may be secured by stitching the suture through a tissue mass of the cavity, or by attaching the suture to a structure introduced into the cavity for stabilizing the tissue of the cavity, such as a suture button.

The invention also provides a method of pelvic surgery wherein a cannula is driven through the pubic bone and into the tissue cavity as described above, and a suture is passed through the cannula and into the cavity. The suture is passed through a structure therein to stabilize the tissue adjacent to the cavity, then the suture is passed back out along the same path through the bone, and both ends of the suture are secured to the pubic bone.

Yet another method of the invention involves driving a cannula through the pubic bone and into a tissue cavity in a first location to make a first path. The suture is then advanced into the cavity along the first path. The suture is passed through a structure of the cavity to stabilize the tissue adjacent to the cavity. The cannula is then driven through the bone and into the cavity along a second path, and the suture is withdrawn from the cavity along the second path. Both ends of the suture are then secured to the pubic bone.

The foregoing methods focus on the path of the suture: the suture may be advanced one-way into the cavity and affixed there, or the suture may be advanced and withdrawn from the cavity along the same path through the bone, or the suture may be advanced and withdrawn along two separate paths through the bone. Regardless which method is used, the tissue cavity of the method may be the vagina. Alternatively, the cavity may be a hiatal cavity made according to a method of the dilator or incision guide aspects of the present invention. Further, the tissue cavity of the method may be a transvaginally created pocket into the plane of the vaginal hiatus. Also regardless which method is used, the method may advantageously be performed on the left side of the cavity and on the right side of the same cavity by piercing the pubic bone on both sides lateral to the pubic symphysis. The method may also include a step of tensioning the suture to elevate or otherwise stabilize the tissue mass.

Further provided is a method of stabilizing a urethral sling relative to the pubic bone. This is done by creating a tissue cavity and creating a path through the pubic bone by driving a guide through the bone. Then a urethral sling is placed into the cavity. A suture is passed through the pubic bone along the path, and is attached to the tissue mass. The suture is then secured to the pubic bone to stabilize the tissue.

Another aspect of the invention provides a driver frame assembly for positioning and stabilizing a bone-piercing guide driver relative to the patient. The driver frame assembly includes an upper clamp and a lower clamp, as well as a catheter, a cavity tongue, and the driver. The upper clamp has a head portion, a descending arm, and a base portion. The head portion has a compression foot for compressing the patient's abdominal surface against the pubic bone. Stabilizing pins extend downward from the compression foot and penetrate the abdominal surface adjacent to the superior surface of the pubic bone. The base portion of the upper frame attaches to the catheter and the tongue. The catheter is used to expand and straighten the urethra; the tongue inserts into the cavity, providing counterpressure to oppose the pressure of the compression foot. The lower clamp has a buttock plate for insertion beneath the patient, so that the patient's weight rests on the plate to secure the frame assembly relative to the patient. The lower clamp also has an ascending arm that connects with the base portion of the upper clamp.

Finally, at least one driver is attached to the descending arm of the upper clamp. There may be more than one driver mounted to the frame assembly, or there may be one driver that drives two bone-piercing guides, which may be displaced to the left and right of center relative to the patient.

This aspect of the invention provides a method for stabilizing pelvic tissue by relatively non-invasive pelvic surgery. The foregoing frame assembly is installed on the patient. The bone-piercing guide is positioned and is driven through the bone and into the cavity. A stabilizing device is passed along the path through the bone created by the guide and secured in the cavity, thus stabilizing the targeted tissue of or adjacent to the cavity. This method may employ two or more guides, or one guide in various positions, to create more than one path through the pubic bone. The path created may be directly through the bone, after removal of the guide, or may be through the guide itself, if the guide is a cannula.

The stabilizing device thus passed through the bone may be a suture, a suture passer, a quick connect device, and the like. The cavity may be the vagina, a cavity of the vaginal hiatus, or a cavity made by entry through the vaginal wall. The method of stabilization may be a suture stitching of the cavity tissue or the placement of a quick connect device to a sling or suture button. The tissue stabilization is achieved by securing the suture to the bone with a quick-connect bone suture fastener. A sling, suture button, or like device that attaches to the suture or quick connect may be positioned in the tissue cavity by using the card discussed above in cooperation with the frame. The tongue of the frame may be adapted to cooperate with the card much like the dilator of the invention, such that the proper placement of the tongue as part of frame installation assures proper positioning of the device to be carried on the card for binding the device to a suture or a quick connect device. This card may be advanced into position in a cavity of the vaginal hiatus, the vagina, or a cavity made in the vaginal wall.

Another aspect of the invention provides a system for attaching a urethral sling to a suture. The system includes a urethral sling and a connector. Part of the sling is a ring member. The ring member has a central opening that cooperates with the sling to allow unidirectional passage of the connector through the opening, and to prevent retrograde passage of the connector through the opening. The connector and ring member may have a variety of configurations. One such configuration provides a ring member having several flanges and a substantially conical connector with a shoulder that contacts the flanges, preventing withdrawal of the connector from the ring member. Another configuration provides a connector having an elongate axial segment and a leading segment that is flexibly perpendicular to the axial segment. This "T" connector may cooperate with a ring member that is simply an opening in the urethral sling. The connectors of any configuration may be a attached to a suture.

This aspect of the invention provides a method for securing a sling for urethral and pelvic floor reconstruction. A sling having a suitable ring member is placed in position in a tissue cavity. A suture with a suitable connector is passed through the pubic bone, and the connector is advanced through the ring member of the sling. The suture is then fastened to the pubic bone, thus securing the sling in the cavity. The cavity may be the vagina, a cavity of the vaginal hiatus, or a cavity in the vaginal wall.

A closely related aspect of the invention provides a system for attaching a securing device to a suture. The system includes a securing device with a ring member, and a connector that attaches to a suture. The ring member and the connector cooperate as described above. The securing device may be a suture button, a staple, or a quick connect.

The method provided in this aspect of the invention is a method for securing a target tissue to the pubic bone. The securing device with a ring member is placed within or adjacent to the target tissue. A suture with a suitable connector is passed through the pubic bone, and the connector is advanced through the ring member of the securing device. The suture is fastened to the pubic bone, thus securing the target tissue to the bone.

Also part of the present invention is a bone eyelet having a sleeve and at least one crosspiece. The sleeve has an outer surface and an inner surface. The outer surface is adapted for inserting into a bone, and the crosspiece is attached to the inner surface to transect the sleeve, providing a plurality of channels in the sleeve. The crosspiece may be a plane or a rod. Alternatively, the crosspiece may be created by a piercing or crimping of the sleeve. The sleeve may have an external friction surface for contacting with the bone. It may have a flange rim for suspending the sleeve at the surface of the bone. The sleeve may also have a conical shape to facilitate advancing the sleeve into and contacting it with the bone.

The invention provides a method for securing a suture to a bone. The bone is pierced and a suture is passed through the bone. Suture ends are passed through at least two channels in the bone eyelet and the bone eyelet is placed in the opening in the bone. The suture ends are then tied, thus securing the suture to the bone. The bone may be pierced with a drill or with a driver as described above. The suture may be connected directly to a tissue or to a medical device, such as a sling, a quick connect device, a suture button, a staple, an implant, or to itself. Appropriate tension on the suture may be provided, for example with use of a suture tensioner.

The invention also provides a quick-connect bone suture fastener for fastening suture to a bone. The suture fastener consists of a sleeve and a sleeve plug. The sleeve has at least two openings through which suture may pass. The sleeve is adapted for inserting into a bone, and has a surface for frictionally contacting the sleeve plug, which functions to occlude at least one of the openings. The friction surface of the sleeve may be threaded for contacting with a threaded sleeve plug; the friction surface also may be a plurality of flanges that overlie the top of the sleeve plug after the plug is inserted into the sleeve. There also may be a friction surface on the outside of the sleeve for contacting with the bone. The sleeve may have a flange rim for suspending the sleeve at the surface of the bone. The sleeve may also have a conical shape to facilitate advancing it into and contacting it with the bone.

This aspect of the invention provides a method for quick connection of a suture to a bone. A bone is pierced and a suture is passed through the bone and through the sleeve. The sleeve is then pressed into the opening in the bone. The sleeve plug is then inserted into the sleeve, and the suture is secured. The bone may be pierced by drilling or by driving a guide through the bone. The suture may be attached to tissue or to a device, as described above. The suture may be tensioned with a suture tensioner prior to placement of the sleeve plug.

BRIEF DESCRIPTION OF THE DRAWINGS

FIG. 16 is an enlarged view of the distal end of the sling application catheter taken along line 16-16 of FIG. 15.

FIG. 17 is a cross-sectional view taken along line 17-17 of the sling application catheter of FIG. 16.

FIG. 18 is an enlarged view of the distal end of a sling application catheter having a reinforcing stiffener within the pouch.

FIG. 19 is a cross-sectional view taken along line 19-19 of the sling application catheter of FIG. 18.

FIG. 20 is an enlarged view of the distal end of a sling application catheter having a pouch made of a porous material.

FIG. 38A is a perspective view of a sling application device.

FIG. 38B is a plan view taken along line 3813-3813 of the sling application device of FIG. 38A showing the tab on the locking button.

FIG. 42 is a side view of an alternate embodiment of the sling application device in which the portion of the shafts proximal to the bend is cylindrical and the portion of the shafts distal to the bend is a flat tube.

FIG. 43 is a cross-sectional view taken along line 43-43 of the portion of the first shaft distal to the bend of the sling application device of FIG. 42.

FIG. 44 is a cross-sectional view taken along line 44-44 of the portion of the first shaft proximal to the bend of the sling application device of FIG. 42.

FIG. 47A is a plan view of the first shaft taken along line 47A-47A of the sling application device of FIG. 47.

FIG. 47B is a plan view of the second shaft taken along line 4713-4713 of the sling application device of FIG. 47.

FIG. 84 is a plan view of the balloon catheter having a flat profile balloon.

FIG. 85 is a cross-sectional view taken along line 85-85 of the balloon catheter of FIG. 84.

FIG. 86 is a cross-sectional view taken along line 86-86 of the balloon catheter of FIG. 84.

FIG. 101b illustrates the insertion of a dilator into the vaginal hiatus over the needle of FIG. 101a.

FIG. 107 is a cross section including a driver as in FIG. 106, depicting the passage of the bone-piercing guide through the pubic bone lateral to the urethra and into the vagina.

FIG. 108a is a transverse cross section taken along the line 108-108 in FIG. 107, showing the distal end of the first jaw of the driver in position in the vagina, with cannulas forming a passage through the pubic bone and into the vagina.

FIG. 108b is a cross section as in FIG. 108a that illustrates passage through the cannulas of a suture and connecting device.

FIG. 109a is a cross section as in FIG. 108a, showing the pubic bone, the urethra, the hiatal region and the vagina, with sutures attached on the right and left sides of the upper vaginal wall.

FIG. 109b is a cross section as in FIG. 109a, showing elevation of the urethra resulting from tensioning of the sutures.

FIG. 110 is a cross section view of the pelvis as in FIG. 102 with the upper clamp of the driver frame assembly in place, articulating with the rigid catheter and the tongue.

FIG. 111a is a cross section taken along the line 111-111 in FIG. 110, and illustrates the hiatal region depicting a flat insertion tongue.

FIG. 111b is a cross section taken along the line 111-111 in FIG. 110, and depicts a concave insertion tongue in a hiatal cavity.

FIG. 111c is a cross section taken along the line 111-111 in FIG. 110, and depicts an additional embodiment of a concave insertion tongue in a hiatal cavity.

FIG. 112 is a cross section view of the pelvis as in FIG. 102 showing the complete driver frame assembly in place.

FIG. 113 is a cross section view taken along the line 113-113 in FIG. 112, showing left and right displacement of the bone-piercing guides mounted on the driver.

FIG. 114 is a cross section as in FIG. 102, and depicts the driver frame assembly with the bone-piercing guides penetrating to the hiatal cavity.

Figure 115:
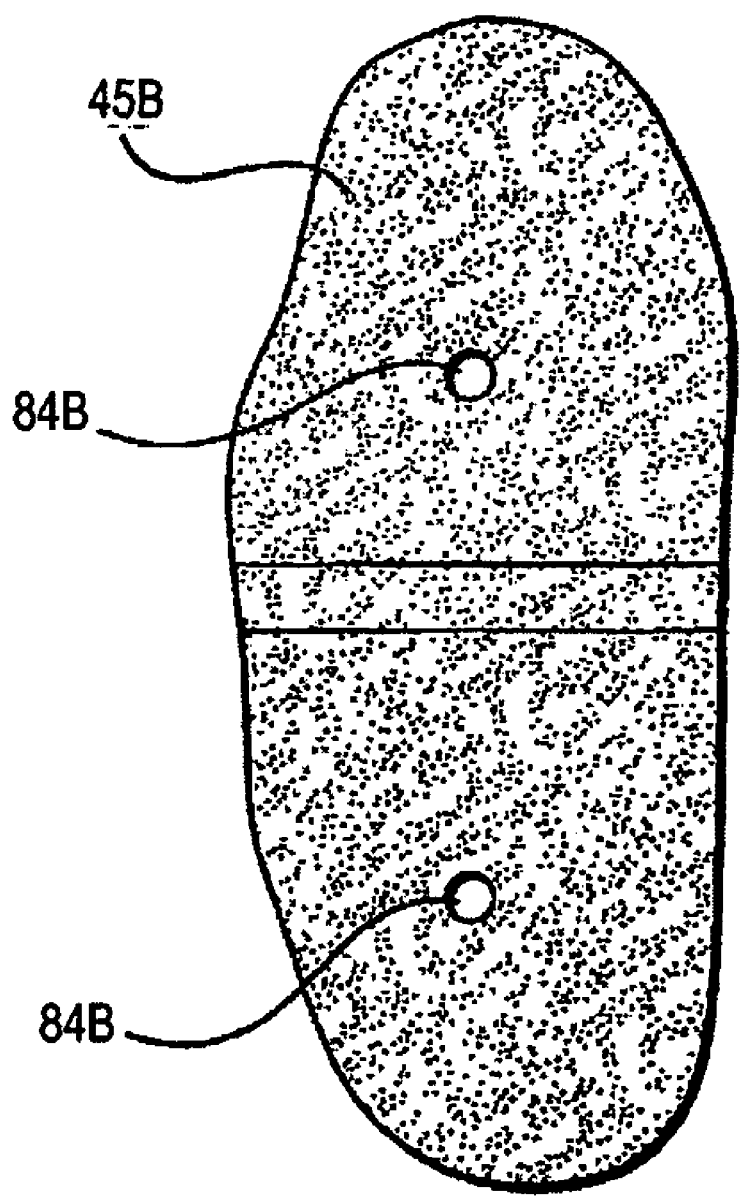

FIG. 115 illustrates the pubic bone with the guides passing through the bone left and right of the pubic symphysis.

Figure 102:
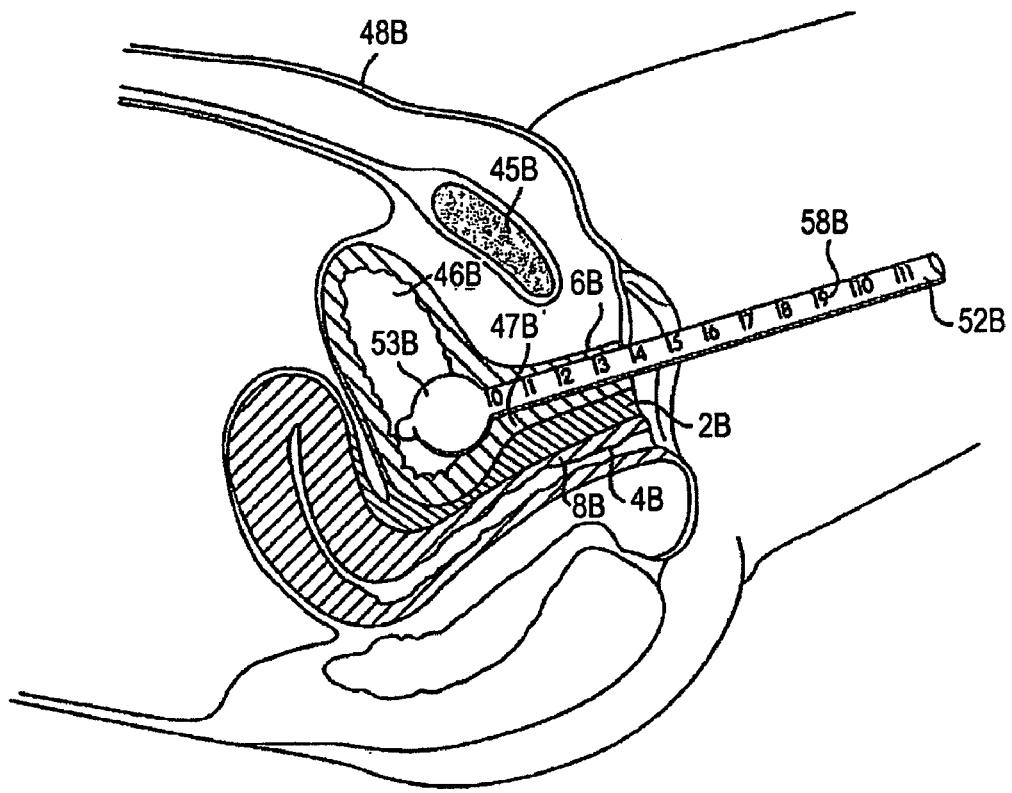
FIG. 102 is a partial longitudinal cross section of the vagina, urethra, and bladder showing a rigid catheter in place in the urethra.
Figure 116:
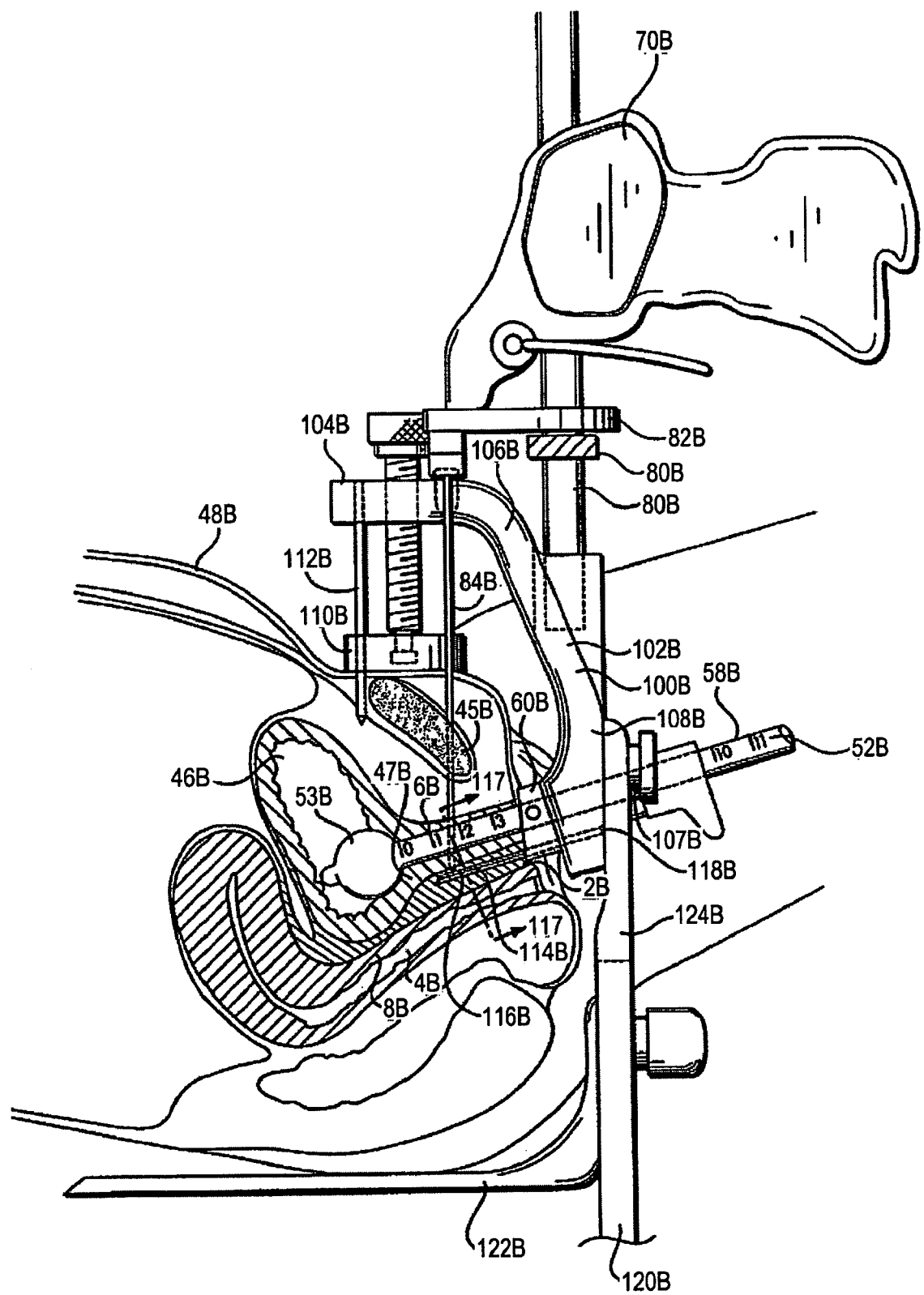

FIG. 116 is a cross section view of the pelvis as in FIG. 102 and the driver frame, with the tongue supporting an insert card and a sling in position.

Figure 117:
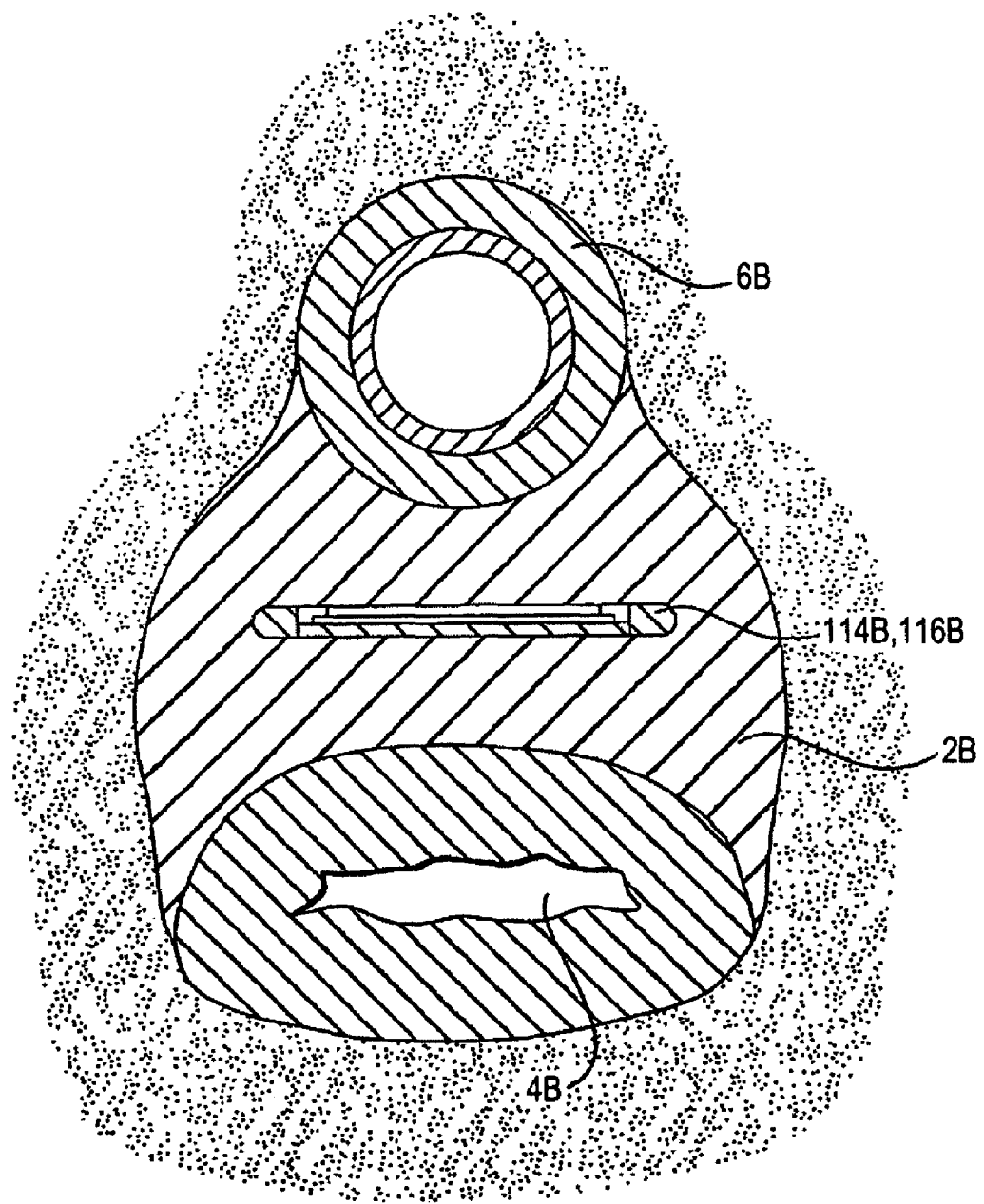

FIG. 117 is a cross section taken along the line 117-117 in FIG. 116, and shows the position of the rigid catheter inside the urethra, the tongue, the insert card, and the sling.

Figure 118:
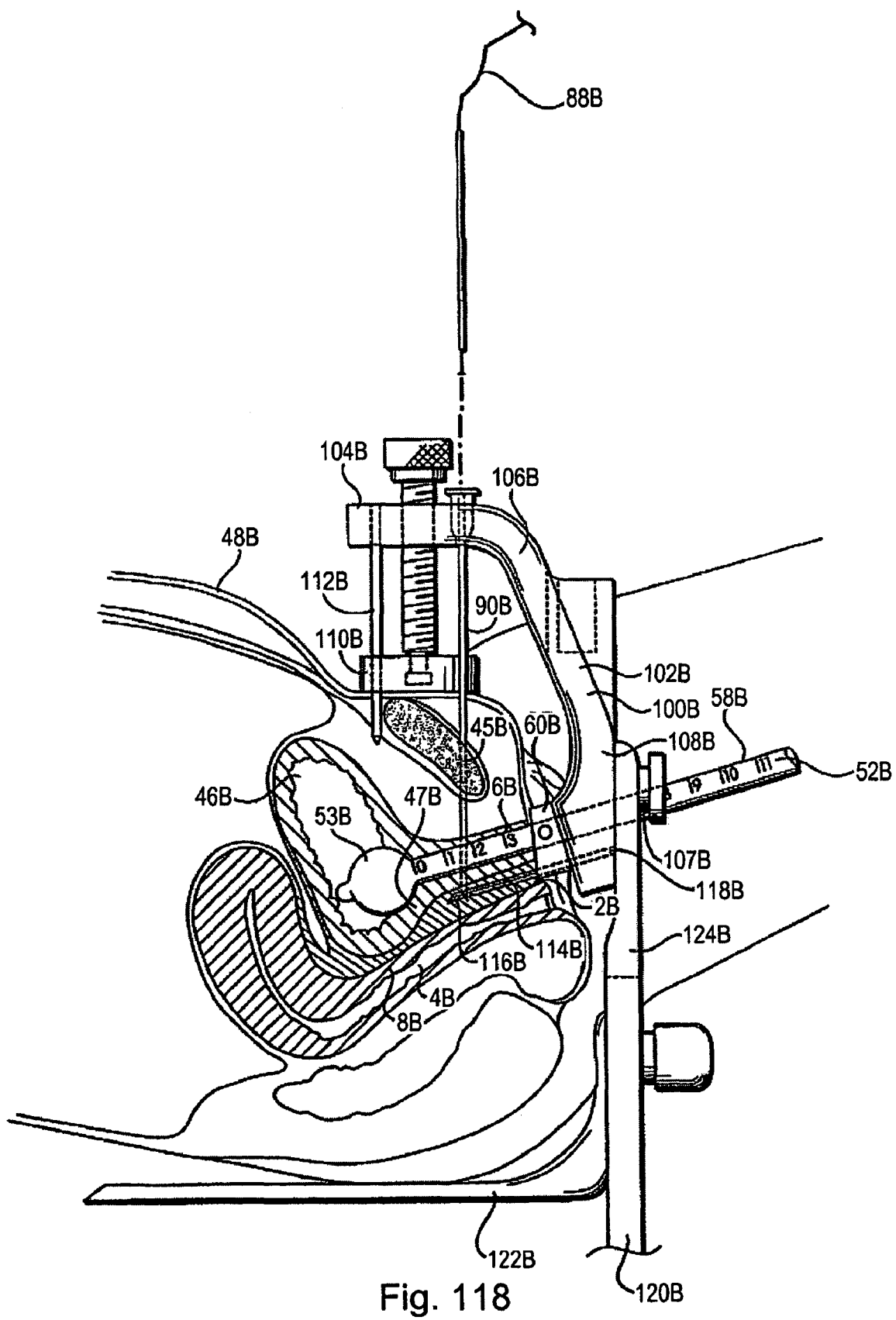

FIG. 118 is a cross section as in FIG. 116 with the driver frame in place, and shows the driver frame with the driver removed and a cannula in position.

Figure 119:
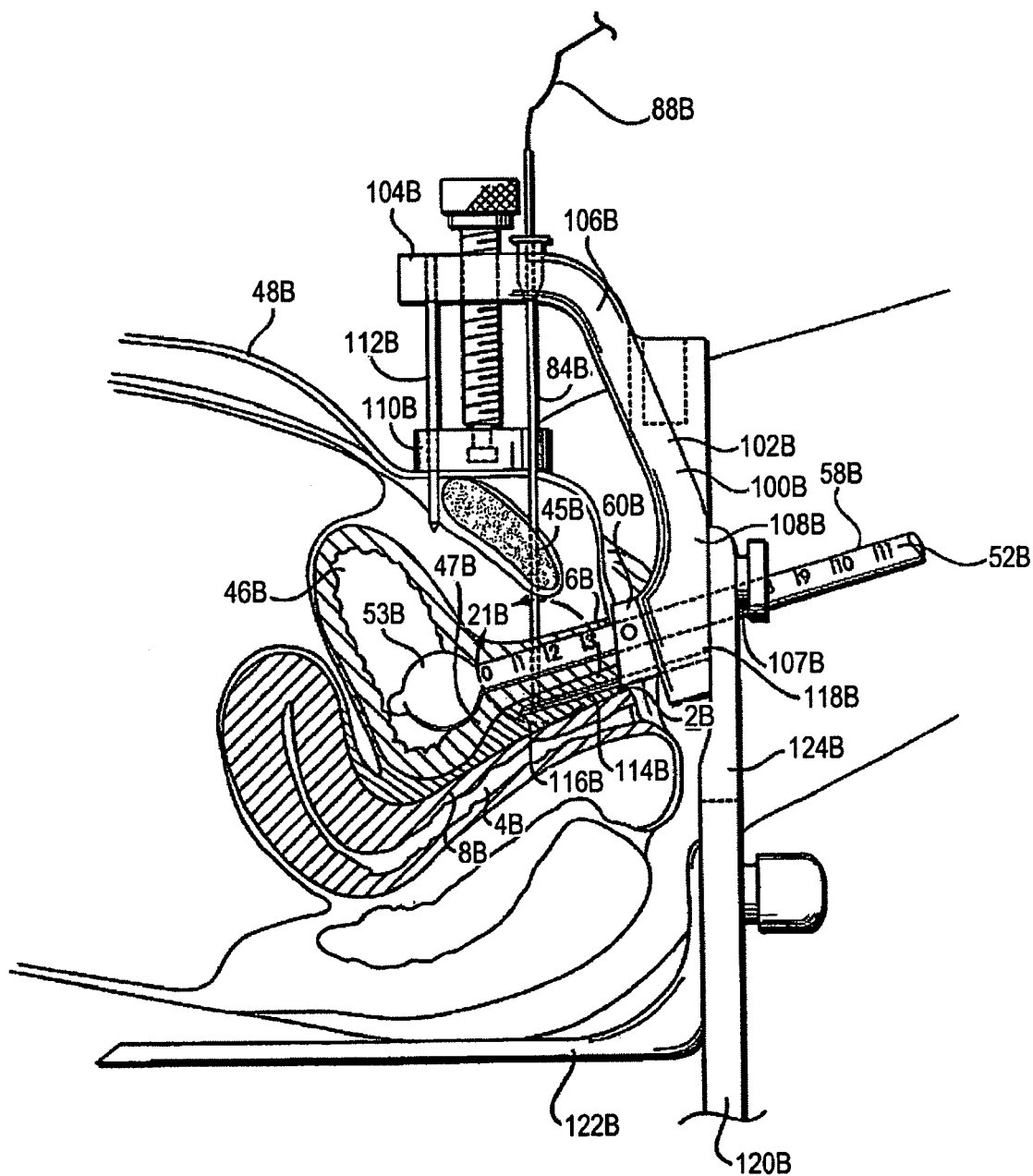

FIG. 119 corresponds to FIG. 118, but shows the driver frame with the cannula in place and a suture with quick-connect device passing through the cannula.

Figure 120:
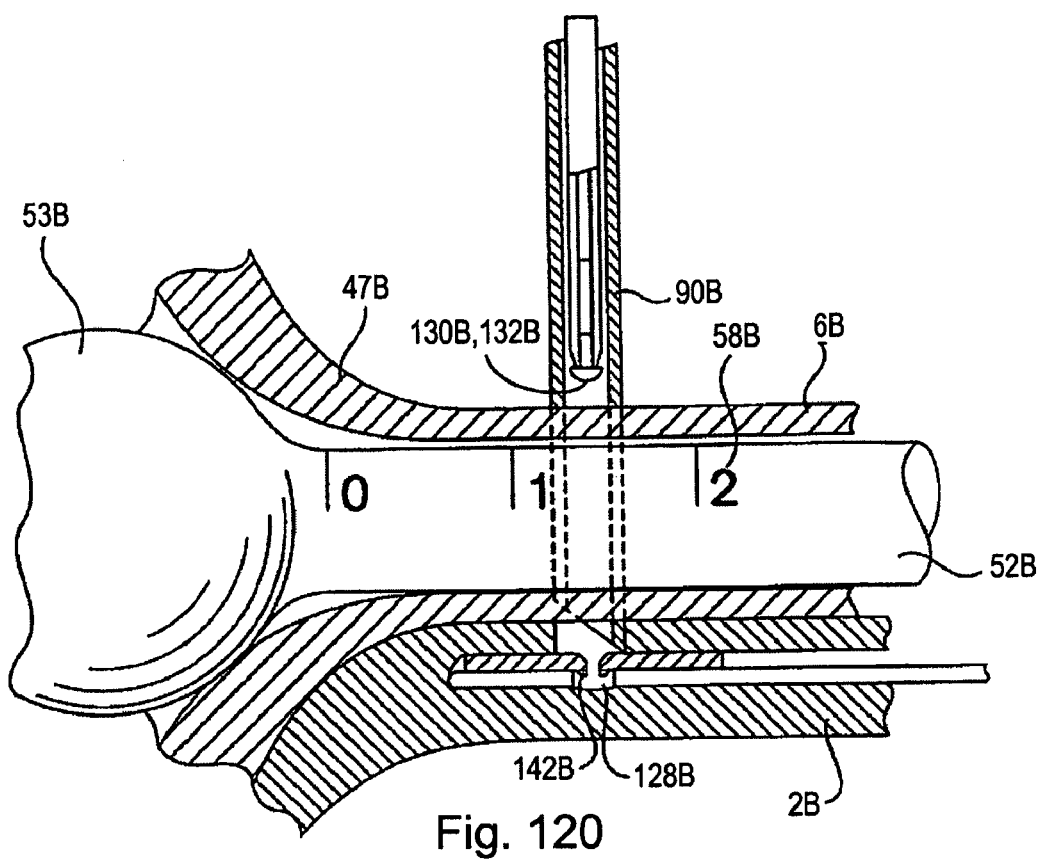

FIG. 120 is a detail view of the area described by the curved arrows in FIG. 119, and shows detail of the quick-connect device passing through the cannula toward the sling.

Figure 121:
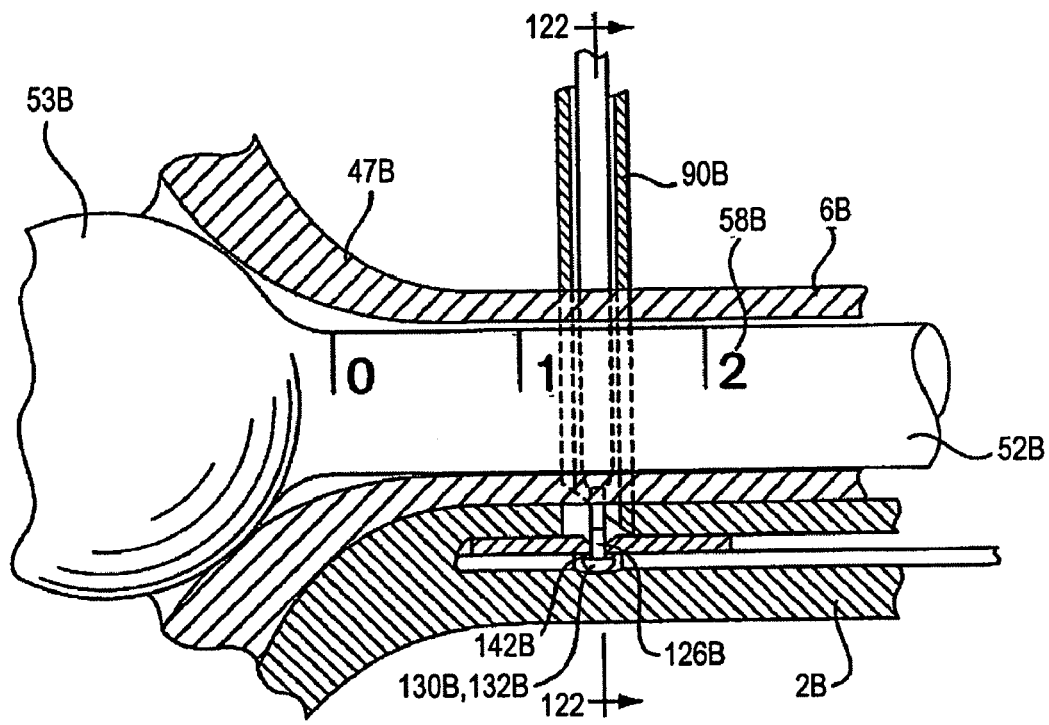

FIG. 121 corresponds to FIG. 120, and provides detail of the quick-connect device articulating with the ring member of the sling.

Figure 122:
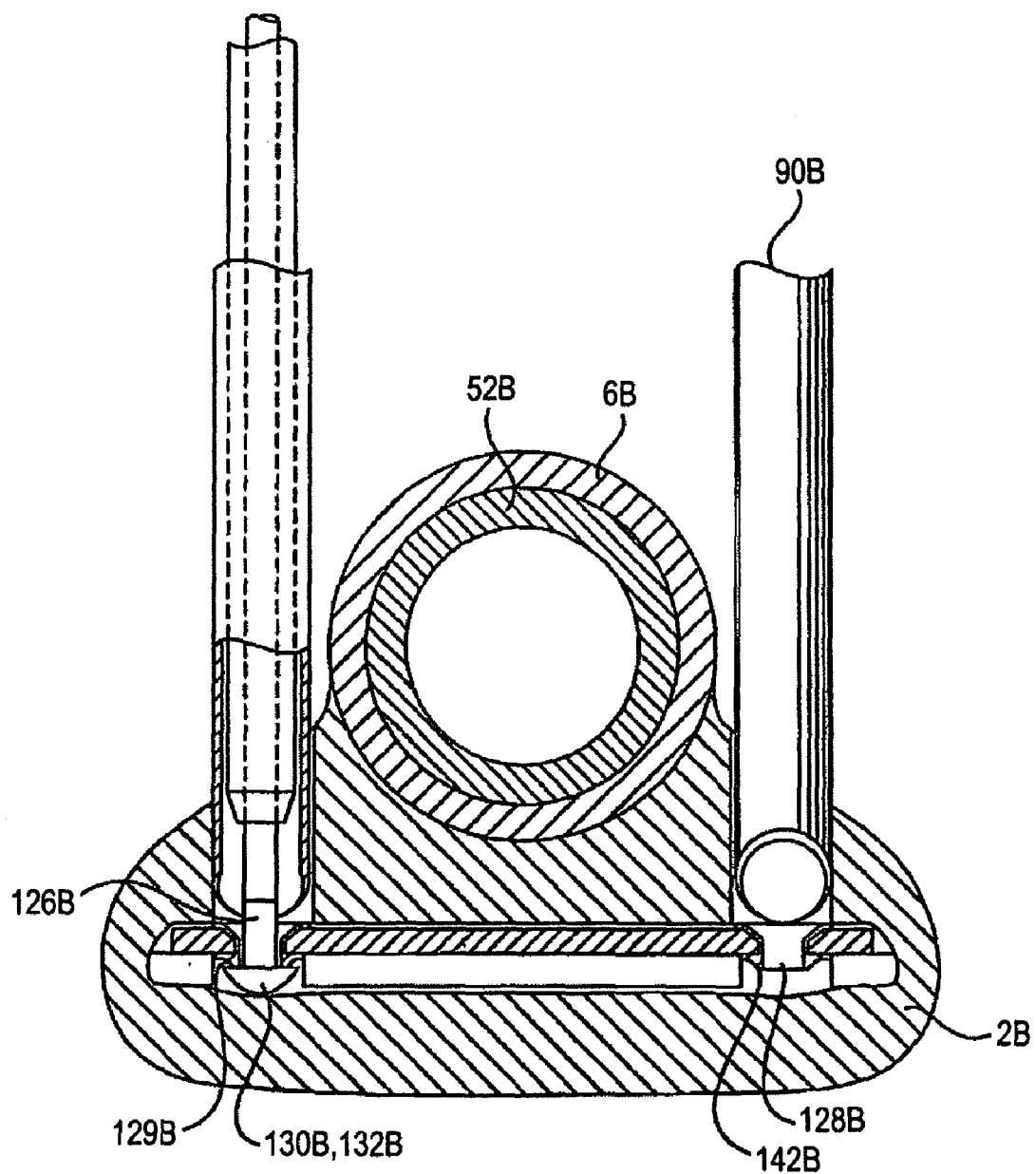

FIG. 122 is a cross section taken along the line 122-122 in FIG. 121, and shows the position of the rigid catheter, left and right side cannulas, and a quick-connect device in the left cannula articulated with the ring member of the sling.

Figure 123A:
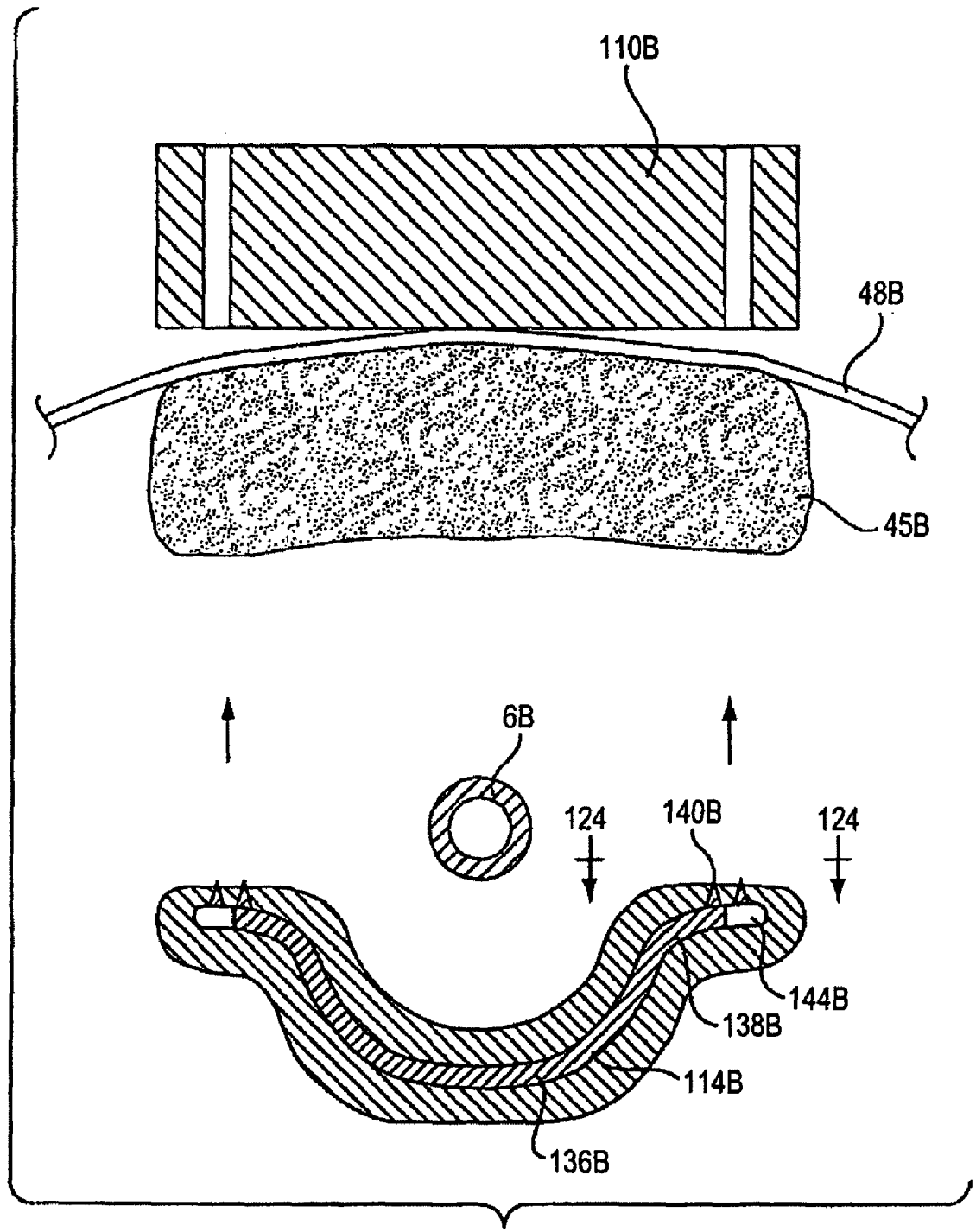

FIG. 123a illustrates in cross section the position of the concave insertion tongue with contact pins relative to the urethra, the pubic bone, and the compression foot of the driver frame assembly, prior to application of counterpressure on the pubic bone by the concave tongue.

Figure 123B:
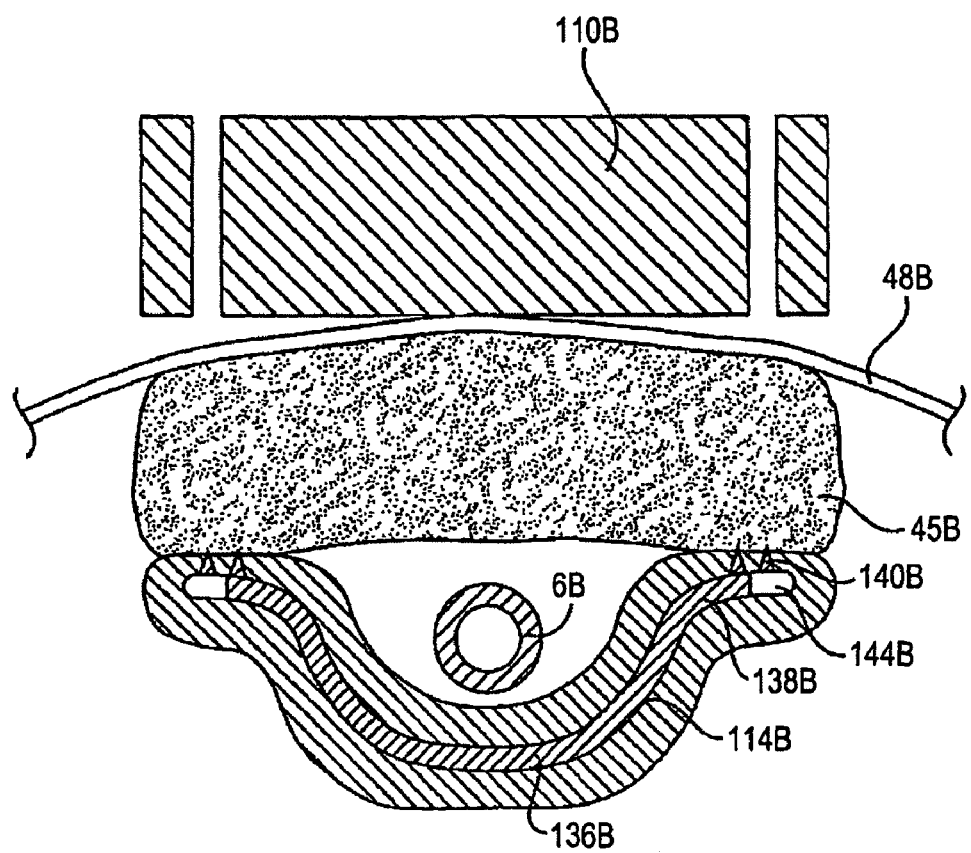

FIG. 123b corresponds to FIG. 123a and shows the concave tongue and contact pins providing counterpressure against the inferior posterior face of the pubic bone.

Figure 124:
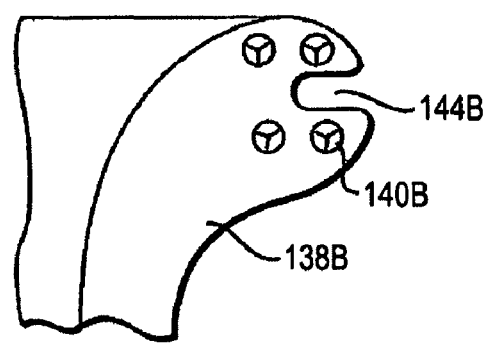

FIG. 124 is a view of the insertion tongue from the direction 124-124 of FIG. 123a, and provides detail of the elevated edge of the concave insertion tongue, showing the position of the contact pins and the passage gap.

Figure 125A:
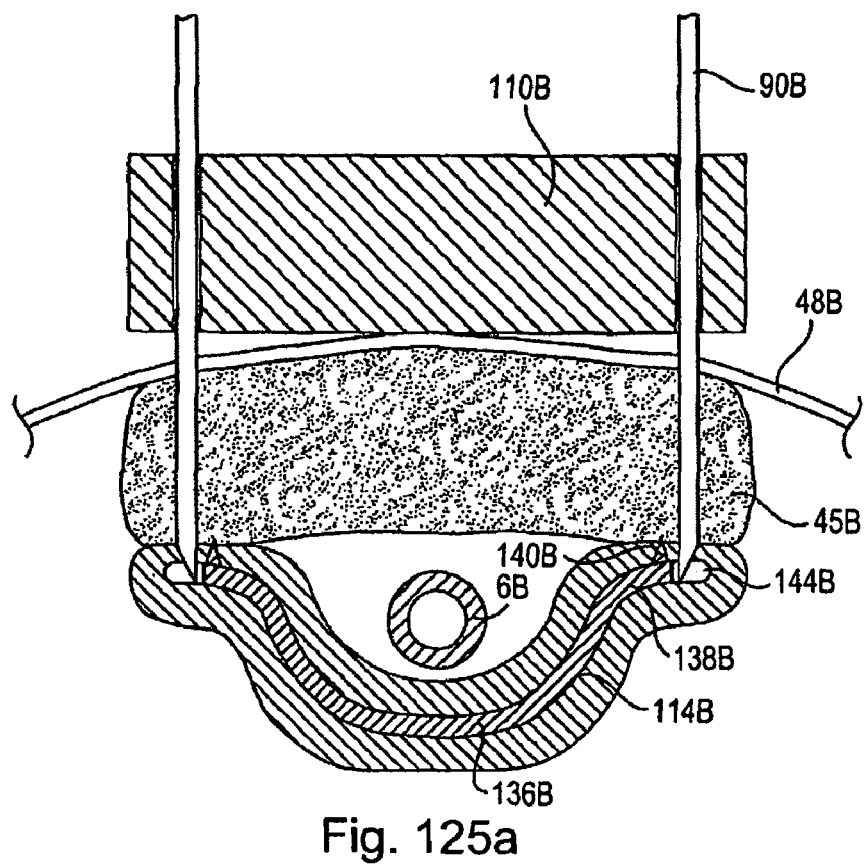

FIG. 125a corresponds to FIG. 123b, and shows the compression foot with bone driver guides passing through the pubic bone and passage gap of the tongue.

Figure 125B:
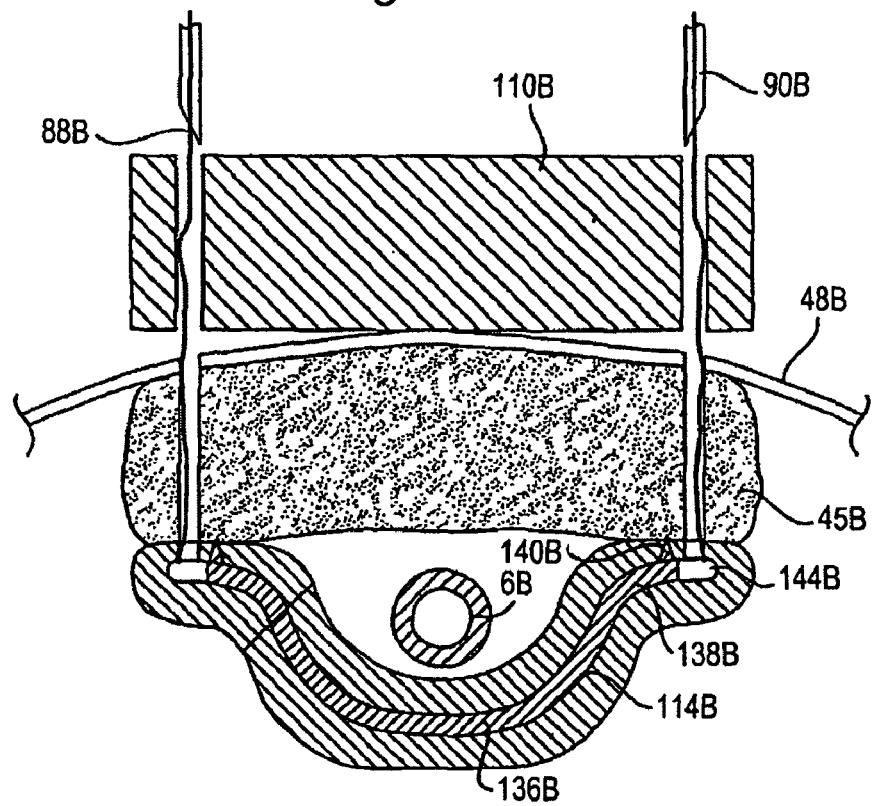

FIG. 125b corresponds to FIG. 125a, and shows the withdrawal of the guides and the position of the sutures.

Figure 126A:
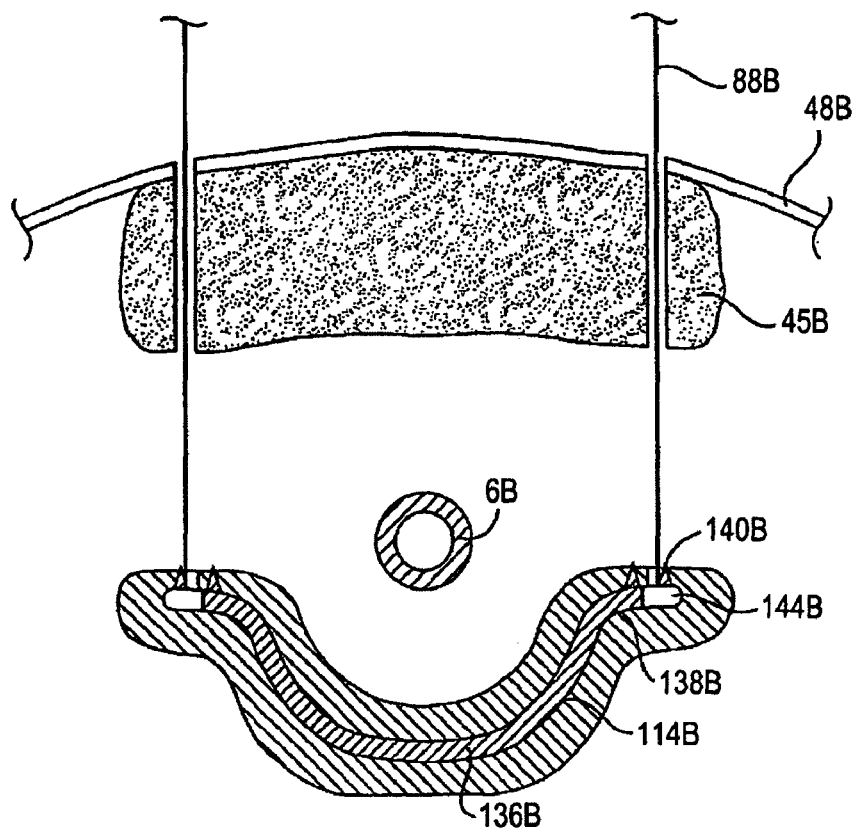

FIG. 126a corresponds to FIG. 125b, and shows the orientation of the sutures, the tongue, and the hiatal cavity before tensioning of the sutures.

Figure 126B:
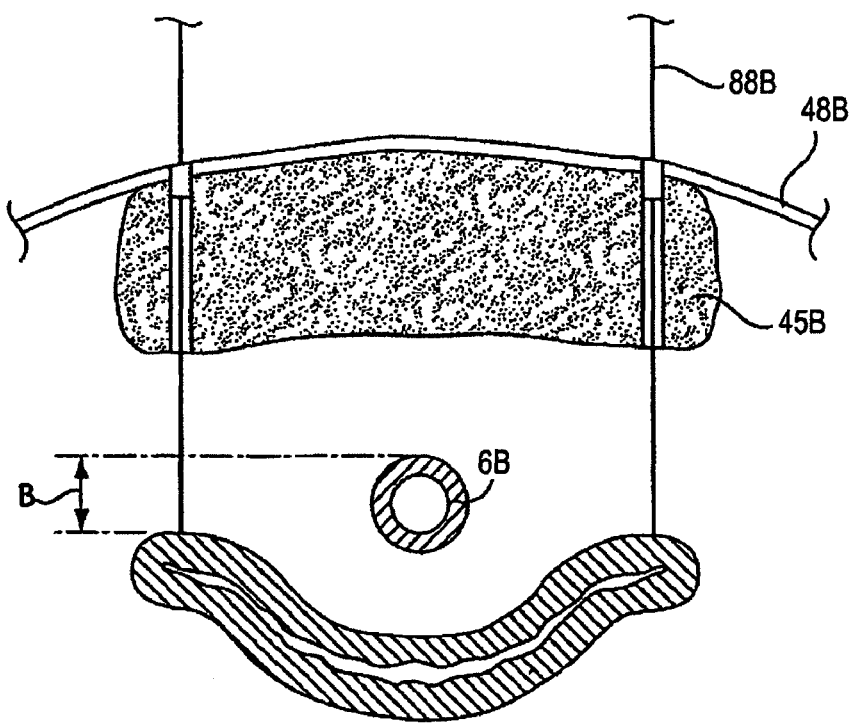

FIG. 126b corresponds to FIG. 126a, and shows the elevation of the hiatal cavity and the urethra after tensioning of the sutures.

Figure 127:
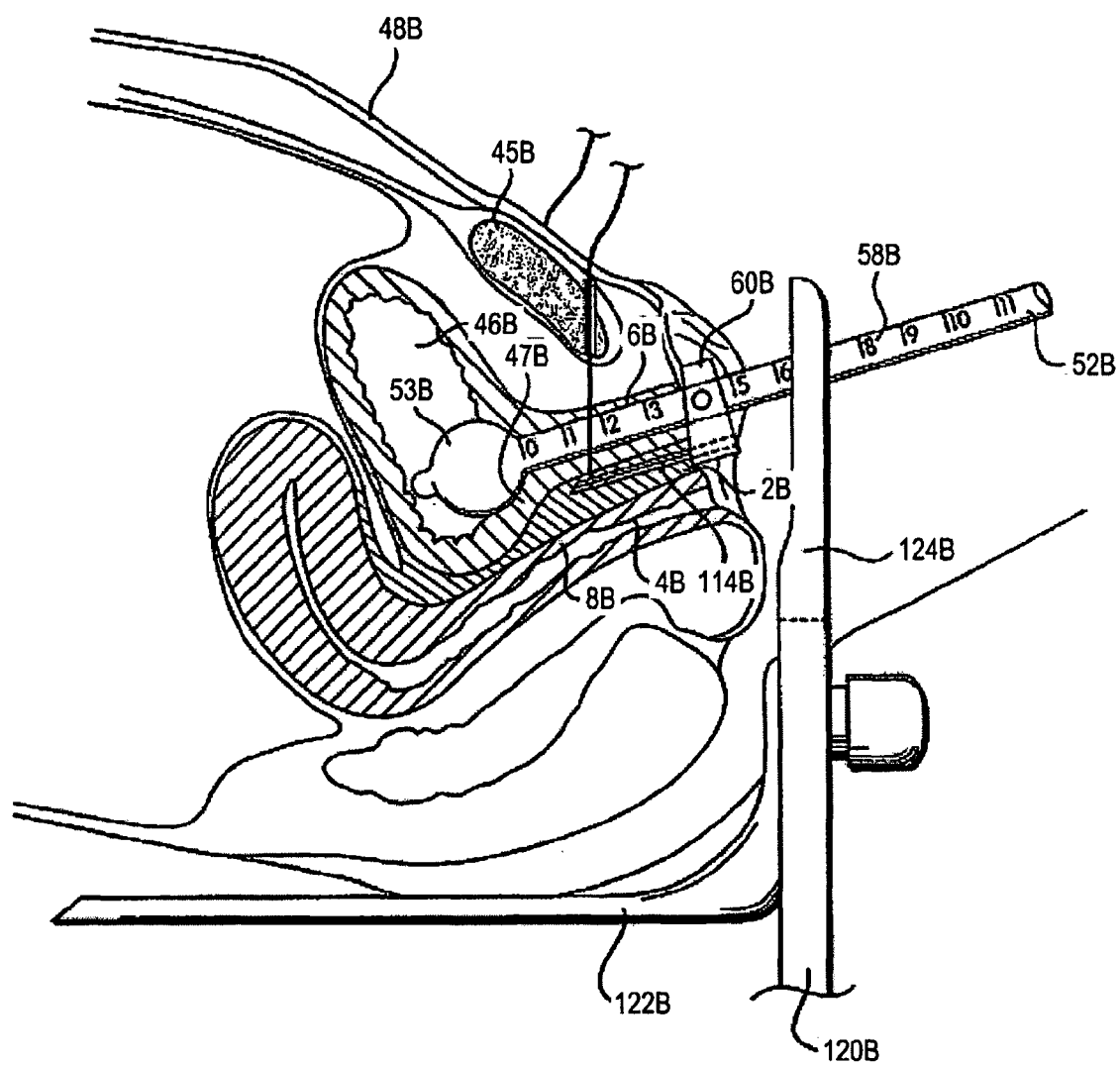

FIG. 127 is a cross section view as in FIG. 102 showing a sling with the ring member of a quick-connect device in place.

Figure 128:
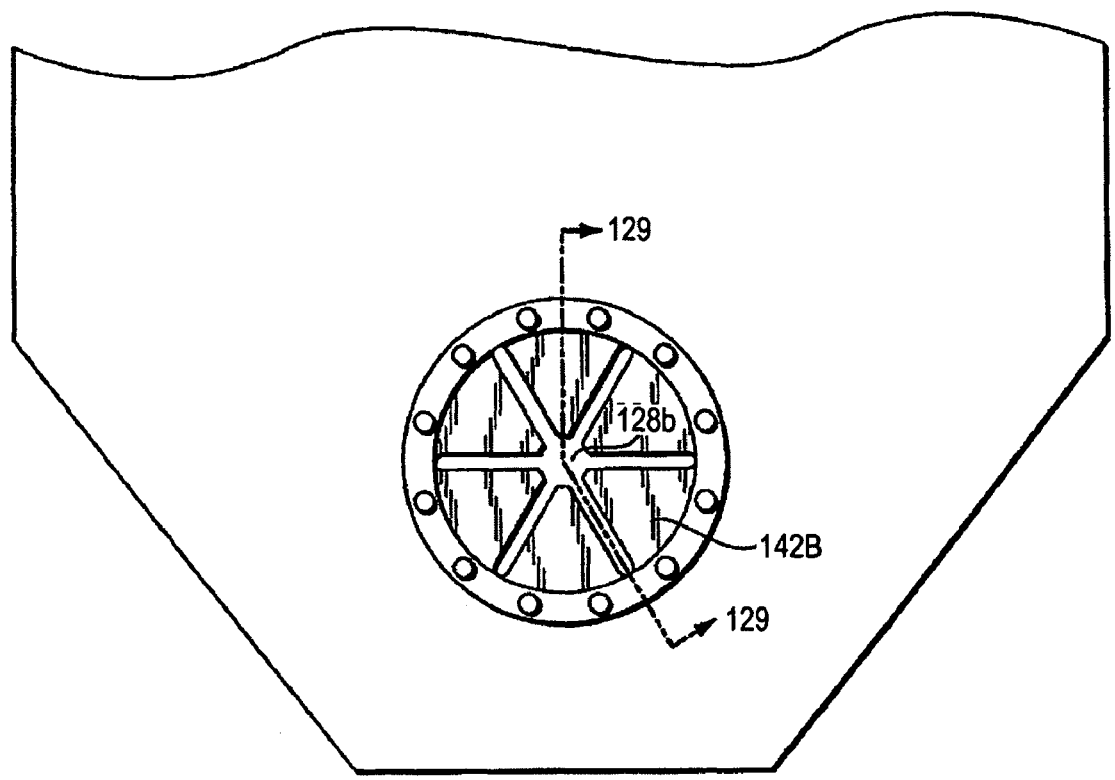

FIG. 128 is a plan view of a sling with the ring member of a quick-connect device in place.

Figure 129:
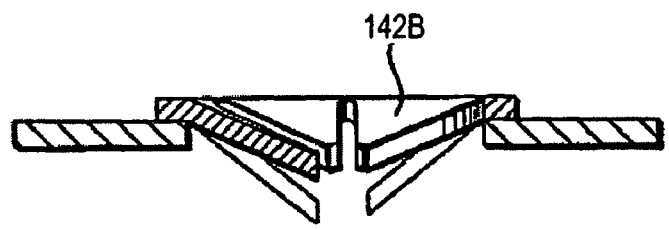

FIG. 129 is a cross section view taken along the line 129-129 in FIG. 128, showing the sling with the quick-connect ring member in place.

Figure 130:
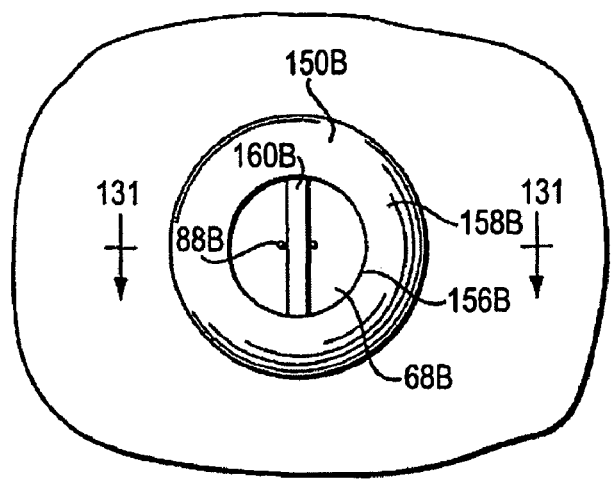

FIG. 130 is a plan view showing the bone eyelet in position in a bone with suture on either side of the crosspiece.

Figure 131:
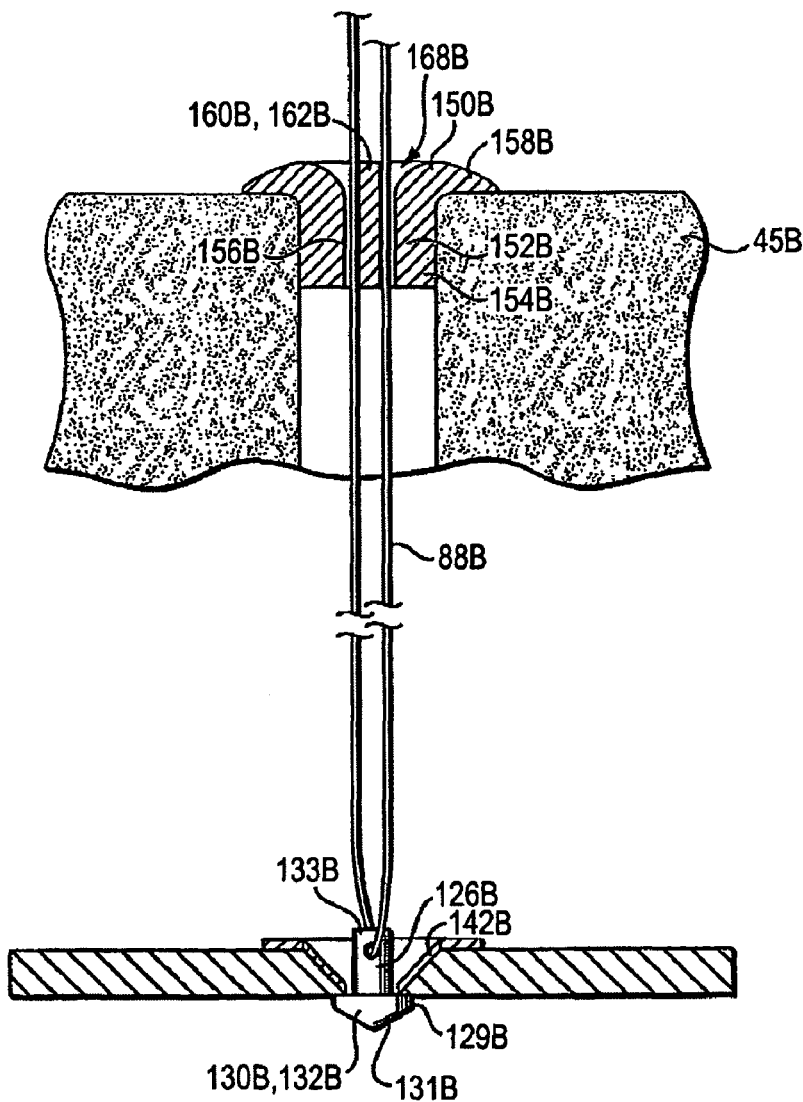

FIG. 131 is a cross section taken along the line 133-133 in FIG. 130, and depicts the bone eyelet with a planar crosspiece in position in the pubic bone and connected by suture to an arrowhead configuration of the quick-connect device articulated with the ring member of the sling.

Figure 132:
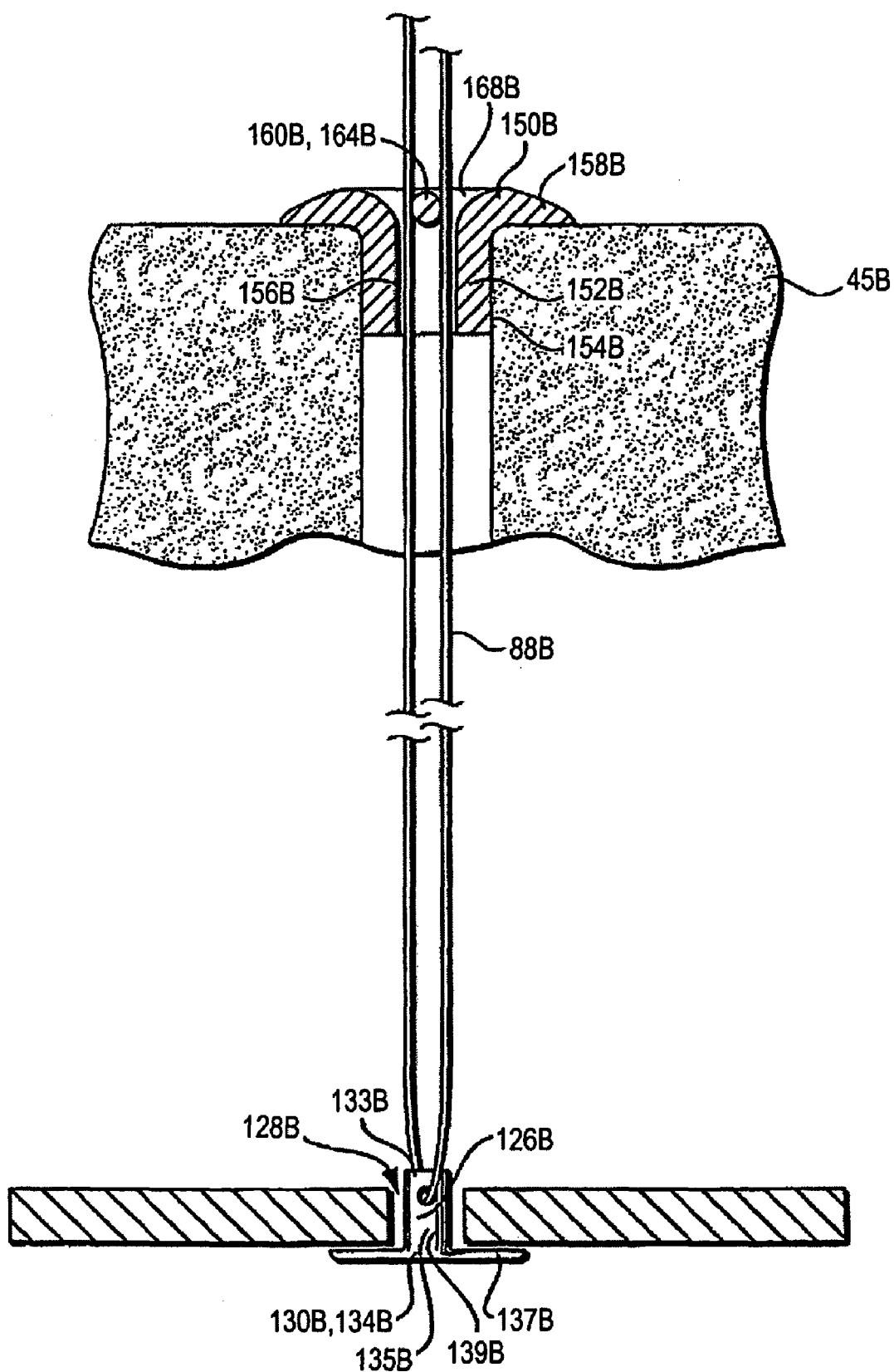

FIG. 132 corresponds to FIG. 131, but shows a bone eyelet with a rod crosspiece in place in the pubic bone connected via suture to a T-configuration of the quick-connect device.

Figure 133:
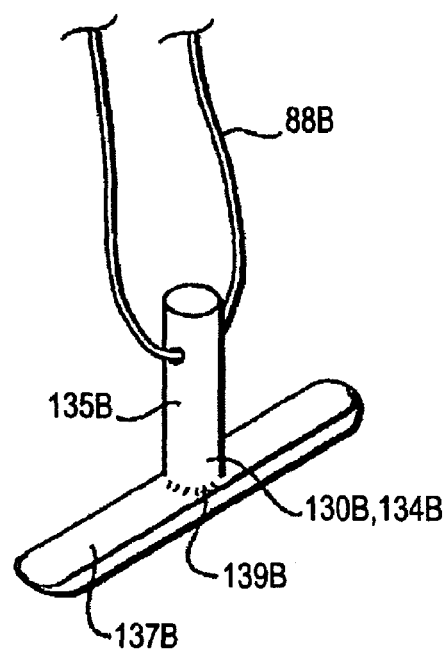

FIG. 133 is a perspective view of the T-configuration of the quick-connect device.

Figure 134:
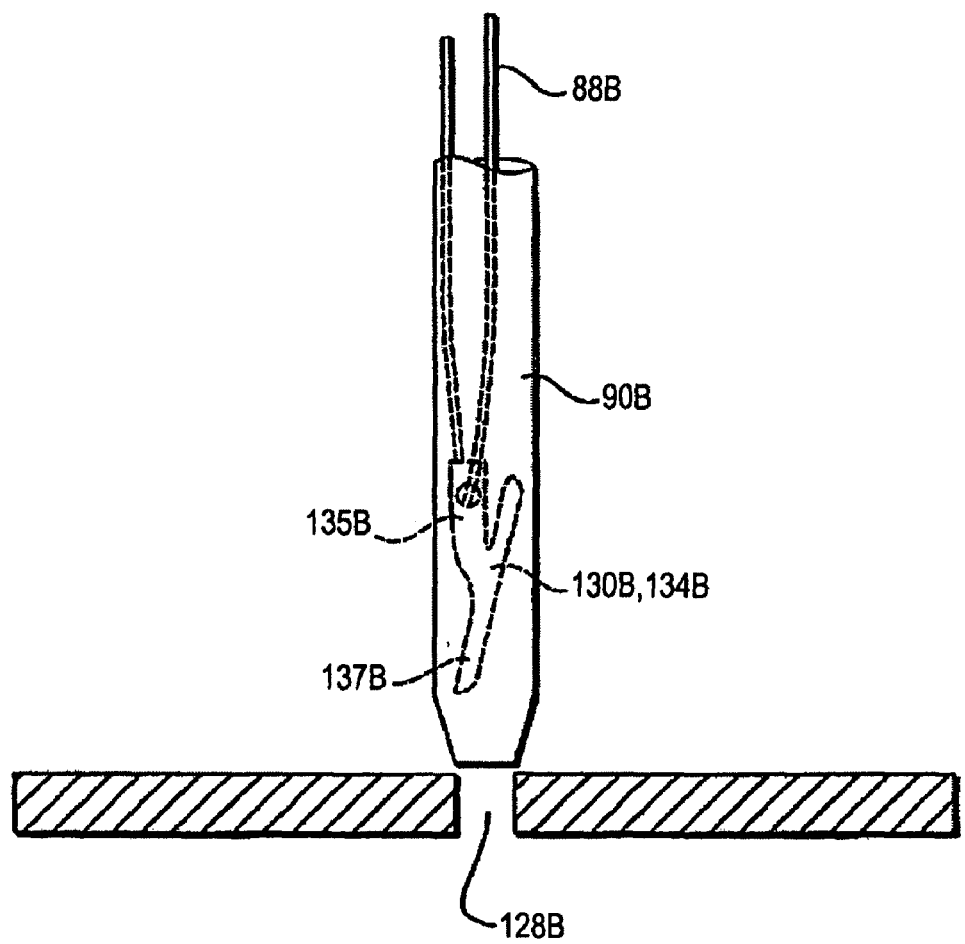

FIG. 134 is a side elevation that depicts the passage of the T-configuration of the quick-connect device through a cannula toward the ring member of a sling.

Figure 135:
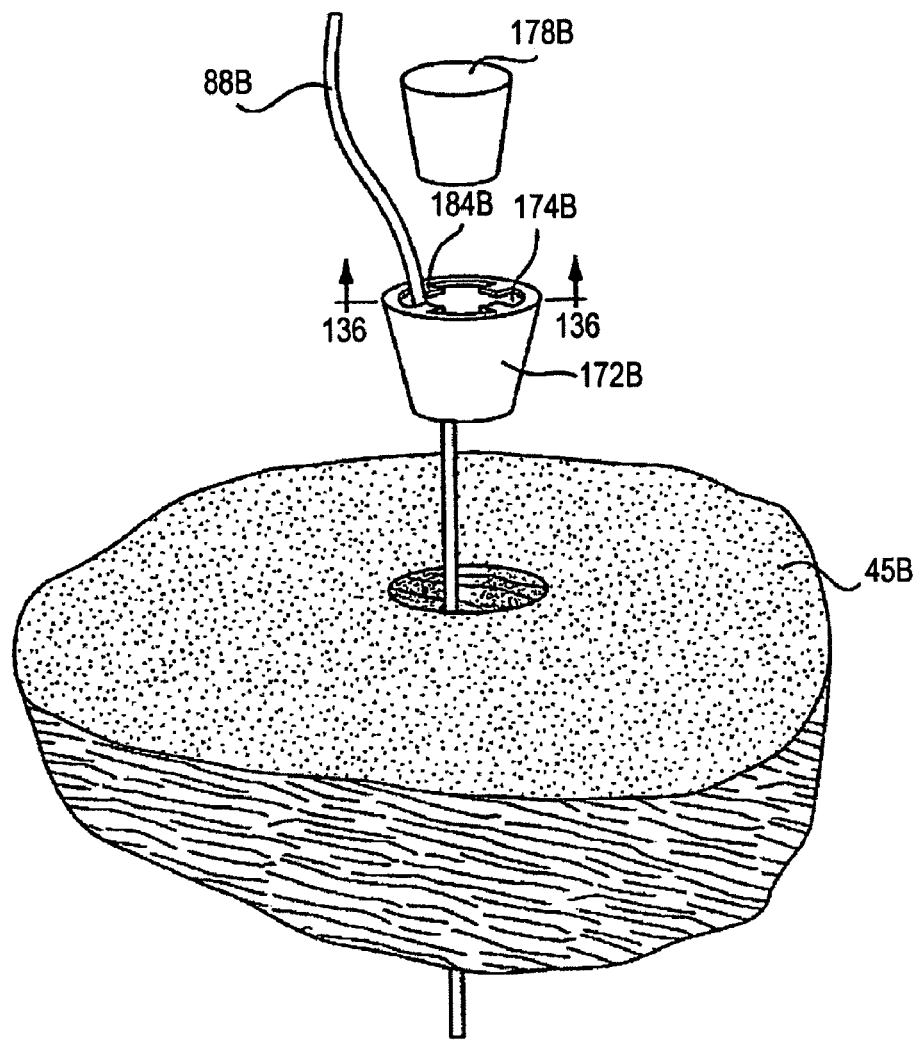

FIG. 135 is a perspective view of a bone suture fastener and a sleeve plug oriented above the pubic bone.

Figure 136A:
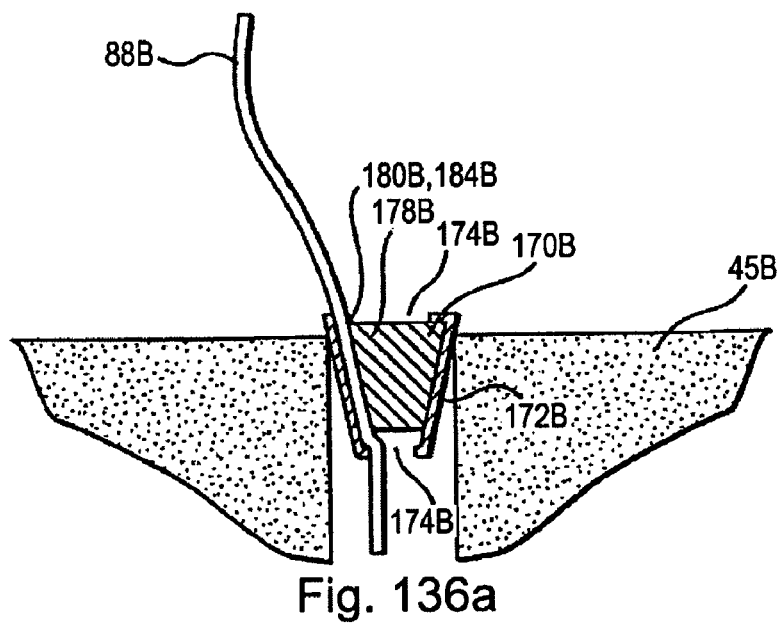

FIG. 136a is a cross-section taken along the line 136-136 in FIG. 135 and illustrates suture passing through the sleeve with the sleeve plug in place.

Figure 136B:
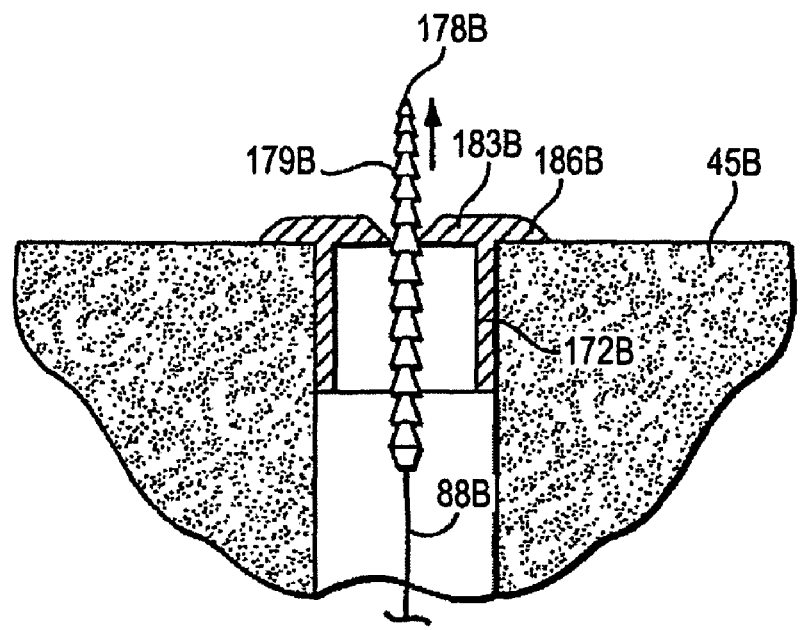

FIG. 136b is a cross section view similar to FIG. 136a showing the zipper-lock configuration of the bone suture fastener with the sleeve plug in place.

Figure 137:
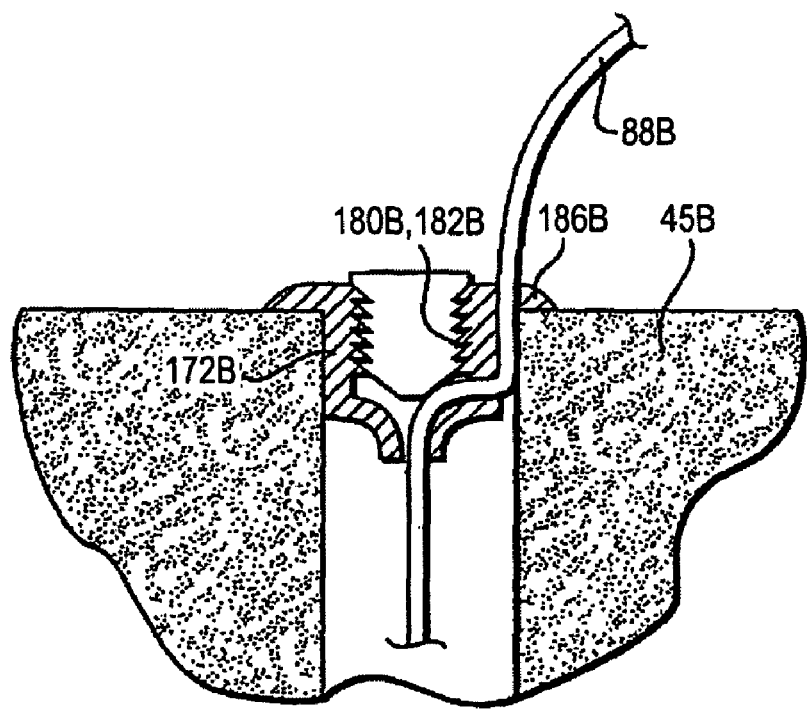

FIG. 137 is a cross section view similar to FIG. 136a showing the threaded configuration of the bone suture fastener with the sleeve plug in place.

DETAILED DESCRIPTION OF THE PREFERRED EMBODIMENTS

Part A

The present invention relates to methods and devices for creating openings or pockets in body tissues and/or dilating body tissues. The guide member placement devices, sling application catheters, tissue dissector/dilators, sling application devices, sling application systems, detachable member sling application devices, retrieval devices, and balloon catheters of the present invention may be used percutaneously or in conjunction with laparoscopic techniques. In such laparoscopic procedures, trocars are placed in the abdomen and the abdomen is insufflated with $CO_2$, causing it to distend. The devices are introduced into the patient's body via the trocars, and the procedure is visualized with a laparoscope.

The devices of the present invention may be used in a wide variety of medical procedures, but are particularly well suited for urethral floor reconstruction procedures such as bladder neck stabilization or suspension procedures in which a sling is used to maintain or improve urinary continence by stabilizing and/or slightly compressing the urethra or by creating a non-moveable pelvic floor. Slings suitable for use in bladder neck stabilization procedures and methods for implanting them are disclosed in U.S. patent application Ser. No. 09/023, 398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

The present invention is particularly well suited for bladder neck stabilization procedures for treating urinary incontinence in females. The bladder neck stabilization procedures for which the present invention is especially well suited involve the creation of an opening or pocket in the tissue between the urethra and the upper vaginal wall, which is called the hiatus. The sling is then inserted in the opening or pocket. Sutures or integral attachment members at the ends of the sling are attached to the pubic bone or surrounding tissue and the tension is adjusted to slightly compress or stabilize the urethra by providing a platform to reduce distension resulting from internal pressures, thereby maintaining or improving urinary continence. Suitable methods and devices for adjusting the tension on the sutures are disclosed in U.S. Pat. No. 5,611,515, issued Mar. 18, 1997 to Benderev et al., the disclosure of which is incorporated herein by reference.

The opening or pocket may be created in a variety of ways. In one approach, the opening or pocket is created by introducing an expandable balloon into the tissue between the urethra and the upper vaginal wall. When the balloon is expanded, the surrounding tissue is dilated or torn, generating an opening or pocket of sufficient size to receive the sling.

In an alternative approach, the opening or pocket is created by hydrodissection. In this approach, a bolus of saline or other sterile solution is injected into the tissue between the urethra and the upper vaginal wall, resulting in an opening or pocket sized to receive the sling. The bolus of saline may be administered by positioning a syringe inside the vagina and piercing the vaginal wall with the needle of the syringe such that the tip of the needle is in the tissue between the urethra and the upper vaginal wall. Alternatively, the bolus of saline may be administered directly into the hiatal tissue without piercing the vaginal wall.

The volume of saline injected into the tissue in the hydrodissection procedure is too large to be rapidly absorbed such that the tissue must separate to accommodate the saline bolus.

Preferably, the volume of saline introduced into the tissue is from about 4 cc to about 10 cc. More preferably, the volume of saline is about 4 to about 5 cc.

In yet another approach, the opening or pocket is created by dissecting the tissue between the urethra and the upper vaginal wall with a combination of blunt dissectors and sharp cutters.

The opening or pocket may be created and the sling may be introduced by taking a variety of routes through the patient's body. In one approach, called the percutaneous approach, the opening or pocket is created by making suprapubic incisions into which a device for introducing an opening or pocket in a body tissue or dilating a body tissue is inserted. The device is advanced through the patient's body tissue into the tissue between the urethra and the upper vaginal wall where the opening or pocket is to be created. In some instances, the device for introducing an opening or pocket in a body tissue or dilating a body tissue may also introduce the sling into the opening.

In another approach, called the hiatal approach, the opening or pocket is created and the sling is introduced by directly accessing the tissue between the urethra and the upper vaginal wall. In this procedure the opening or pocket can be created without making suprapubic or vaginal incisions.

In other approaches, the opening or pocket is created directly in the tissue between the urethra and the upper vaginal wall and the sling is introduced with a device advanced into the opening or pocket from a suprapubic or vaginal incision.

The devices and procedures described briefly above are discussed in greater detail in the following sections. It will be appreciated by those of skill in the art that any of the disclosed devices and methods for creating an opening or pocket can be combined with any of the disclosed devices and methods for introducing a sling into the opening or pocket.

Guide Member Placement Device

One aspect of the present invention relates to methods in which the sling is introduced over a guide member and devices for use in such methods. The guide member may be a suture, guidewire, or other structure suitable for guiding a sling to a desired location.

In one embodiment, the opening or pocket in which the sling is introduced is created first and the guide member is then passed through the opening or pocket. In this embodiment, the opening or pocket may be created using any of the techniques disclosed herein, including expandable balloons and hydrodissection.

Alternatively, the opening or pocket may be created during guide member placement by extending and retracting a blunt dissector on a guide member placement device.

In yet another embodiment, the opening or pocket in which the sling is introduced is created by the sling application catheter disclosed herein after the guide member is positioned.

Devices and methods for using a guide member to introduce a sling in the tissue between the urethra and the upper vaginal wall will now be discussed in greater detail.

One aspect of the present invention relates to guide member placement devices for applying a guide member under the urethra in a less invasive manner without puncturing the vaginal wall.

In general, the guide member placement device comprises a shaft having a proximal end, a distal end, and a lumen extending therethrough. The lumen is adapted for receiving a guide member.

Preferably, the shaft is rigid. It is also preferred that the proximal end of the shaft is attached to a handle having a lumen extending therethrough. Preferably, the guide member placement device has a blunt dissection tip with a lumen extending therethrough. The blunt dissection tip is preferably located at the distal end of the shaft. It is also preferred that the blunt dissection tip is on a blunt dissector which is within the shaft and is extendable from and retractable in the shaft.

Preferably, the lumen in the blunt dissector is in fluid communication with the lumen in the handle. Preferably, the blunt dissector is axially movable and can be extended from and retracted in the shaft. Preferably, the blunt dissector is made of rigid plastic or flexible metal. For example, the blunt dissector may be a coil of stainless steel. The blunt dissector may be solid and may be made of metals such as stainless steel, spring steel, Elgiloy, Nitinol, or other generally elastic metals. The blunt dissector may also be a rigid plastic such as nylon or Acrylonitrile Butadiene Styrene (ABS).

The guide member placement device has an engaging member at the distal end of the shaft which is complementary to or otherwise adapted to be attached to an engaging member at the distal end of the shaft of a second guide member placement device, such that the shafts of the two guide member placement devices can be attached to one another with the lumens of the blunt dissectors in each shaft in fluid communication with one another.

Figure 1:
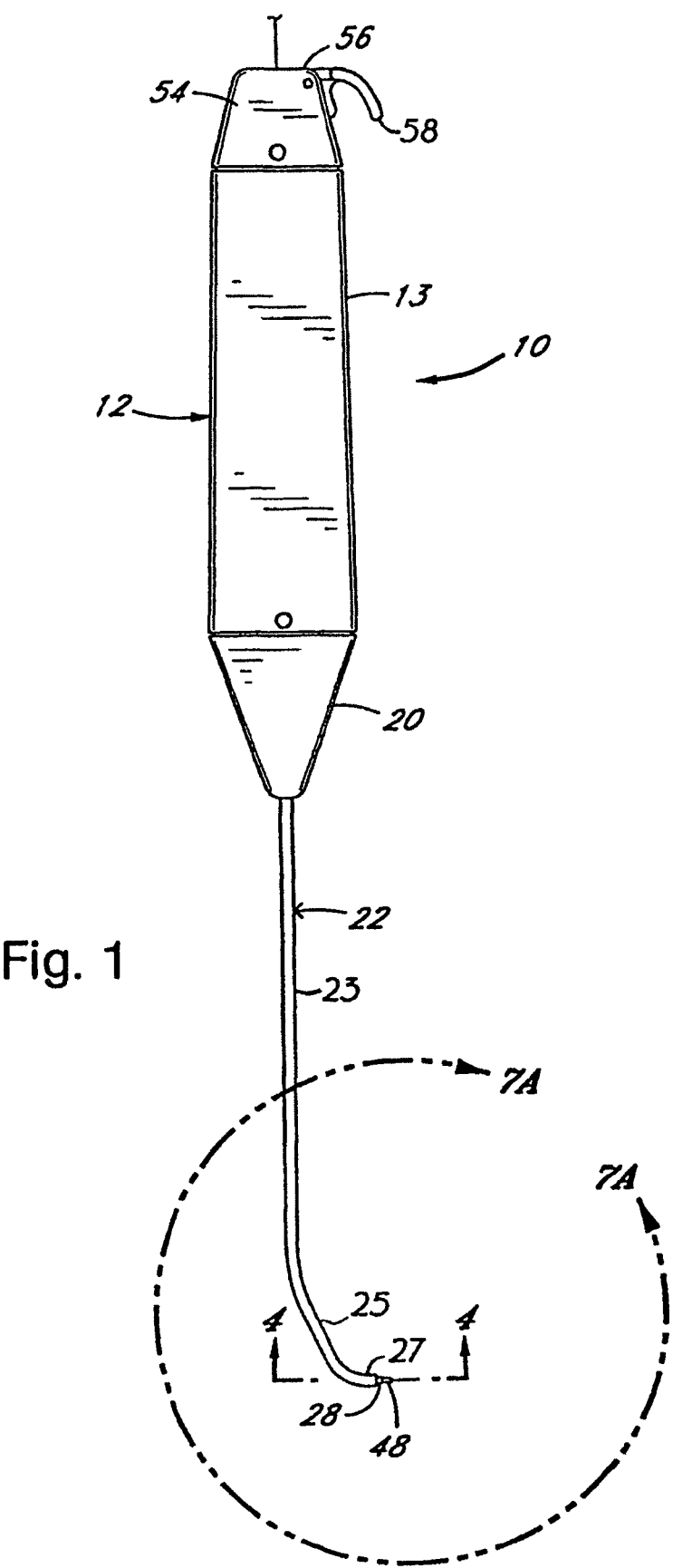
FIG. 1 is a side view of an embodiment of a guide member placement device having a male connector at the distal end of the shaft.
Figure 2:
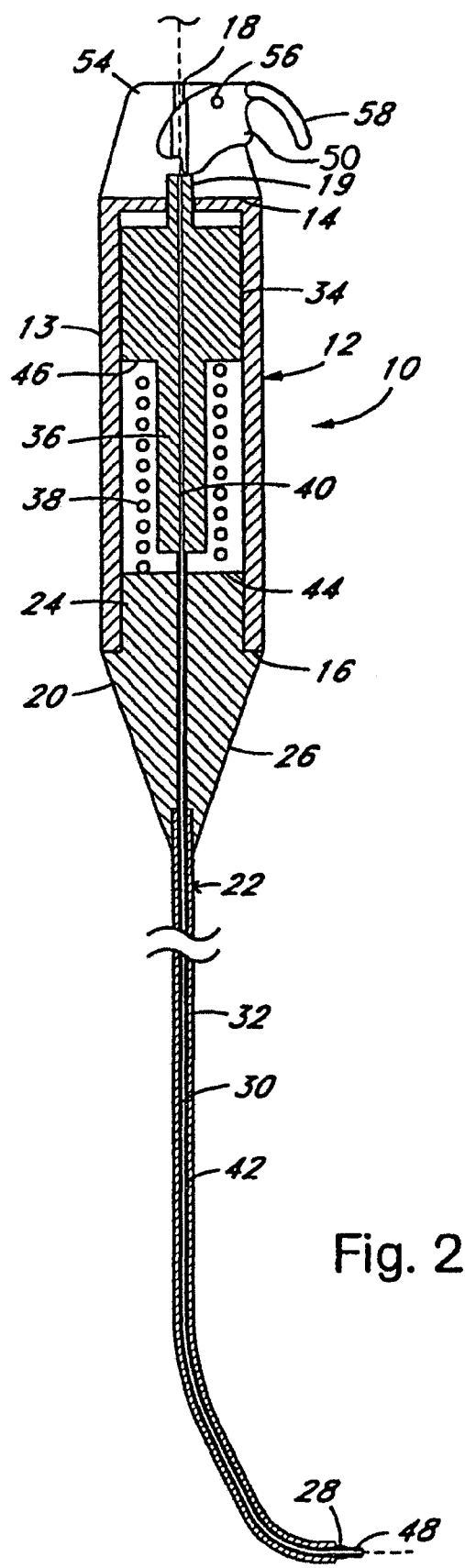
FIG. 2 is an assembled cross-sectional view of the guide member placement device of FIG. 1 showing the internal structure of the device.
Figure 3:
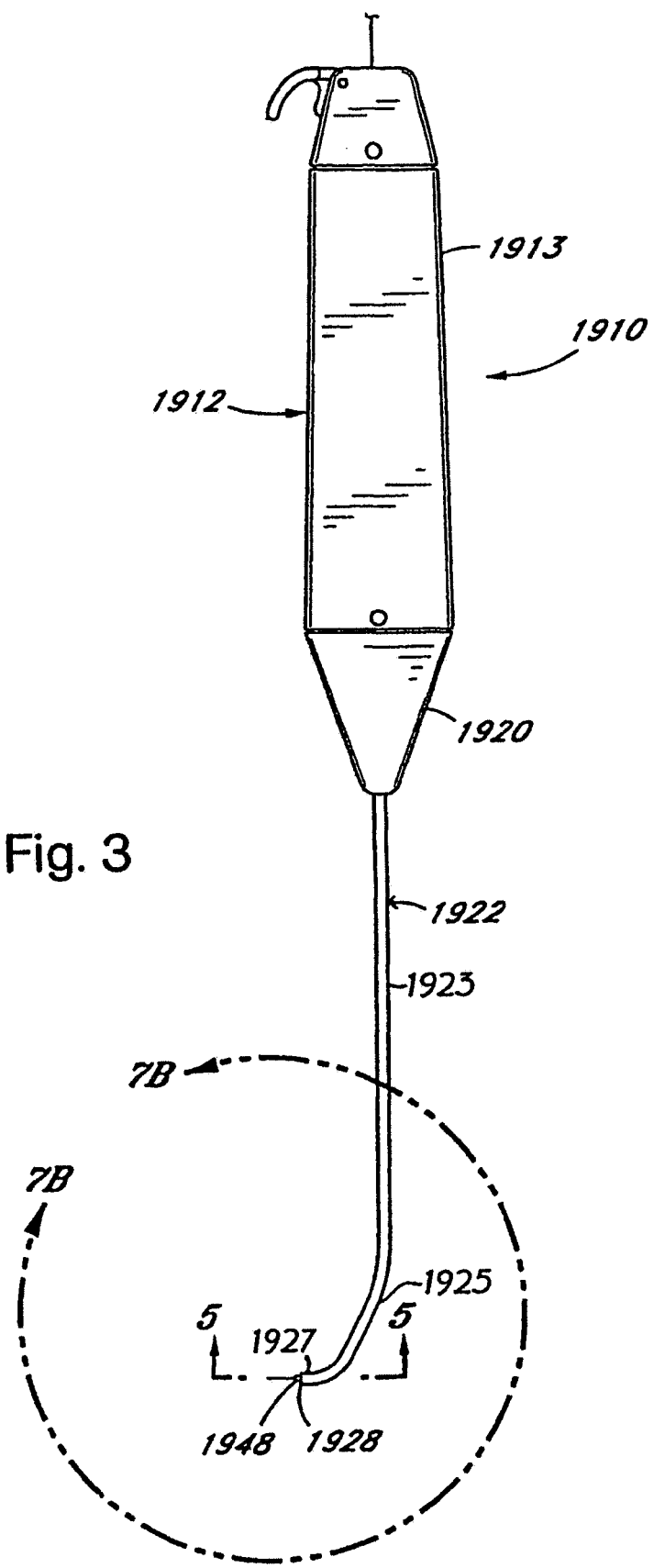
FIG. 3 is a side view of an embodiment of a guide member placement device having a female connector at the distal end of the shaft.

Referring to FIGS. 1, 2 and 3, there are disclosed guide member placement devices 10, 1910 in accordance with one aspect of the present invention. Handle 12, 1912 serves both as a gripping area for the physician and as a support structure for the guide member placement device. Handle 12, 1912 preferably comprises a hollow tubular body 13, 1913. The handle 12, 1912 is preferably of such a size to be easily gripped by a user. For instance, in one embodiment, the handle is approximately 0.75 inches (20 mm) in diameter and approximately 4 inches (110 mm) in length. Preferably, handle 12, 1912 is provided with knurling or other surface texturing to produce a high friction gripping surface.

A support 20, 1920 is preferably mounted such that it extends from the distal end of the handle 12, 1912 to provide a mounting support for the shaft 22, 1922. The support 20, 1920 acts as a transition member from the handle 12, 1912 to support the shaft 22, 1922.

The shaft 22, 1922 is an elongate member with its proximal end inserted within or secured to the support 20, 1920. The shaft 22, 1922 may be attached to the support 20, 1920 in any variety of manners, including brazing, threading or other means well known to those of skill in the art.

The shaft 22, 1922 extends distally from the support 20, 1920 and is preferably within the range of from about 6 inches to about 10 inches in length.

Figure 7A:
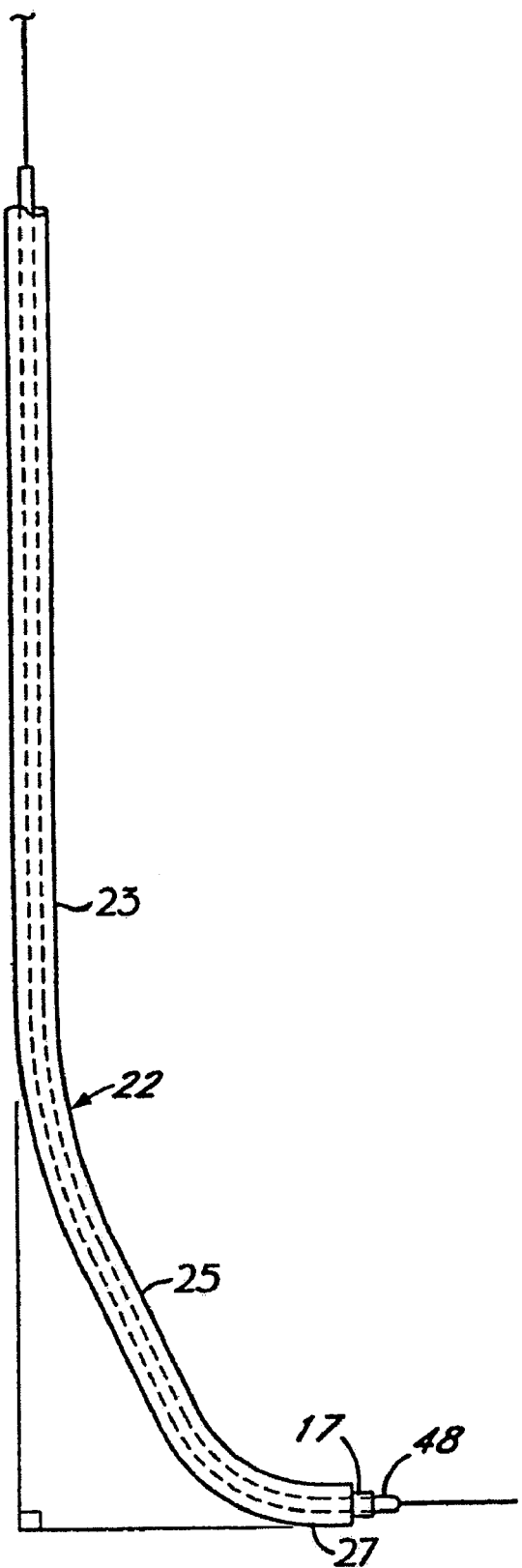
FIG. 7A is an enlarged view of the distal portion of the shaft of the guide member placement device taken along line 7A-7A of FIG. 1.
Figure 7B:
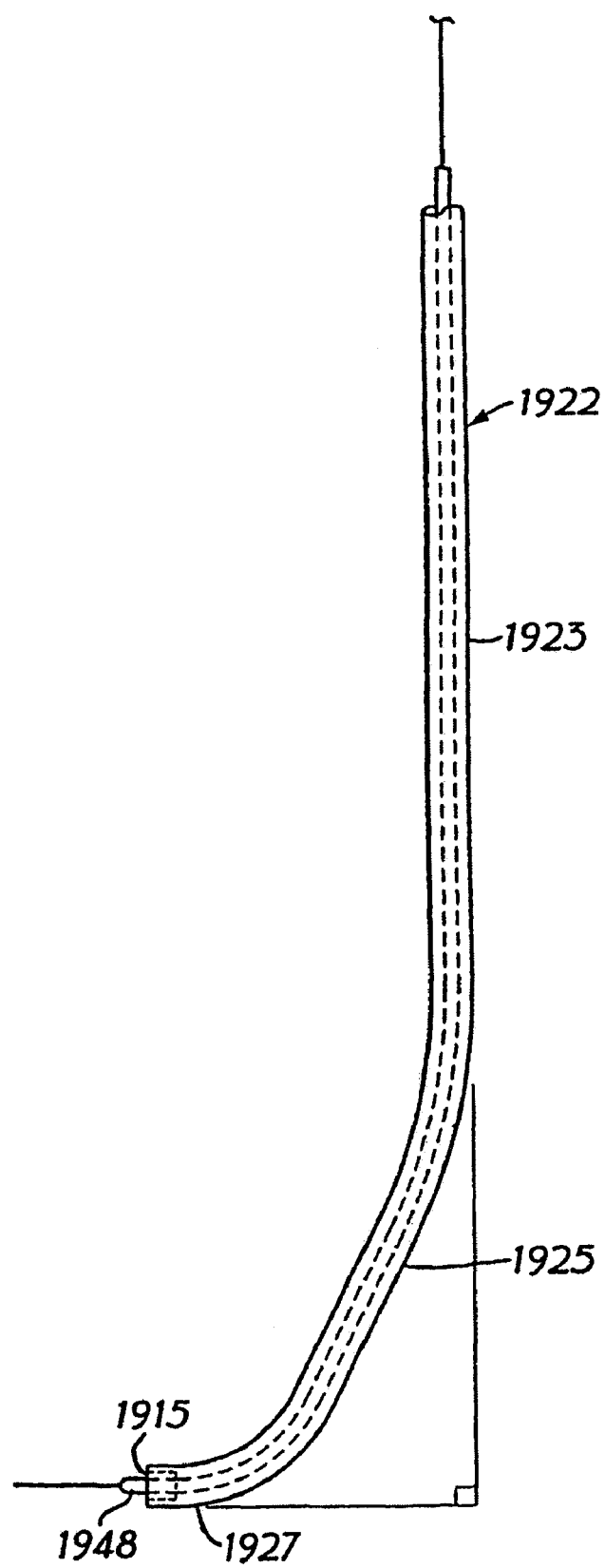
FIG. 7B is an enlarged view of the distal portion of the shaft of the guide member placement device taken along line 7B-7B of FIG. 3.
Figure 7C:
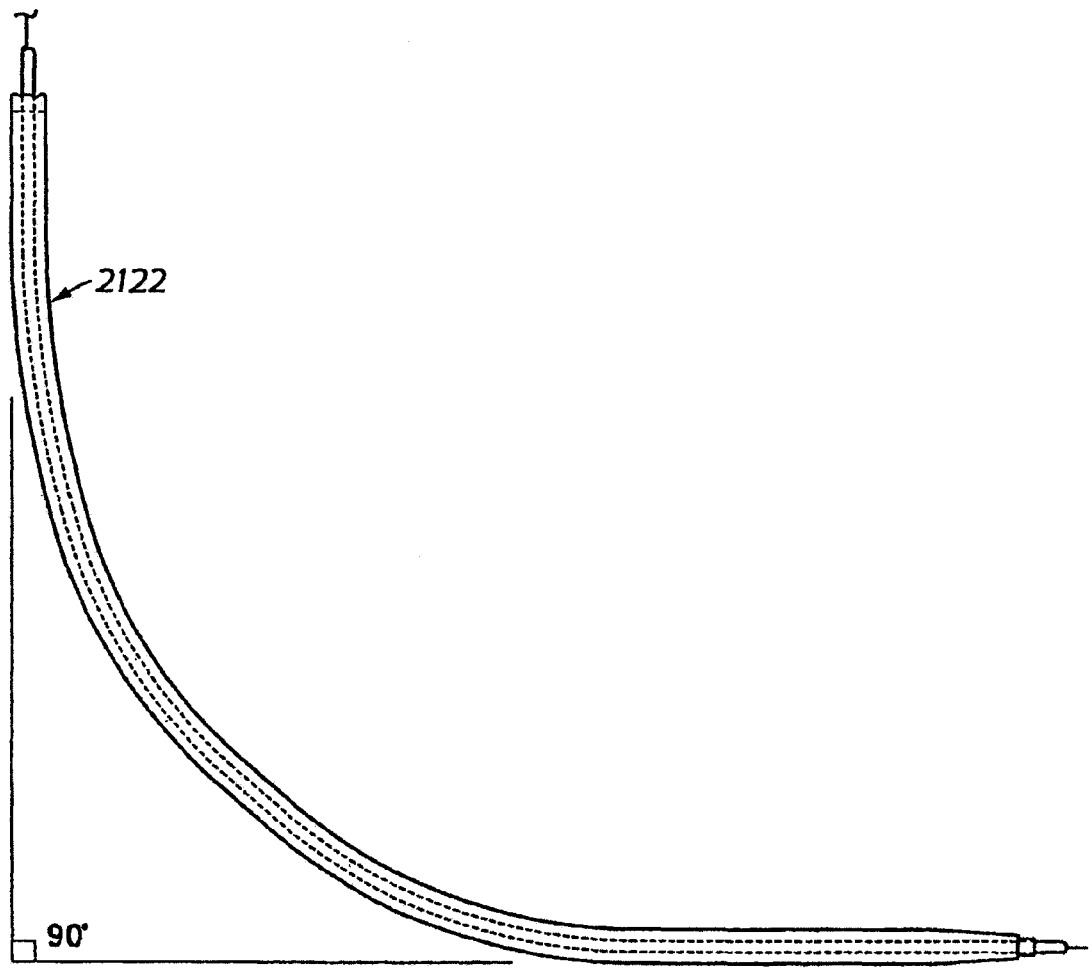
FIG. 7C is an enlarged view of the distal portion of the shaft of a guide member placement device having an alternate shaft configuration in which the curve is smoothly curved.
Figure 7D:
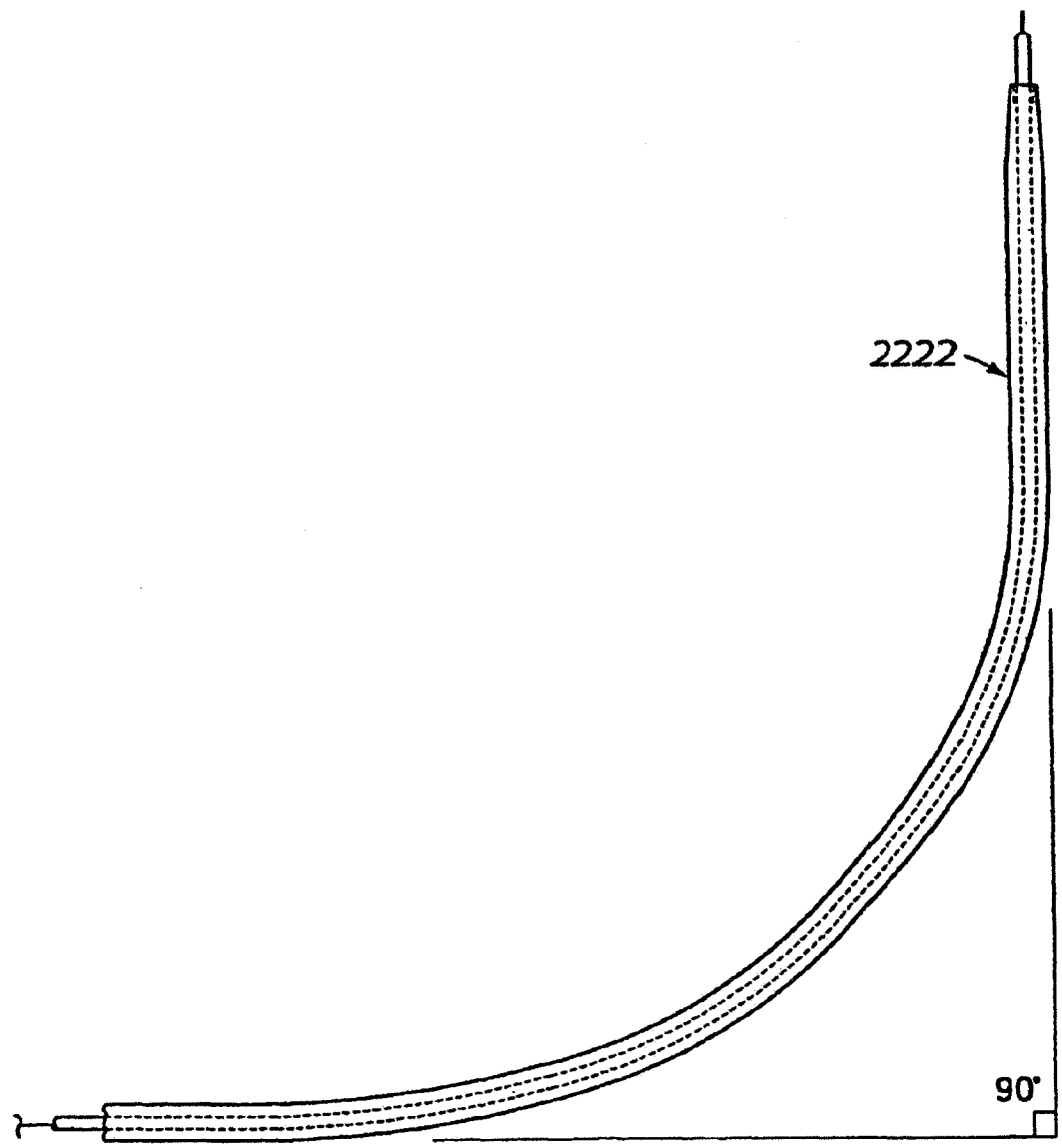
FIG. 7D is an enlarged view of the distal end of the shaft of a guide member placement device having an alternate shaft configuration in which the curve is smoothly curved.

The shaft 22, 1922 has a lumen 30 extending therethrough. A preferred embodiment of the distal end of the shaft is shown in FIGS. 7A and 7B. In this embodiment, the shaft 22, 1922 has a straight proximal section 23, 1923, a bent intermediate section 25, 1925, and a distal end 27, 1927. In an alternate embodiment, the shaft 2122, 2222 may be smoothly curved as shown in FIGS. 7C and 7D. In the embodiments of FIGS. 7A-7D, the distal end of the shaft is preferably oriented at an angle of 90° relative to the straight proximal section of the shaft. Preferably, the curve of the shaft is smooth to facilitate movement of the blunt dissector 32 within the shaft.

As will be understood by one of skill in the art, the dimensions and curvature of the shaft 22, 1922 may vary depending on anatomical considerations and the type of procedure in which it is intended to be used.

Figure 4:
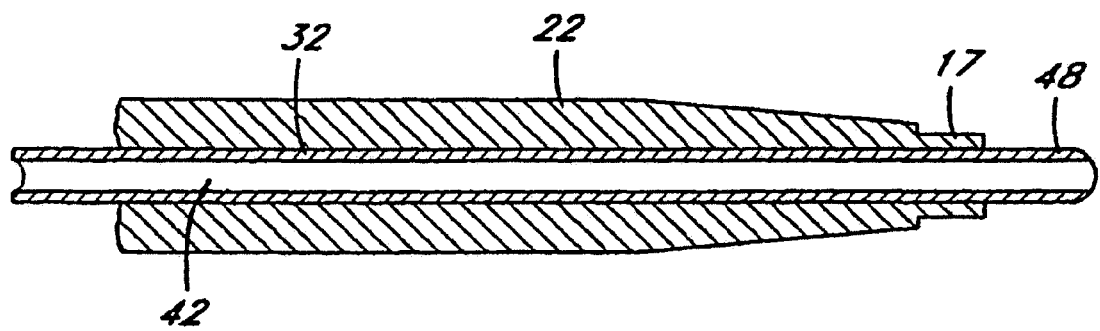
FIG. 4 is an enlarged cross-sectional view taken along line 4-4 of the distal end of the shaft of a guide member placement device of FIG. 1.
Figure 5:
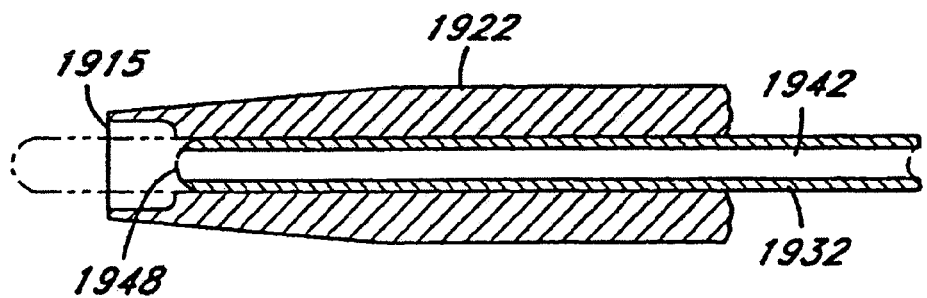
FIG. 5 is an enlarged cross-sectional view taken along line 5-5 of the distal end of the shaft of the guide member placement device of FIG. 3.

The distal ends 27, 1927 of the shafts 22, 1922 of the guide member placement devices 10, 1910 are provided with engaging members 28, 1928 which are complementary to each other, such that the shafts 22, 1922 of the two guide member placement devices 10, 1910 are adapted to be attached to one another. In one embodiment of the guide member placement device 10, depicted in FIGS. 1 and 2, the engaging member comprises a male connector 17 as illustrated in the enlarged cross-sectional view of FIG. 103. The male connector 17 on the guide member placement device 10 shown in FIGS. 1 and 2 is complementary to the female connector 1915 on the guide member placement device 1910 shown in FIG. 3 and shown in the enlarged cross-sectional view in FIG. 4. As shown in the enlarged cross-sectional view of FIG. 6, the male connector 17 on the guide member placement device 10 of FIGS. 1, 2 and 4 engages the female connector 1915 on the guide member placement device 1910 of FIGS. 3 and 5 and attaches the two guide member placement devices 10, 1910 together such that the lumens 42, 1942 of the blunt dissectors 32, 1932 of each of the two devices are in fluid communication with one another. When desired, the male connector 17 disengages from the female connector 1915, permitting the two guide member placement devices 10, 1910 to be separated.

While the complementary engaging members 28, 1928 of the embodiments shown in FIGS. 1-5 are male and female connectors, those skilled in the art will appreciate that a number of alternative configurations can be employed for the engaging members, and the present invention contemplates such alternative configurations.

FIG. 2 is a cross-sectional view showing the internal structure of the guide member placement device 10 having a male connector at the distal end of the shaft. The internal structure of the embodiment of the guide member placement device 1910 having a female connector at the end of the shaft is similar to that shown in FIG. 2. Thus, the internal structure will only be described with respect to the device having a male connector.

As shown in FIG. 2, the handle 12 has a proximal end wall 14 and a distal end wall 16. The support 20 as illustrated is provided with a generally cylindrical proximal section 24 for engagement within the distal end of the handle 12 and a tapered distal section 26 for securing the shaft.

The shaft 22 is preferably no more than about 0.1 inches (2.5 mm) in diameter and is provided with at least one central lumen 30 for acceptance of an axially movable blunt dissector 32. The blunt dissector 32 is mounted within the handle 12 and extends through the support 20 and the shaft 22. The blunt dissector 32 is preferably provided at its proximal end with a relatively large diameter body portion 34 adapted for reciprocal motion within tubular handle 12. Body portion 34 is preferably provided with a slightly smaller diameter recessed portion 36 for receiving a return spring 38 which biases the blunt dissector 32 in the proximal direction and has a lumen 40 extending therethrough which is in fluid communication with the lumen 42 of the narrow portion of the blunt dissector. Alternatively, any of a variety of well known means can be utilized to provide a proximal bias on the blunt dissector 32.

The length of body portion 34 is less than the axial length of the cavity within handle portion so that the body portion 34 has an axial range of motion within the range of from about 2 mm to about 10 mm, and preferably about 0.12 inch (3 mm). The proximal end wall 44 of the support 20 which extends into the handle 12 acts as one limiting stop for distal travel of body portion 34. The distal surface of the end wall 14 of the handle limits proximal travel of body portion 34. Spring 38 pushes against an' annular shoulder 46 on body portion 34, biasing the blunt dissector 32 15 proximally.

The distal end of blunt dissector 32 is provided with a blunt dissection tip 48 having a lumen therethrough. Spring 38 normally biases the blunt dissector 32 towards a first retracted position within the distal end of shaft 22 such that the blunt dissection tip 48 does not extend from the shaft 22. Axial distal force on body portion 34 extends the blunt dissection tip 48 into a second position in which it extends from the shaft 22. Although the blunt dissection tip 48 may be extended and retracted in any number of ways, such as by use of a knob or button, it is preferred that a rotatable cam 50 be used.

The cam 50 is attached to a post 54 extending proximally from the handle 12 and having a lumen 18 therein which is in fluid communication with the lumen 40 in the recessed position of the blunt dissector and the lumen 42 in the narrow portion of the blunt dissector. The cam 50 is rotatably mounted about a pin 56 which extends along an axis perpendicular to the longitudinal axis of the shaft 22. The proximal end of the body portion has a rod 19 which extends proximally through an opening in the proximal end wall 14 of the handle.

The cam 50 has of least a two position engaging surface which, when rotated into position, engages the rod 19 of the body portion. In a first position, the cam 50 is biased by the return spring 38 to a position in which the blunt dissection tip 48 is fully retracted within the shaft 22. In a second position, the bias imposed by return spring 38 is overcome and engaging surface of the cam 50 engages the rod 19 such that the blunt dissection tip 48 is extended outwardly from the shaft 22. The cam 50 is preferably provided with an actuator portion 58 which extends radially outwardly and which may be used by the operator for rotating the cam.

Alternatively, other means such as pneumatic force generating means, hydraulic force generating means, piezoelectric force generating means, and electric force generating means may be used to overcome the bias of the spring and extend the blunt dissection tip 48.

It is preferred that this instrument be manufactured from a sterilizable material having sufficient rigidity for its intended purpose. Many acceptable materials are well known in the art, such as stainless steel for the shaft 22, and stainless steel or a plastic for the handle portion 12.

Alternatively, the guide member placement device may be made in a disposable form. In this embodiment, the components preferably are made of a suitable thermoplastic. In particular, the thermoplastic Cycolac 2679F made by General Electric Plastics has been found suitable, which is Acrylonitrile Butadiene Styrene (ABS). Preferably, the shaft 22, blunt dissector 32, and return spring 38 are made of stainless steel.

The use of the guide member placement devices of FIGS. 1-7D in a representative bladder neck stabilization procedure employing a sling is described below and depicted in FIGS. 8-14. However, those skilled in the art will appreciate that the guide member placement device may also be used in a number of other surgical procedures requiring introduction of a guide member.

Figure 8:
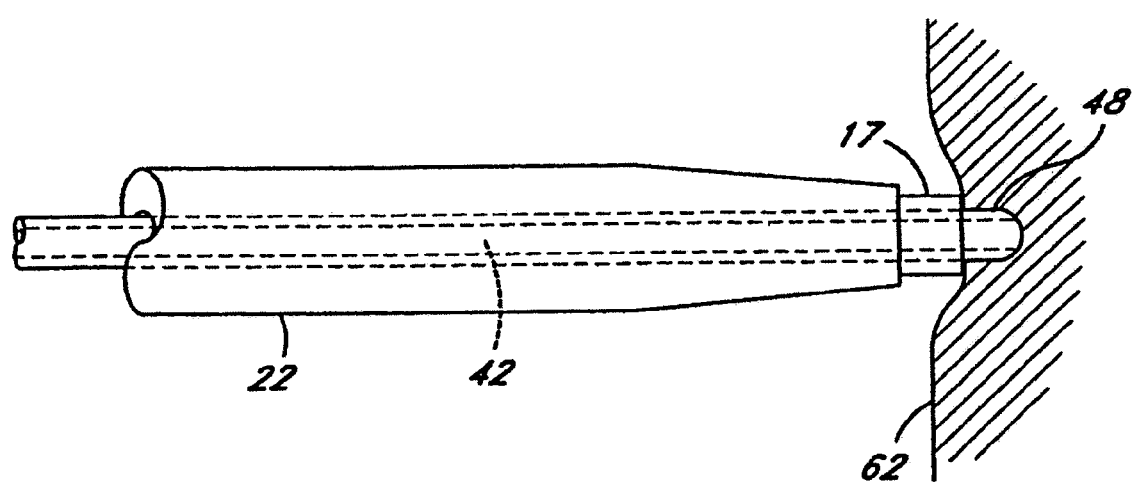
FIG. 8 shows the blunt dissection tip extending into a tissue from the distal end of the shaft of a guide member placement device having a male connector to create an opening in the tissue.
Figure 11:
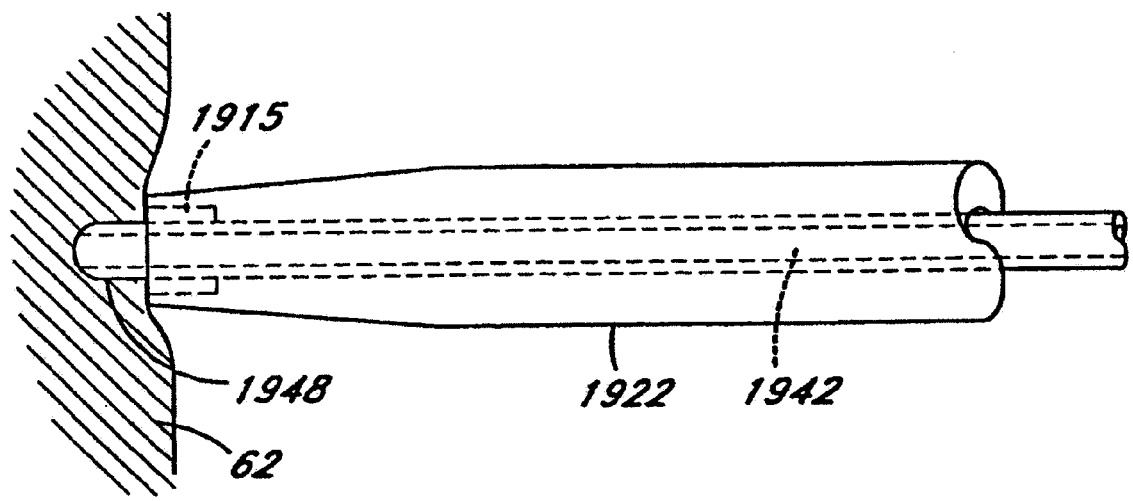
FIG. 11 shows the blunt dissection tip extending into a tissue from the distal end of the shaft of a guide member placement device having a female connector to create an opening in the tissue.

The following procedure is intended to place a guide member in the tissue between the urethra and the vaginal wall without puncturing the vaginal wall. A Foley catheter is placed in the bladder to identify the bladder neck. The guide member placement device is percutaneously inserted into the body. For example, a pair of approximately one inch suprapubic incisions 60 and 61, shown schematically in FIG. 9, may be made over the pubic tubercles and dissection may be carried down to the area of the rectus fascia. A first guide member placement device 10 is placed within one of the incisions and advanced along the back side of the pubic bone so that the distal tip of the shaft 22 is in contact with the bone/fascial surface to decrease the risk of puncturing the bladder. As resistance is felt, the cam 50 is pressed to extend the blunt dissection tip 48 from the distal end of the shaft 22, thereby creating an opening in the body tissue 62 as shown in FIGS. 8 and 11. The cam 50 is then released, retracting the blunt dissection tip 48 into the shaft 22, and the device 10 is advanced through the opening in the body tissue. This process results in the creation of a first opening in the body tissue.

Figure 9:
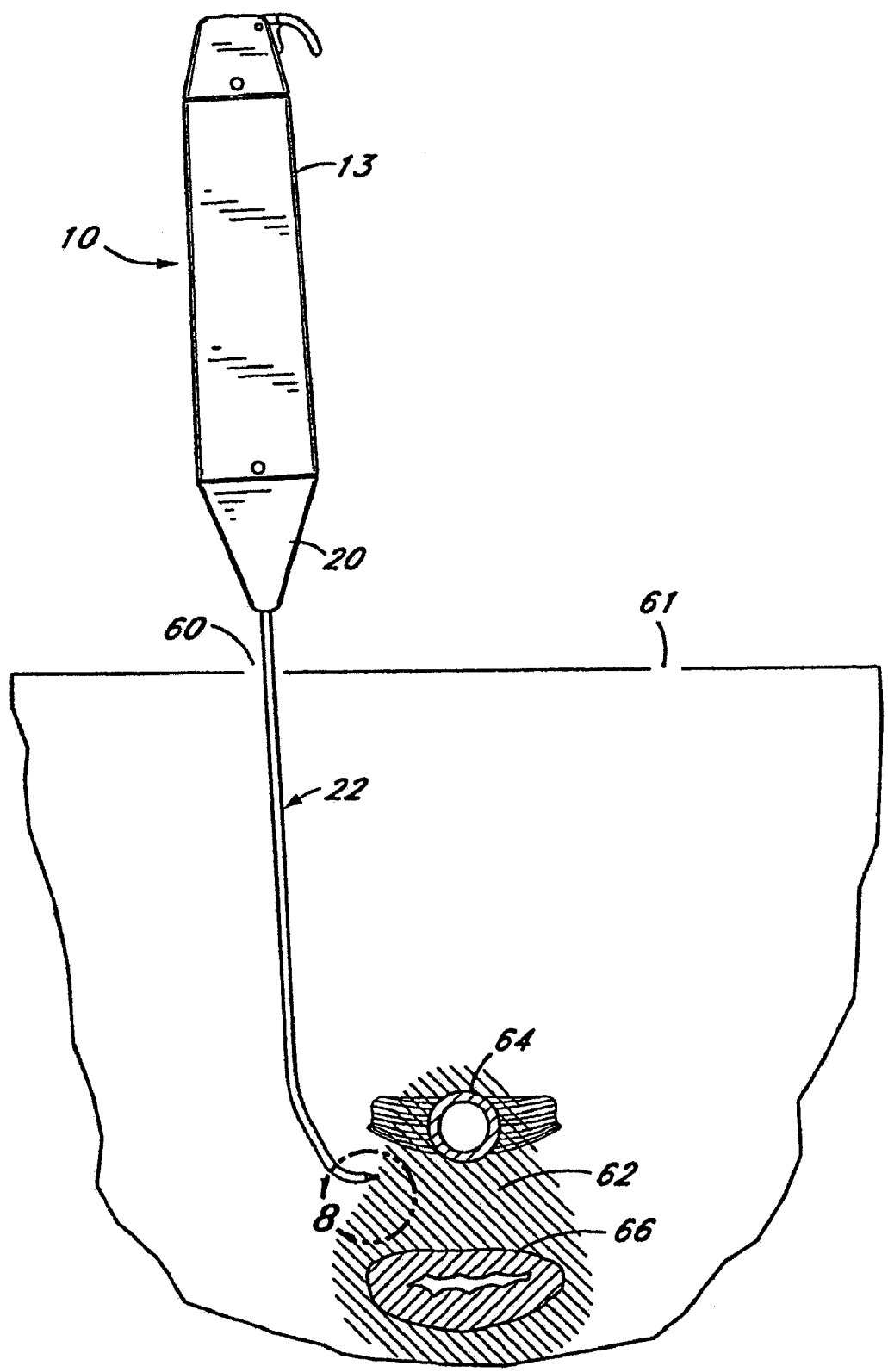
FIG. 9 shows a first guide member placement device that has been inserted into a first suprapubic incision and advanced into the body tissue.
Figure 10:
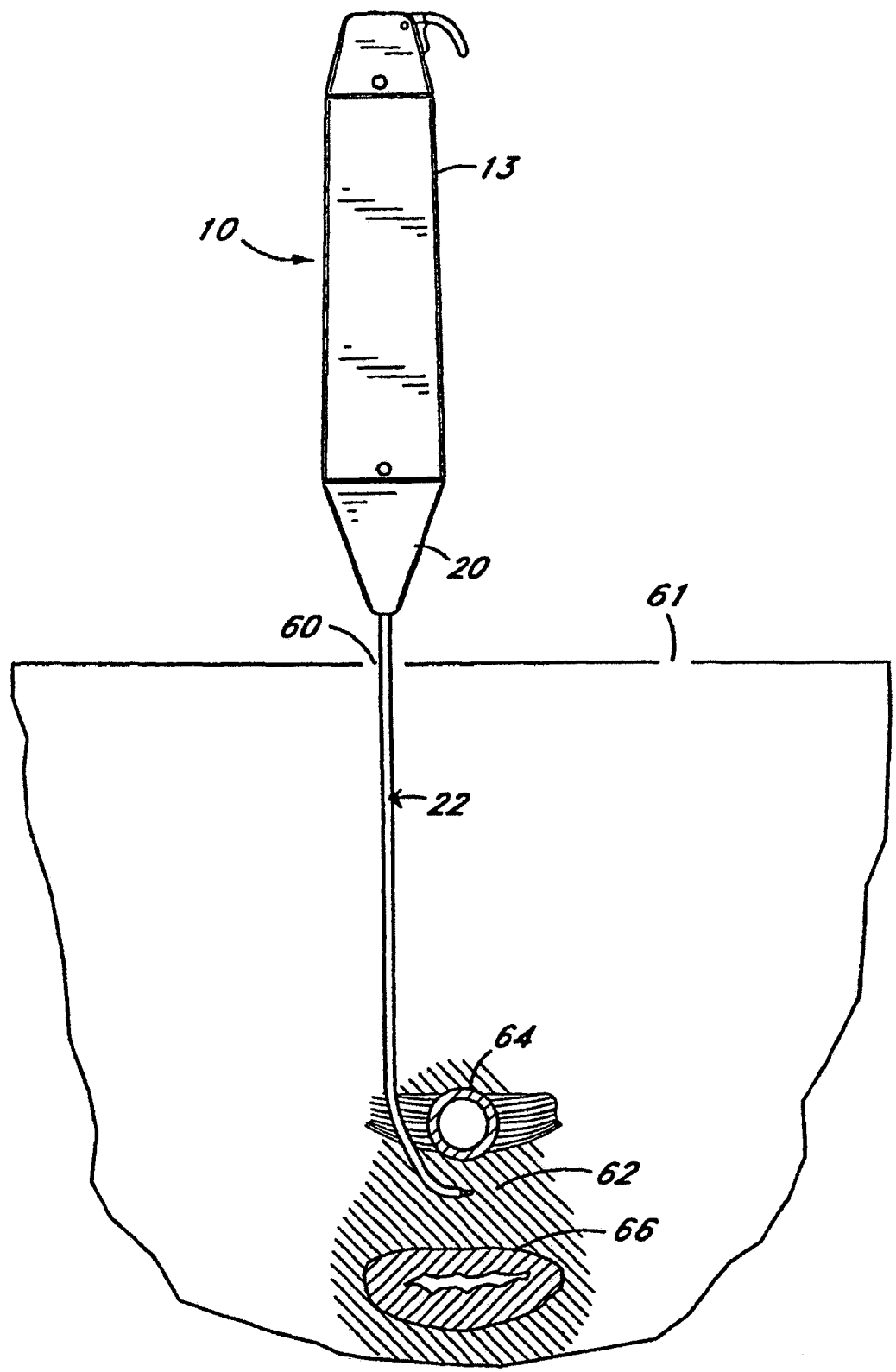
FIG. 10 shows a guide member placement device that has been advanced into the tissue between the urethra and the upper vaginal wall such that the distal end of the shaft extends transversely between the urethra and the upper vaginal wall in the plane defined by the longitudinal axes of the urethra and the vagina.

The first guide member placement device 10 is advanced until it is positioned under the urethra 64 within the tissue 62 lying between the urethra 64 and the upper vaginal wall 66 as shown in FIG. 9. The blunt dissection tip 48 is extended and retracted during advancement of the guide member placement device 10 so as to create an opening in the tissue. Advancement of the guide member placement 10 device with extension and retraction of the blunt dissection tip 48 is continued until the distal end of the shaft 22 is positioned approximately midline to the urethra 64 as shown in FIG. 10 such that the distal end of the shaft 22 extends transversely between the urethra 64 and the upper vaginal wall 66 in the plane defined by the longitudinal axes of the urethra and the vagina.

Alternatively, a pocket or opening in the tissue between the urethra and the vagina may be created beneath the bladder neck prior to insertion of the first guide member placement device using the devices and methods described below. In this embodiment, the first guide member placement device 10 is advanced such that the distal end of the shaft is in the pocket or opening and the device is positioned as described above.

As the guide member placement device 10 is advanced, the elastic upper vaginal wall tents. This tenting can be utilized to determine the position of the guide member placement device 10. The guide member placement device is advanced until tenting is apparent at the desired location.

Figure 6:
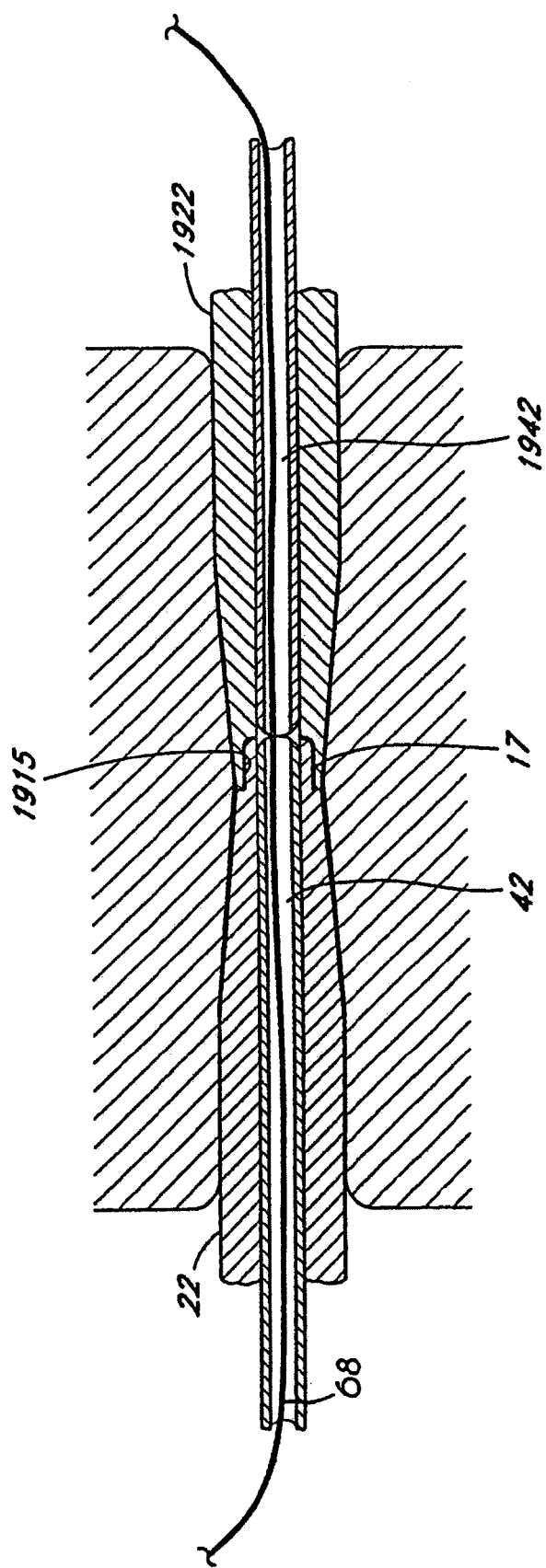
FIG. 6 is a cross-sectional view showing the distal ends of the shafts of the guide member placement devices of FIGS. 1 and 3 coupled through their male and female connectors.
Figure 12:
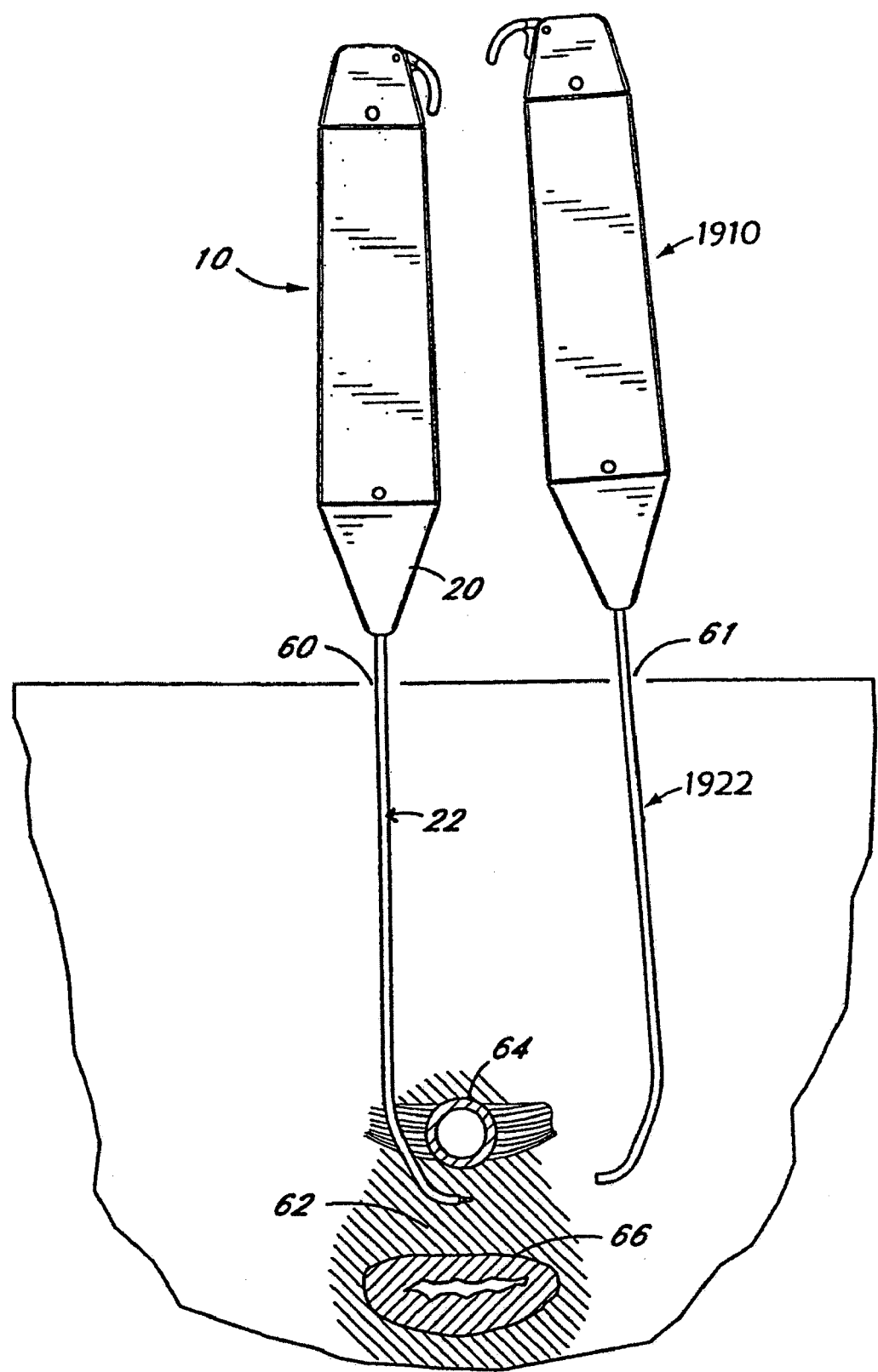
FIG. 12 shows a second guide member placement device that has been inserted into a second suprapubic incision and advanced into a body tissue.

The above process is repeated with a second guide member placement device 1910 as shown in FIG. 12. The second guide member placement device 1910 has an engaging member 1928 complementary to that of the first guide member placement device 10 as shown in FIG. 6. The blunt dissection tip 1948 of the second guide member placement device 1910 is extended and retracted to create a second opening in the body tissue as described above and shown in FIG. 11.

The second guide member placement device 1910 is advanced to a position approximately midline to the urethra 64 such that the distal end of the shaft 1922 extends transversely between the urethra 64 and the upper vaginal wall 66 in the plane defined by the longitudinal axes of the urethra and the vagina.

Alternatively, in the embodiment in which the pocket or opening in the tissue between the urethra and the vagina is created prior to insertion of the first guide member placement device, the second guide member placement device is advanced into the pocket or opening.

The second guide member placement device 1910 is then aligned with the first guide member placement device 10.

Figure 13:
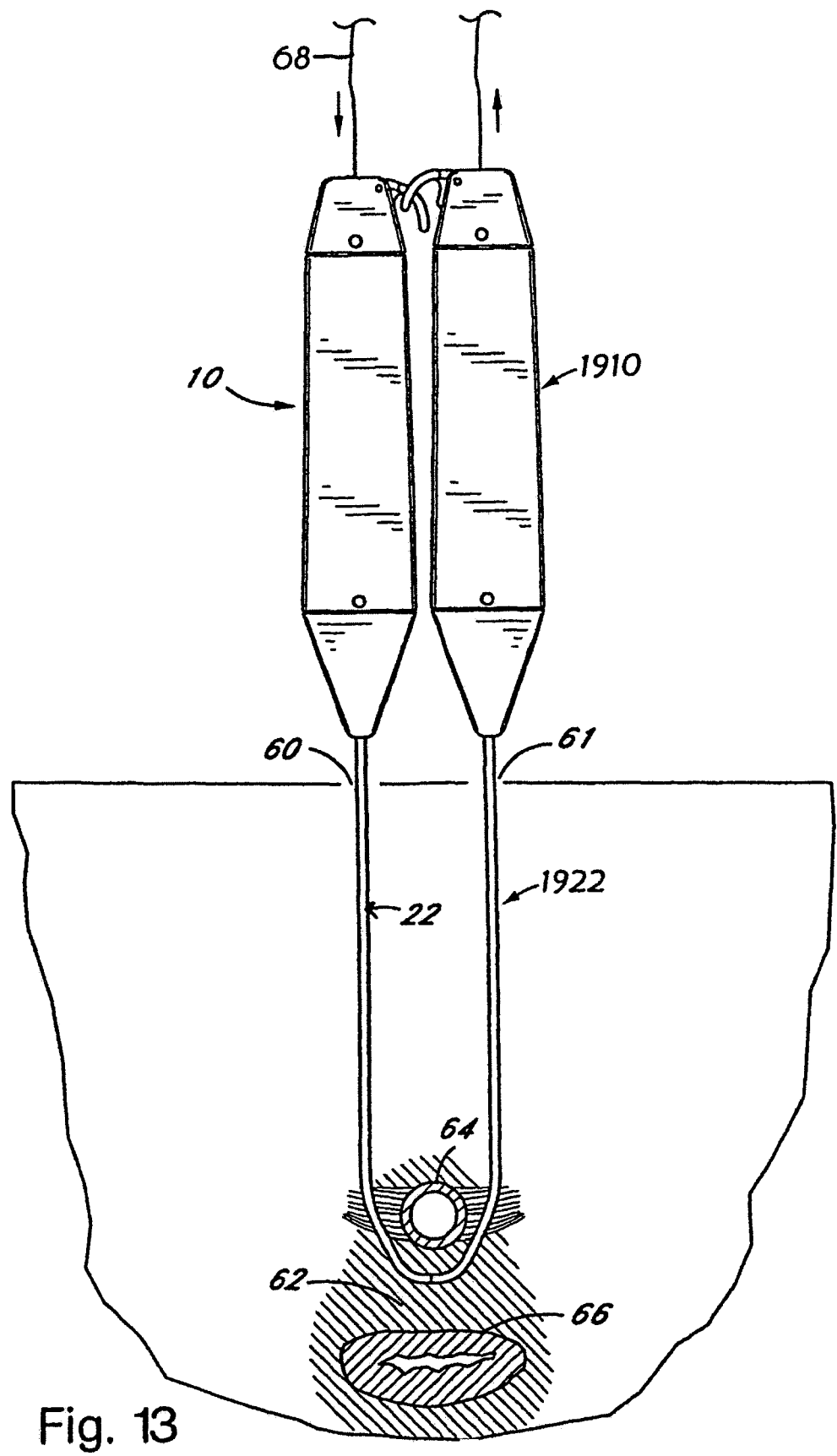
FIG. 13 shows the first and second guide member placement devices in the tissue between the urethra and the upper vaginal wall with the distal ends of their shafts connected to one another.

The first and second guide member placement devices 10 and 1910 are then joined through their engaging members 28, 1928, creating a continuous opening in the tissue 62 between the urethra 64 and the upper vaginal wall 66, as shown in FIG. 13. In an alternative embodiment, in addition to joining the two shafts, the two handles may also be coupled together and secured to one another.

After joining of the two guide member placement devices 10, 1910, the lumens 42, 1942 of the blunt dissectors are in fluid communication with one another, as shown in FIG. 6. As shown in FIGS. 13 and 2, a guide member 68 is then inserted into the lumen 18 in the handle 12 of the first guide member placement device 10 and advanced through the lumens 40, 1940, 42, 1942 of the blunt dissectors of the first and second guide member placement devices 10, 1910 until it exits from the handle 1912 of the second guide member placement device.

Figure 14:
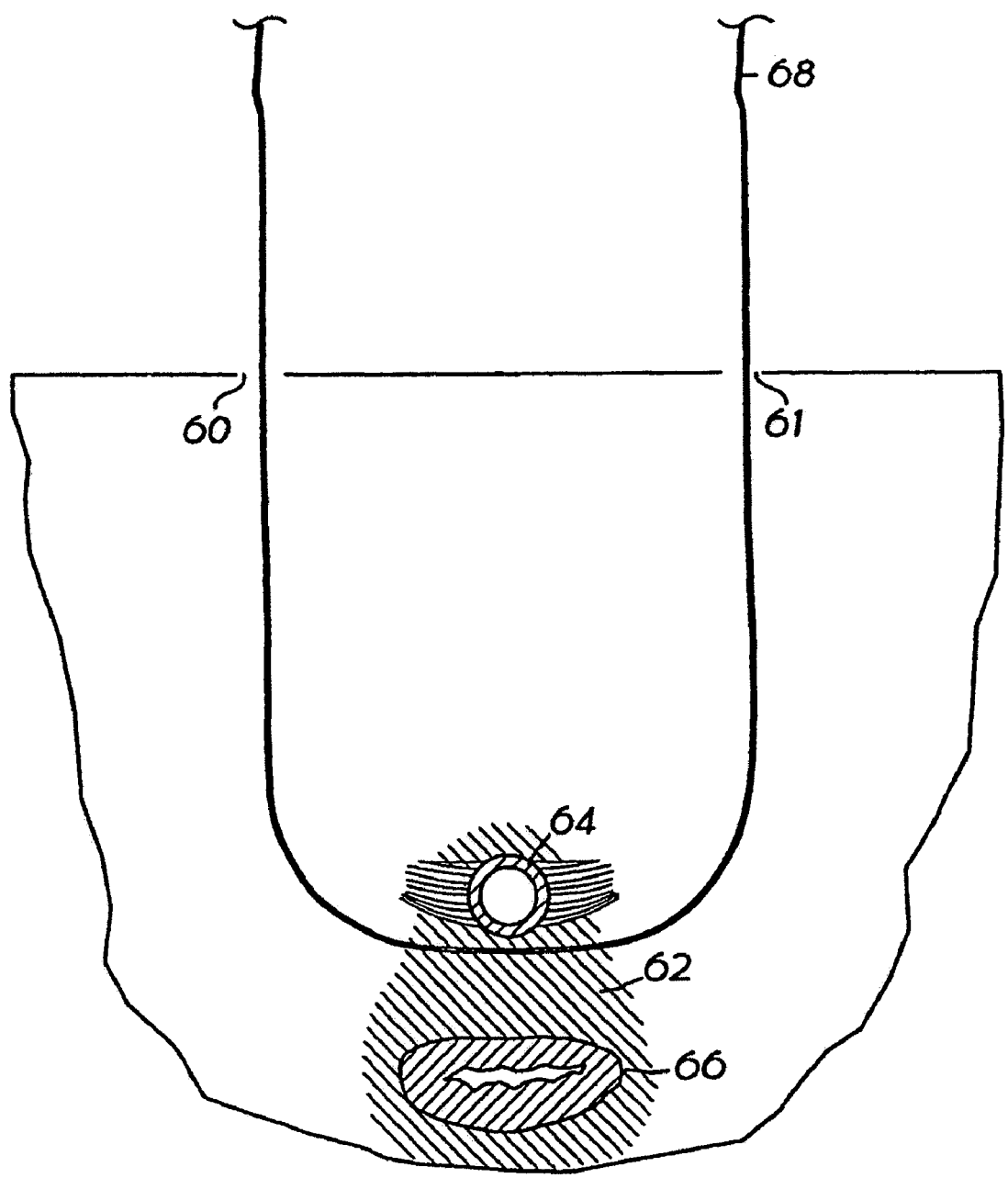
FIG. 14 shows a guide member extending between the two suprapubic incisions after removal of the first and second guide member placement devices.

The engaging members 28, 1928 of the two guide member placement devices 10, 1910 are then disengaged from one another and the devices 10, 1910 are removed from the patient's body, leaving the guide member 68 in place, as shown in FIG. 14.

The guide member 68 may then be used to introduce a sling attached to a sling application catheter in order to stabilize the bladder neck or stabilize the urethral floor as described in the following sections.

In alternative embodiments of the method, rather than using the blunt dissection tips 48 of the guide member placement devices to create the continuous opening in the tissue, the guide member placement device may be inserted to a pre-formed opening in the tissue between the urethra and the upper vaginal wall. The pre-formed opening may be created by hydrodissection or with balloon catheters as described below. The steps of this embodiment of the method are similar or identical to the method described above. However, if desired, this embodiment of the method can be practiced with guide member placement devices having a blunt dissector which is fixed in a position in which it is extended from the shaft.

In an alternative embodiment of the method, the guide member placement device may be advanced through a trocar into the tissue between the urethra and the upper vaginal wall. In another embodiment, the guide member placement device may be viewed laparoscopically during the procedure to ensure proper positioning and assist in the alignment of the first and second guide member placement devices.

Sling Application Catheter

Another aspect of the present invention is a sling application catheter for introducing a sling into an opening or pocket in the patient's body tissue. In particular, the sling application catheter of the present invention can be used in urethral floor reconstruction procedures, such as bladder neck stabilization procedures, to introduce a sling into the tissue between the urethra and the upper vaginal wall in a less invasive manner than the techniques currently in use.

Generally, the sling application catheter comprises a catheter having a sling therein which is releasably engaged with the catheter. Preferably, the sling is releasably engaged by a pouch in the catheter. Preferably, the sling application catheter is adapted to be guided along a guide member. The guide member may be a suture, guide wire, or other structure suitable for guiding the sling application catheter to a desired location.

The sling application catheter may be attached to the guide member, suture, or other guiding device in numerous ways. For example, the catheter may have a lumen extending therethrough through which the guide member passes. The guide member may pass along the full length of the lumen, thereby extending entirely through the catheter. Alternatively, the guide member may extend partially through the lumen but exit the catheter along its length through an opening in the wall of the catheter.

In yet another embodiment, a loop with an aperture therein may be attached to the catheter. In this embodiment, the guide member passes through the loop to guide the catheter along the length of the guide member. Those skilled in the art will appreciate that there are a variety of other ways to permit the sling application catheter to travel along the guide member, and the present invention contemplates such additional approaches.

Preferably, the sling application catheter is long enough to span between an insertion site in the patient's body and an exit site in the patient's body. The insertion site and exit site are positioned on either side of the location to which the sling is to be delivered.

The catheter may be a continuous cylinder with a lumen extending therethrough. Alternatively, the surface of the catheter may be partially open with a slot therein which is narrower than the width of the guide member, suture or other guiding device. Preferably, the distal end of the catheter has a tapered tip to facilitate its passage through the body tissue.

The pouch permits the sling to be handled without damage, maintains a barrier preventing microorganisms from contacting the sling, provides handling flexibility, and ensures that the sling is introduced into the opening or pocket in the patient's body tissue in the desired orientation. The pouch may be made of a variety of materials such as polyethylene terephthalate (PET), polyethylene (PE), vinyl, polyester and ethylene vinyl acetate (EVA). Preferably, the pouch is made of PET.

Preferably, the pouch is flat to facilitate delivery of the sling in a flat orientation. However, the pouch may also be conical, or rolled conical, and be provided with means for flattening the sling after delivery. Alternatively, the sling application catheter may be used in conjunction with slings made from materials which adopt a flat configuration after delivery.

Preferably, the pouch is clear or translucent to permit visualization of the sling within. In some embodiments, the pouch is made of a porous material such as polyethylene, polyethylene terephthalate or vinyl. In one embodiment, the pouch is adapted to receive a sling long enough to pass between a first suprapubic incision on one side of the urethra and a second suprapubic incision on the opposite side of the urethra.

In an alternative embodiment, the pouch may be adapted to receive a sling having a shorter length than the slings used with the embodiment described above. Such slings are attached to the pubic bone by sutures.

Long and short slings suitable for use with the present invention are described in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

The length of the pouch may be varied depending upon the length of the sling with which the sling application catheter is to be used.

Figure 15:
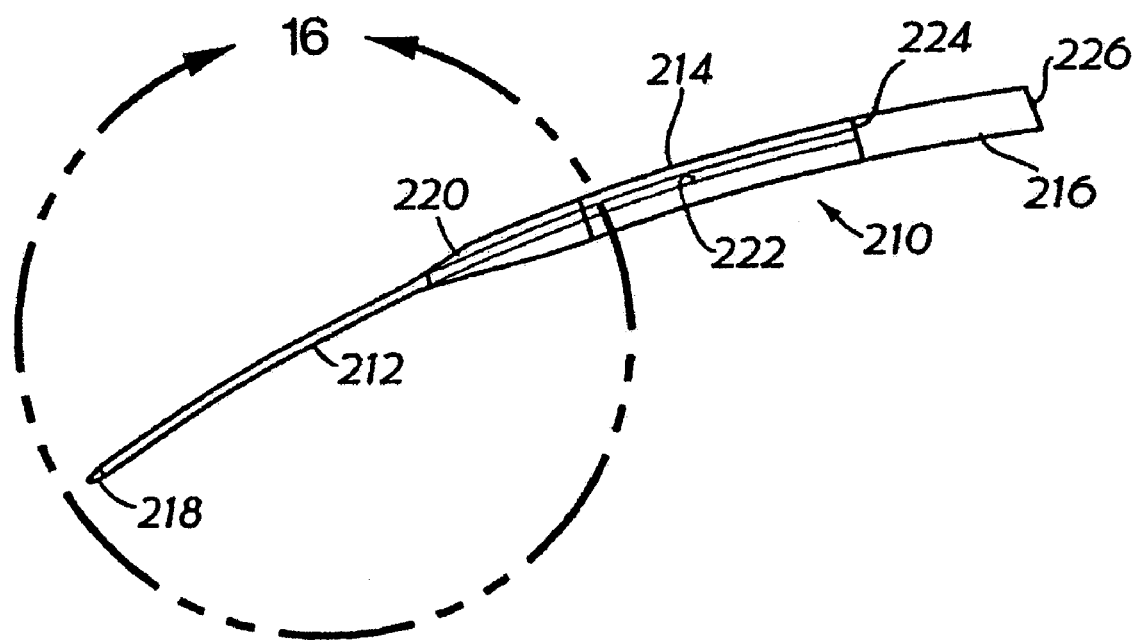
FIG. 15 is a plan view of a sling application catheter.

One embodiment of a sling application catheter 210 according to the present invention is shown in FIGS. 15 and 16. The sling application catheter of FIG. 15 comprises a catheter 212 and a pouch 214 adapted to releasably engage a sling 216 attached thereto. The distal end 218 of the catheter is tapered and extends beyond the distal end 220 of the pouch. The distal end 220 of the pouch is also tapered to facilitate its passage through the patient's body tissue. A lumen 222 extends through the catheter.

A cross section of the sling application catheter 210 of FIG. 15 with a sling 216 inside the pouch 214 is shown in FIG. 17. The sling 216 depicted in FIG. 15 is sufficiently long to pass between two suprapubic incisions on opposite sides of the urethra. Preferably, the sling 216 extends beyond the proximal end 224 of the pouch of the sling application catheter to permit the proximal end 226 of the sling to be grasped or secured.

Alternatively, shorter slings which are attached to the pubic bone via sutures may be used. The sling 216 may have sutures or integral attachment members extending bilaterally therefrom. Long and short slings suitable for use with the present invention are disclosed in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference. In such an arrangement, a suture or integral attachment member extends beyond the proximal end 224 of the pouch and can be grasped or secured by the physician to withdraw the sling from the pouch.

As illustrated in FIGS. 18 and 19, in alternative embodiments of the sling application catheter 310, the pouch 314 has a reinforcing stiffener 328. The reinforcing stiffener 328 may be on the interior or the exterior of the pouch 314. The stiffener 328 provides rigidity and prevents distortion of the sling 316 during passage through the patient's body tissue, as well as permitting the sling application catheter 310 to dilate or tear an opening in the patient's body tissue as it passes therethrough. In this manner, the sling application catheter 310 may be used to create an opening in the tissue between the urethra and the upper vaginal wall in which the sling is introduced. The stiffener 328 may also provide a bending effect which permits the sling to follow an axial bend along its width. Finally, the stiffener 328 reduces damage to the sling material during handling.

The stiffener 328 may be made of any of a variety of materials compatible with the above described considerations such as polyethylene, polypropylene, or acrylic. Preferably, the stiffener 328 provides approximately a 1 cm radius of bending.

In some embodiments, the stiffener 328 is made of a porous material such as polyethylene or polyethylene terephthalate having pores which permit a solution to access the sling during a soak as described below.

Preferably, the sling 216 introduced into the opening in the patient's body is sterile. In this regard, FIG. 20 depicts a further embodiment of the sling application catheter 410, in which the pouch 414 has pores 411 to permit rehydration of slings made of natural materials and antibiotic or saline soaks of the sling in the pouch prior to introduction of the sling into the patient. In this embodiment, the pouch 414 may be made of a variety of materials, such as PE, PET or vinyl. Preferably, the porous material has pore sizes ranging from about 100 microns to about 0.25 inches. Preferably, the pouch 414 is made of vinyl having a pore size of 0.125 inches.

The sling application catheters described above may be used in a variety of procedures in which delivery of a sling to an opening or pocket in the patient's body tissue is desired. A representative method in which the sling application catheter of FIGS. 15-20 are used to deliver a sling in a bladder neck stabilization procedure is described below and depicted in FIGS. 21-23. While the procedure is described with particular reference to the sling application catheter 210 of FIG. 15, those skilled in the art will appreciate that the sling application catheters 310, 410 of FIGS. 18 and 20 may also be used in the procedure.

Figure 21:
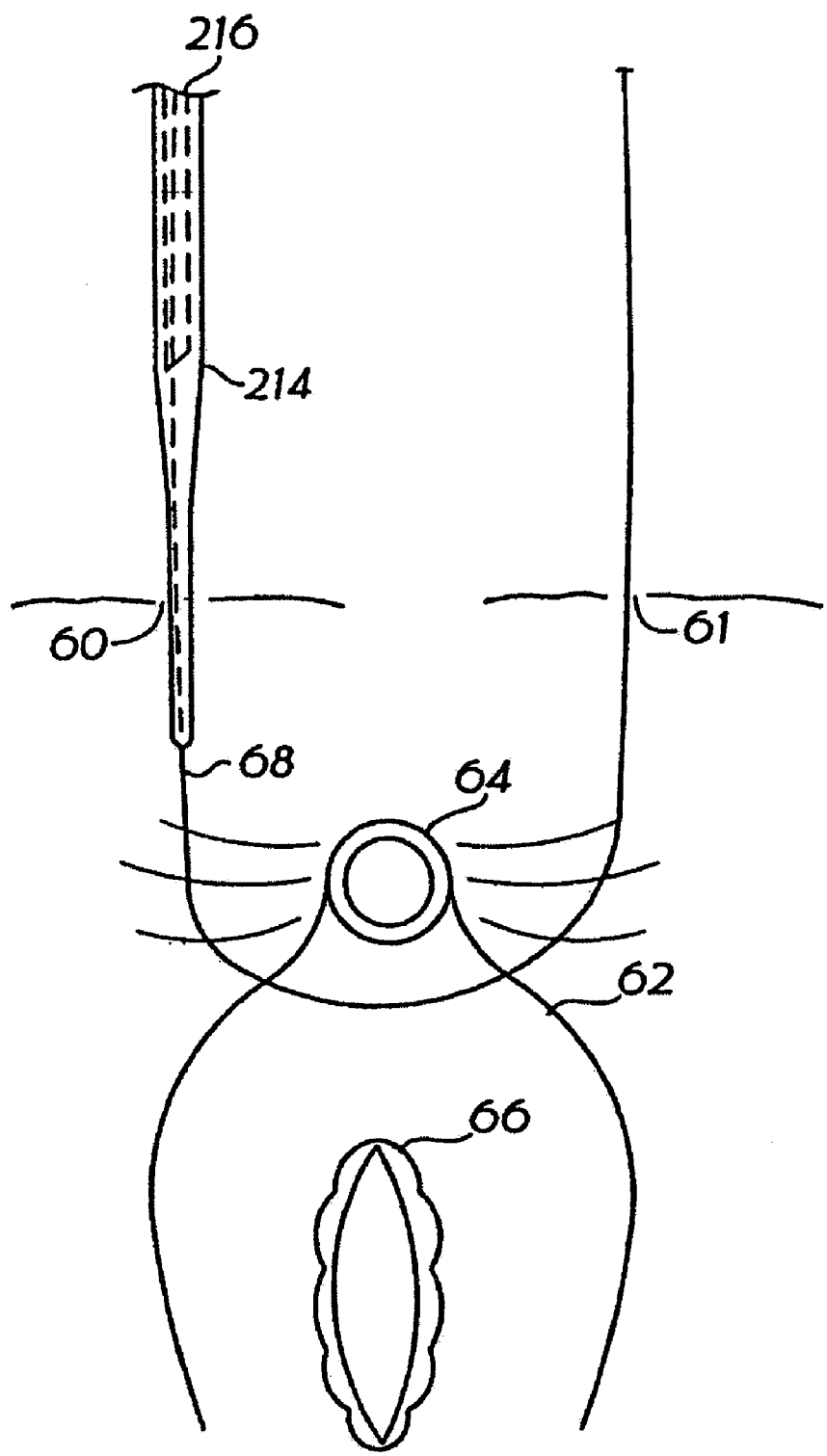
FIG. 21 shows a sling application catheter being inserted into a first suprapubic incision with a guide member extending through the lumen of the catheter.

A guide member 68 is introduced into the tissue between the urethra and the upper vaginal wall using a device such as the guide member placement devices 10, 1910 described above. As illustrated in FIG. 21, the guide member extends between two suprapubic incisions 61 and 62 on opposite sides of the urethra 64. As shown in FIG. 21, the end of the guide member 68 extending from the first suprapubic incision 60 in the patient's body is inserted into the lumen 222 of the catheter 212 such that the guide member passes 68 entirely through the catheter 212. A sling 216 capable of passing beneath the urethra and through the abdominal tissue on opposite sides of the urethra 64 is inserted into the pouch 214 such that the proximal end 226 of the sling extends from the proximal end 224 of the pouch.

Alternatively, a shorter sling 216 may be used. Such shorter slings may be attached to the pubic bone by sutures. In this embodiment, the sling may have sutures or integral attachment members extending bilaterally and may be inserted into the pouch so that a suture or integral attachment member extends from the proximal end of the pouch.

Long and short slings suitable for use with the sling application catheter are described in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

Figure 22:
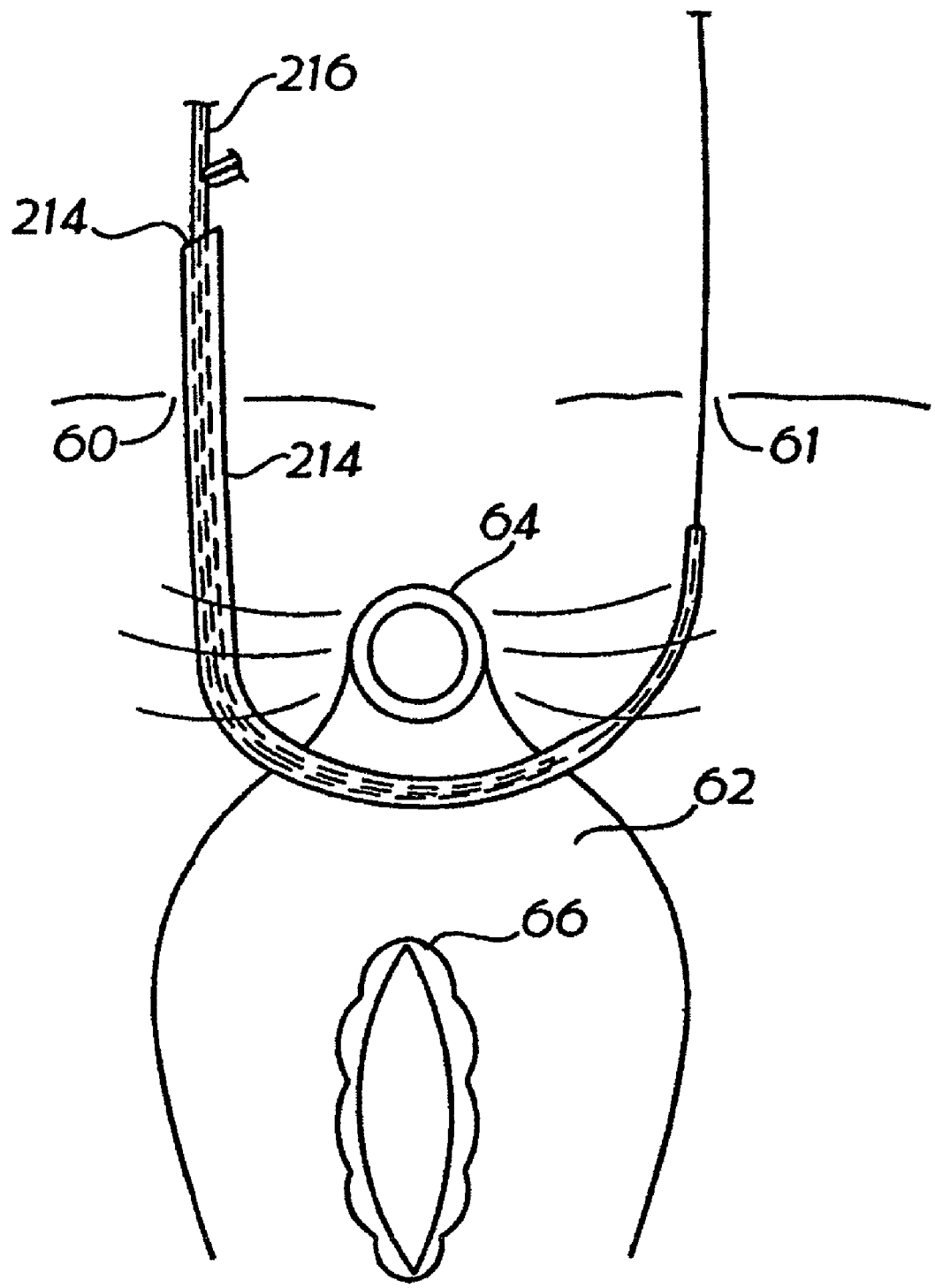
FIG. 22 shows the sling being withdrawn from the pouch of a sling application catheter that has been advanced into the tissue between the urethra and the upper vaginal wall.
Figure 23:
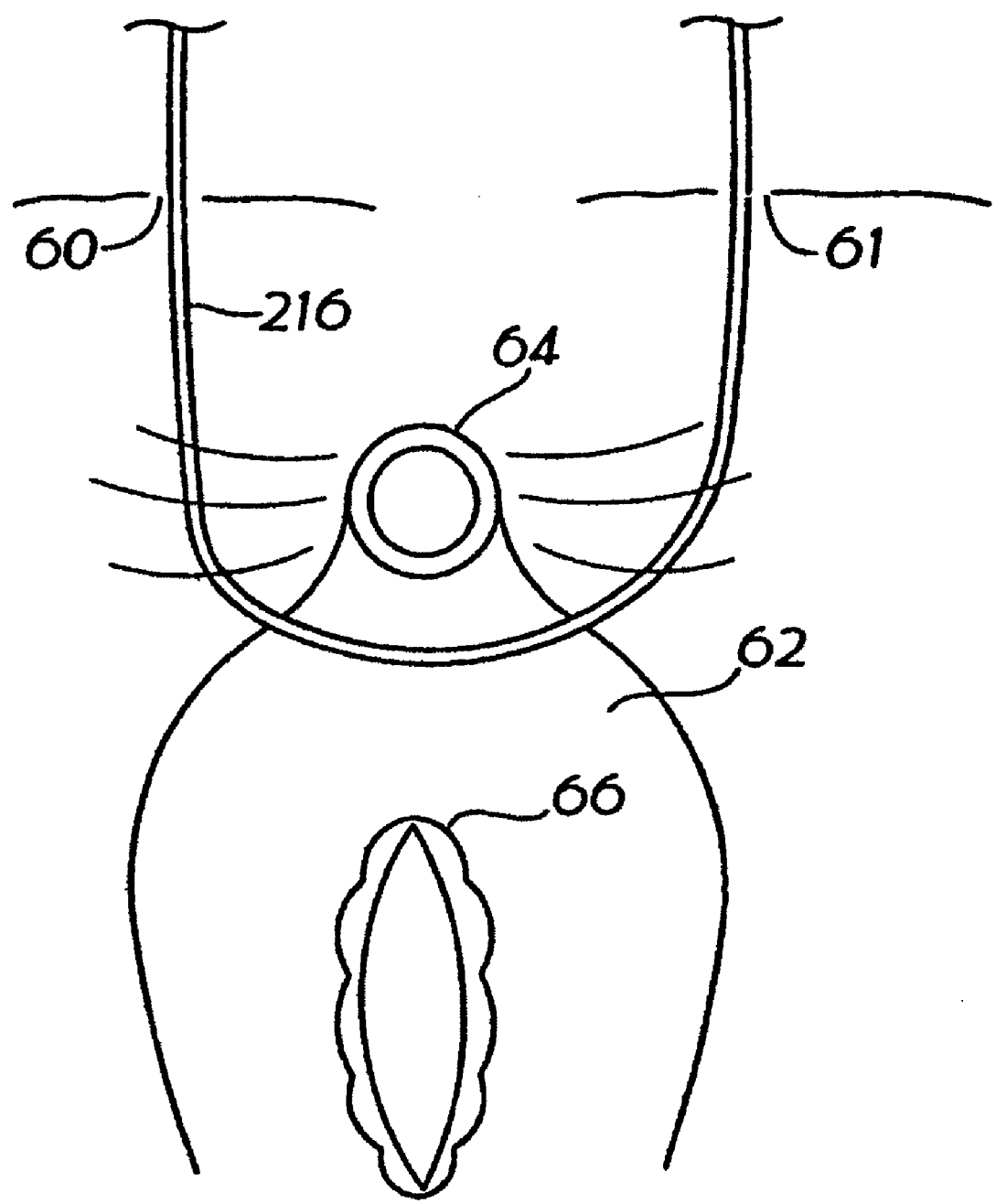
FIG. 23 shows the sling extending between the first and second suprapubic incisions and passing through the tissue between the urethra and the upper vaginal wall.

The physician percutaneously inserts the sling application catheter and advances it along the guide member. For example, the sling application catheter may be inserted through a first suprapubic incision 60. As the pouch 214 passes beneath the urethra 64, the physician grasps the portion of the sling or the suture or integral attachment member extending from the proximal end of the pouch while continuing to advance the sling application catheter 210, causing the sling 216 to be withdrawn from the pouch 214 as illustrated in FIG. 22. The sling application catheter is advanced until it exits the patient's body at a second suprapubic incision 61, leaving the sling extending between the first 60 and second 61 incisions as shown in FIG. 23.

Alternatively, when the shorter slings are used, the sutures or integral attachment members extend from the first and second incisions.

Following the completion of the preceding procedures, the sling 216 is located in the tissue 62 between the urethra and the upper vaginal wall.

Following implantation, the sling or sutures or integral attachment members extending therefrom may be sewn, stapled, riveted, or anchored to any of a variety of structures, such as the pubic bone, Cooper's ligament or rectus fascia to stabilize or stabilize the bladder neck or to stabilize the pelvic floor. For example, the long sling may be attached directly to the pubic periosteum using staples, clips, or sutures or may be attached to the pubic bone with short sutures attached to a bone anchor implanted in the pubic bone or fastened to the pubic bone with a headed nail or screw-like anchoring device.

The slings may be used to stabilize the bladder neck as described in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997. The tension on the sling may be adjusted as appropriate, using approaches such as those described in U.S. Pat. No. 5,611,515, issued Mar. 18, 1997 to Benderev et al., the disclosure of which is incorporated herein by reference, to support the bladder neck or stabilize the urethral floor, thereby maintaining or improving urinary continence.

Tissue Dissector/Dilator

Another aspect of the present invention is a tissue dissector/dilator 510 for creating an opening or pocket in a body tissue and dilating the opening or pocket with an expandable dilator. The tissue dissector/dilator finds particular application in urethral floor reconstruction procedures, such as bladder neck stabilization procedures in which the tissue between the female urethra and the upper vaginal wall is dissected and dilated to facilitate placement of a therapeutic sling device designed to alleviate incontinence.

The tissue dissector/dilator can be used in percutaneous approaches in which the sling is introduced into an opening or pocket in the tissue between the urethra and the upper vaginal wall without entry of the vaginal canal. Such procedures are described in detail below.

The tissue dissector/dilator generally comprises a body with a non-compliant shaft attached thereto. Preferably, the shaft has at least one lumen extending therethrough.

A dissector for creating an opening or pocket in the body tissue is carried on the shaft. The dissector may be on the exterior of the shaft or in the interior. Preferably, the dissector is within the lumen of the shaft and is axially movable such that it is capable of being extended from and retracted in the shaft to create an opening in the body tissue.

A dilator for dilating the opening or pocket is also carried on the shaft. The dilator may be on the exterior of the shaft or in the interior. Preferably, the dilator is within the lumen of the shaft and is axially movable such that it is capable of being extended from and retracted in the shaft. Preferably, the dilator is expandable and collapsible.

Preferably, the dissector and the dilator are integral. Alternatively, the movable dissector and the dilator can be separate elements of the tissue dissector/dilator. Preferably, both the dissector and the dilator are axially movable.

In yet another embodiment, the dissector and the dilator are not integral parts of the tissue dissector/dilator. In this embodiment, the dissector and the dilator are distinct devices which can be inserted into the shaft of the tissue dissector/dilator at the point in the surgical procedure in which tissue dissection or dilation is required.

Figure 24:
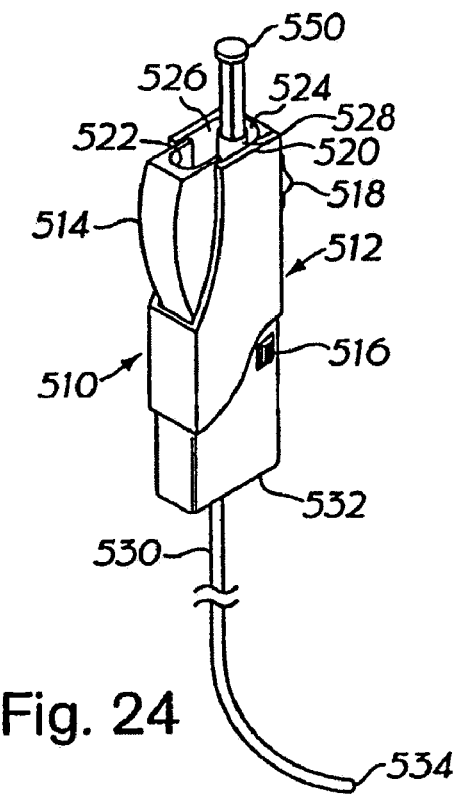
FIG. 24 is a plan view of a tissue dissector/dilator in which the spring return button is at the most proximal point and the blunt dissection tip and the expandable balloon are retracted within the shaft.

A representative embodiment of the tissue dissector/dilator 510 is shown in FIG. 24. As shown in FIG. 24 the body 512 comprises a trigger 514, a locking wheel 516, and a spring return button 518. In the embodiment of FIG. 24, the trigger 514 and the upper section 520 of the body each have a slot 522 and 524 therein which together define an aperture 526 adapted to receive a syringe 528 therein. However, those skilled in the art will appreciate that the body 512 can have a number of configurations compatible with the intended use of the- tissue dissector/dilator and the present invention encompasses such additional configurations.

Figure 25:
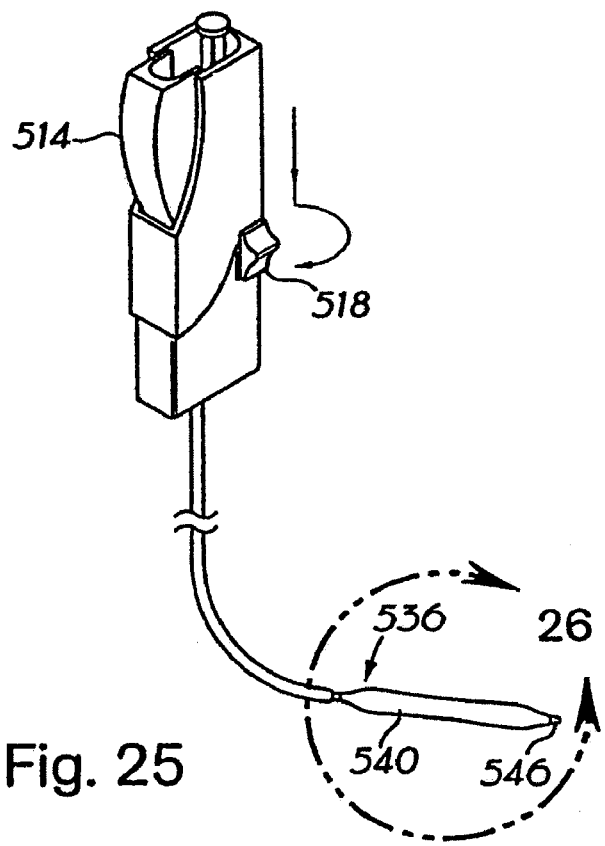
FIG. 25 is a plan view of the tissue dissector/dilator in which the spring return button has been advanced to the locked position and the expandable balloon and blunt dissection tip are fully extended from the shaft.

The spring return button 518 can slide along a slot in a vertical face of the body. As shown in FIG. 24, the spring return button 518 is biased towards a first position at the proximal end of the slot by a spring. As shown in FIG. 25, the spring return button 518 can slide to a second position in which it is locked in place. As illustrated in FIG. 25, in the locked position, the spring return button 518 fits into a groove on the body 512 and is located on a face of the body perpendicular to the face on which the spring return button 518 is located in the unlocked state.

The spring return button 518 may have an internal extension inside the body which has a proximal section adapted to receive a syringe tip.

As illustrated in FIG. 24, the shaft 530 is attached to the bottom portion 532 of the body 512 and has a lumen extending therethrough. The shaft 530 may be fabricated from a number of non-compliant materials sturdy enough to resist torque applied while the device is advanced through the body tissue. Preferably the shaft 530 is made of stainless steel.

Preferably, the shaft 530 curves towards its distal end 534. Preferably, the curve is a small radius curve. Preferably, the distal end 534 of the shaft is at an angle of about 90° relative to the proximal portion of the shaft. However, those skilled in the art will appreciate that the curve in the shaft 530 may vary depending on anatomical considerations and the type of procedure in which the tissue dissector/dilator is to be used.

Figure 26:
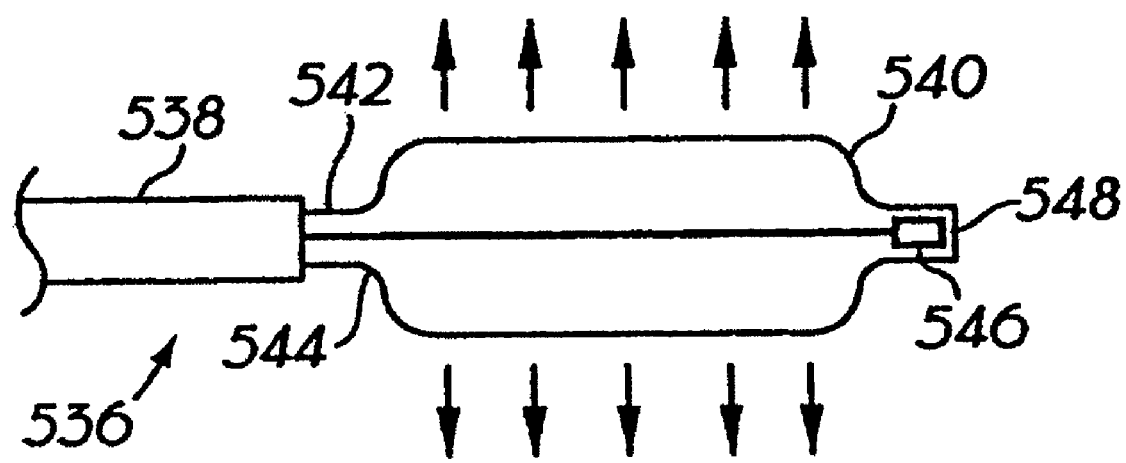
FIG. 26 is a side view of a balloon catheter with a blunt dissection tip at its distal end.

As shown in FIG. 25, a balloon catheter 536 is located within the lumen of the shaft 530 and is engaged by the spring return button 518. As illustrated in FIG. 26, the balloon catheter 536 comprises an outer tube 538 having a lumen extending therethrough and an expandable balloon 540 in the lumen of the outer tube 538. An inflation tube 542 with a lumen therein is located at the proximal end 544 of the expandable balloon and is in fluid communication with the interior of the balloon 540. Preferably, the expandable balloon 540 has a blunt dissection tip 546 at its distal end 548.

The inflation tube 542 may be made of any of a number of materials, such as PE or PET. Preferably, the inflation tube 542 is made of a non-compliant or minimally compliant material.

In the embodiment of FIG. 26, the expandable balloon 540 has a cylindrical shape when expanded. Preferably, the dimensions of the balloon are adapted for dilating an opening or pocket in the tissue between the urethra and the upper vaginal wall. The length of the balloon is dependent upon the direction in which it is oriented relative to the urethra in the procedure being used to create the pocket or opening. When the balloon is oriented perpendicular to the urethra the balloon is preferably 4-6 cm in length, with an effective width of 2 cm to create a pocket or opening of approximately 5 cm in length and 2 cm in width.

When used in procedures in which the balloon is oriented parallel to the urethra the balloon may be shorter than those used in procedures in which the balloon is perpendicular to the urethra. Balloons used in such procedures may also have a larger diameter than those used in procedures in which the balloon is perpendicular to the urethra. Balloon catheters having a plurality of balloons side by side or flat profile balloons, such as those described in more detail below, are also well suited for such procedures.

Preferably, the balloon expands radially but does not increase in length when 30 expanded.

The blunt dissection tip 546 is preferably cylindrical in shape. Preferably, the blunt dissection tip 546 is about ¼ inch in length.

The blunt dissection tip 546 may be fabricated from a variety of materials which are rigid enough to facilitate their use in blunt dissection of a body tissue. The tip of the balloon may be formed into a solid tip which functions as the blunt dissection tip. Alternatively, the blunt dissection tip 546 may comprise the same material as the inflation tube 542. In yet another embodiment, the blunt dissection tip may be stainless steel.

The balloon catheter may also have a second lumen therein for receiving a guide member. In this embodiment, a guide member may be placed through the aperture in the body, pass through the shaft, and extend out of the distal tip of the shaft, permitting the tissue dissector/dilator to be used to place a guide member in the opening or pocket created in the body tissue. The guide member may be a suture, guide wire, or other structure suitable for guiding a sling to a desired location.

In another embodiment, the balloon catheter may have a third lumen therein for irrigation or for receiving diagnostics, such as an ultrasound catheter. The third lumen may also be used for passage of an implant, such as fibrin glue or a bladder neck suspension or stabilization sling, such as those described in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

Figure 27:
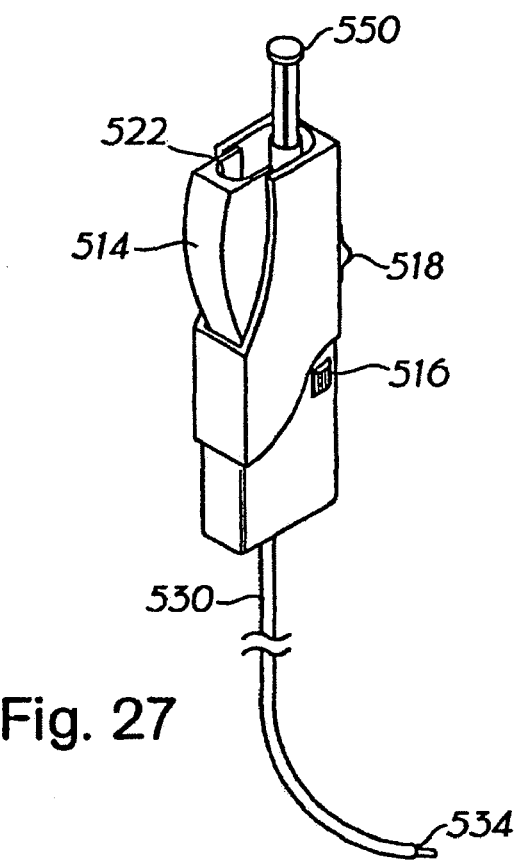
FIG. 27 is a plan view of a tissue dissector/dilator in which the spring return button has been advanced towards the distal end of the slide and the blunt dissection tip extends from the shaft.

As shown in FIG. 24, when the spring return button 518 is positioned at the most proximal point of its path in the vertical face of the body 512, the balloon catheter 536, including the blunt tip 546 and the expandable balloon 540, is retracted within inside the shaft 530. As illustrated in FIG. 27, when the spring return button 518 is moved towards the distal end of the slot, force is communicated to the balloon catheter 536 causing it to move axially towards the distal end 534 of the shaft, such that the blunt dissection tip 546 extends out of the shaft 530. If the spring return button 518 is then released, the bias from the spring will cause the spring return button 518 to return to the most proximal point of the slot, thereby returning the blunt dissection tip 546 to a fully retracted position within the shaft 530. Preferably, the spring return button 518 provides a one to one stroke motion to the blunt dissection tip 546. When the spring return button 518 is locked at its most distal position, the expandable balloon 540 and the blunt dissection tip 546 protrude from the distal end 534 of the shaft, as shown in FIG. 25.

As shown in FIG. 24, the proximal end of the body is adapted to receive a syringe 528 therein. The syringe 528 comprises a plunger 550, a reservoir, and a tip. The tip of the syringe engages the proximal section of an internal extension of the spring return button 518. As illustrated in FIG. 25, when the spring return button 518 is placed in the locked position, the syringe 528 moves into the body 512 and is positioned so as to permit the plunger 550 to engage the trigger 514. The tip of the syringe contacts the locking wheel 516 and engages a luer connection thereon. When the locking wheel 516 is tightened, the syringe 528 is firmly fixed in place such that the reservoir of the syringe is in fluid communication with the lumen of the balloon catheter.

Figure 28:
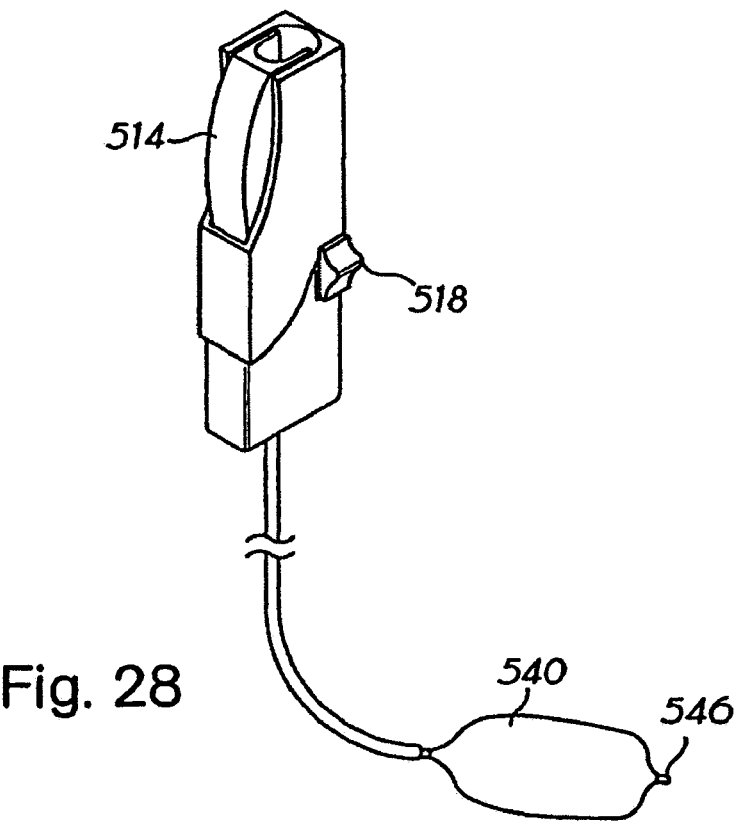
FIG. 28 is a plan view a tissue dissector/dilator in which the trigger has been squeezed, causing the balloon to inflate.

With the spring return button 518 in the locked position, the plunger 550 of the syringe engages the trigger 514, such that squeezing the trigger 514 causes the plunger 550 of the syringe to be depressed. When the reservoir of the syringe is filled with a fluid, such as sterile saline or sterile water, squeezing the trigger 514 causes the fluid to be dispensed from the syringe 528 into the lumen of the inflation tube 542, thereby inflating the expandable balloon as illustrated in FIG. 28. The trigger 514 contains a return spring, such that when the trigger 514 is released from the squeezed position, the trigger returns to its original position, drawing the plunger 550 of the syringe upward and thereby creating a vacuum in the syringe reservoir which draws the fluid from the expandable balloon 540 and deflates the balloon. The plunger 550 and the trigger 514 may be interconnected through a variety of structures familiar to those skilled in the art. For example, they may be interconnected through a rack and pinion gear.

Figure 29:
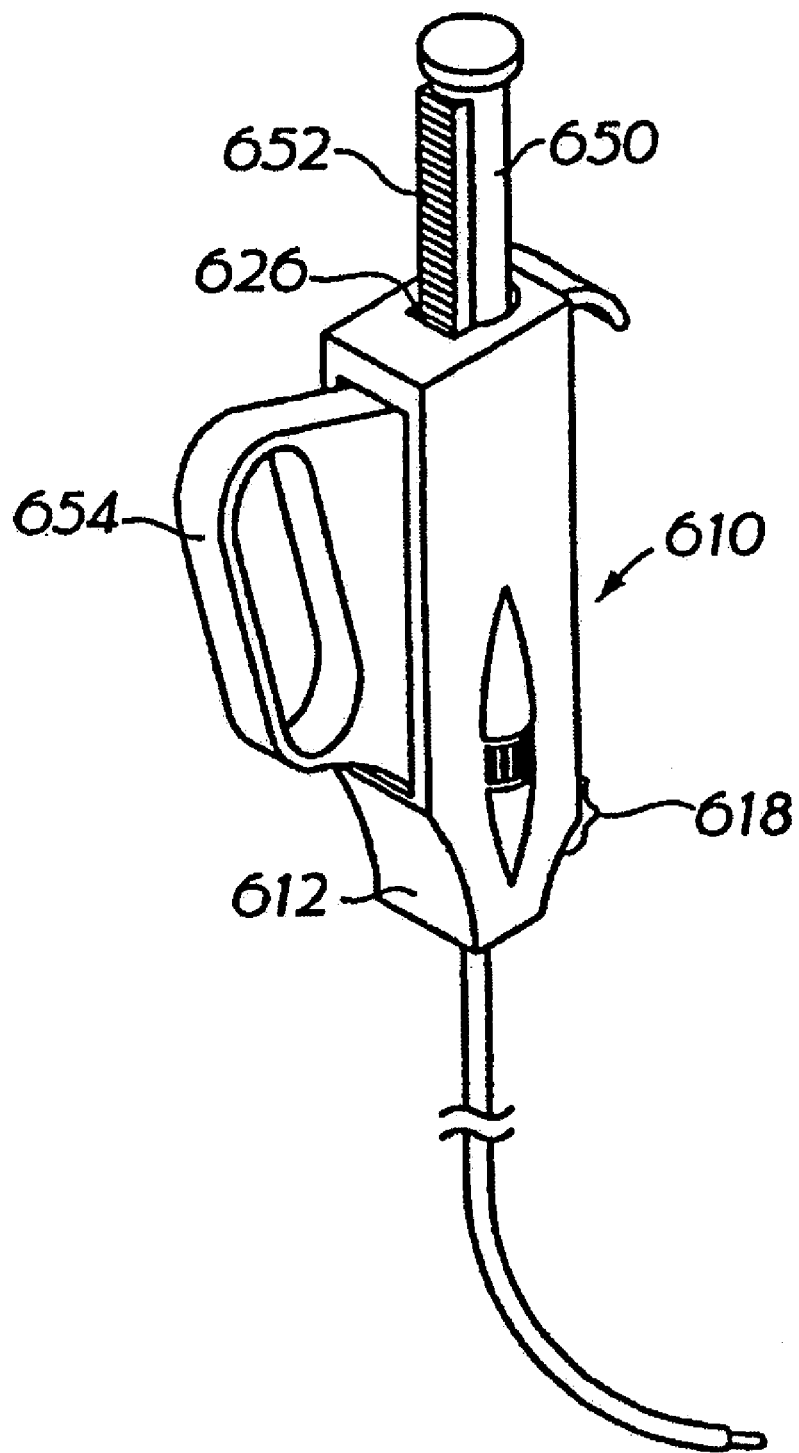
FIG. 29 is a plan view of an alternate embodiment of the tissue dissector/dilator.

An alternative embodiment of the tissue dissector/dilator 610 is shown in FIG. 29. In this device, the trigger 654 has an alternate shape as shown in FIG. 29 and engages a set of teeth 652 on the plunger 650 of the syringe. The body has a central aperture 626 therein which receives the syringe. Additionally, in this embodiment the locked position of the spring return button 618 is close to the bottom of the body 612 and the spring return button 618 is on the same face of the body in its locked and unlocked states.

While several embodiments of the tissue dissector/dilator have been described above, those skilled in the art will appreciate that alternative configurations are compatible with the function of the device. Such additional configurations are within the scope of this invention.

The following section describes the use of the tissue dissector/dilator in the context of a percutaneous bladder neck stabilization or suspension procedure in which a sling is utilized for treating urinary incontinence in females. However, those skilled in the art will recognize that the tissue dissector/dilator may also find application in a variety of other procedures in which it is necessary to introduce an opening into a body tissue and subsequently dilate that opening. While the procedure is described with particular reference to the tissue dissector/dilator 510 shown in FIGS. 24, 25, 27 and 28, those skilled in the art will appreciate that the tissue dissector/dilator 610 shown in FIG. 29 may also be used in the procedure.

The shaft of the tissue dissector/dilator is inserted percutaneously. For example, percutaneous insertion may be through a one inch transverse incision made over a pubic tubercle with dissection is carried down to the area of the rectus fascia. The tissue dissector/dilator 510, 610 is guided through the patient's body tissue along the back side of the pubic bone while maintaining the distal end of the shaft in contact with the pubic bone. If resistance is encountered while advancing the tissue dissector/dilator through tissue, the spring return button 518 may be repetitively partially depressed and allowed to return to its most proximal position through the action of the biasing spring. This process results in repetitive extension of the blunt dissection tip 546 out of the shaft 530 and retraction of the blunt dissection tip 546 back into the shaft 530, thereby dissecting an opening in the body tissue through which the device is passing.

Figure 30:
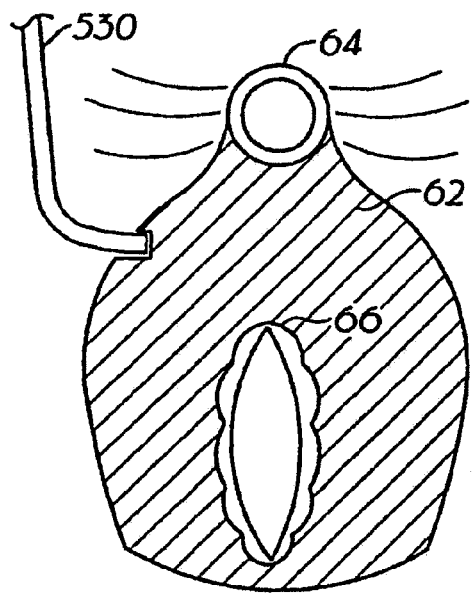
FIG. 30 shows the distal end of the shaft of a tissue dissector/dilator being advanced until it intersects the tissue between the urethra and the upper vaginal wall at approximately mid-thickness and in a direction which would permit the expandable balloon to advance perpendicular to the axial direction of the urethra.

The tissue dissector/dilator 510 is advanced until tenting is observed on the upper vaginal wall. As shown in FIG. 30, the user then manipulates the distal end of the shaft 534 until it intersects the tissue 62 between the urethra 64 and the upper vaginal wall 66 at approximately mid-thickness and in a direction which would permit the expandable balloon to advance perpendicular to the axial direction of the urethra.

Figure 31:
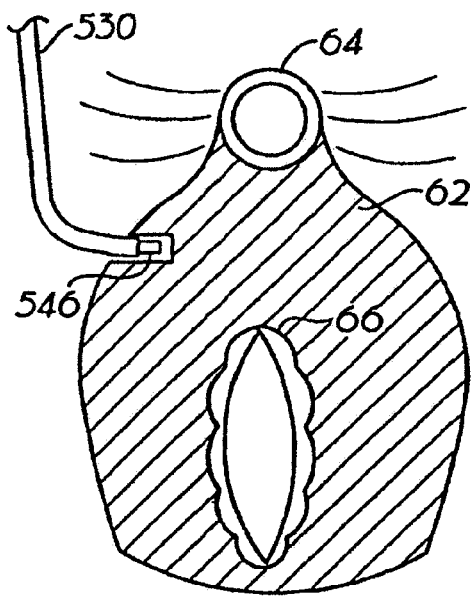
FIG. 31 shows the blunt dissection tip being extended from the distal end of the shaft into the tissue between the urethra and the upper vaginal wall thereby dissecting a first opening in the tissue.

As illustrated in FIG. 31, the tissue 62 between the urethra 64 and the upper vaginal wall 66 is then blunt dissected by repetitively extending and retracting the blunt dissection tip 546 using the spring return button 518 as described above, thereby creating an opening in the tissue. The dissection process is repeated until an opening is created in the tissue 62 which is large enough to permit the expandable balloon 540 to be fully extended from the shaft 530 such that the distal end of the shaft extends transversely between the urethra 64 and the upper vaginal wall 66 in the plane defined by the longitudinal axes of the urethra and the vagina, as shown in FIG. 32.

Figure 32:
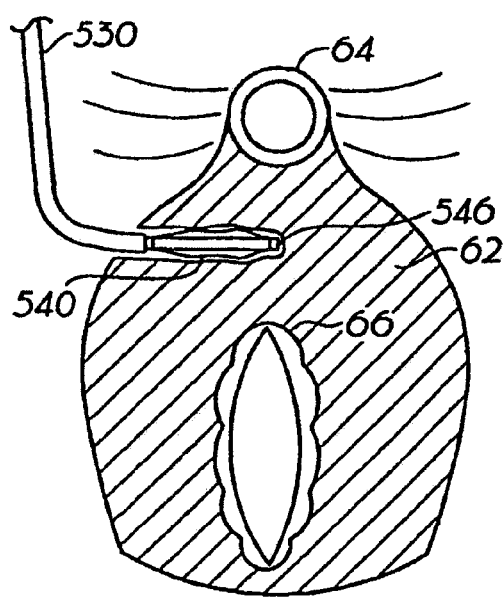
FIG. 32 shows the expandable balloon extended into the first opening in the tissue between the urethra and the upper vaginal wall which was created with the blunt dissection tip.
Figure 33:
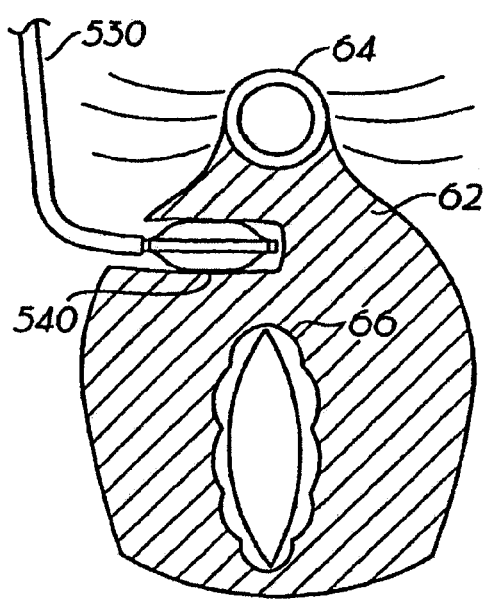
FIG. 33 shows the balloon being expanded in the first opening in the tissue thereby dilating the first opening.

The spring return button 518 is advanced to its locked position in which the expandable balloon 540 is fully extended into the opening in the body tissue, as shown in FIG. 32. The syringe 528 is locked in place such that its reservoir is in fluid communication with the lumen of the inflation tube 542 of the balloon catheter 536 and its plunger 550 engages the trigger 514. The trigger 514 is squeezed to dispense the saline solution inside the reservoir of the syringe through the inflation tube 542 of the balloon catheter 536 and into the expandable balloon 540, causing the balloon 540 to expand. Expansion of the balloon 540 dilates the body tissue, creating a first opening therein as shown in FIG. 33.

The trigger 514 is then released and is returned to its original position through the action of the return spring. As the trigger returns to its original position, a vacuum is created in the reservoir of the syringe 528, thereby drawing the fluid out of the expandable balloon 540 and causing the balloon 540 to deflate.

The trigger 514 can be squeezed and released multiple times, if necessary, until the opening in the body tissue expands. The expandable balloon 540 and blunt dissection tip 546 are then retracted into the shaft 530.

Figure 34:
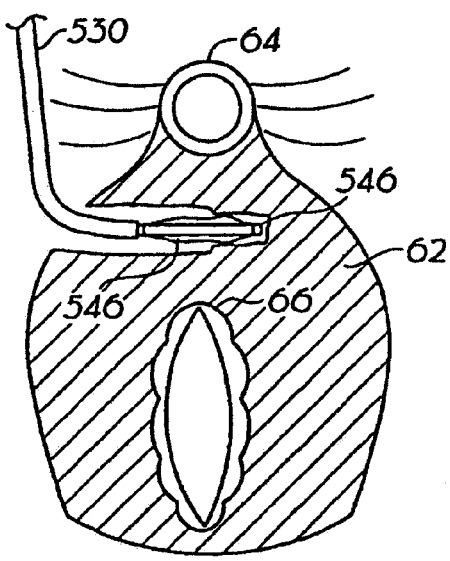
FIG. 34 shows a second tissue dissector/dilator with its blunt tip dissecting a second opening in the tissue between the urethra and the upper vaginal wall which is aligned with the first opening in the tissue.
Figure 35:
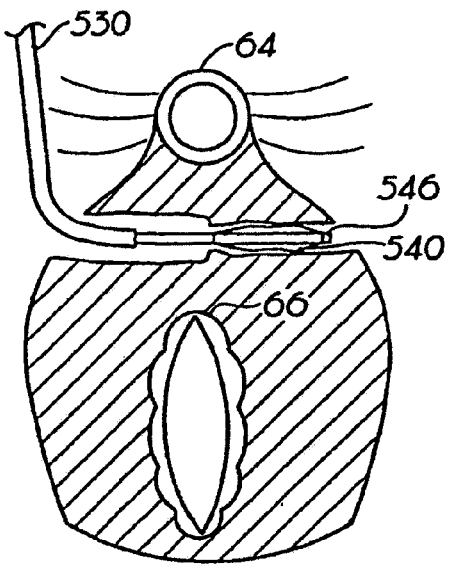
FIG. 35 shows the expandable balloon extended into the second opening.
Figure 36:
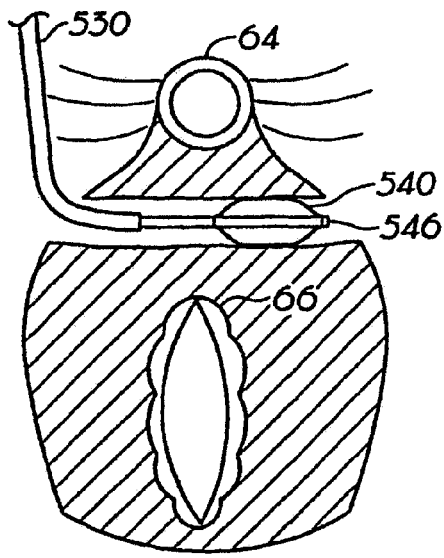
FIG. 36 shows the expandable balloon expanded within the second opening thereby dilating the body tissue.
Figure 37:
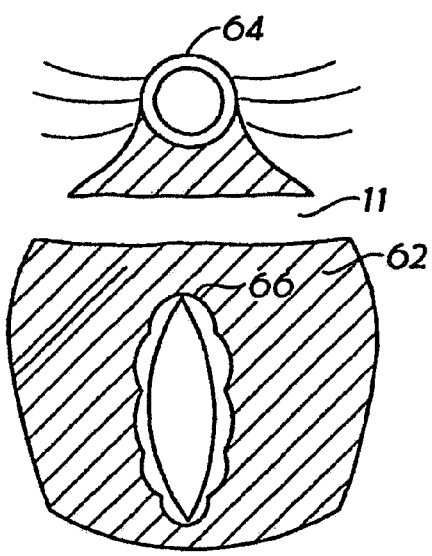
FIG. 37 shows a continuous opening in the tissue between the urethra and the upper vaginal wall.

The above dissection and expansion steps can be repeated while advancing the tissue dissector/dilator through the tissue between the urethra and the upper vaginal wall, as shown in FIGS. 34-36. The dissection and expansion steps may be repeated until a continuous dilated opening or pocket 11 exists in the tissue 62, as shown in FIG. 37. Following the creation of the continuous dilated opening or pocket, the tissue dissector/dilator is removed from the patient's body.

Alternatively, the continuous dilated opening or pocket 11 can be created from both sides of the urethra. In this procedure, a first tissue dissector/dilator is advanced approximately to the midline of the urethra while dissecting and expanding the tissue 62 as described above to create a first opening in the body tissue. The first tissue dissector/dilator may be removed from the body, or, in the embodiments described below in which two tissue dissector/dilators are interconnected to pass a guide member or suture through the patient's body, the first tissue dissector/dilator may remain in the patient's body.

A second tissue dissector is percutaneously inserted. This may be accomplished through a second suprapubic incision made on the opposite side of the urethra from the first suprapubic incision. A second tissue dissector/dilator 510 is inserted into the second incision and advanced through the body tissue until it is aligned with the first opening in the body tissue. Correct alignment of the second tissue dissector/dilator with the first opening in the body tissue is determined through visualization of tenting of the vaginal wall and through tactile sensation. The blunt dissector tip 546 of the second tissue dissector/dilator 510 is extended and retracted from the shaft 530, thereby creating a second opening in the body tissue which is joined to the first opening in the body tissue. The expandable balloon 540 is extended into the second opening and expanded within the second opening, thereby dilating the body tissue. When the second tissue dissector/dilator 510 is removed from the patient's body a continuous dilated opening or pocket 11 exists in the tissue 62, as shown in FIG. 37.

In both of the above methods, a sling may be introduced into the opening or pocket using the sling application devices described herein to suspend or stabilize the pelvic floor.

In the embodiment in which the balloon catheter has a second lumen for receiving a guide member, the tissue dissector/dilator may be used to introduce a guide member as follows. After creation of the first opening or pocket but before removal of the first tissue dissector/dilator from the body, a guide member, suture, guide catheter, or webbing is introduced into the second lumen of the catheter. When the first tissue dissector/dilator is removed from the body, the guide member is left in place.

After creation of the continuous pocket but before removal of the second tissue dissector/dilator from the body, the guide member in the first pocket is introduced into the second lumen of the catheter of the second tissue dissection/dilator and advanced therethrough. When the second tissue dissector/dilator is removed from the body after creation of the continuous pocket, the guide member remains in place and extends between both suprapubic incisions, passing under the urethra and through the continuous pocket. Alternatively, the tissue dissector/dilator may have an engaging member at the distal end of the shaft, permitting two devices to be interconnected with their lumens in fluid communication as described above for the guide member placement device. In this embodiment, the guide member, suture, guide catheter, or webbing is passed through the interconnected lumens of the first and second tissue dissector/dilators as described above in regard to the guide member placement device. Thus the guide member, suture, guide catheter or webbing extends between the two suprapubic incisions and passes through the tissue between the urethra and the upper vaginal wall.

The guide member can then be used to introduce a sling into the opening or pocket as described above.

In yet another embodiment, the tissue dissector/dilator may be used in transvaginal procedures. For example, the tissue dissector/dilator may be inserted through the upper vaginal wall rather than through suprapubic incisions. In this embodiment the device is advanced into the tissue 62 between the urethra and the upper vaginal wall and the balloon is expanded to create an opening or pocket as described above.

Sling Application Device and Sling Application System

Another aspect of the present invention is a sling application device for inserting a sling into an opening or pocket in a body tissue. The sling application device provides access to the tissue between the urethra and the upper vaginal wall and introduces a sling into a pocket or opening in that tissue. In some embodiments, the sling application device creates the pocket or opening into which the sling is inserted. In other embodiments, the sling application device introduces the sling into a pre-formed pocket or opening. The device may be used in percutaneous methods alone or in laparoscopic procedures.

Another sling application device for introducing a sling into the tissue between the urethra and the upper vaginal wall is currently available. This device comprises two shafts, each having a central lumen, which can be clamped together via horizontally extending tabs present at the proximal end of each shaft. Rotation of a lever on one of the horizontal tabs clamps the two tabs together, thereby locking the two shafts to one another.

The currently available device is used to introduce a sling into the tissue between the urethra and the upper vaginal wall as follows. The two shafts are introduced into incisions on opposite sides of the urethra in the unlocked configuration. The shafts are advanced through the patient's tissue until they are located underneath the urethra with the lumens of the two shafts aligned. The lever is then rotated to the locked position, fixing the two shafts together. A sharp blade is inserted through the lumen of one of the two shafts such that it contacts the tissue between the distal ends of the shafts. As the blade is advanced through the tissue between the distal ends of the shafts, the tissue is dissected. Eventually, the blade enters the lumen of the second shaft, thereby creating a continuous opening in the tissue between the urethra and the upper vaginal wall.

The two shafts are unlocked and one of them is removed from the patient's body. A suture is inserted into the eye of the blade and the blade is advanced into the opening in the tissue between the urethra and the upper vaginal wall. A right angle clamp is then used to grasp and follow the suture into the tissue between the urethra and the upper vaginal wall. When the jaws of the right angle clamp are spread, an enlarged opening sized to receive a sling is created. The sling is then guided along the suture and introduced into the enlarged opening.

As will be apparent from the following description, the present sling application device provides several advantages over the currently available device. For example, the present device eliminates the use of a right angle clamp to create the sling receiving opening which is required with the currently available device. Moreover, the sling introducer permits the sling application device to introduce the sling without the use of a guiding suture as required with the currently available device. A further advantage of the present device and methods for using the device is that when the pocket or opening is created by hydrodissection the procedure can be performed without cutting the tissue between the two shafts of the sling application device. Furthermore, with the present device, it is not necessary to seat the distal ends of the shaft together before locking the two halves of the device to one another.

The present sling application device generally comprises a first and a second shaft. The first and second shafts have a central lumen which is sized to allow a sling to advance therethrough. The lumens of the first and second shafts may also be sized to allow a sling introducer to pass therethrough. Preferably, the shafts of the present sling application device are sufficiently wide to create or maintain an opening in the tissue capable of receiving the sling.

Preferably, the sling application device further comprises a first handle attached to the first shaft and a second handle attached to the second shaft. The first and second handles have openings therein which are in fluid communication with the lumens in the shafts to which the handles are attached. Preferably, the first and second handles are adapted to be connected to one another.

The present sling application device includes an adjuster for incrementally adjusting the distance between the distal ends of the first and second shafts. The adjuster allows the distance between the distal ends of the shafts to be slowly decreased while monitoring the patient to ensure that the urethra is not pinched during the procedure. This feature is absent from the currently available device, which has only two configurations, the locked and unlocked configurations described above. Preferably, the adjuster engages the first and second handles.

Preferably, the upper portions of the distal ends of the first and second shafts are indented relative to the lower portions of the distal ends to reduce the possibility of pinching of the urethra during the sling implantation procedure. This feature is absent from the currently available device, increasing the risk of damage to the urethra when that device is used.

The shafts of the present sling application devices are adapted to receive several components during the sling application procedure such that the sling application device can be used as part of a sling introduction system. The sling introduction system generally comprises the sling application device, a blunt dissector and a sling introducer. In some embodiments, the sling introduction system may further comprise a sharp tissue cutter.

A representative embodiment of the sling application device 710 is shown in FIG. 38A. As shown in FIG. 38A, the sling application device 710 comprises a first handle 712 and a second handle 714, having first 716 and second 718 shafts, respectively, attached thereto. The first and second handles have openings 725, 727 and therein which are adapted to receive a sling or sling introducer. The first and second shafts 716, 718 are adapted for insertion into a body tissue and have central lumens 711 and 713, respectively, which extend therethrough. The lumens of first and second shafts are in fluid communication with the openings in the first and second handles and are adapted to receive a sling or sling introducer. The first and second shafts 716, 718 have dimensions adapted for creating or maintaining a pocket or opening in the body tissue and for receiving a sling introducer. The sling application device also comprises an adjuster 720 for adjusting the distance between the first shaft 716 and the second shaft 718. Preferably, the adjuster 720 is an articulating lock. As shown in FIG. 38A, the first handle 712 has a generally rectangular distal portion 722, an indented region 724, and a generally rectangular proximal portion 726 having a width less than the width of the generally rectangular distal portion 722. One face of the first handle 712 has a rectangular recess 728 open at each end for receiving an extension 730 on the second handle.

As shown in FIG. 38B, the first handle has a locking button 732 with a tab 717 thereon which is adapted to engage a groove 734 in the extension 730 section which is disposed between the first handle 712 and the second handle 714, thereby locking the two handles together. Alignment of the first handle 712 with the second handle 714 during locking is achieved by placing alignment pin 756 in alignment hole 758. However, those skilled in the art will appreciate that other means for aligning the handles and locking them together may also be used.

Figure 39:
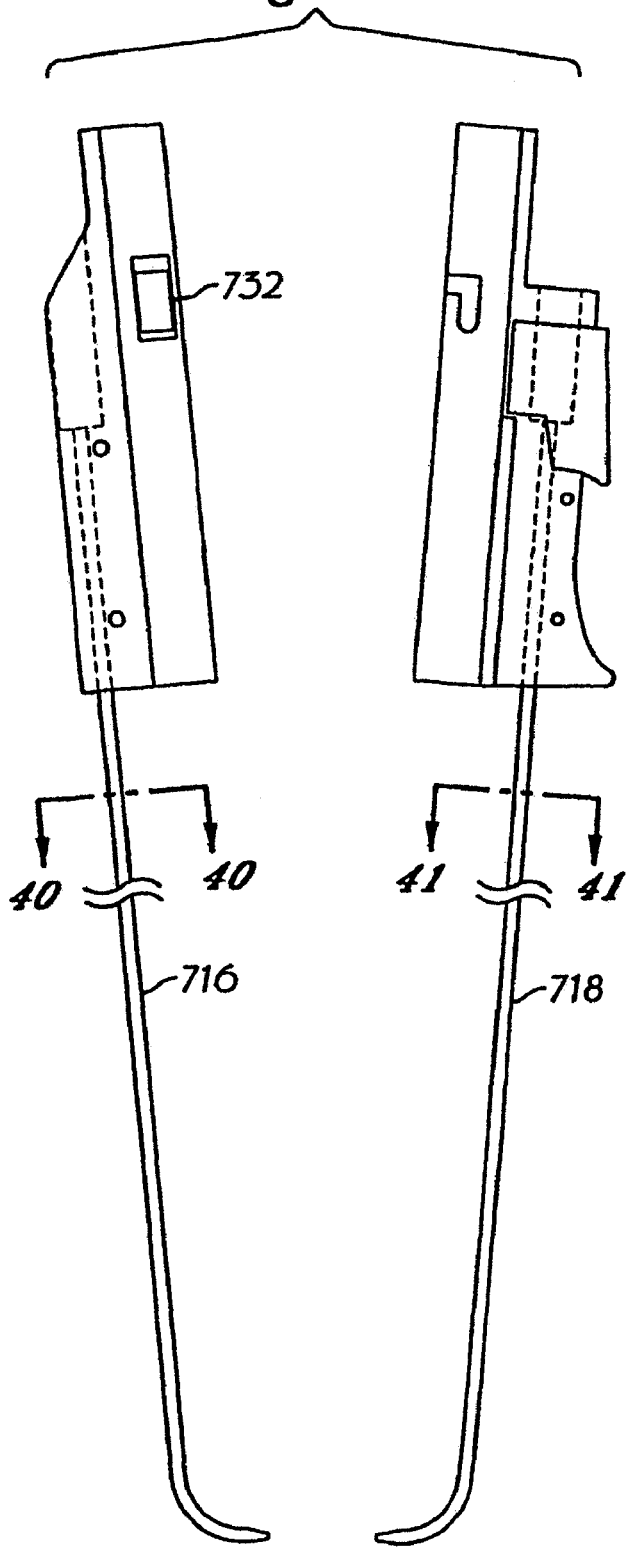
FIG. 39 is a side-view of the sling application device.
Figure 40:
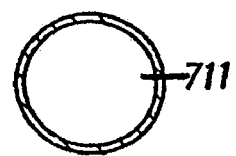
FIG. 40 is a cross-sectional view taken along line 40-40 of the first shaft of the sling application device of FIG. 39.
Figure 41:
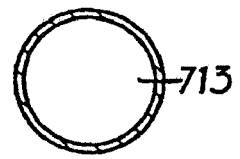
FIG. 41 is a cross-sectional view taken along line 41-41 of the second shaft of the sling application device of FIG. 40.

A first shaft 716 with a central lumen therethrough extends through the first handle 712. As shown in FIGS. 39, 40 and 41, the first shaft 716 is cylindrical and curves toward its distal end 736. The first shaft 716 may be from about 3 inches to about 10 inches in length, with an outer diameter from about ³⁄₁₆ inch to about ⅝ inch with a wall thickness from about 0.010 inch to about 0.020 inch. Preferably, the first shaft 716 is from about 6 inches to about 8 inches in length, with an outer diameter from about 0.187 inch to about 0.275 inch. However, those skilled in the art will appreciate that the preceding dimensions may vary depending on ahatornical considerations and the type of procedure being performed.

The first shaft 716 may be made of a variety of materials, including stainless steel and aluminum. Preferably, the first shaft 716 is made from stainless steel.

The first shaft 716 is curved near its distal end. Preferably, the first shaft 716 curves through an arc from about 80° to about 90°. More preferably, the first shaft 716 curves through an arc of about 90°.

In an alternate embodiment of the sling application device 810, shown in FIGS. 42, 43 and 44, the portion of the first shaft 816 proximal to the curve is cylindrical and the portion of the first shaft 816 distal to the curve is a flat tube. The flat tube may have a variety of cross sectional shapes such as rectangular, hexagonal or oval. The first shaft 816 is curved as described above for the embodiment in which the shaft is cylindrical.

Figure 45:
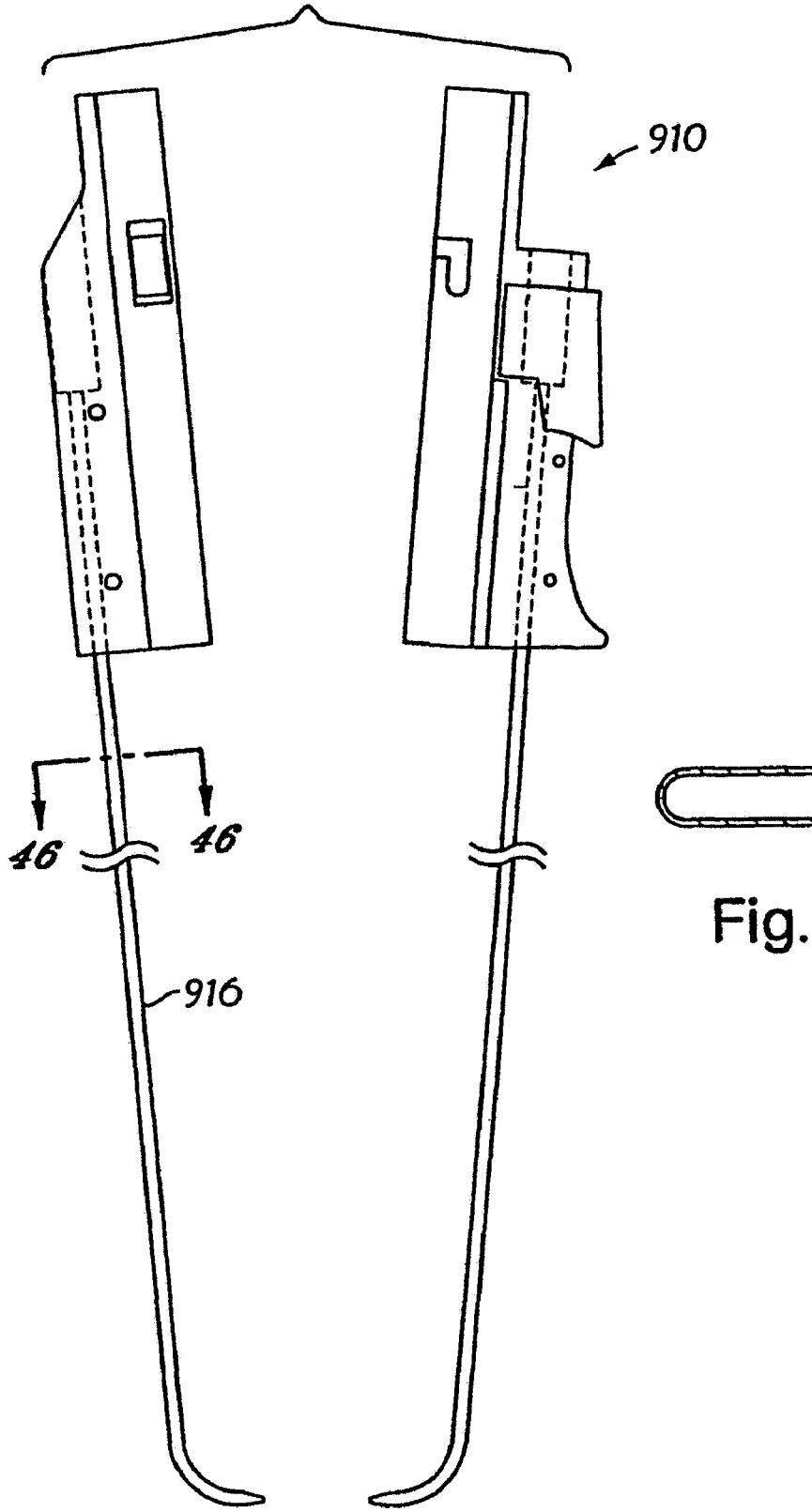
FIG. 45 is a side view of an alternate embodiment of the sling application in which the shafts are flat along their entire length.
Figure 46:
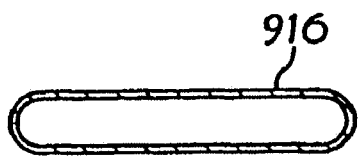
FIG. 46 is a cross-sectional view taken along line 46-46 of the first shaft of the sling application device of FIG. 45.

In a further embodiment of the sling application device 910, the first shaft 916 comprises a tube which is flat along its entire length as shown in FIGS. 45 and 46. The first shaft 916 is curved towards its distal end as described above for the embodiment in which the shaft is cylindrical.

Preferably, the first shaft has a side bend. In accordance with this embodiment, the first shaft can be flat, cylindrical, or flat in some portions and cylindrical in others as described above with respect to the sling application devices 710, 810, 910 discussed above.

Figure 47:
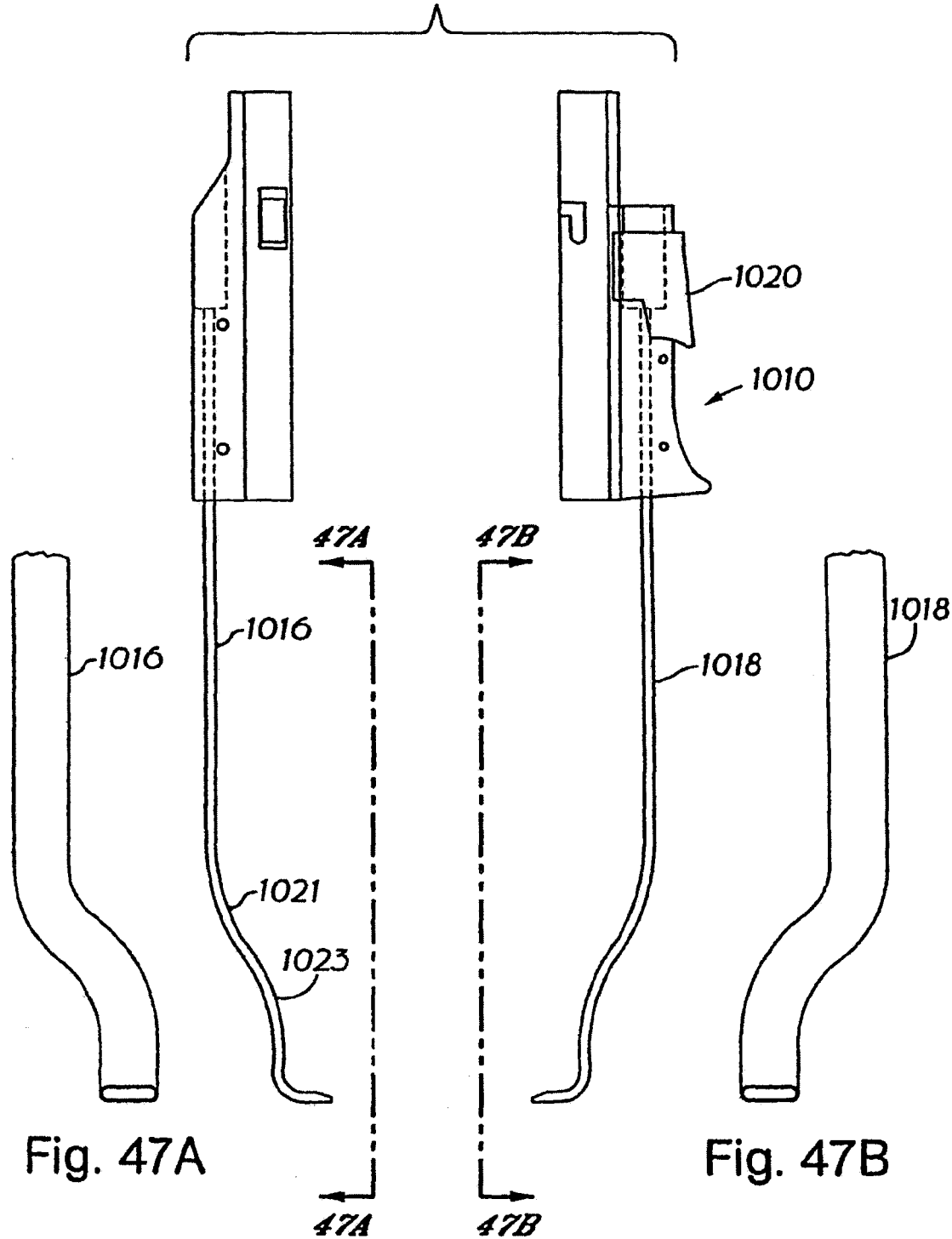
FIG. 47 is a side view of an alternate embodiment of the sling application device in which the shafts have a side bend.

FIGS. 47, 47A and 47B show a sling application device 1010 in which the shafts have a side bend. In this embodiment, the first shaft 1016 is flat and has a first curved section 1021 and a second curved 1023 section along its length. Preferably, the portion maximum offset between the first curved section 1021 and the second curved section 1023 is from about 1 inch to about 3 inches. As shown in FIGS. 47 and 47B, the second shaft 1018 has the same structure as the first shaft 1016. Preferably, the first and second shafts 1016, 1018 undergo a smooth transition from cylindrical to elliptical or flat. More preferably, the portion of the shaft proximal to the first curved section 1021 is cylindrical and the portion of the shaft distal to the first curved section is flat. Preferably, the radius of curvature of the second curve is not planar with the axial plane of the portion of the shaft. The adjuster 1020 in this embodiment may be the same as the adjuster described above.

Figure 48:
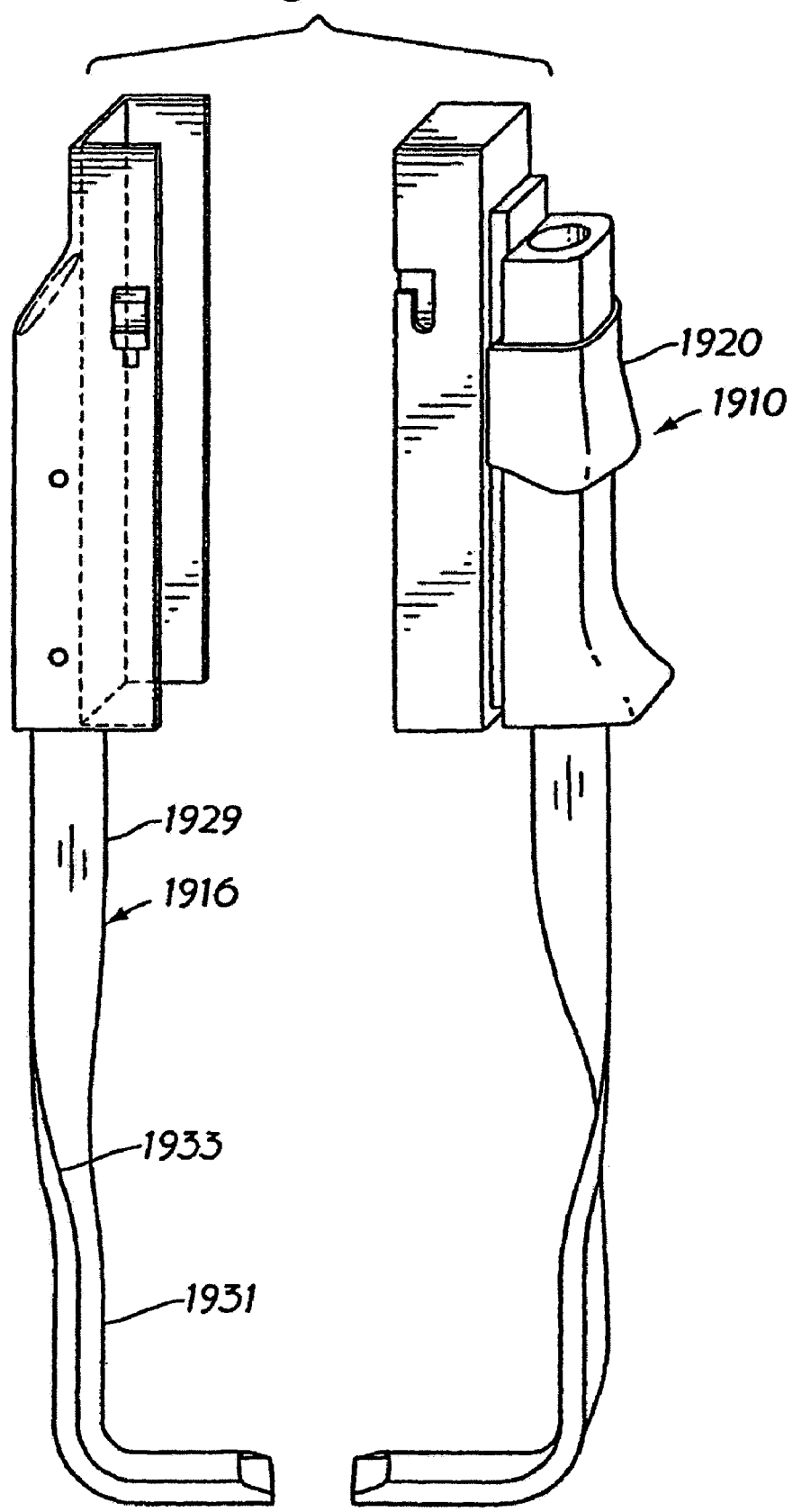
FIG. 48 is a side view of a sling application device in which the shafts have a 90° twist.

Alternatively, the shaft may have a 90° twist as shown in FIG. 48. In this embodiment of the sling application device 1910, the proximal portion 1929 of the first shaft 1916 is oriented at an angle of 90° relative to the distal portion 1931 of the first shaft, with a transitional section 1933 disposed between the proximal section of the first shaft 1929 and the distal section of the first shaft 1931. The adjuster 1920 in this embodiment may be the same as the adjuster described above.

Figure 56:
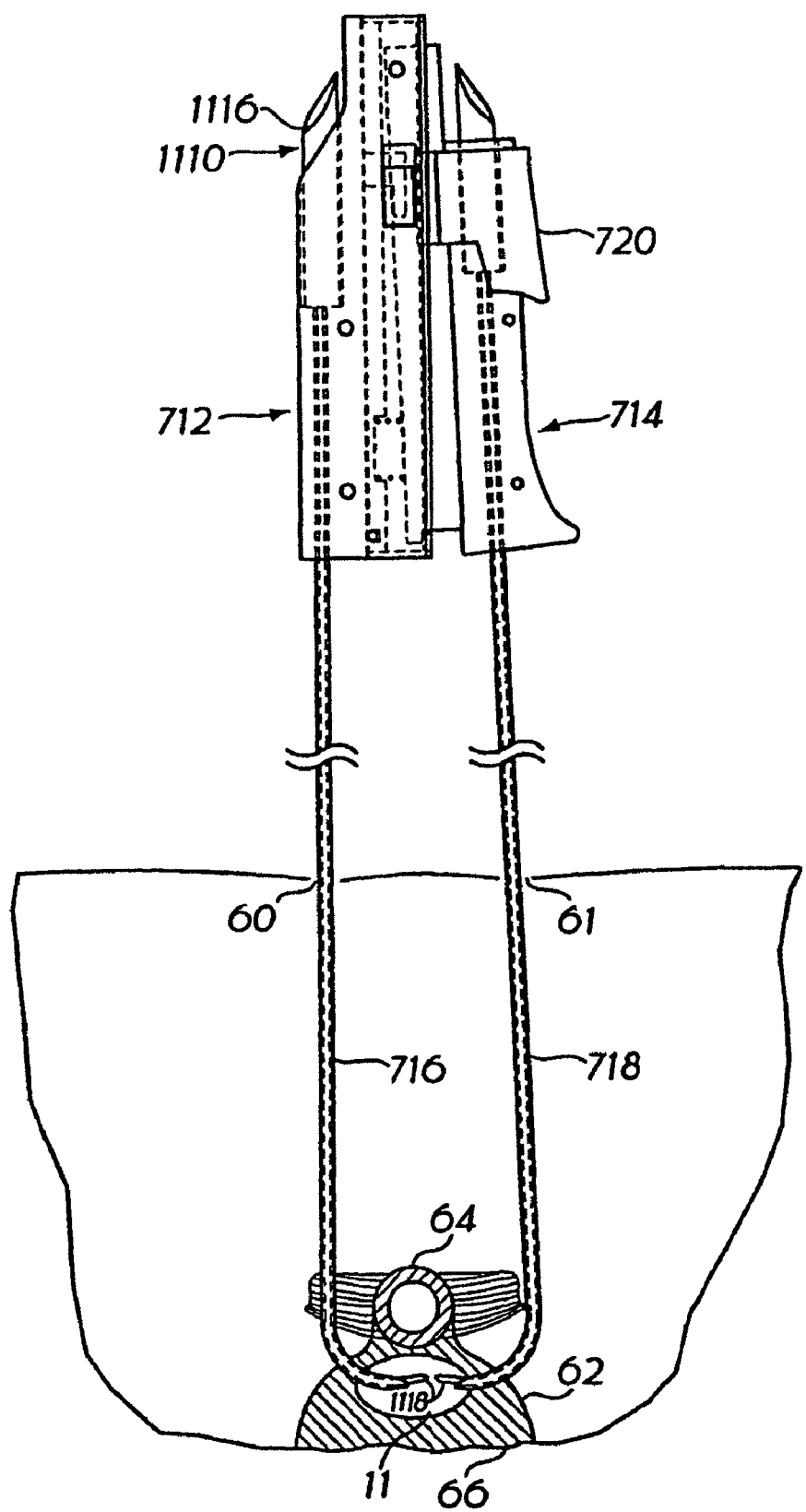
FIG. 56 shows the first and second handles of the sling application device locked together.
Figure 57:
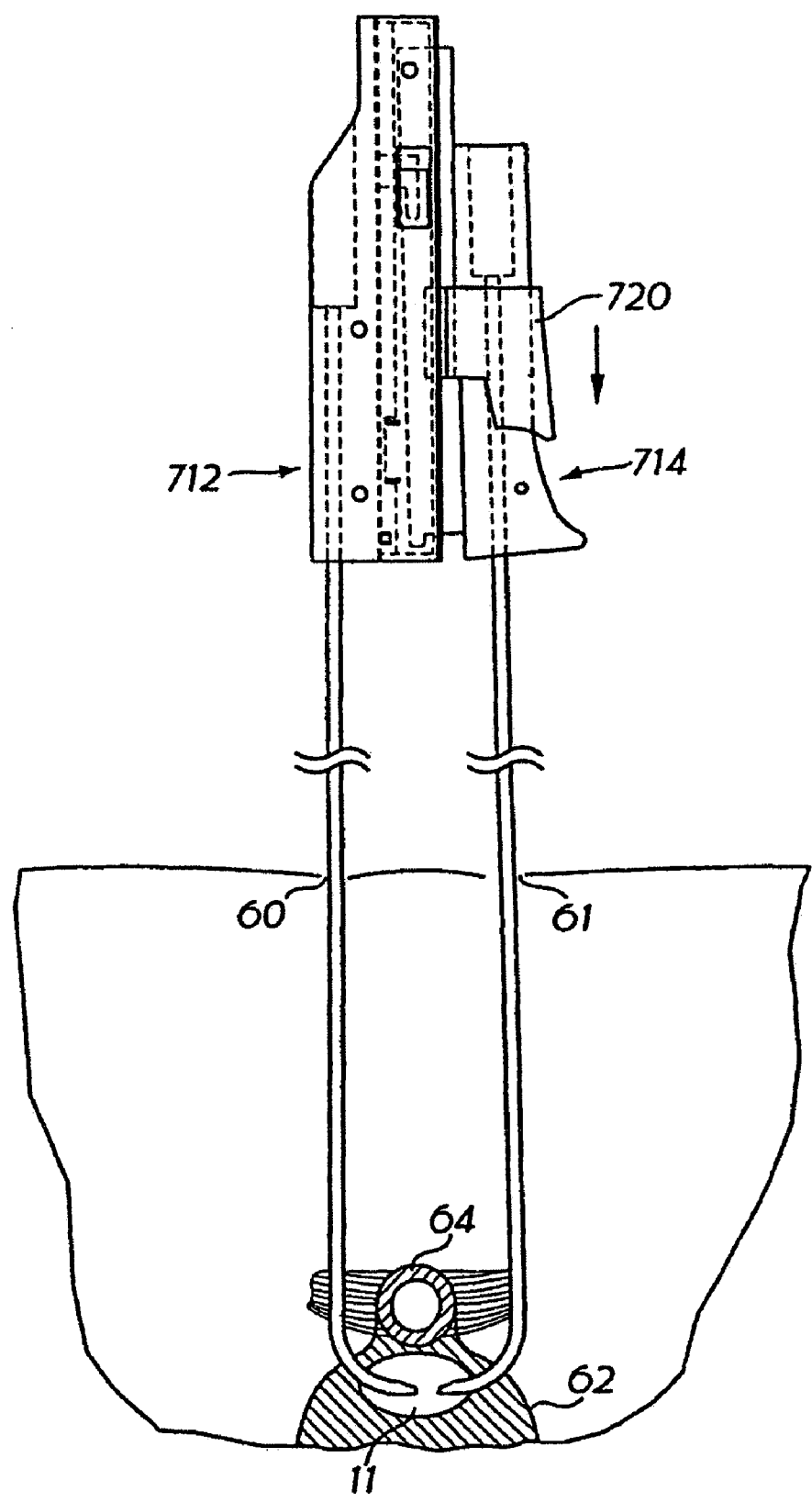
FIG. 57 shows the distance between the distal ends of the first and second shafts of the sling application device being decreased as the adjuster is advanced to a position in between the proximal point and the distal point of the guide.
Figure 58:
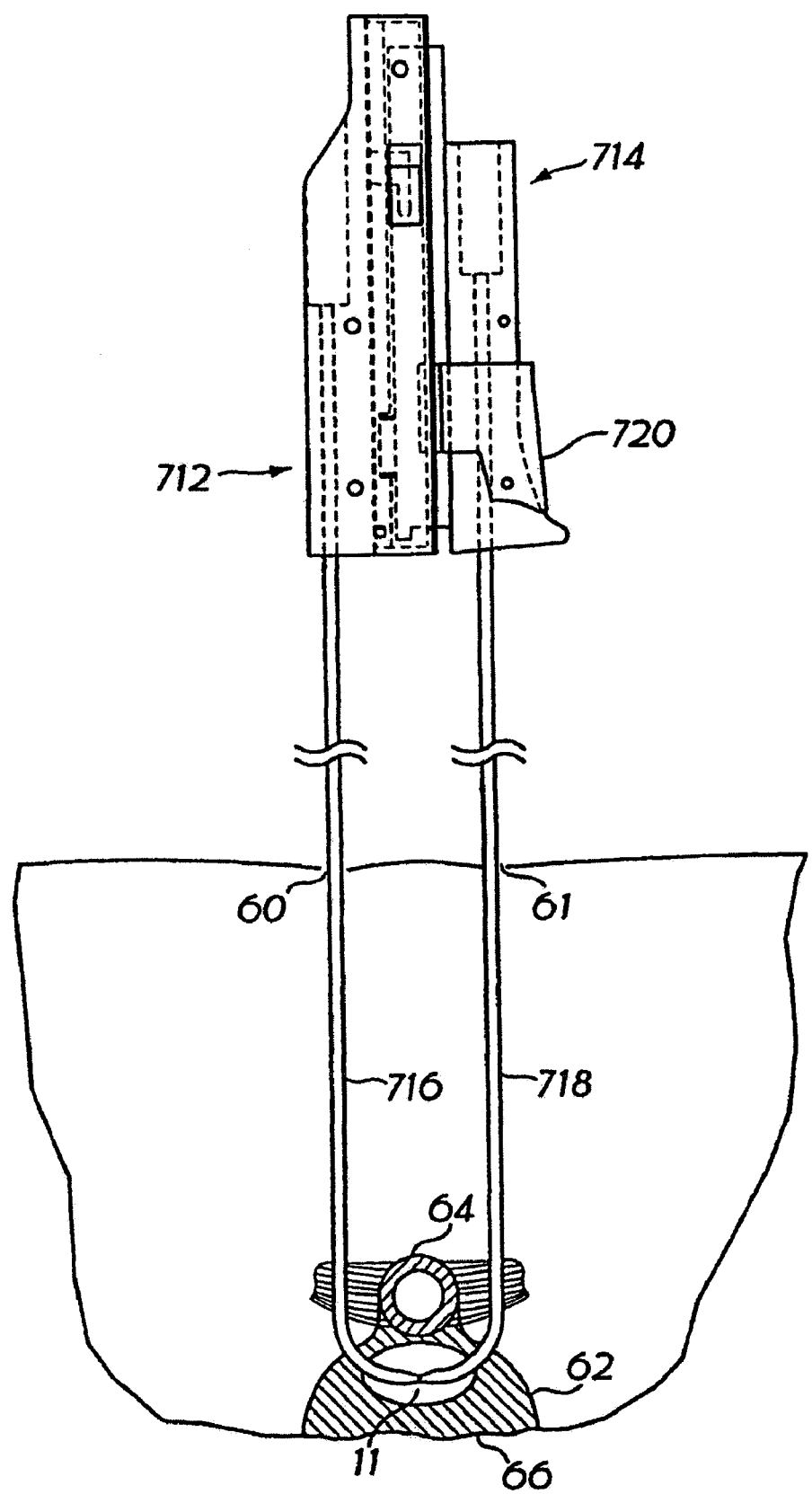
FIG. 58 shows the tissue between the distal ends of the first and second shafts of the sling application device being compressed when the adjuster is advanced to the distal end of the guide.

Referring to FIG. 38A, one face 746 of the second handle is adapted to enable the physician to firmly grasp it when advancing the device through tissue. An adjuster 720 is slidably mounted on face 746. The adjuster 720 slidably engages a guide 748 on the bottom of the first handle 712. The guide 748 is hingedly connected to the extension 730 and is biased away from the extension 730 by a biasing means such as a spring 754 (indicated in FIG. 56) disposed between the guide 748 and the extension 730. Tabs 750 on the adjuster 720 fit into grooves 752 between the sides of the extension 730 and the sides of the guide 748 such that the adjuster 720 moves along the guide 748 between a proximal end and a distal end. When the two handles have been locked together, moving the adjuster 720 along the guide 748 adjusts the distance between the distal ends of the first and second shafts 716, 718 as depicted in FIGS. 56-58, which are discussed in greater detail below. However, those skilled in the art will appreciate that there are other adjuster designs compatible with the operation of the present device, and such designs are specifically contemplated in the present invention.

As the adjuster 720 is moved towards the distal extreme of the guide 748, the resistance of the spring biasing the guide away from the extension 730 is overcome and the distance between the distal ends of the first and second shafts 716, 718 decreases. As the adjuster 720 is moved towards the proximal extreme of the guide 748, the spring pushes the guide 748 away from the extension 730 and the distance between the distal ends of the first and second shafts 716, 718 increases.

The second handle 714 has a second shaft 718 extending therethrough. The second shaft 718 may have the same configurations and be made of the same materials as described above with regard to the first shaft 716. Preferably, the second shaft of the second handle has the same configuration as the first shaft of the first handle with which it is to be used, as illustrated in FIGS. 38-48.

Figure 49:
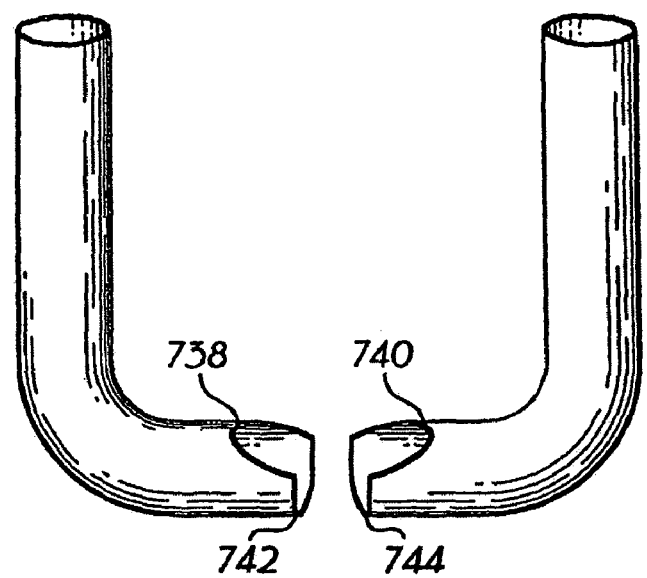
FIG. 49 is a perspective view of the distal ends of the first and second shafts of a sling application device in which the upper edges of the distal ends of the shafts are slightly indented relative to the lower edges.

Preferably, as shown in FIG. 49, the upper edges 738 and 740 of the distal ends of the first and second shafts 736, 715 are slightly indented relative to the lower edges 742 and 744 to reduce the possibility of the urethra being pinched during the sling implantation procedure.

A further aspect of the present invention is a blunt dissector for dissecting the body tissue without scoring or creasing the tissue or bone with which it comes in contact. The blunt dissector is adapted for insertion into the first and second shafts of the sling application device and protrudes from the distal ends of the shafts. The blunt dissector can be used as a component in the sling application system.

Figure 50:
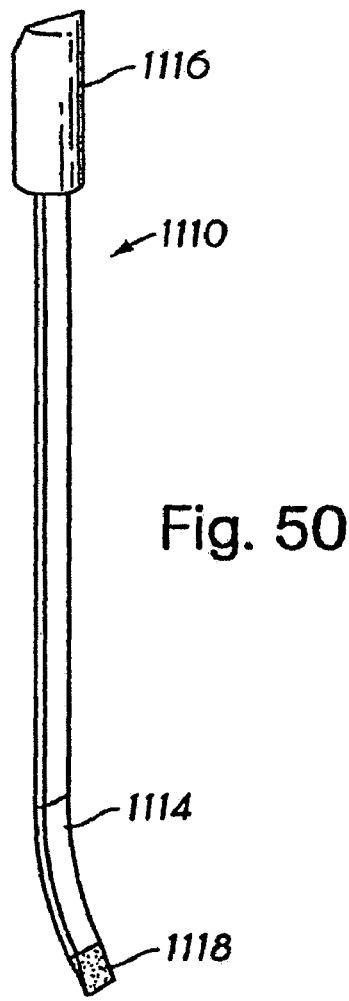
FIG. 50 is a side view of an obturator for use with the sling application device.

The blunt dissector may be an obturator 1110 as shown in FIG. 50. The obturator comprises an elongate, flat shaft 1112 interposed between a flexible section 1114 located at the distal end of the shaft and a handle 1116 located at the proximal end of the shaft 1112. When the obturator 1110 is inserted into the first and second shafts 716 and 718 of the sling application device, the flexible section 1114 bends to permit the obturator 1110 to conform to the curves near the distal ends of the shafts 716 and 718. The flexible section 1114 has a generally rigid tip 1118 at its distal end which extends from the distal ends of the first and second shafts 716 and 718 when the obturator 1110 is inserted therein. The generally rigid tip 1118 prevents scoring of the tissue or bone with which it comes in contact when the first and second shafts 716, 718 are advanced through tissue. In an alternate embodiment, the flexible section may have an opening near its distal end to increase flexibility.

The shaft 1112 of the obturator may be made of a variety of materials such as polycarbonate, nylon, polypropylene, and Acrylonitrile Butadiene Styrene (ABS). A preferred material is ABS.

The flexible section 1114 of the obturator may be made of any of a number of materials, including polycarbonate, nylon, polypropylene, and ABS. Preferably, the flexible section 1114 is made of ABS.

The generally rigid tip 1118 of the obturator may be made of materials such as polycarbonate, nylon, polypropylene, and ABS. Preferably, the generally rigid tip 1118 is made of ABS.

When the obturator 1110 is inserted into the first and second shafts 716, 718, the generally rigid tip of the obturator 1118 protrudes from the distal ends of the shafts 716, 718. Preferably, the generally rigid tip 1118 protrudes a distance of from about 0.1 inch to about 0.25 inch from the lower edges 742, 744 of the distal end of the shafts 716, 718. More preferably, the generally rigid tip 1118 protrudes a distance of about 0.20 inch from the lower edges 742, 744 of the distal end of the shafts 716, 718.

Yet another aspect of the present invention is a sling introducer 1210 adapted for releasably engaging a sling 1211 and introducing the sling 1211 into the body tissue without the use of sutures. The sling introducer 1210 can be used as a component in the sling application system and is adapted for insertion into and advancement through the first and second shafts 716, 718 of the sling application device 710. Alternatively, the sling introducer can be used in conjunction with laparoscopic trocars.

Figures 51, 52:
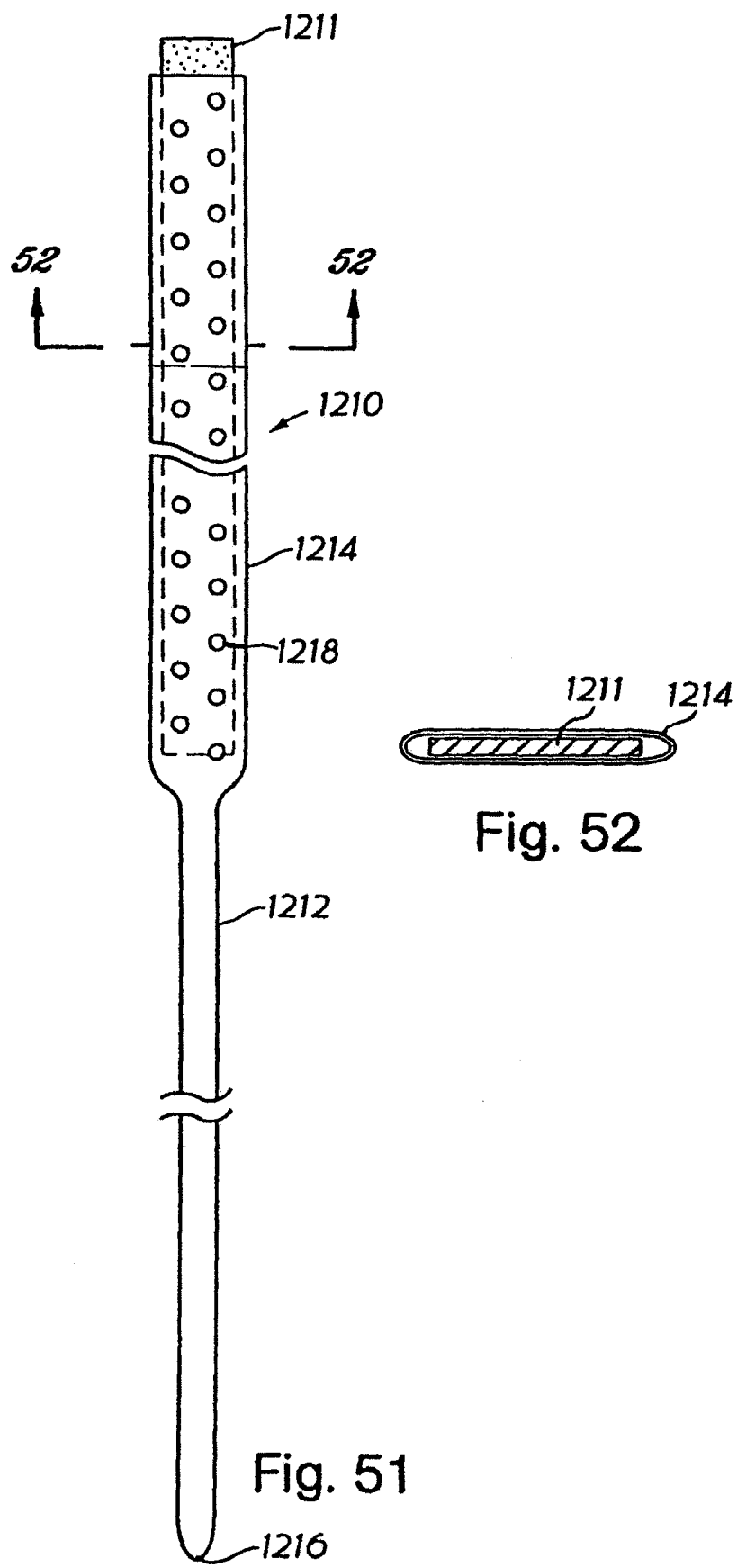
FIG. 51 is a plan-view of a sling introducer.
FIG. 52 is a cross-sectional view taken along line 52-52 of the sling introducer of FIG. 51.

A representative sling introducer 1210 is shown in FIGS. 51 and 52. The sling introducer 1210 can be made of any of a number of materials such as polyethylene, PET or vinyl. Preferably, the sling introducer 1210 is made of generally rigid vinyl.

The sling introducer 1210 of FIG. 51 has a narrow elongate distal tip 1212 and a pouch 1214 at the proximal end. The elongate distal tip 1212 of the sling introducer of the sling introducer is configured to pass through the first and second shafts 716, 178 of the sling application device. The sling introducer 1210 is sufficiently long to permit the distal tip 1216 of the sling introducer to protrude from the proximal end of the opening 725 in the first handle of the sling application device 710 while the sling 1211 protrudes from the proximal end of the opening 727 in the second handle of the sling application device 710.

The pouch 1214 of the sling introducer is sized to receive a sling 1211 therein. The slings 1211 introduced with the sling introducer 1210 can be long enough to extend between two suprapubic incisions or may be shorter slings designed to be attached to the pubic bone with sutures. Long and short slings suitable for use with the present invention are disclosed in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

The pouch 1214 is relatively flexible, and is preferably made of a soft, pliable plastic such as polyethylene, PET or vinyl. In some embodiments, the pouch 1214 may be reinforced by a stiffener to provide some rigidity along the edges as discussed above. The proximal end of the pouch 1214 may be sufficiently wide to maintain the sling 1211 in a flat orientation. Alternatively, the pouch of the sling introducer 1210 may be rolled up such that the sling is also in a rolled configuration. During introduction of the sling into the opening or pocket in the body tissue, the sling 1211 may be converted to a flat configuration.

In one embodiment, the pouch 1214 has pores 1218 therein as shown in FIG. 51 to facilitate re-hydration or soaking treatments of the sling materials. In particular, the porous pouch 1214 permits solutions in which the pouch. is placed to contact the sling inside the pouch. Such solutions include saline solutions and antibiotic solutions. In this way, the pores facilitate treatments in which the sling is soaked in antibiotics to prevent the growth of microorganisms on the surface of the sling after the sling 1211 is introduced into the body. The pores also permit gas sterilization of the sling while it is inside the pouch.

In this embodiment, the pouch 1214 may be made of a variety of materials, such as PE, PET, or vinyl. Preferably, the pouch is made of clear material to permit visualization of the sling when it is inside the pouch. Preferably, the pouch has pore sizes from about 0.10 inch to about 0.25 inch. Preferably, the pouch 1214 is made of vinyl having a pore size of about 0.125 inch.

In alternate embodiments, the pouch 1214 may be nonporous. Such pouches may be made of the same materials as described above for the porous pouches. However, the nonporous pouches do not have pores formed therein.

Figure 53:
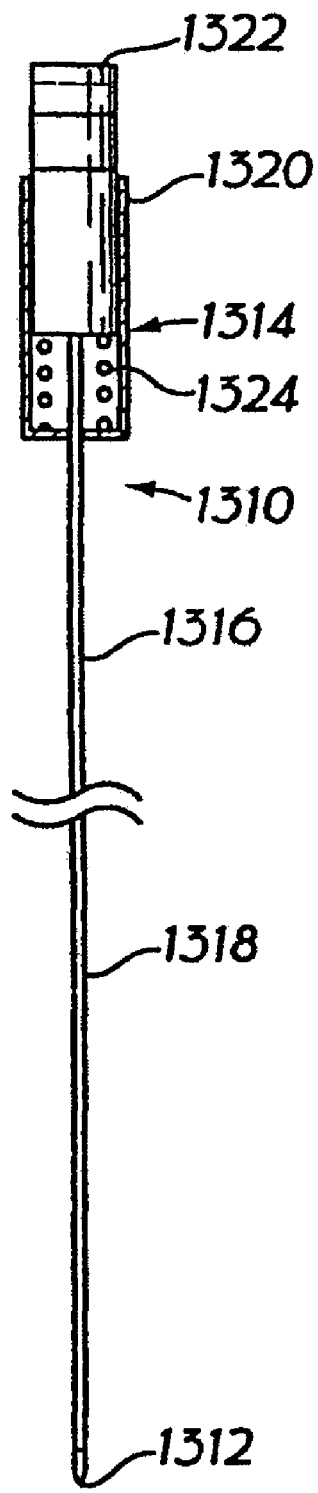
FIG. 53 is a cross-sectional view of a cutter showing the internal structure of the device.

Yet another aspect of the present invention is a tissue cutter 1310, 1312 for cutting tissue disposed between the distal ends of the first shaft and the second shaft. As shown in FIG. 53, the tissue cutter 1310 comprises a razor 1312 housed in a razor assembly 1314. A flexible catheter 1316 extends from the distal portion of the razor assembly 1314. A lumen 1318 extends through the catheter 1316. The width of catheter 1316 of the tissue cutter is slightly smaller than the width of the second shaft 718 of the sling application device 710, such that the catheter 1316 can be inserted inside the second shaft 718. The tissue cutter 1310 can be used as a component of the sling application system.

In the tissue cutter shown in FIG. 53, the razor assembly 1314 comprises a handle 1320 having a thumb button 1322 at its proximal end and an elongate catheter 1316 adapted to receive the razor 1312 therein. The thumb button 1322 is movable between a proximal position and a distal position and is biased towards the proximal position by a spring 1324 inside the handle. When the thumb button 1322 is depressed, the resistance of the spring 1324 is overcome, and the thumb button 1322 engages the razor 1312, moving the razor 1312 to a position in which it protrudes from the distal end of the catheter 1316. When the thumb button 1322 is released, the razor retracts inside the catheter.

The razor 1312 is slightly smaller in width than the lumen of the catheter 1316. The width of the razor 1312 is generally the same as the desired width of the sling 1211 which will be inserted according to the procedure described below. In addition, as shown in FIG. 53, the razor 1312 is slightly tapered at its distal end.

Although several embodiments of the sling application device and the components of the sling application system have been described above, those skilled in the art will appreciate that other configurations are compatible with the operation of the device and the system. For example, a spring biased trigger on the first handle of the sling application device may substitute for the articulating lock for adjusting the distance between the distal ends of the first and second shafts. Such additional configurations are also contemplated by the present invention.

The sling application device is used as follows. The method is performed with the patient in the dorsal lithotomy position. In some methods a pocket or opening 11 is created in the tissue between the urethra and the upper vaginal wall using any of the methods and devices disclosed herein. In such methods, the first and second shafts 716 and 718 maintain the opening or pocket in a configuration in which the sling can be introduced.

Alternatively, the sling application device can be used to create the opening or pocket 11 in the tissue between the urethra and the upper vaginal wall.

Both the methods in which the sling application device maintains the opening or pocket and the methods in which the sling application device creates the opening or pocket are described below.

Each of the above described embodiments of the sling application device can be used according to the method described below and shown in FIGS. 54-65.

Figure 54:
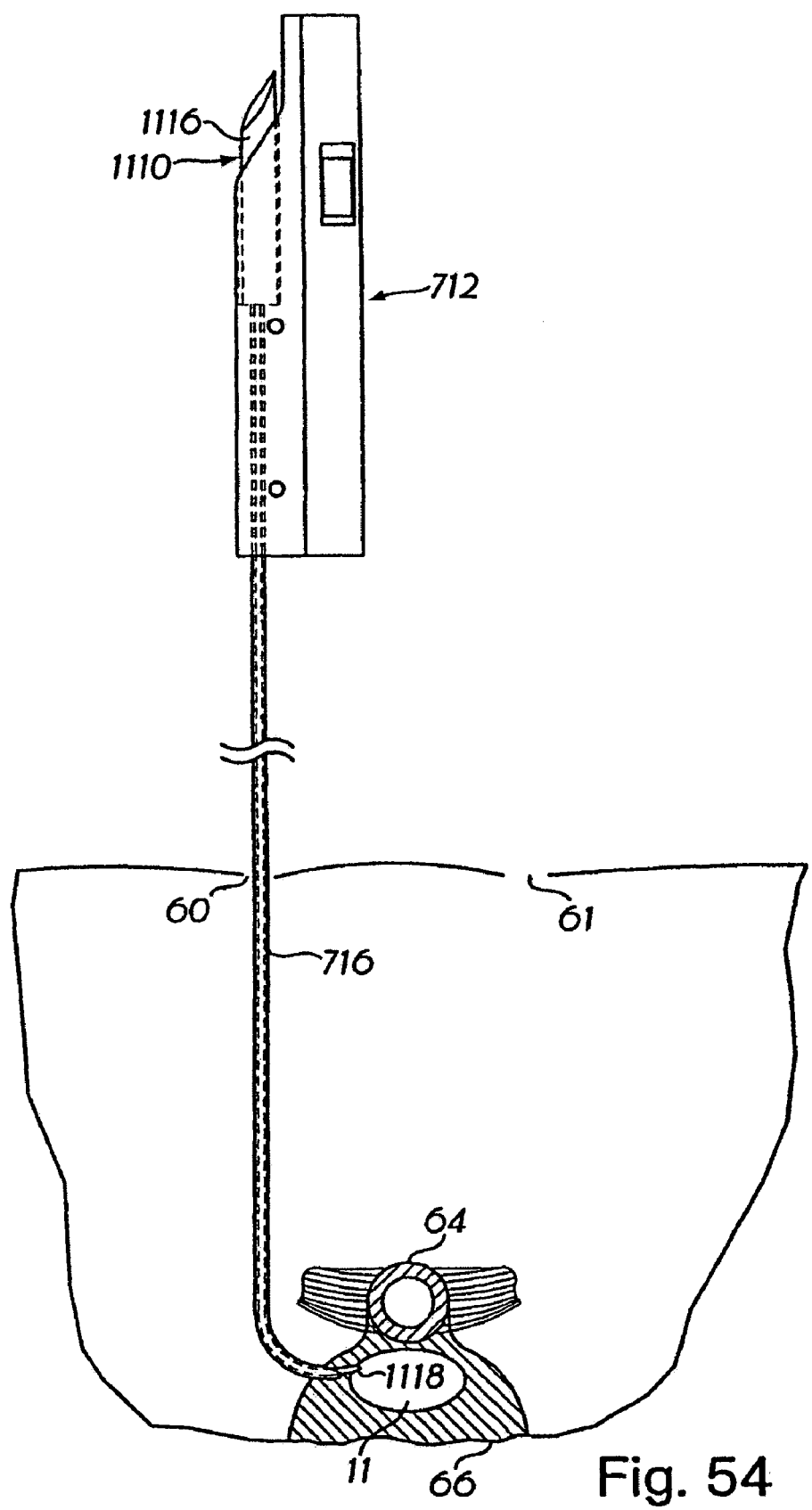
FIG. 54 shows the first shaft of the sling application device being advanced into a pre-formed opening in the tissue between the urethra and the upper vaginal wall.

After inserting an obturator 1110 into the lumen 711 of the first shaft such that the generally rigid tip 1118 extends from the distal end of the first shaft, the first shaft 716 is inserted percutaneously. For example, the first shaft 716 may be inserted into a first suprapubic incision 60, which is preferably approximately 1 to 1.5 inches in length, and is located above a pubic tubercle. The first shaft 716 is advanced into the patient's body and guided along the back side of the pubic bone to the upper vaginal wall. Once the vaginal wall is tented, placement is visually realized and lateral placement can then be adjusted. As shown in FIG. 54, the sling application device is then rotated 90° such that the distal end of the first shaft 716 is directed perpendicular to the urethra 64 facing the tissue 62 between the urethra 64 and the upper vaginal wall 66, creating and/or maintaining an opening or pocket in the tissue between the urethra and the upper vaginal wall. With the embodiments shown in FIGS. 47 and 48, the sling application device will rotate 90° as the device passes along the back of the pubic bone.

Figure 55:
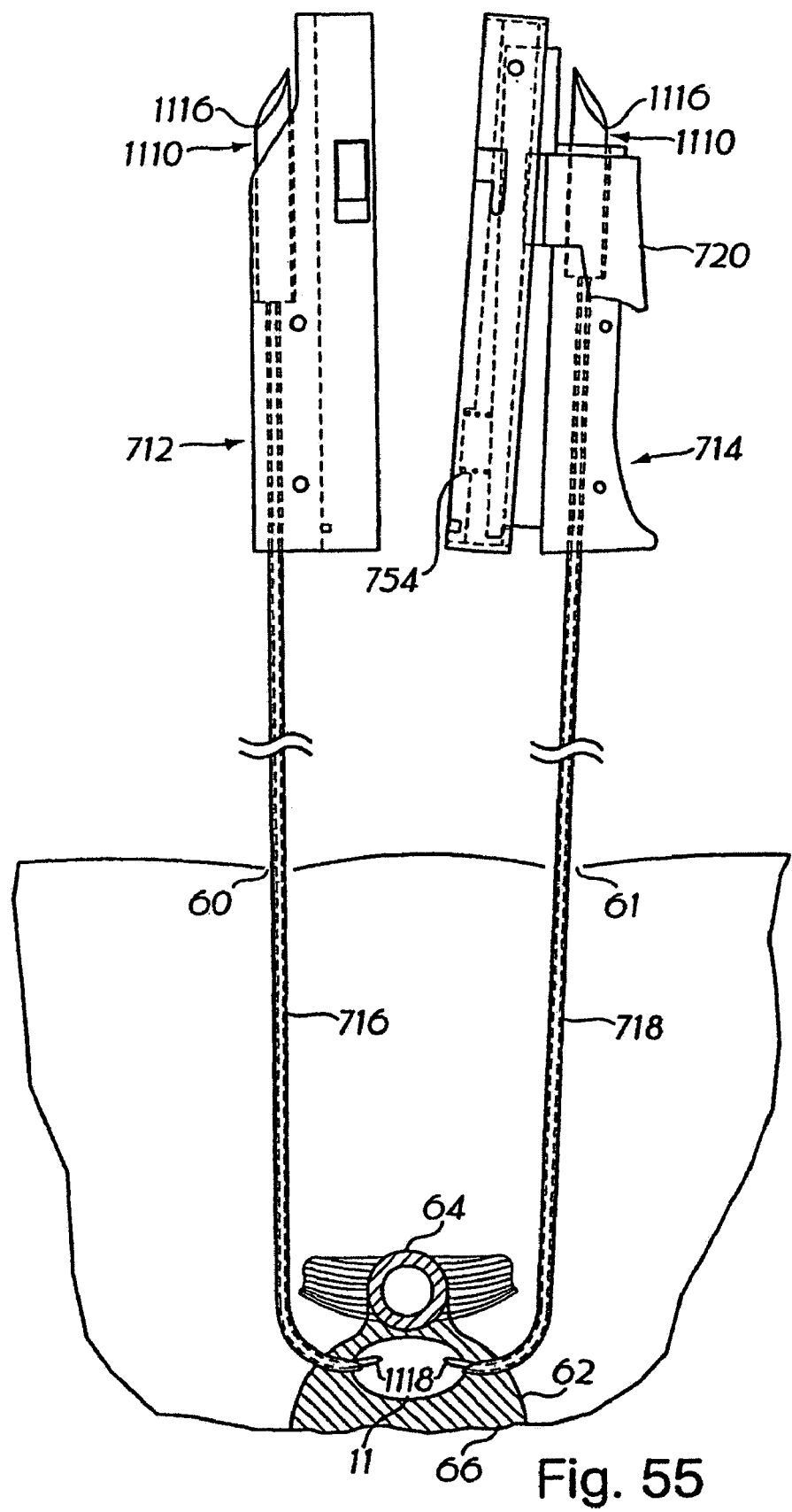
FIG. 55 shows the distal ends of the first and second shafts of the sling application device opposing each other in the opening in tissue between the urethra and the upper vaginal wall.

After inserting an obturator 1110 into the lumen 713 of the second shaft such that the generally rigid tip 1118 extends from the distal end of the second shaft 718, the second shaft 718 is inserted percutaneously. For example, the second shaft may be inserted into a second suprapubic incision 60, which is preferably approximately 1 to 1.5 inches in length, and is located above a pubic tubercle. The second shaft 718 is advanced into position as described above such that the distal end of the second shaft 718 is perpendicular to the urethra 64 facing the tissue 62 between the urethra 64 and the upper vaginal wall 66, thereby creating and/or maintaining an opening in the tissue between the urethra and the upper vaginal wall. As shown in FIG. 55, at the completion of this step, the distal ends of the first and second shafts 716, 718 oppose each other in the tissue 62 between the urethra 64 and the upper vaginal wall 15 66.

After the sling application device is in position, the obturators 1110 are removed from the first and second shafts 716, 718 and the first 712 and second 714 handles are locked together with the adjuster 720 at its most proximal point, as shown in FIG. 56. The adjuster 720 is advanced towards the distal extreme of the guide 748, progressively decreasing the distance between the distal ends of the first and second shafts 716, 718 as shown in FIGS. 57 and 58. During this process, the physician may observe the inner wall surface of the urethra 64 with a cystoscope to avoid pinching the urethra. The physician also observes the upper vaginal wall 66 to avoid pinching. When the first and second shafts 716, 718 have been properly positioned, no pinching is observed at either the inner wall of the urethra or the upper vaginal wall. Correct placement is confirmed through touch and by visualizing a bulge in the upper vaginal wall at the desired positions.

Once correct placement has been obtained, the adjuster 720 is advanced to the distal extreme of the guide 748, compressing the tissue 62 between the distal ends of the first and second shafts 716, 718, as shown in FIG. 58.

Figure 59:
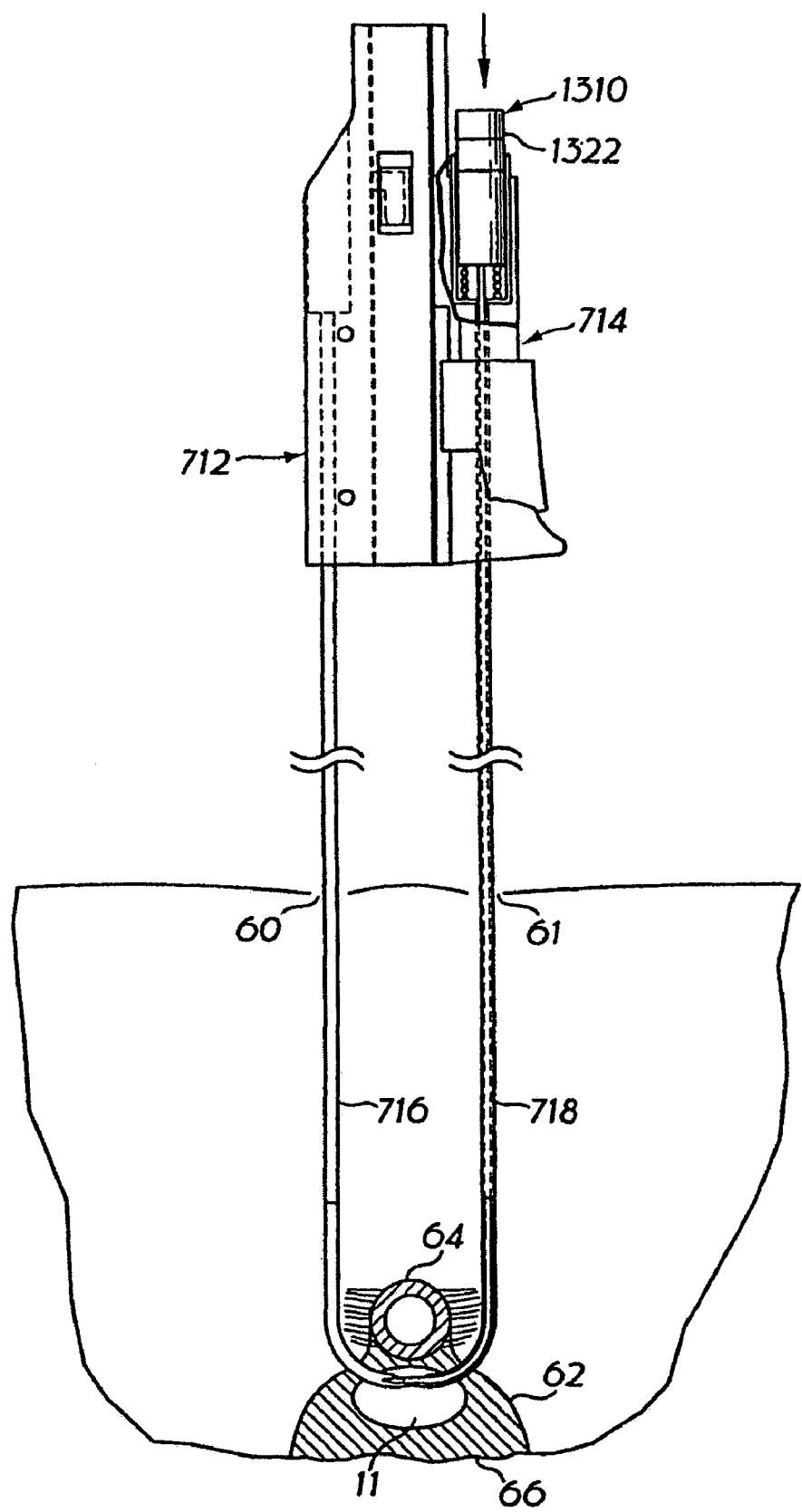
FIG. 59 shows an opening in the tissue between the urethra and the upper vaginal wall being created by a cutter dissecting the tissue between the distal ends of the first and second shafts of the sling application device.

In the methods in which the sling application device 710 creates the pocket or opening in the tissue between the urethra and the upper vaginal wall, the tissue cutter 1310 is then inserted into the second shaft 718 as shown in FIG. 59. When the thumb button 1322 of the razor assembly 1314 is depressed, the razor 1312 extends out of the distal end of the second shaft 718 and cuts the tissue 62 disposed between the distal ends of the first and second shafts 716, 718, creating a continuous opening 11 or pocket sized to receive the sling. The thumb button 1322 of the razor assembly 1314 is then released, causing the razor 1312 to retract within the second shaft 718. The razor assembly 1314 is then removed from the second shaft 718.

Figure 60:
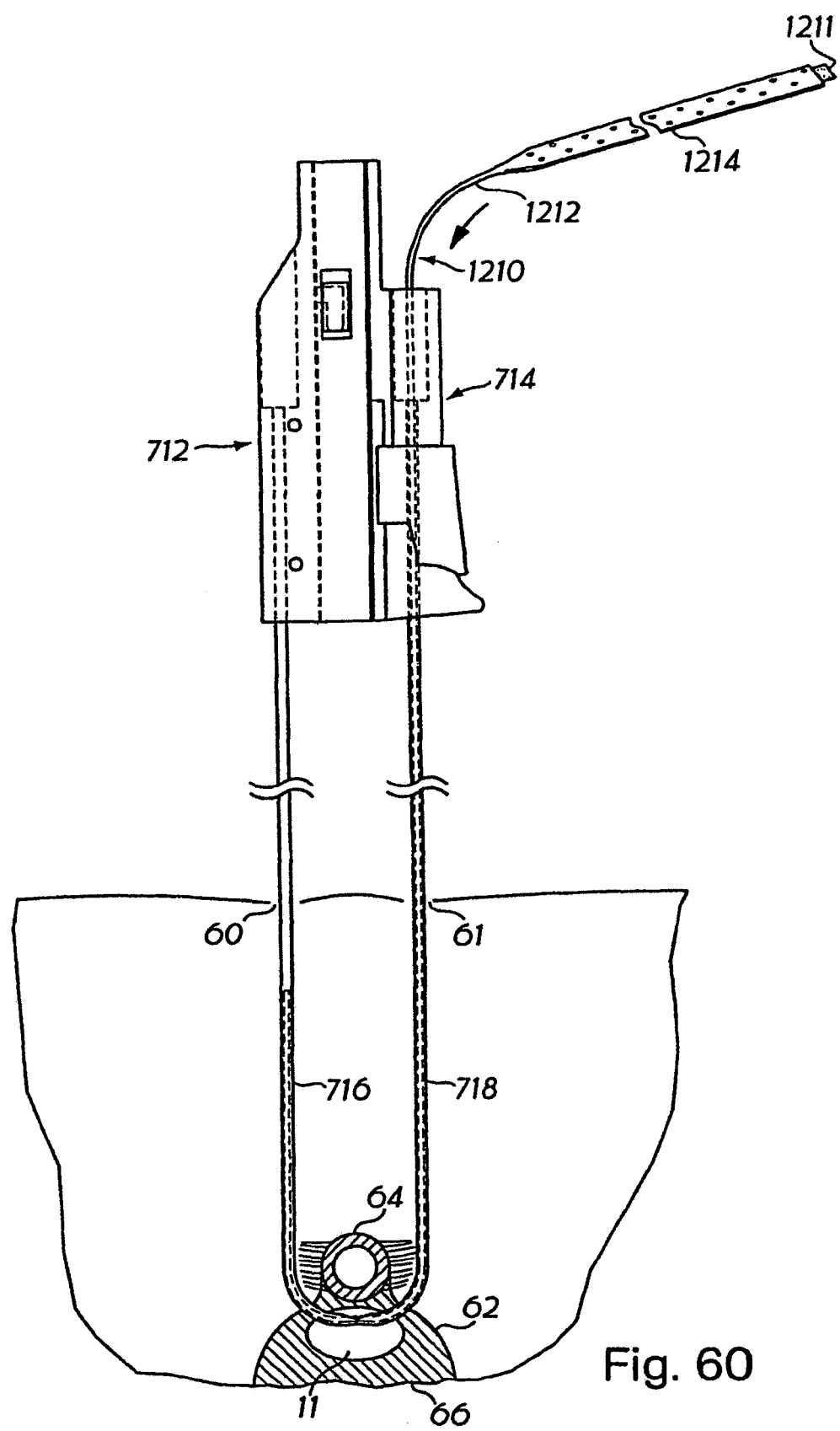
FIG. 60 shows the sling introducer being inserted into the second shaft of the sling application device.

In both the methods in which the sling application device maintains the pocket or opening and the methods in which the sling application device creates the pocket or opening, a sling or a sling introducer 1210 having a releasably engaged sling 1211 attached thereto is inserted through the opening 727 of the second handle and into the lumen of the second shaft 718, as shown in FIG. 60. The proximal end of the sling 1211 extends beyond the proximal end of the sling introducer 1210. Long and short slings suitable for use with the present invention are disclosed in U.S. patent application Ser. No. 09/023, 398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

Preferably, a porous sling introducer 1210 is used and the porous sling introducer 1210 with the sling 1211 attached thereto is soaked in a wetting and/or antibiotic solution as described above prior to insertion into the first shaft.

Figure 61:
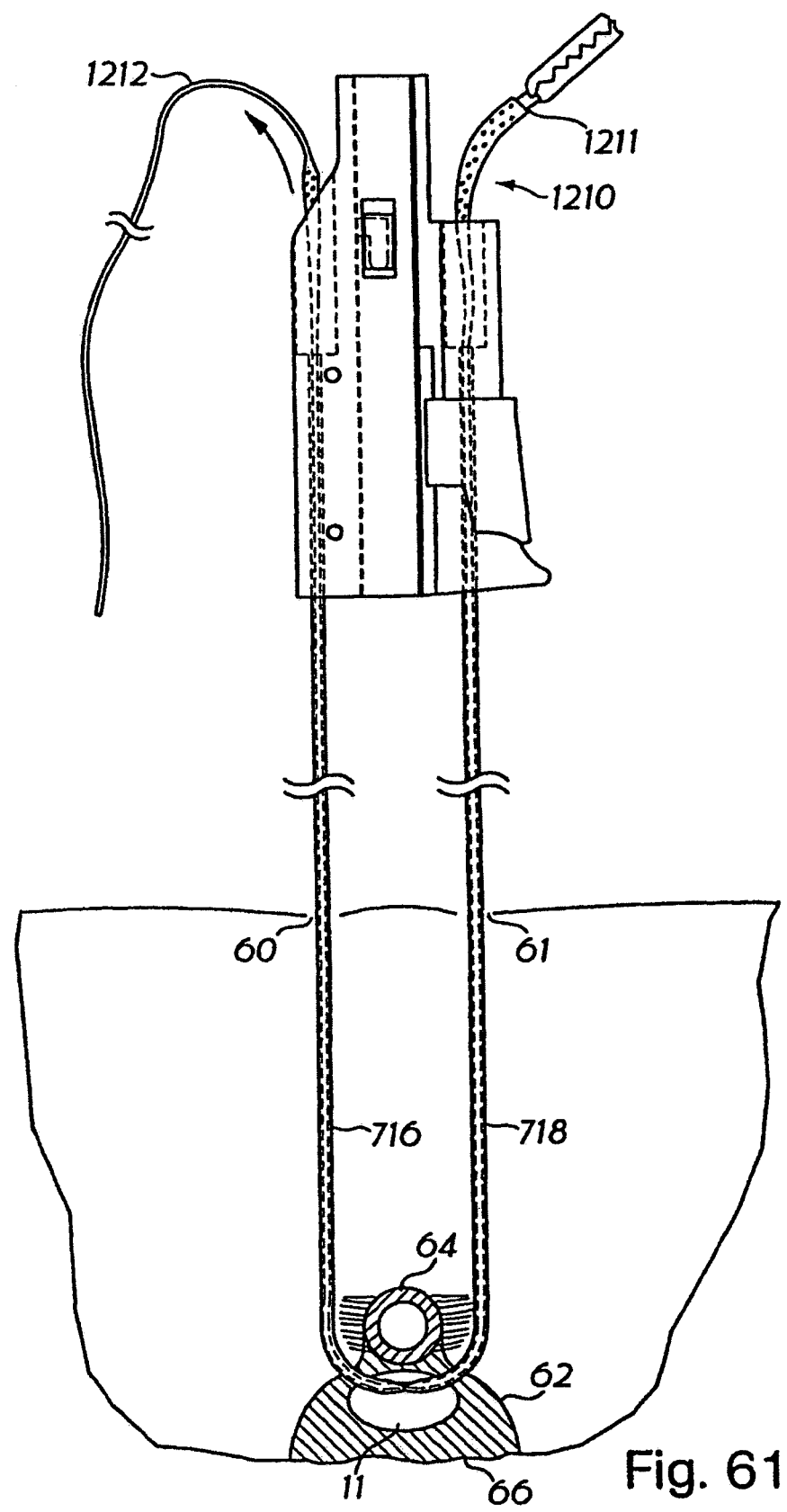
FIG. 61 shows the sling being withdrawn from the sling introducer as the sling introducer is advanced through the tissue between the urethra and the upper vaginal wall.
Figure 62:
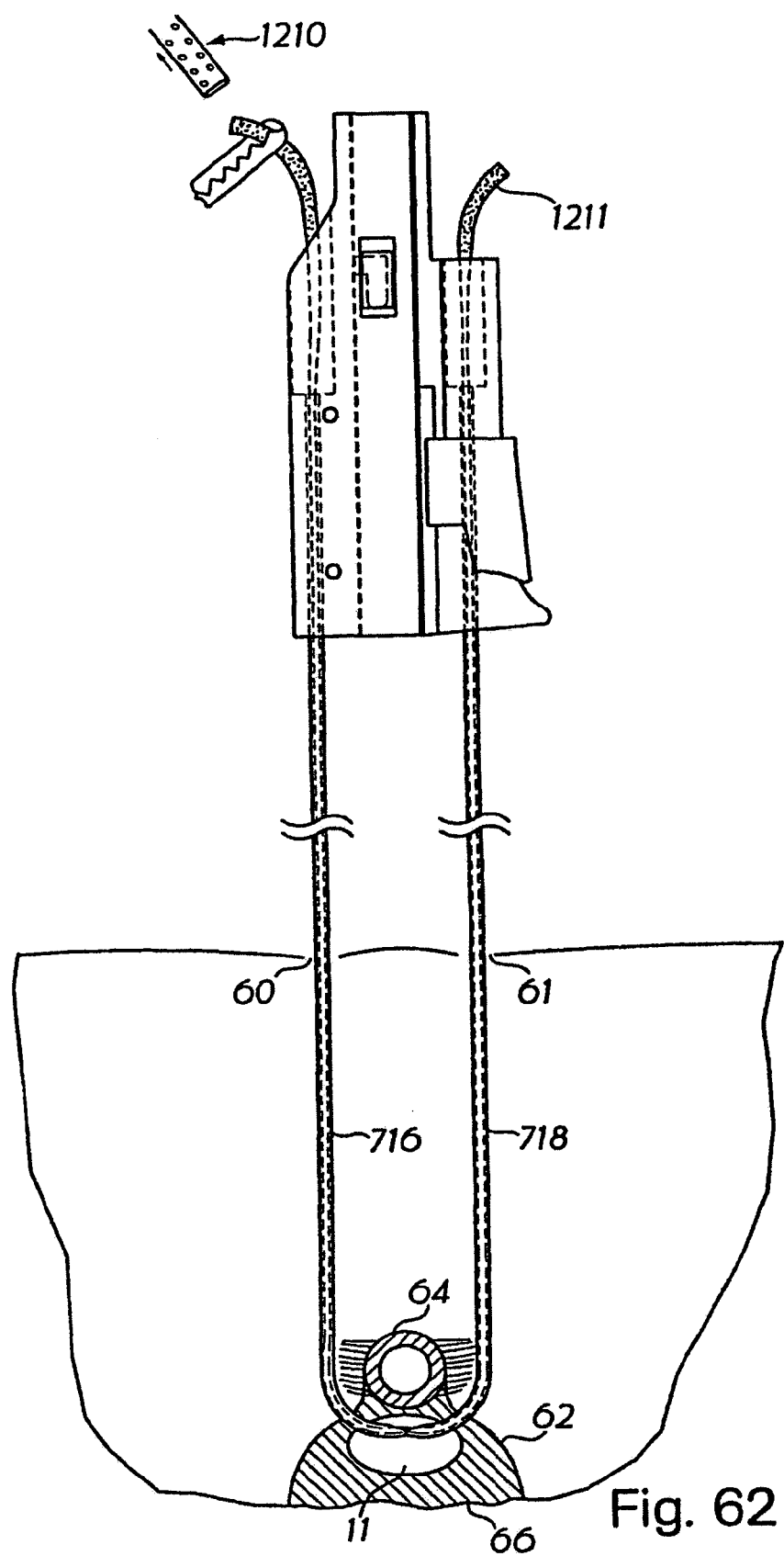
FIG. 62 shows the sling fully withdrawn from the sling introducer and located within the first and second shafts of the sling application device.
Figure 63:
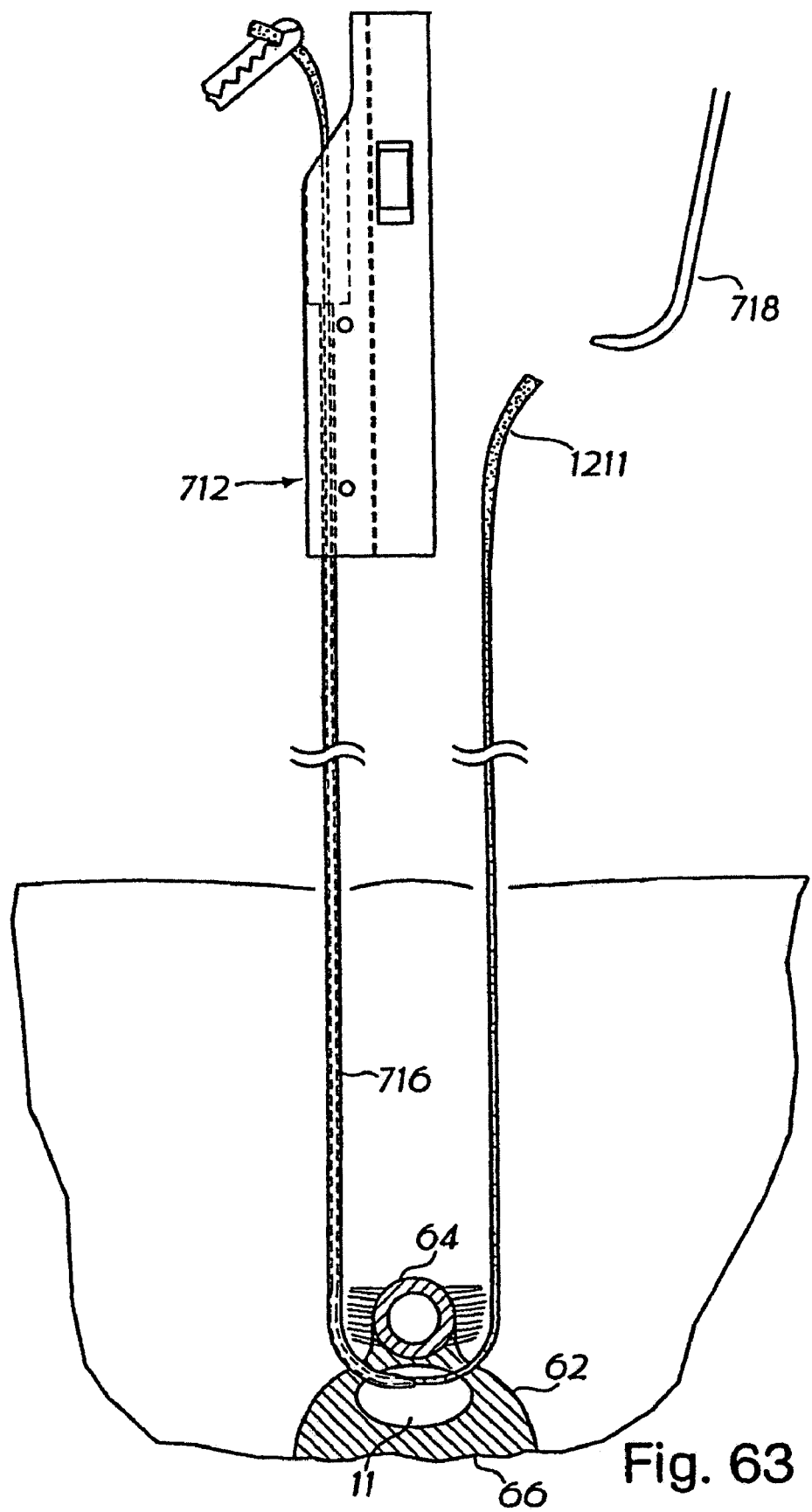
FIG. 63 shows the second shaft of the sling application device being removed from the patient's body.

The elongate distal end 1212 of the sling introducer is advanced through the 2 opening 727 in the second handle, into the lumen of the second shaft 718, into the lumen of first shaft 716, and out the opening 725 in the first handle as shown in FIG. 61. While holding the proximal end of the sling 1211, the elongate distal end 1212 of the sling introducer 1210 is pulled. The sling introducer 1210 is advanced until it exits the opening in the first handle 725, leaving the sling 1211 within the first and second shafts 716, 718, as shown in FIG. 62. Following this step, the sling 1211 is located within the first 716 and second 718 shafts and extends out of the proximal ends of the openings 725, 727 in the first and second handles. As shown in FIG. 63, the end of the sling 1211 extending out of the proximal end of the opening in the first handle is grasped and the second shaft 718 is removed from the patient's body, leaving the sling 1212 in the opening 11 in the tissue which was formerly occupied by the second shaft.

Figure 64:
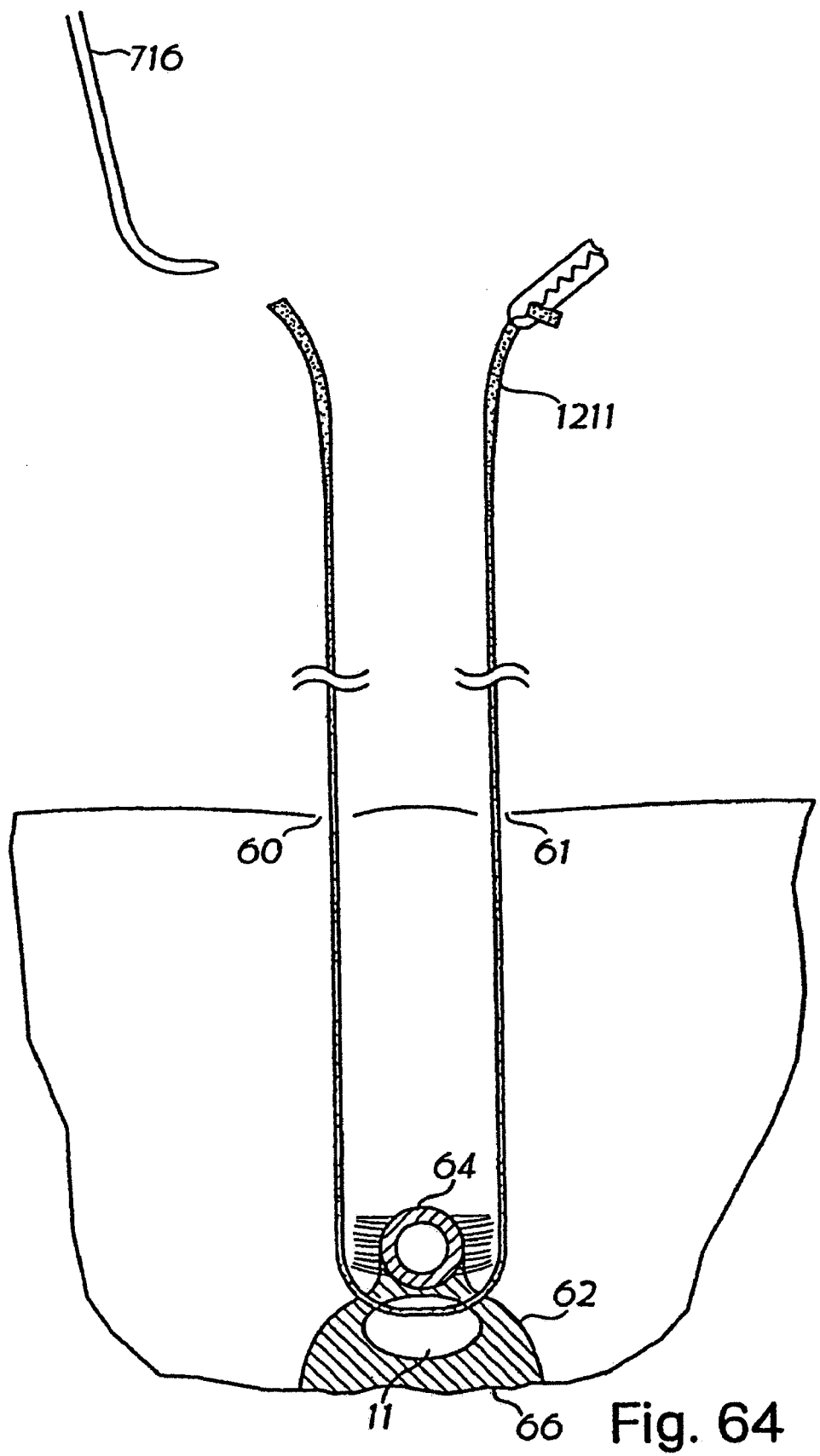
FIG. 64 shows the first shaft of the sling application device being removed from the patient's body.
Figure 65:
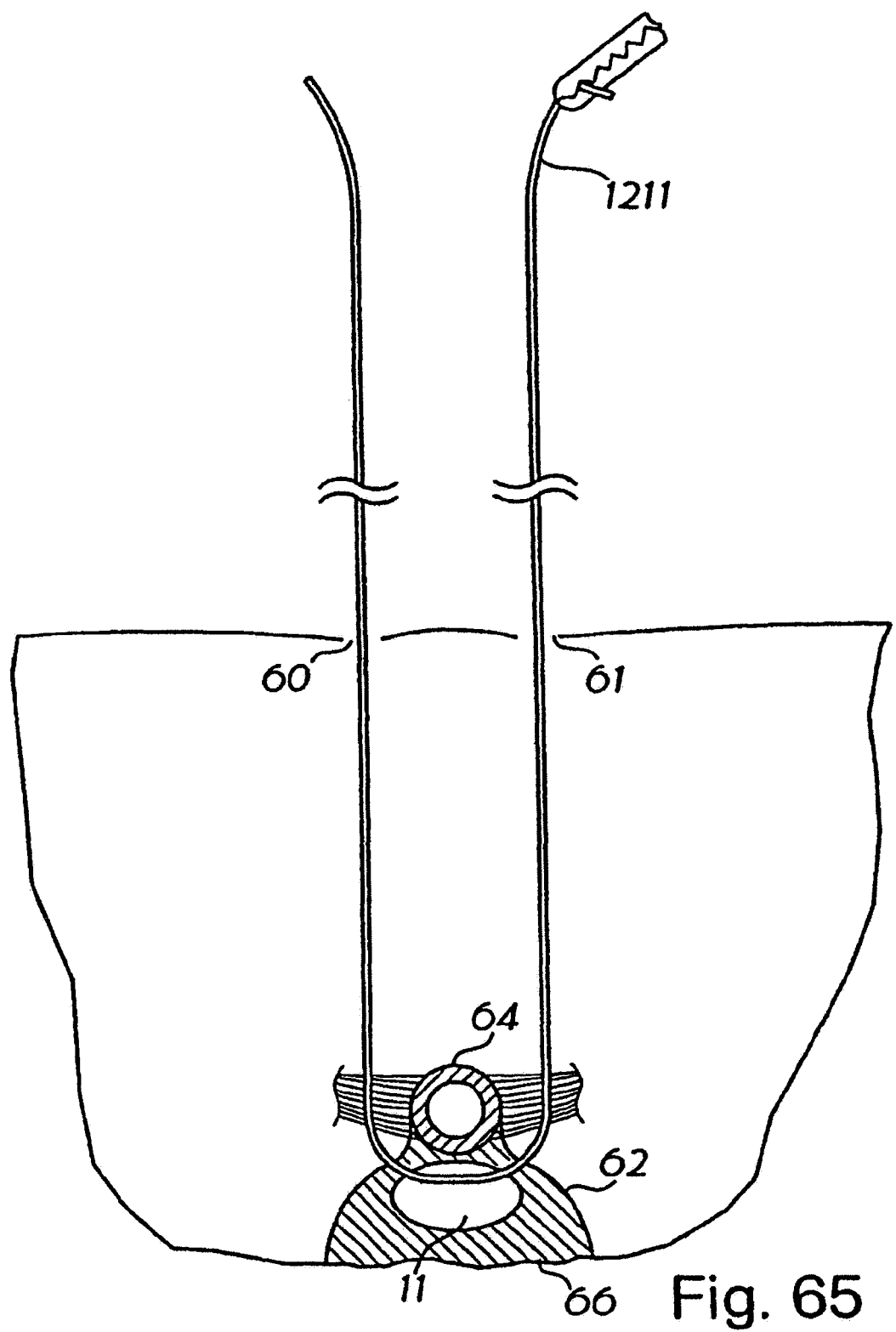
FIG. 65 shows the sling extending between the suprapubic incisions and passing through the tissue between the urethra and the upper vaginal wall.

As shown in FIG. 64, the proximal end of the sling 1212 which had formerly been inside the second shaft 718 is grasped, and the first shaft 716 is removed from the patient's body. After this procedure, the sling 1211 passes through the continuous opening in the patient's body tissue created by the above procedure, as shown in FIG. 65.

The sling 1212 may then be secured to a structure, such as the pubic bone by anchoring, stapling, riveting, or sewing to suspend or stabilize the bladder neck or create a platform to stabilize the urethral floor using approaches such as those disclosed in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, the identically titled U.S. Provisional Patent Application Ser. No. 60/038,379, filed Feb. 13, 1997, and U.S. Pat. No. 5,611,515, issued Mar. 18, 1997 to Benderev et al., the disclosures of which are incorporated herein by reference. Tension on the sling may be adjusted using procedures such as those disclosed in the U.S. Pat. No. 5,611,515, issued Mar. 18, 1997 to Benderev et al., the disclosure of which is incorporated herein by reference, to support the bladder neck or stabilize the urethral floor, thereby maintaining or improving urinary continence.

Detachable Member Sling Application Device and Retrieval Device

Another aspect of the present invention relates to a detachable member sling application device resembling the guide member placement device discussed above.

In general, the detachable member sling application device comprises a housing with an introduction shaft having a lumen extending therethrough connected to the housing. A detachable member is located on the distal end of the introduction shaft, the detachable member being connected to at least one of the sutures attached to the sling. The lumen in the shaft of the detachable member sling application device is capable of receiving a sling therein. Preferably, the sling is in an accordion like configuration when inside the lumen. The accordion like configuration may consist of random folds.

Optionally, the detachable member sling application device may further comprise an axially movable needle located inside the lumen of the introduction shaft. The needle, which comprises a needle shaft and a sharpened point, is extendable from the introduction shaft.

As illustrated in FIGS. 66-81, the shaft bends toward its distal end in the same manner as discussed above with regard to the guide member placement device.

A detachable member sling application device 1410-according to the present invention is depicted in FIGS. 66-79. The detachable member sling application device comprises a housing 1412 and a shaft 1414 with a lumen 1416 extending therethrough. The shaft 1414 has an engaging member 1411 near its distal tip for engaging a detachable member. Preferably, the engaging member 1411 comprises an annular ring on the outer surface of the shaft.

An axially movable inner shaft 1440 is located inside the shaft 1414 and is extendable therefrom and retractable therein. The axially movable inner shaft 1440 has a lumen extending therethrough. Movement of the axially movable inner shaft 1440 is controlled by an actuator 1442 which pivotally engages the housing 1412. Pivoting the actuator 1442 distally causes the axially movable inner shaft to move distally.

An axially movable plunger 1444 is located inside the axially movable inner shaft 1440 and is extendable therefrom and retractable therein. Movement of the axially movable plunger 1444 is controlled by a button 1446 which slidably engages the housing 1412. The button 1446 is movable between a first proximal position, a second intermediate position, and a third distal position. When the button 1446 is in first proximal position, sharpened point 1425 of the axially movable needle 1422 is retracted in the detachable member.

An axially movable needle 1422 having a shaft 1423 and a sharpened point 1425 at its distal end passes through an aperture in a deployment member 1448 which is located inside a detachable member 1424 located at the distal end of the shaft 1414. A spring 1413 is disposed between the deployment member 1448 and the detachable member 1424. The engaging member 1411 on the distal end of the shaft 1414 releasably engages the detachable member 1424. Preferably, the detachable member comprises a cup.

The detachable member 1424 has an engaging surface 1426 which engages the distal end of the shaft and a connecting member 1450. The connecting member 1450 is connected to at least one suture 1428 attached to a sling 1418 located in the lumen of the shaft 1414. Preferably, the sling 1418 is in an accordion like configuration inside the shaft 1414 to reduce the amount of space it occupies.

When the button 1446 is in the intermediate position, -the sharpened point 1425 of the axially movable needle 1422 is extended from the detachable member 1424 so as to permit the tissue to be easily punctured while the device is advanced. When the button 1446 is in the distal position, the axially movable needle 1422 is maximally extended from the detachable member 1424 such that the shaft 1423 protrudes from the detachable member 1424 to permit extension through the hiatal area into the vagina for ease of grasping and securing.

Figure 67:
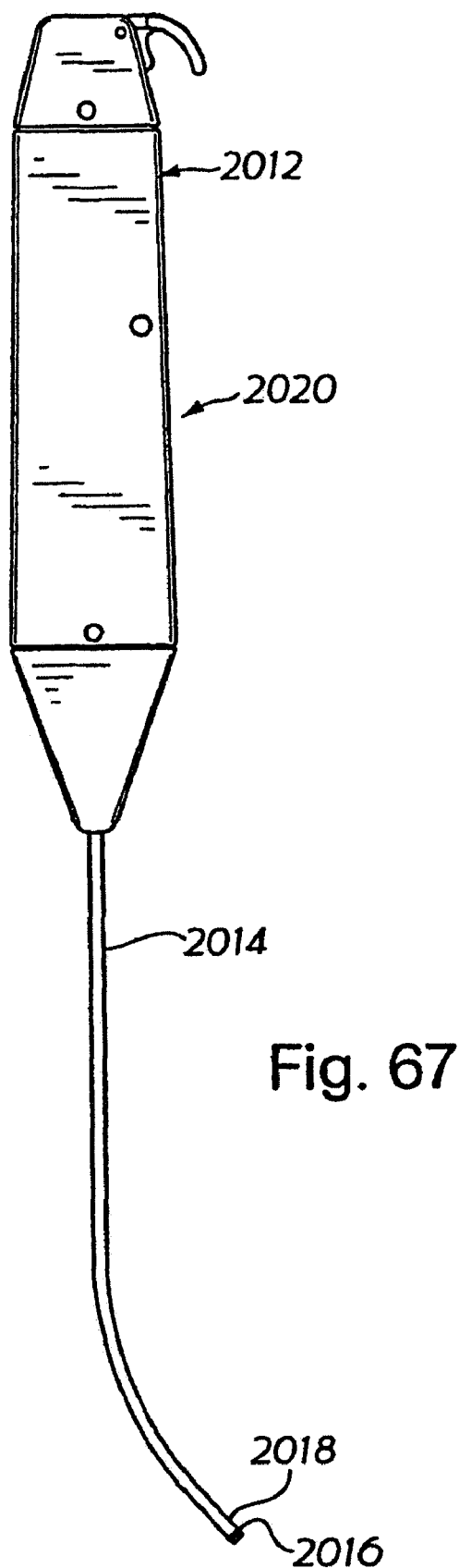
FIG. 67 is a side view of a retrieval device.

Another aspect of the present invention is a retrieval device for introducing a sling into an opening or pocket in a body tissue. One embodiment of the retrieval device is illustrated in FIG. 67. The retrieval device 2010 comprises a handle 2012 attached to a shaft 2014 having an engaging member 2016 near its distal end.

The handle 2012 of the retrieval device may have a variety of configurations which may vary depending on anatomical considerations and the type of procedure being performed. For example, the handle may have a similar configuration as that of the detachable member sling application device shown in FIG. 66.

Figure 66:
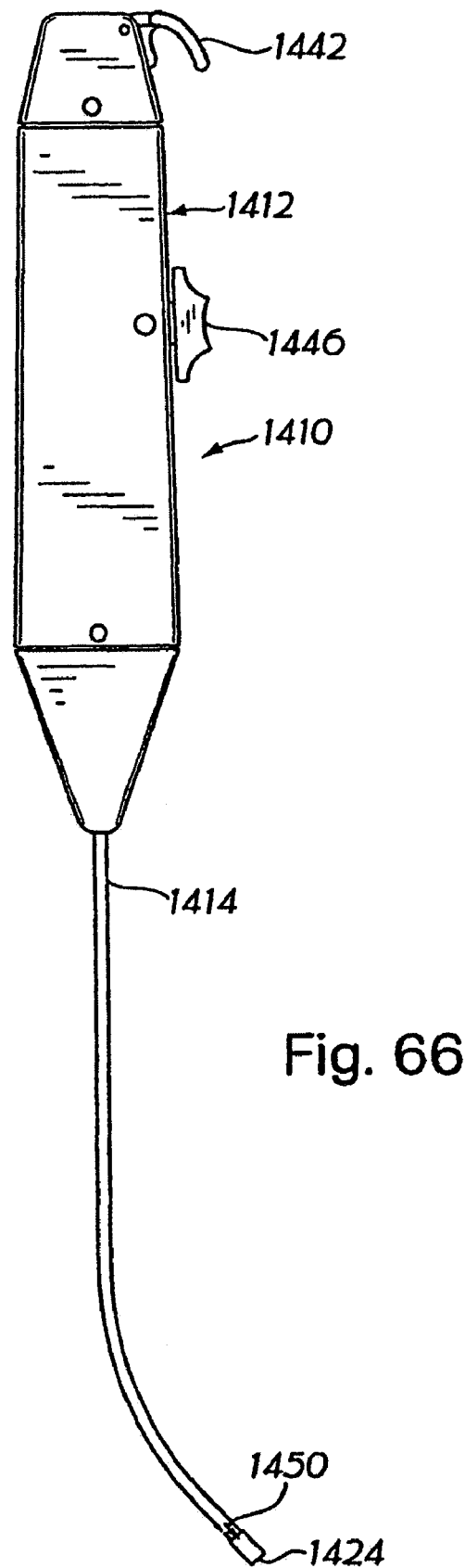
FIG. 66 is a side view of a detachable member sling application device.

Similarly, the shaft 2014 of the retrieval device may have the same configuration as the shaft 1414 of the detachable member sling application device 1410 shown in FIG. 66. Preferably, the engaging member 2016 comprises an annular ring on the outer surface of the shaft 2014.

In one embodiment, the retrieval device 2010 may be a modified detachable member sling application device 1410 having a hollow or solid shaft and lacking the actuator 1442, the button 1446, the detachable member 1424, the sling 1418, and the mechanism inside the shaft for deploying the detachable member.

The distal end of 2018 the shaft 2014 of the retrieval device has an engaging member 2016 adapted to engage the detachable member 1424. Preferably, the engaging member 2016 comprises an annular ring on the outer surface of the shaft. The shaft 2014 of the retrieval device may be solid or may have a hollow interior.

Although the detachable member sling application device 1410 and the retrieval device 2010 described above and depicted in FIGS. 66 and 67 may be used in a variety of procedures, a representative procedure for using the device to apply a sling beneath the female urethra is described below and depicted in FIGS. 68-81.

The first step of the procedure involves creating an opening or pocket 11 in the tissue 62 between the urethra 64 and the upper vaginal wall 66 into which the sling 1418 can be introduced. The opening or pocket 11 may be created in a variety of ways, including those described herein and in U.S. patent application Ser. No. 09/023,398, entitled "Stabilization Sling for Use in Minimally Invasive Pelvic Surgery" (VESITEC.023A) filed Feb. 13, 1998, now issued U.S. Pat. No. 6,042,534, issued Mar. 28, 2000, and the identically titled U.S. Provisional Patent Application Ser. No. 60/038,379, filed Feb. 13, 1997, the disclosures of which are incorporated herein by reference.

Figure 68:
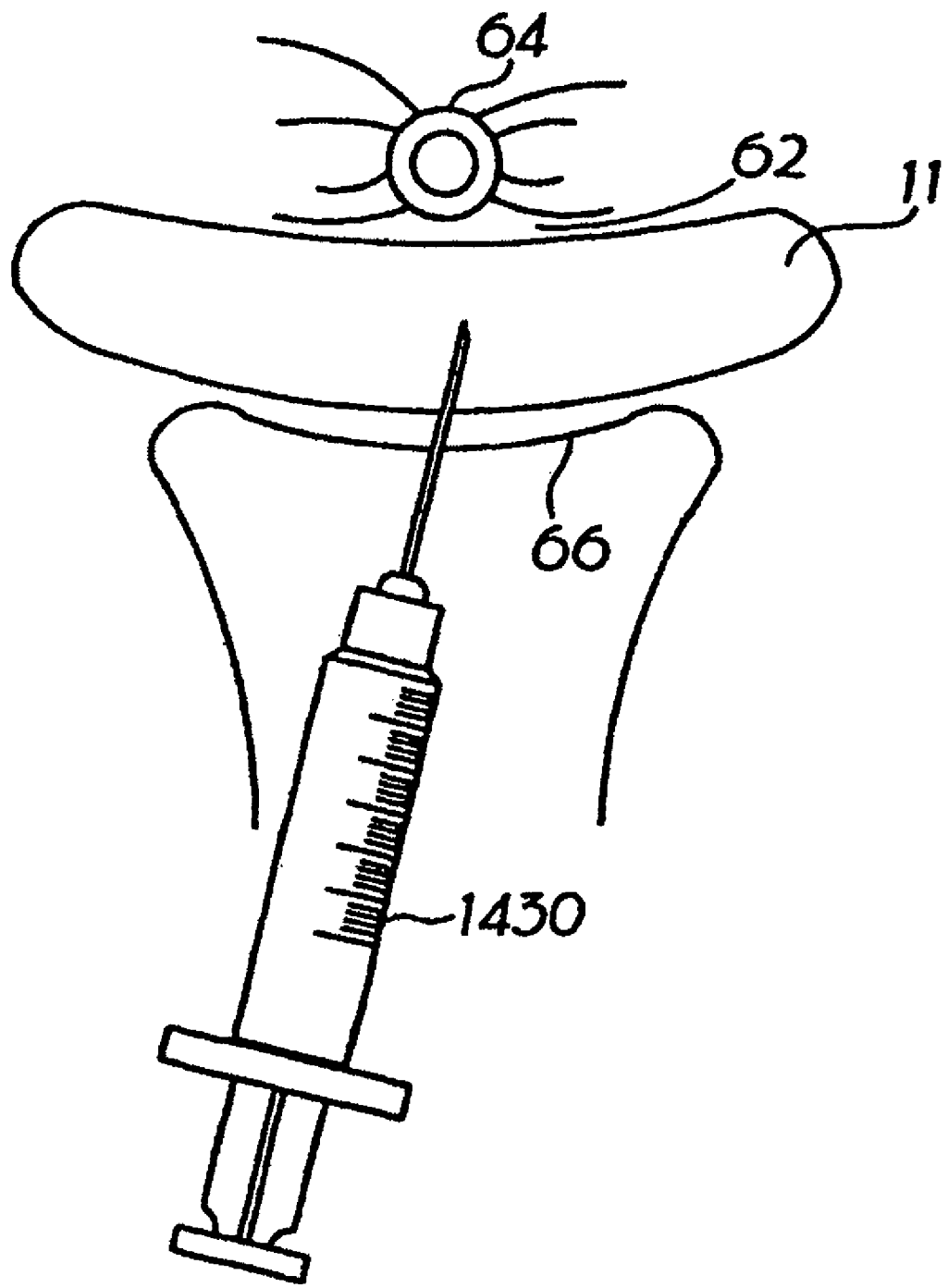
FIG. 68 shows the creation of an opening in the tissue between the urethra and the upper vaginal wall by hydrodissection.
Figure 69:
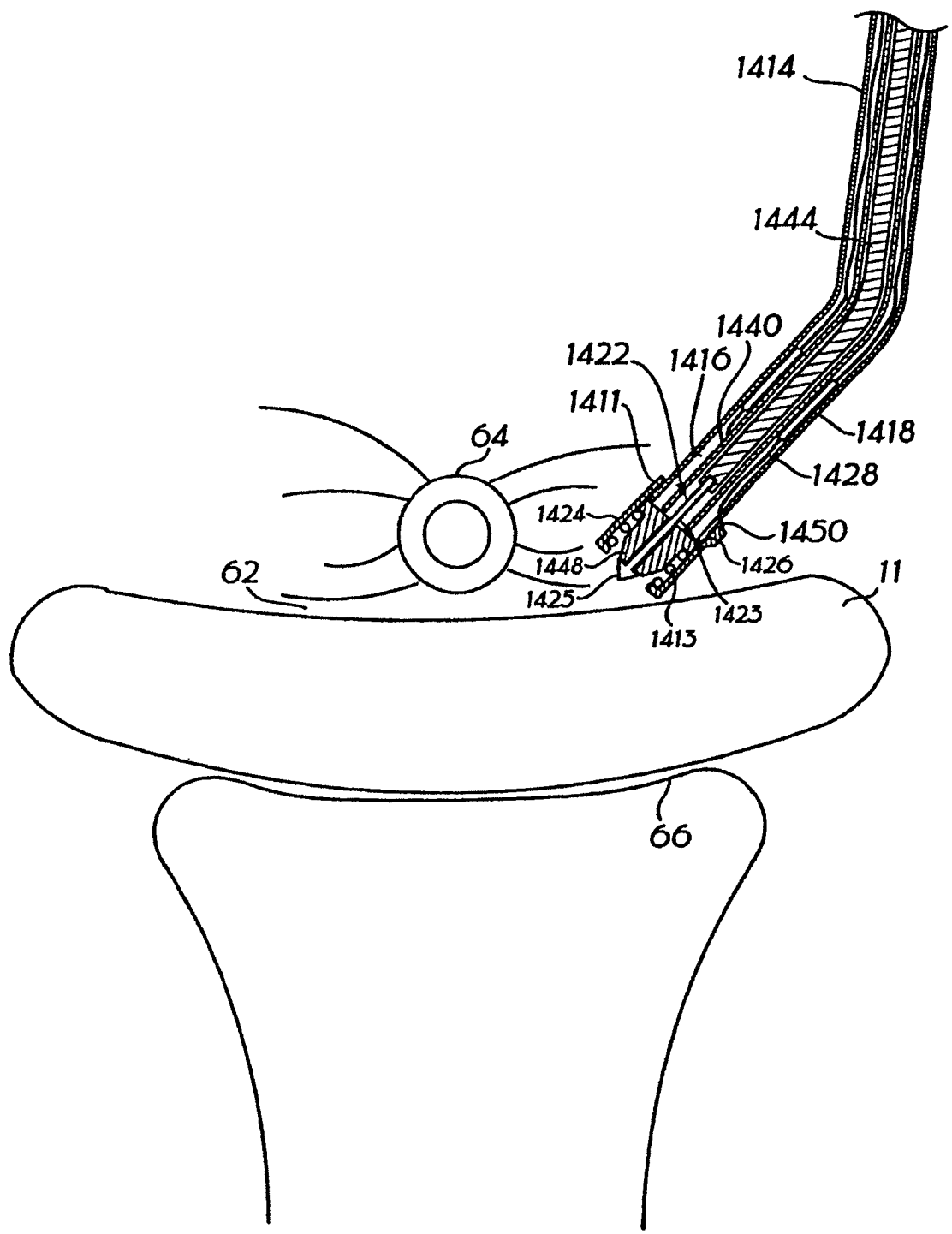
FIG. 69 shows the shaft of a detachable member sling application device sling application device being advanced to a pocket or opening in the tissue between the urethra and the upper vaginal wall.

A preferred method of creating the pocket involves hydrodissection. As shown in FIG. 68, a syringe 1430 filled with saline is inserted through the vaginal wall 66 into the tissue 62 between the urethra and the upper vaginal wall. A bolus of saline is dispensed into the tissue, creating an opening or pocket 11 therein as shown in FIG. 68. Preferably, the bolus comprises about 4 cc of saline. The shaft 1414 of the detachable member sling application device is inserted percutaneously. For example, the shaft 1414 may be inserted percutaneously through a first suprapubic incision 61. The shaft 1414 of the detachable member sling application device 1410 is inserted therein. The shaft 1414 of the detachable member sling application device 1410 is advanced through the patient's body tissue along the back side of the pubic bone to the opening or pocket 11 created in the tissue 62 between the urethra 64 and the upper vaginal wall 66, as shown in FIG. 69. During advancement of the shaft 1414, the button 1446 may be advanced from the most proximal position, in which the sharpened point 1425 of the needle is within the detachable member 1424, to the intermediate position, in which the sharpened point 1425 of the needle extends from the detachable member. In particular, the sharpened point 1425 may be extended to dissect through muscle groups.

Figure 70:
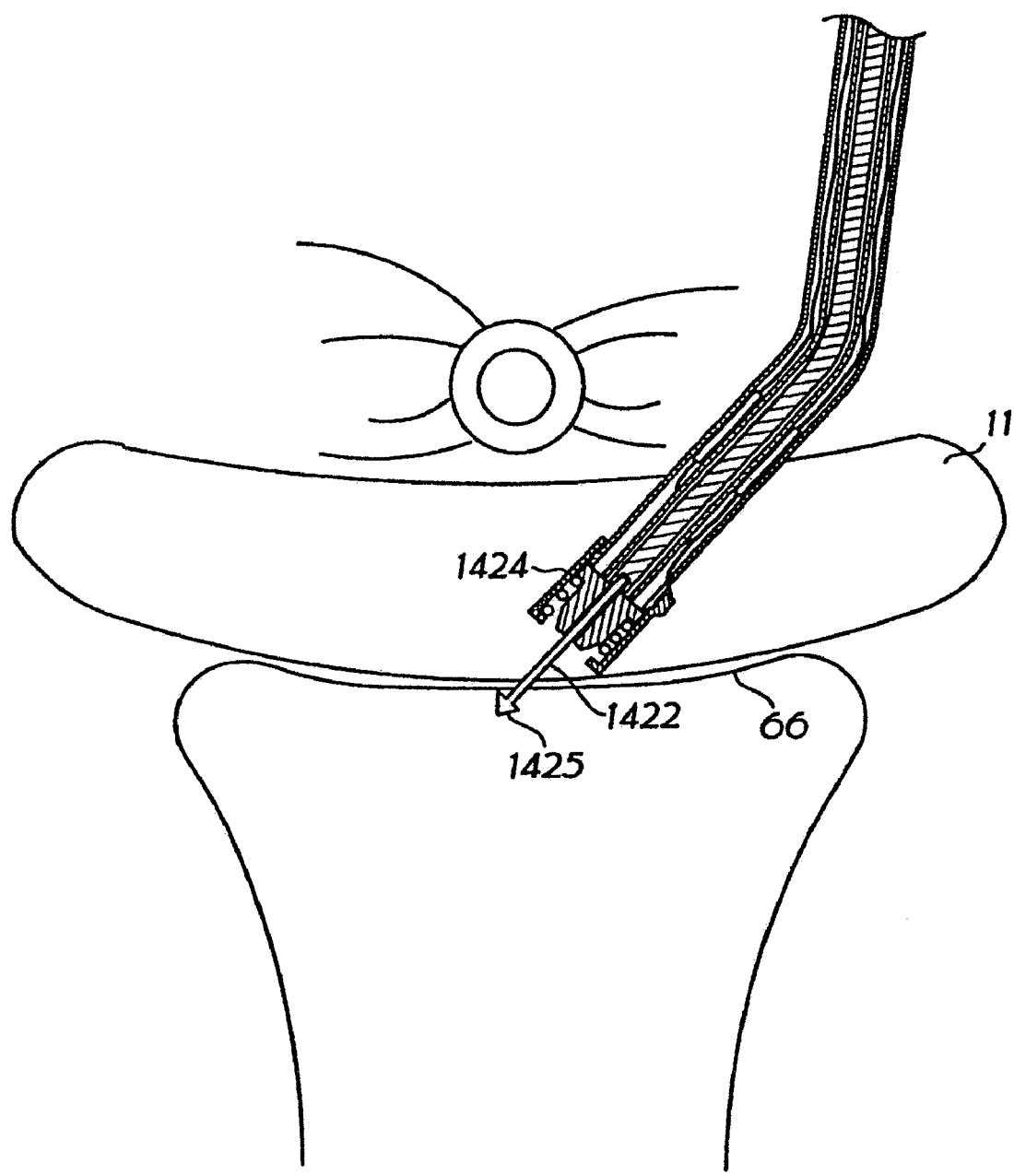
FIG. 70 shows the sharpened point of the needle of the detachable member sling application device extending through the upper vaginal wall.
Figure 71:
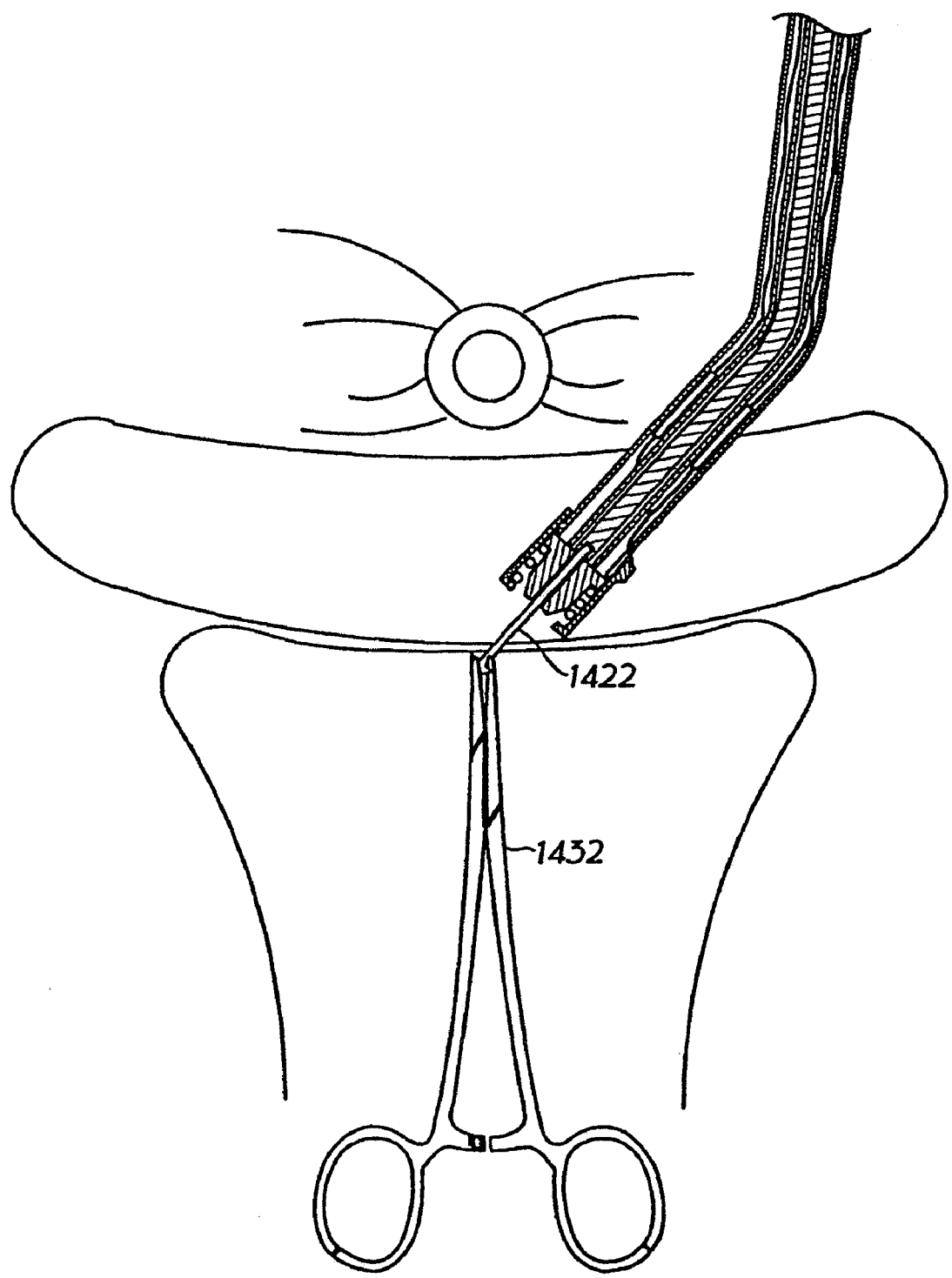
FIG. 71 shows the needle of the detachable member sling application device being secured on the vaginal side with a hemostat.

The distal end of the shaft 1414 is advanced percutaneously or laparoscopically to the bottom of the pocket or opening 11 and the button 1446 is advanced to the most distal position, in which the needle 1422 is maximally extended and the sharpened point 1425 passes through the upper vaginal wall 66 as shown in FIG. 70. The needle 1422 is secured on the vaginal side with a device such as a hemostat 1432 as shown in FIG. 71.

Figure 72:
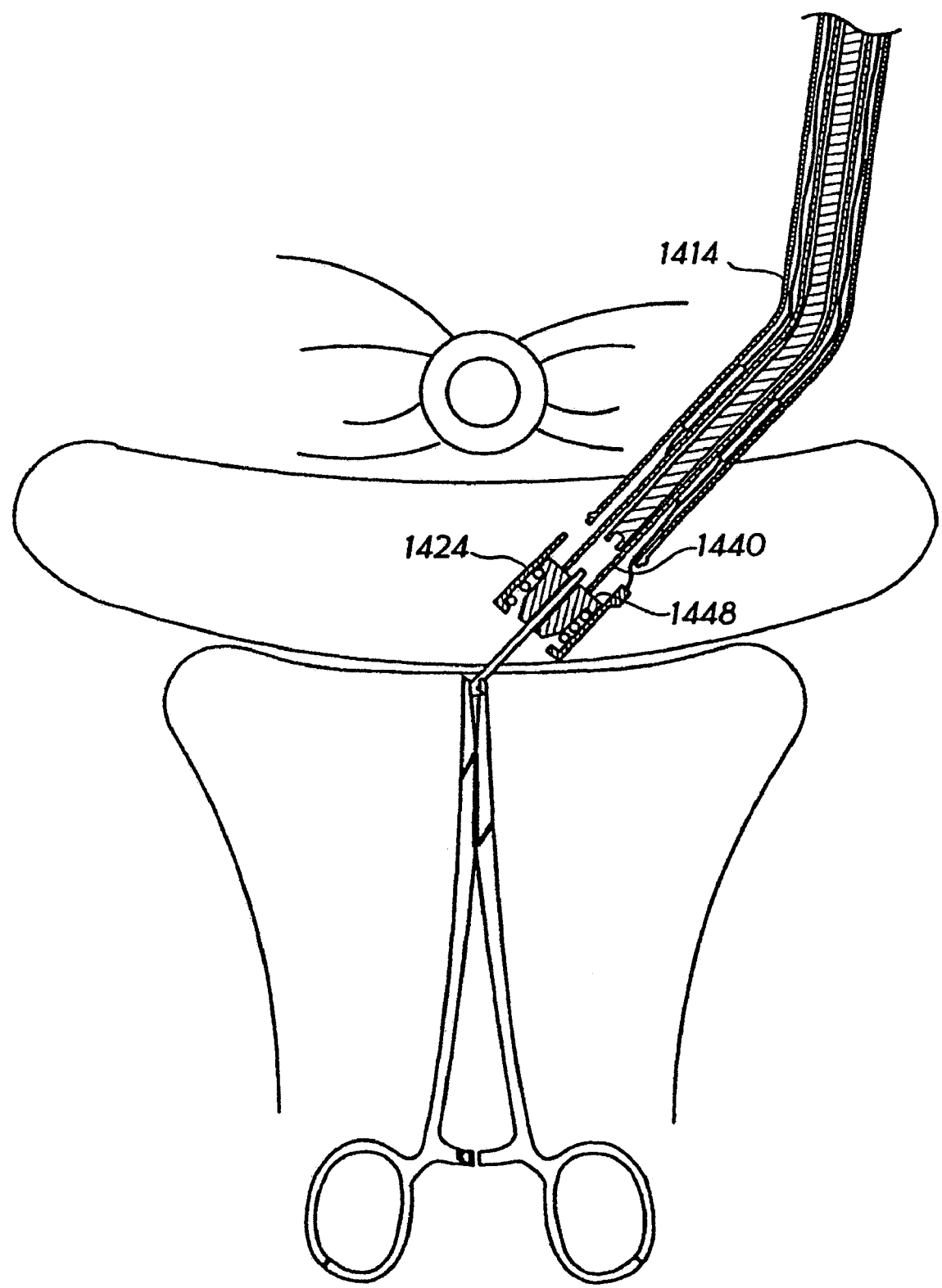
FIG. 72 shows the detachable cup being detached from the distal end of the shaft of the detachable member sling application device.

As shown in FIG. 72, the detachable member 1424 is then detached from the distal end of the shaft 1414 by pivoting the actuator 1442 distally, thereby causing the inner shaft 1440 to move distally such that it contacts the deployment member 1448 and pushes the detachable member 1424 off the distal end of the shaft 1414.

Figure 73:
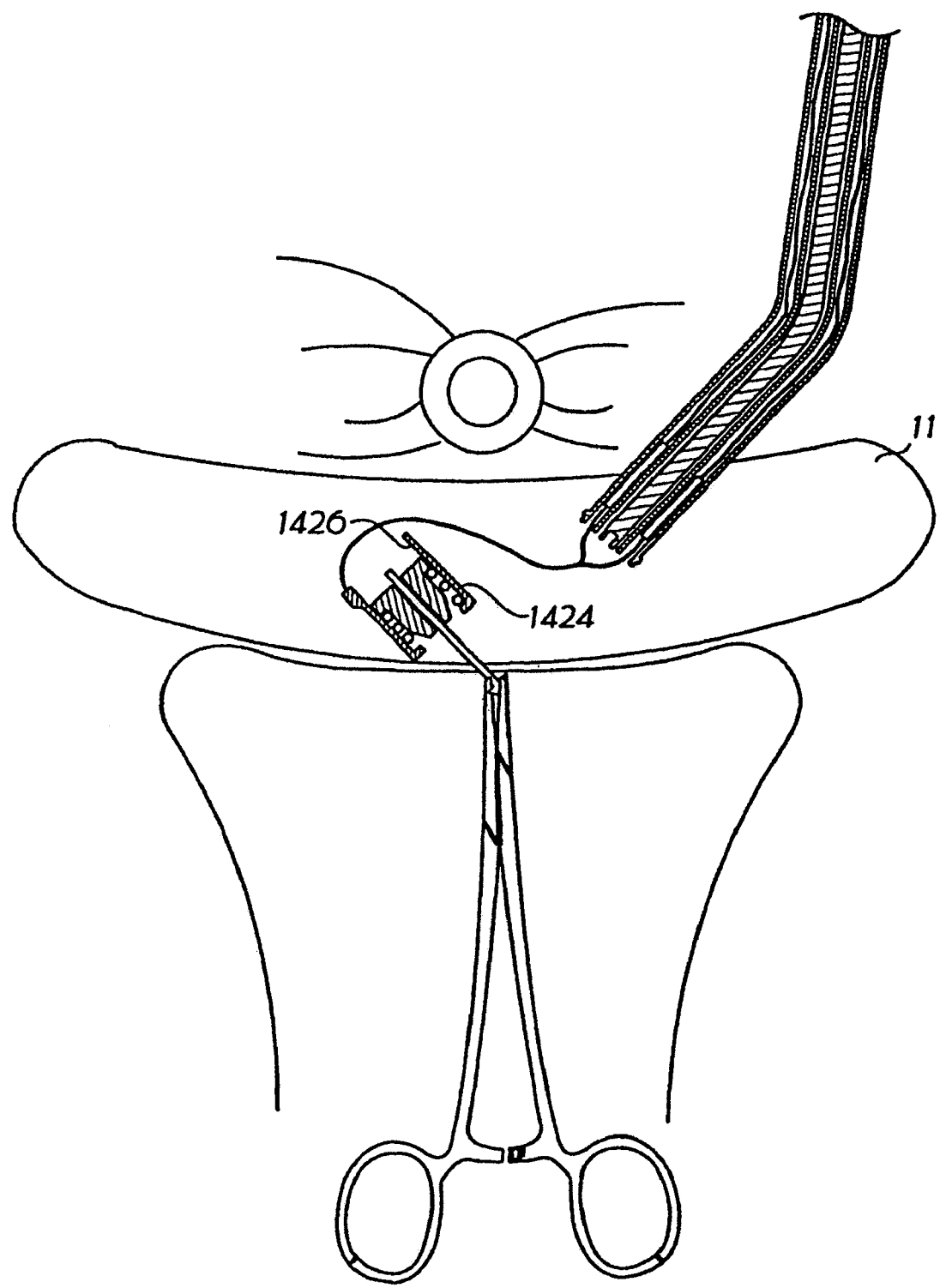
FIG. 73 shows the needle of the detachable member sling application device being toggled.

As illustrated in FIG. 73, the needle 1422 is toggled within the pocket or opening 11 such that the engaging surface 1426 of the detachable member will be accessible to the engaging member 2016 of a retrieval device 2010. Preferably, the needle is toggled from about 30° to about 150°. More preferably the needle is toggled from about 60° to about 120°. In a highly preferred embodiment, the needle is toggled about 90°.

As will be appreciated by those skilled in the art, other methods of positioning the detachable member for engaging the engaging member of a retrieval device may be used with embodiments of the detachable member sling application device which do not have the axially movable needle.

Figure 74:
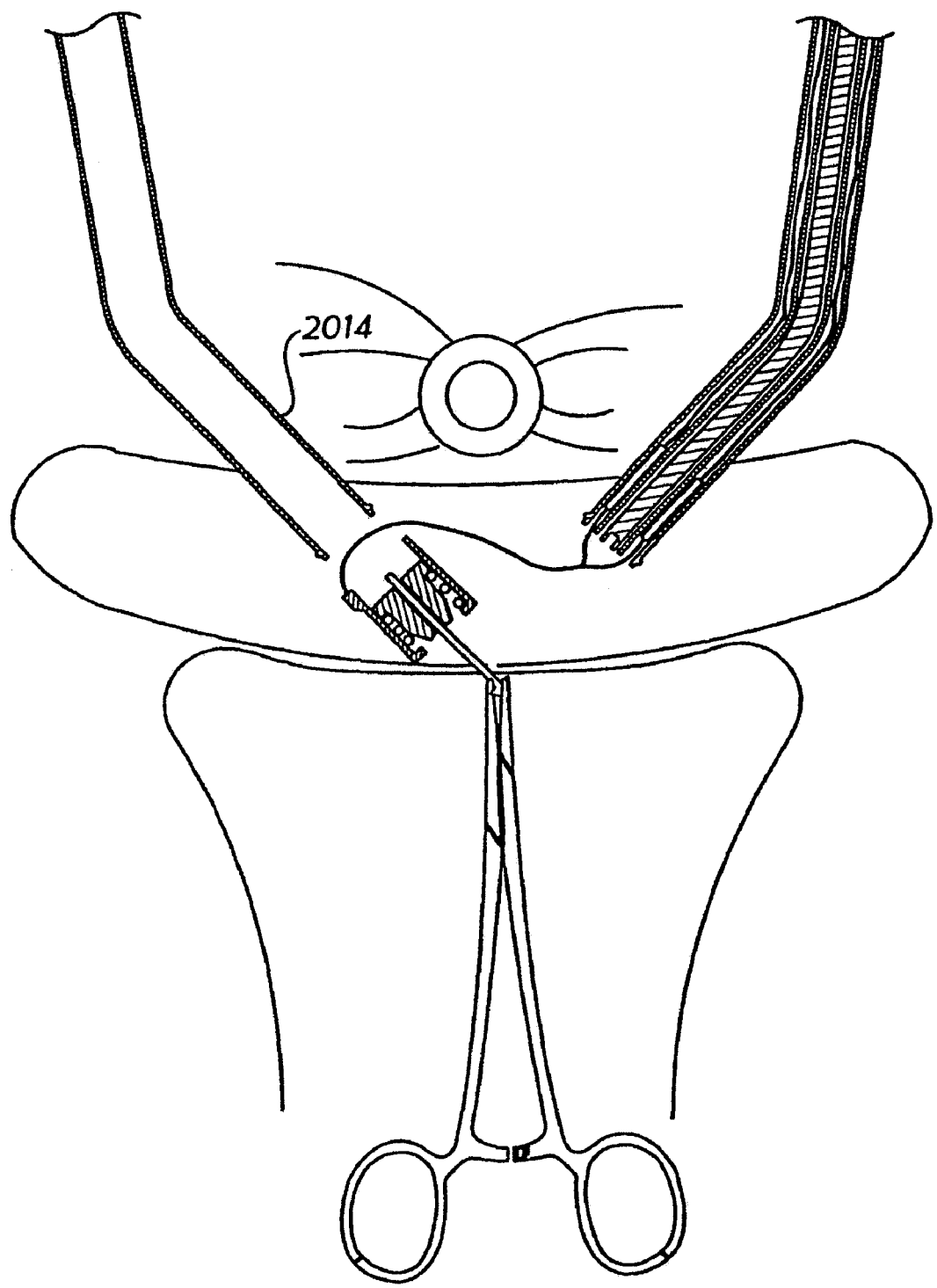
FIG. 74 shows the shaft of a retrieval device being advanced through a second suprapubic incision into the pocket.

The shaft 2014 of a retrieval device is advanced percutaneously or laparoscopically into the opening or pocket 11 as shown in FIG. 74. For example, the shaft may be advanced into the opening or pocket through a second suprapubic incision 60.

Figure 75:
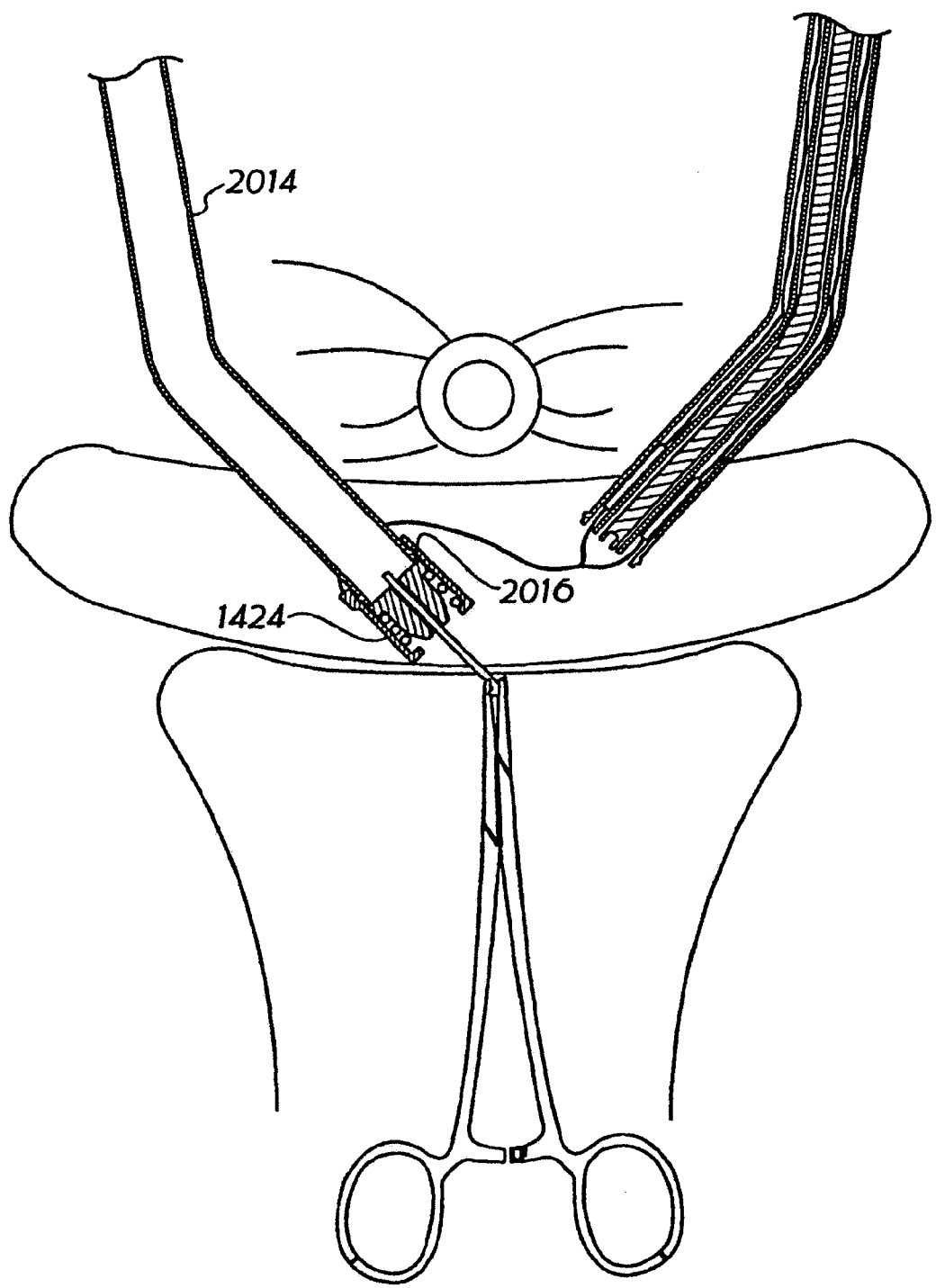
FIG. 75 shows the shaft of the retrieval device being inserted into the detachable cup and engaging the detachable cup.
Figure 76:
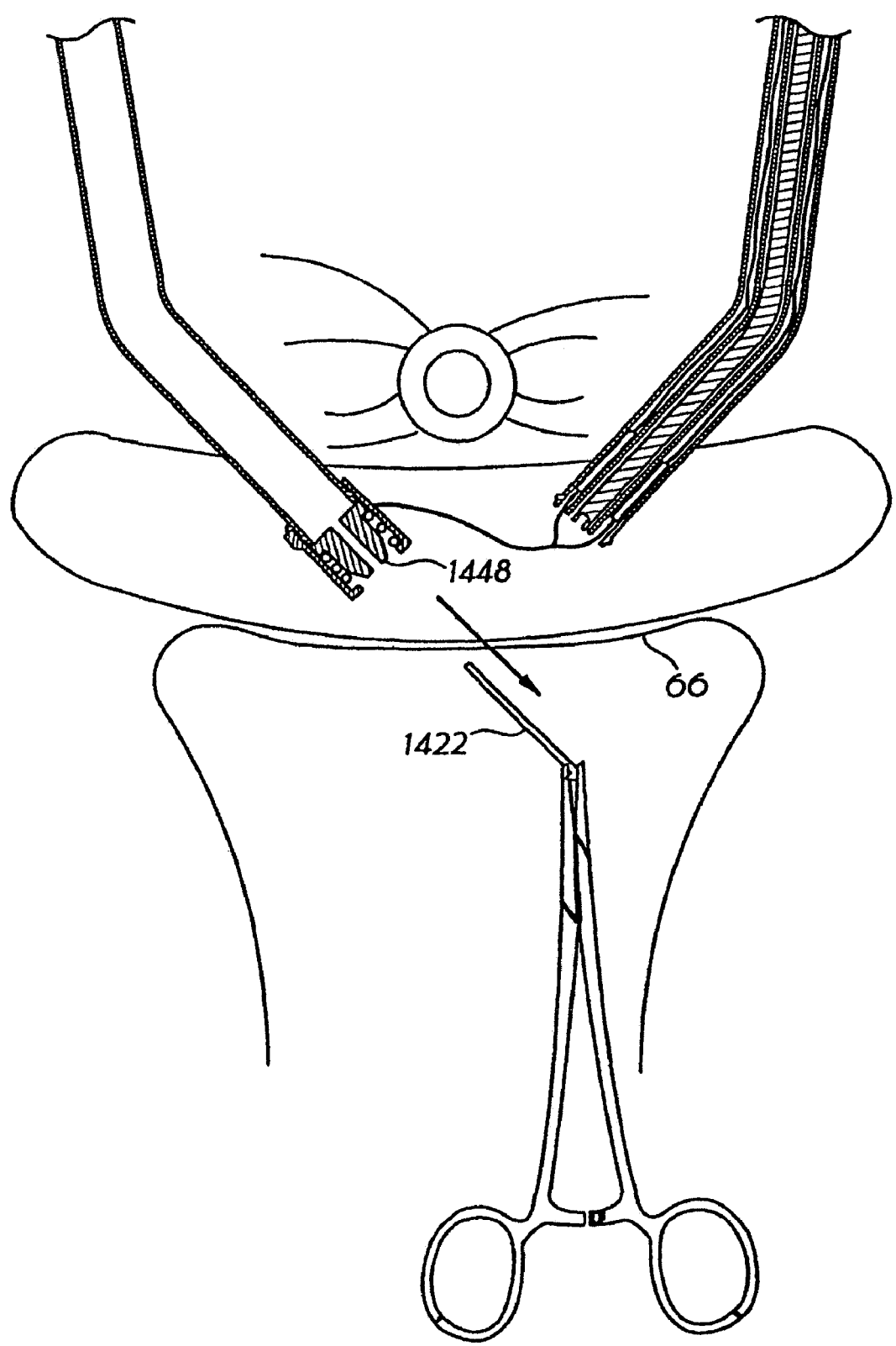
FIG. 76 shows the needle being removed from the vagina.

The distal end of the shaft 2014 of the retrieval device is inserted into the detachable member 1424 and the engaging member 2016 engages the engaging surface 1426 of the detachable member 1424 as shown in FIG. 75. As shown in FIG. 76, the needle 1422 protruding through the vaginal wall 66 is then pulled out of the deployment member 1448 and removed from the vagina so as not to draw bacteria back into the pelvic area.

Figure 77:
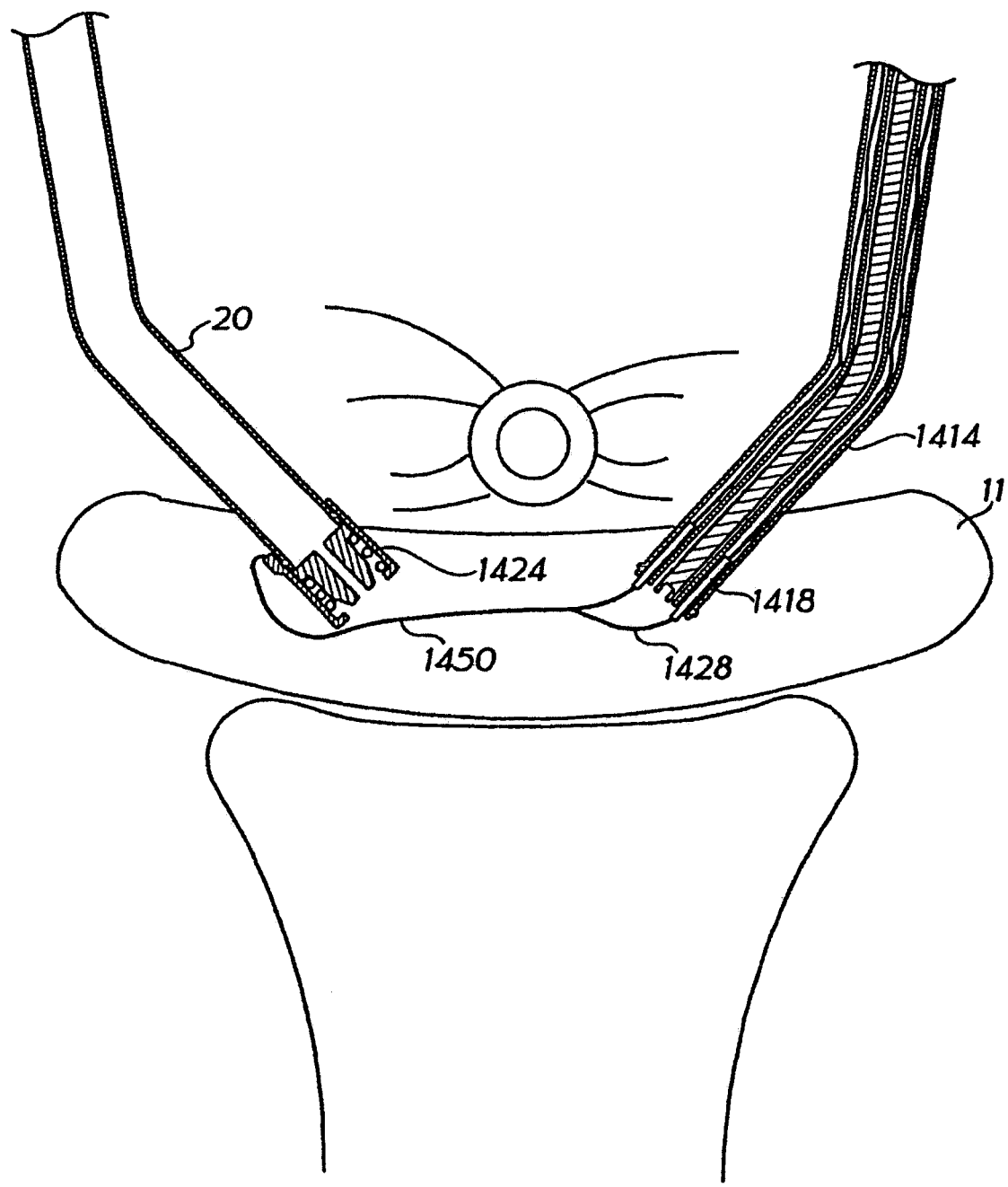
FIG. 77 shows the sutures connected to the sling being pulled out of the shaft of the detachable cup sling application device.
Figure 78:
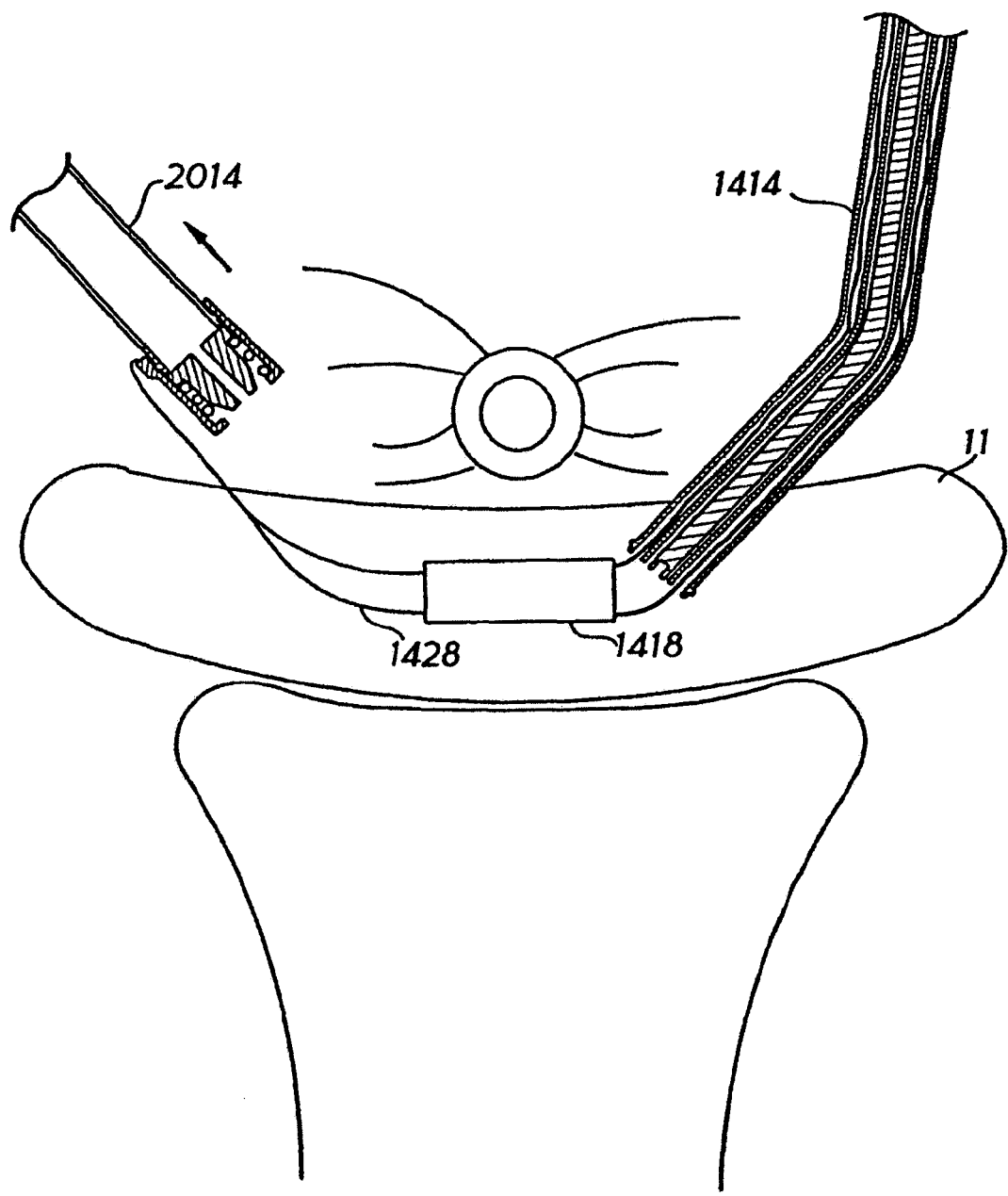
FIG. 78 shows the shaft of the retrieval device being withdrawn from the pocket or opening, pulling the sling out of the shaft of the detachable member sling application device.

As the shaft 2014 of the retrieval device is withdrawn from the pocket or opening 11, the connecting member 1450 on the detachable member 1424 pulls the sutures 1428 connected to the sling 1418 out of the shaft 1414 of the detachable member sling application device 1410, as illustrated in FIG. 77. As the shaft 2014 of the retrieval device is withdrawn further from the pocket or opening 11, the sling 1418 and the sutures 1428 connected thereto are pulled out of the shaft 1414 of the detachable member sling application device 1410, as illustrated in FIG. 78.

Figure 79:
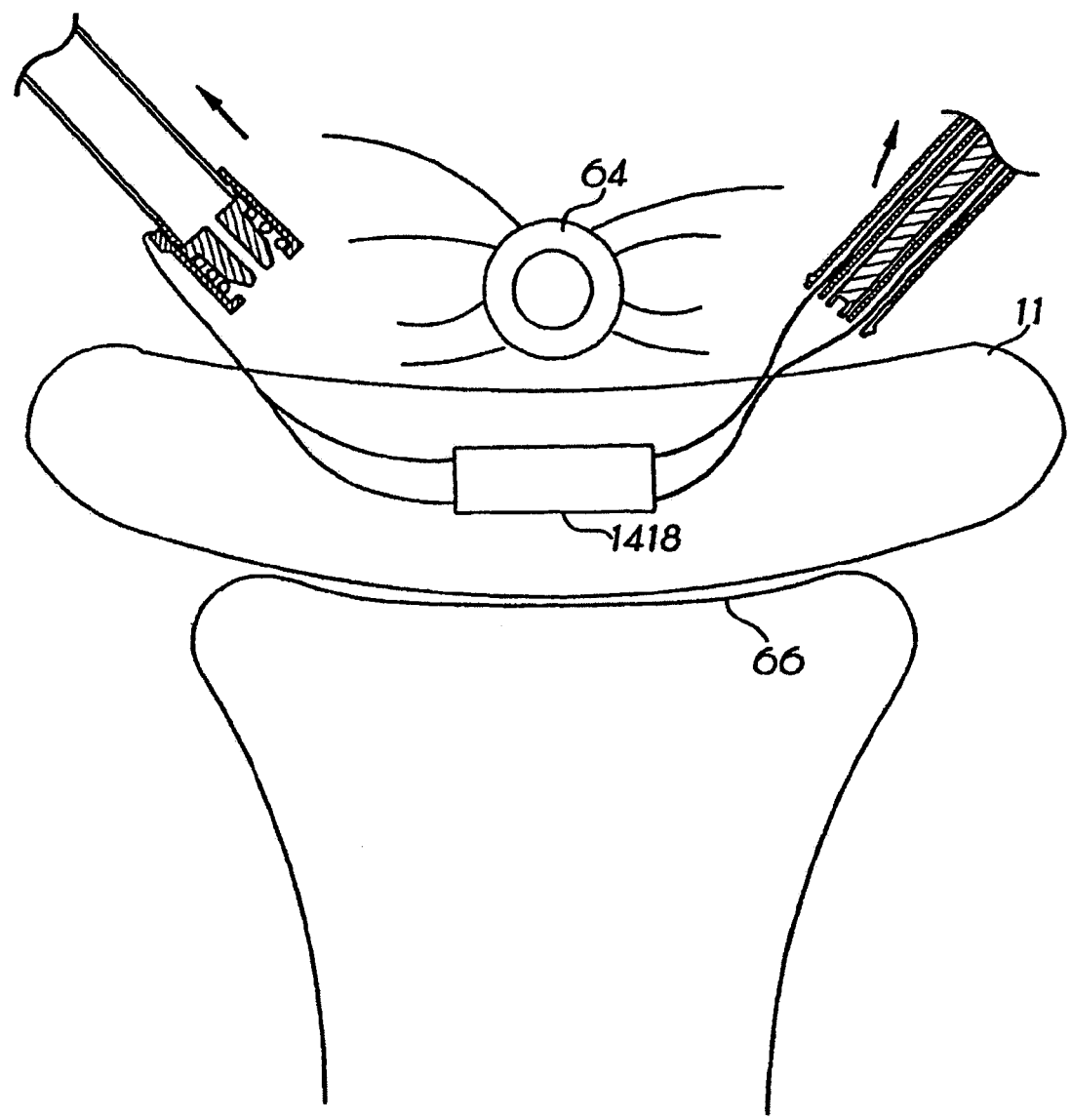
FIG. 79 shows the shafts of the retrieval device and the detachable member sling application device being withdrawn from the pocket.
Figure 80:
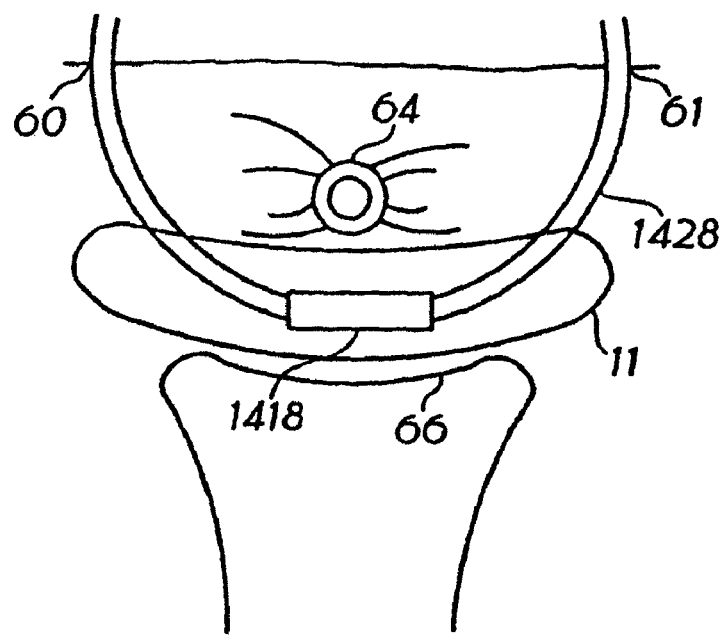
FIG. 80 shows the sling located in the opening in the tissue between the urethra and the upper vaginal wall with the sutures extending through the incisions to the outside of the patient's body.

The shaft 1414 of the detachable member sling application device 1410 and the shaft 2014 of the retrieval device 2010 are withdrawn from the patient's body as shown in FIG. 79. The sling 1418 is thereby left in the opening or pocket 11 between the urethra 64 and the upper vaginal wall 66 such that the sutures 1428 extend from the first and second suprapubic incisions 60, 61 patient's body, as shown in FIG. 80.

Figure 81:
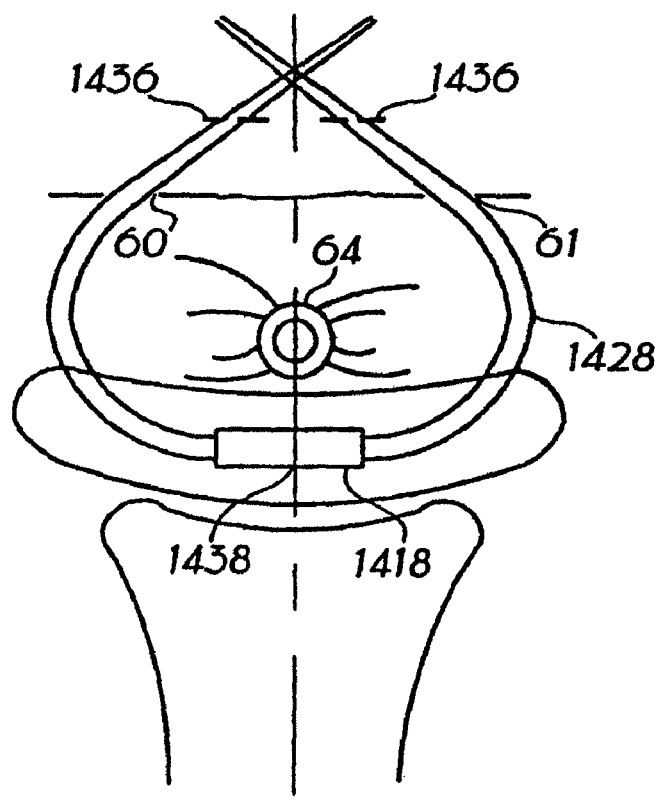
FIG. 81 shows the marks on the sutures being aligned to ensure centering of the sling beneath the urethra within the opening in the tissue between the urethra and the upper vaginal wall.

Preferably, the sutures 1428 or integral attachment members attached to the sling 1418 have markings 1436 thereon for ensuring that the sling 1418 is properly centered beneath the urethra in the opening or pocket 11. The markings 1436 on the sutures or integral attachment members are equidistant from the center 1438 of the sling. Following placement of the sling 1418 in the opening or pocket 11, the physician crosses the sutures 1428 as shown in FIG. 81. When the markings 1436 on the sutures 1428 or integral attachment members are positioned along a line extending transversely to the patient's abdomen, as shown in FIG. 81, the sling 1418 is properly centered in the pocket or opening 11.

The sling can then be attached to a bone anchor or other structures, and tensioned to support the bladder neck or stabilize the urethral floor, thereby maintaining or improving urinary continence, using approaches such as those described in U.S. patent application Ser. No. 09/023,398, entitled "Stabilization Sling for Use in Minimally Invasive Pelvic Surgery" (VESITEC.023A), filed Feb. 13, 1998, now issued U.S. Pat. No. 6,042,534, issued Mar. 28, 2000, the identically titled U.S. Provisional Patent Application Ser. No. 60/038,379, filed Feb. 13, 1997 and U.S. Pat. No. 5,611,515, issued Mar. 18, 1997 to Benderev et al., the disclosures of which are incorporated herein by reference.

Tissue Expander Grasping Device, and Balloon Catheters

A further aspect of the invention relates to hiatal techniques for creating an opening or pocket in the tissue between the urethra and the upper vaginal wall and devices for use in the hiatal techniques. The hiatal methods can be practiced without the necessity for a vaginal incision, thus minimizing the risk of infection from the procedure.

As will be described in greater detail below, in the hiatal approach a lumen is created in the hiatal tissue between the urethra and the upper vaginal wall. The lumen is then expanded to create an opening or pocket of a size sufficient to accept a sling. The opening or pocket is then held open with the tissue expander while a first suture or flexible guide member is percutaneously advanced into the opening or pocket. The guide member may be a suture, guide wire, or other structure suitable for guiding a sling to a desired location. The first suture or flexible guide member is grasped with a grasping device and withdrawn through the lumen and out of the body. The process is repeated with a second suture or flexible guide member on the opposite side of the urethra. The two sutures or flexible guide members are then tied together to create a guide for delivering a sling into the pocket. The knotted section of the suture or guide member is then translocated outside of the body so that the progress of the sling along the suture or guide member is unimpeded.

Alternatively, the sling may be attached to the sutures extending outside of the body, rolled or restuffed, and drawn into the body through the lumen by pulling on the sutures.

As discussed above, after creation of the lumen in the hiatal tissue, the lumen is expanded to create a pocket or opening. One aspect of the present invention relates to balloon catheters for expanding the lumen and creating the pocket or opening. The balloon catheters generally comprise an outer tube having a lumen extending therethrough and at least one expandable balloon inside the outer tube. The expandable balloon has a blunt dissection tip at its distal end having sufficient rigidity to allow it to create an opening in a body tissue when contacting the tissue.

One embodiment of a balloon catheter 536 suitable for use in the hiatal approach was described above and is shown in FIG. 26.

In the embodiment shown in FIG. 26, there is a single expandable balloon 540. In an alternative embodiment of the balloon catheter, there is more than one balloon. This embodiment permits the creation of an opening or pocket wide enough to accommodate the sling using balloons having a smaller diameter than would a single balloon capable of creating a pocket of that width. In this way, tearing of tissue above and below the pocket is minimized.

Figure 82:
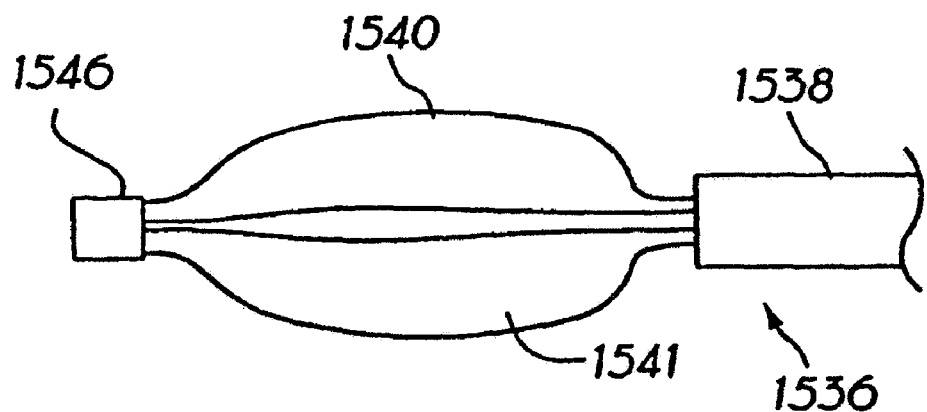
FIG. 82 is a side view of a balloon catheter having two expandable balloons joined at their distal ends.

FIG. 82 shows a preferred embodiment 1536 in which there are two expandable balloons 1540 and 1541 in the lumen of the outer tube 1538 which are joined at their distal ends. Preferably, the expandable balloons are joined at their distal ends by a blunt dissection tip 1546. The blunt dissector tip may comprise a plastic or metal cap. Alternatively, the ends of the two balloons may be potted together. In the embodiment of FIG. 82, the two balloons have a common inflation tube. However, those skilled in the art will appreciate that the balloons may also have separate inflation tubes.

Figure 83:
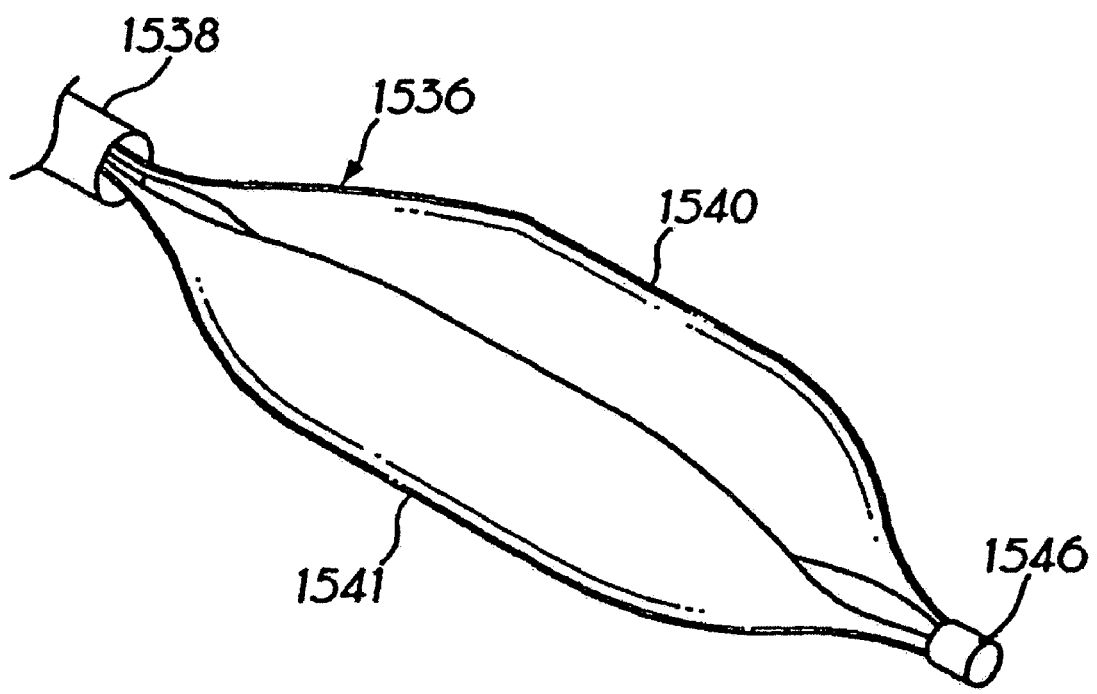
FIG. 83 shows the balloon catheter of FIG. 82 with the balloons expanded.

FIG. 83 shows the embodiment of FIG. 82 in which the balloons 1540, 1541 have been inflated. As illustrated in FIG. 83, the balloons 1540, 1541 have a generally cylindrical configuration when inflated. In this embodiment, each balloon 1540, 1541 may be from about 2 cm to about 3 cm in length and has a diameter when expanded of from about 1 cm to about 2.5 cm. In a preferred embodiment, each balloon 1540, 1541 is from about 2 cm to about 3 cm in length and has a diameter when expanded of from about 1.5 cm to about 2 cm. More preferably, each balloon is about 2.75 cm in length and 2.5 cm in diameter when expanded.

Some physicians prefer procedures which take place beneath the pelvic floor so as to avoid any unnecessary disruption of muscle, the slings are preferably about 1.5 cm to about 6 cm in length and about 2 cm in width. More preferably, the slings used in such procedures are 2.5 cm to 4 cm in length, although longer slings may be more manageable for general surgeons since they allow for slippage off center during 30 placement.

Other physicians prefer procedures which break through the pelvic floor and produce scarring which may reinforce the area. In such procedures, the slings may be as long as 20-25 cm. These long slings minimize the length of attaching suture and permit more tissue ingrowth while providing security against suture breakage. Preferably, the slings used in such procedures are about 2 cm wide.

Those skilled in the art will appreciate that the sling dimensions can be varied as appropriate. In any case, however, it is preferred that the balloon on the balloon catheter is appropriately sized to create a pocket or opening capable of accommodating the sling.

Alternatively, a balloon catheter 1636 having a flat profile balloon 1640 may be used to create the lumen. The flat profile balloon 1640 is capable of forming a flat pocket sized to receive a sling while avoiding the unnecessary dilation or tearing of tissue above and below the sling pocket which may occur if a cylindrical balloon was used to create the pocket. Preferably, the flat profile balloon 1640 has a square or rectangular shape when inflated. However, those skilled in the art will appreciate that other shapes are compatible with the present invention and that the shape may be readily modified to be compatible with the particular device or procedure used.

The flat profile balloons 1640 are preferably made of two sheets of noncompliant material such as mylar, polyethylene, or PET. Alternatively, the balloons may be made by blow molding.

A flat profile balloon 1640 according to the present invention is shown in FIG. 84. As illustrated, the balloon 1640 has a series of internal non-expansive ribs 1650 which serve to maintain a shallow profile after expansion, direct the flow of air to promote even unrolling during expansion, reduce buckling in critical areas after expansion, and provide a conduit structure which delivers a consistent expansion of tissue into the desired shape. The internal structure of the catheter and balloon 1640 are further illustrated in the cross sectional views of FIGS. 85 and 86.

As illustrated in FIG. 84, the balloon 1640 is located at the distal end of a generally rigid inflation tube 1642 which extends through the interior of the balloon 1640. The inflation tube 1642 provides a generally rigid support structure during advancement and placement of the balloon 1640 in the body tissue. Preferably, the inflation tube 1642 has a series of fill holes 1658 in the interior of the balloon 1640 which promote uniform inflation of the balloon. However, those skilled in the art will appreciate that a single fill hole may also be used.

In one embodiment, shown in FIG. 85, the inflation tube 1642 has two lumens in its interior. One lumen, the guide lumen 1652, is adapted to receive a guide member, while the other lumen, the inflation lumen 1654, is for inflation of the balloon and is in fluid communication with the interior of the balloon. In an alternative embodiment, the catheter has a single inflation lumen.

Those skilled in the art will appreciate that the catheter may be provided with more than two lumens to accommodate other instruments necessary to perform the surgical procedure.

The inflation tube has a luer tip 1656 at its proximal end which is adapted to engage a syringe filled with saline or sterile water. When the plunger of the syringe is depressed, fluid is force through the inflation lumen 1642 and out of the fill holes into the interior of the balloon, causing the balloon 1640 to inflate. When the plunger of the syringe is retracted, a vacuum is created, drawing the fluid out of the balloon 1640 and causing the balloon to deflate 1640.

In a preferred embodiment, the balloon 1640 is rolled on the exterior surface of the inflation tube 1642 to reduce its entry profile.

Those skilled in the art will appreciate that the above described balloon catheters 536, 1536, 1636 can be used to dilate body tissues in contexts other than the hiatal procedures discussed below. For example, the balloon catheters 536, 1536, 1636 may be utilized in the tissue dissector/dilator 510 described above, or may be used to create a pre-formed opening for receiving the guide member placement devices 10, 1910, the sling application devices 710, 810, 910, 1010, or the detachable member sling application devices 1410 described above.

Additionally, the balloon catheters 536, 1536, 1636 of the present invention can also be used to create the opening or pocket in the tissue between the urethra and the upper vaginal wall in transvaginal incontinence treatments. In such transvaginal procedures the balloon catheter is inserted through the upper vaginal wall into the area in which the opening or pocket is to be made. The balloon is then expanded, creating the opening or pocket for receiving a sling. In some instances, the physician may use the balloon catheters' in conjunction with transvaginal bone anchor implantation devices such as those disclosed in the copending U.S. patent application Ser. No. 08/744,439 entitled "Transvaginal Anchor Implantation Device," filed Nov. 8, 1996, the disclosure of which is incorporated herein by reference. However, use of the balloon catheters in conjunction with transvaginal bone anchor implantation devices may impact the expense of such procedures.

The balloon catheters described above and depicted in FIGS. 2B and 82-86 may be introduced into the body in a number of ways. In one method a needle or guide member is inserted into the hiatal tissue to the desired location. The needle or guide member is inserted into the guide lumen of the catheter. The catheter is advanced along the guide member or needle to the desired location. A syringe filled with saline or sterile water is attached to the luer tip at the end of the catheter and the plunger of the syringe is depressed, ejecting the fluid from the syringe and causing the balloon to inflate. The inflated balloon dilates or tears the tissue thereby creating a shallow opening or pocket adapted to receive a sling.

In an alternate procedure, a hollow needle or trocar is introduced into the body tissue and advanced to the desired location. A balloon catheter, which may have a single inflation lumen, is passed through the lumen of the needle or trocar and advanced to the end. The needle or trocar is partially withdrawn from the patient's body to expose the balloon. The balloon is inflated and deflated as described above to create an opening or pocket adapted to receive a sling.

Further aspects of the present invention relate to tissue expanders 1710 for expanding an opening or pocket in a body tissue and grasping devices 1810 for grasping a suture advanced into the opening or pocket.

In general, the tissue expander comprises a tube with a lumen extending therethrough, an expandable and collapsible member attached to the tube for insertion into the opening within the body tissue and expansion thereof, and an expansion and collapse control in communication with the expandable and collapsible member for moving the expandable and collapsible member between a first position in which it is collapsed and a second position in which it is expanded.

Figure 87:
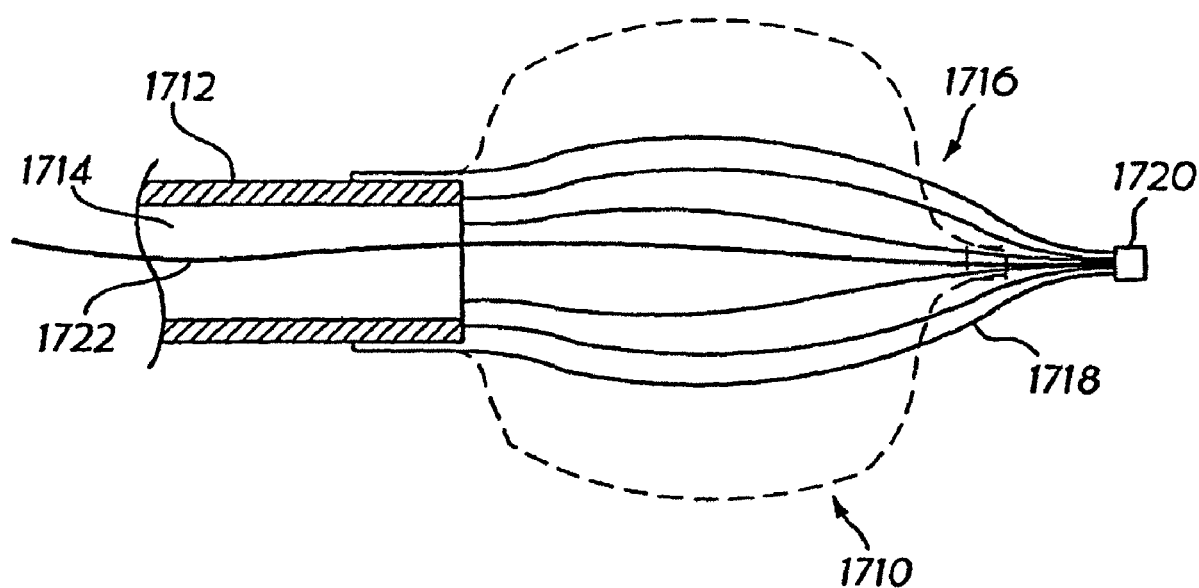
FIG. 87 is a cross-sectional view of a tissue expander.

One embodiment of a tissue expander 1710 according to the present invention is shown in FIG. 87. The tissue expander comprises a tube 1712 with a lumen 1714 extending therethrough. Preferably, the lumen 1714 of the tube 1712 is of sufficient diameter to permit a visualizer, such as a fiberoptic scope, and a grasping device to be simultaneously housed therein.

An expansion basket 1716 is attached to the tube 1712. Preferably, the expansion basket 1716 comprises a plurality of wires 1718 joined at their distal ends by a tip 1720 which is connected to a pull wire 1722. The expansion basket 1716 is movable between a first position in which it is collapsed (indicated with solid lines) and a second position in which it is expanded (indicated with dashed lines) as shown in FIG. 87. When the pull wire 1722 is pulled towards the proximal end of the device, the expansion basket 1716 moves to the expanded position. When the pull wire 1722 is released, the expansion basket 1716 collapses.

The expansion basket 1716 may be fabricated from a variety of materials such as stainless steel or Nitinol. Preferably, the expansion basket 1716 is made of stainless steel.

The expansion basket 1716 may expand the tissue from about 0.25 inch to about 1.5 inches. Preferably, the expansion basket 1716 expands the tissue from about 0.5 inch to about 1.25 inches. In a highly preferred embodiment, the expansion basket 1716 expands the tissue about one inch.

In an alternative embodiment of the tissue expander, a self-expanding net or a self-expanding mesh tube may be used in place of the expansion basket.

A further aspect of the present invention relates to a grasping device which is adapted to fit inside the lumen of the tube of the tissue expander described above. When inserted into the lumen of the tube of the tissue expander, the grasping device is axially movable and extendable from and retractable in the lumen of the tube. Generally, the grasping member comprises a catheter with a grasper on its distal end.

Figure 88:
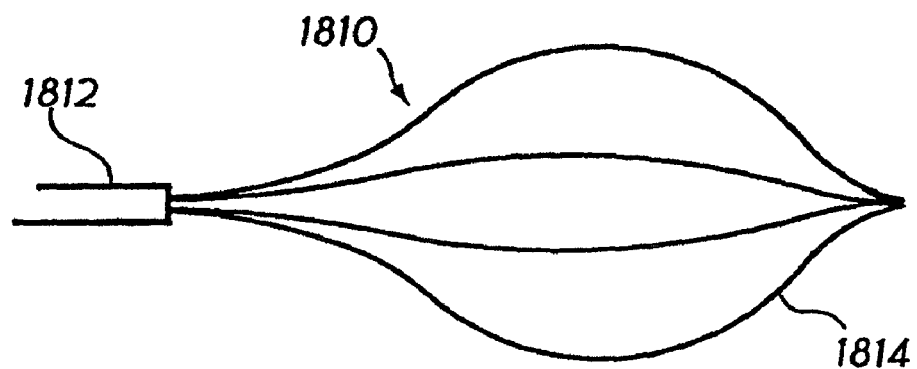
FIG. 88 is a side view of a grasping device.

A grasping device 1810 according to the present invention is shown in FIG. 88. The grasping device 1810 comprises an elongate member 1812 and self expanding grasping basket 1814 attached to the distal end of the elongate member 1812.

Preferably, the grasping device 1810 is adapted to fit inside the tube 1712 of the tissue expander 1710. When the self-expanding grasping basket 1814 is inside the lumen of the tube 1712 of the tissue expander 1710, it is held in a collapsed configuration by the tube 1712. However, when the self-expanding grasping basket 1814 is extended outside the tube 1712, it expands. Preferably, in its expanded state, the self-expanding grasping basket 1814 on the grasping device 1810 fits inside the expansion basket 1716 of the tissue expander 1710. When the grasping device 1810 is retracted back into the lumen 1714 of the tube 1712 it collapses.

The above grasping devices 1810 and tissue expanders 1710 can be used in a wide variety of surgical procedures in which it is necessary to expand an opening in a body tissue and grasp a suture which has been advanced into the expanded opening. For illustrative purposes, the use of the above devices in a hiatal bladder neck stabilization procedure is described below.

Figure 89:
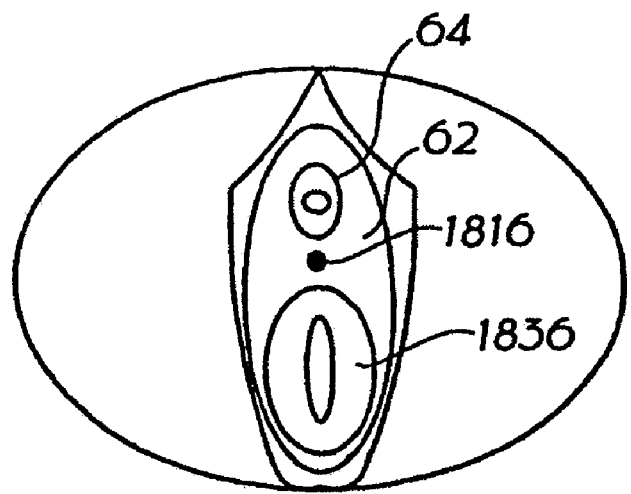
FIG. 89 shows the target site for insertion of a device for creating a lumen in the hiatal tissue between the urethra and the upper vaginal wall.

FIG. 89 shows the urethra 64, the vagina 1836, the hiatal tissue 62 between the urethra and the upper vaginal wall, and a target site 1816 for insertion of a device for creating a lumen 1818 in the hiatal tissue. In the hiatal bladder neck stabilization procedure disclosed herein, the urethra 64 is straightened prior to creation of the lumen 1818 in the hiatal tissue.

Figure 90:
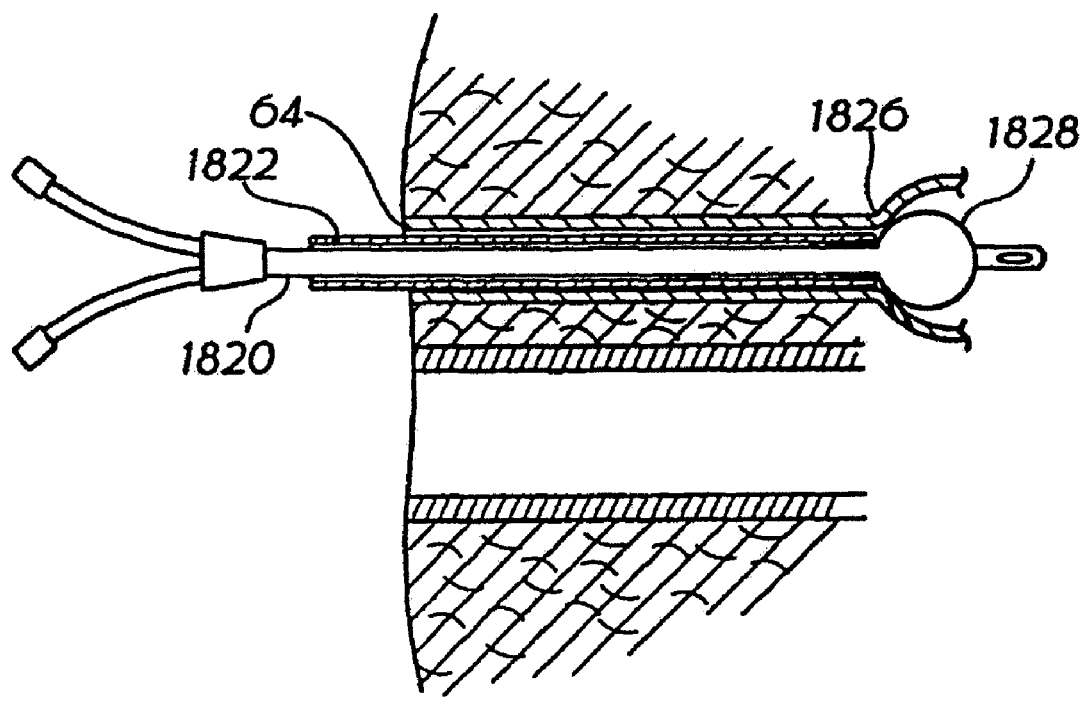
FIG. 90 shows the urethra straightened with a Foley catheter.

As shown in FIG. 90, the urethra 64 can be straightened with a Foley catheter 1820 inside a large bore tube 1822. The large bore tube 1822 fits securely over the Foley catheter and extends out of the urethra. Preferably, the large bore tube is sufficiently firm to rigidify the Foley catheter.

Preferably, the large bore tube 1822 comprises a metal shaft. In a preferred embodiment the metal shaft includes a means to measure the length of the urethra from the bladder neck to the proximal end. In some embodiments, the large bore tube 1822 has guide means thereon which allow the needle 1830 or other dissecting device for dissecting the hiatal tissue, such as a cutter knife, to be guided to the desired site. Such devices are described in U.S. patent application Ser. No. 09/023,533, entitled "Method and Apparatus for Minimally Invasive Pelvic Surgery," (VESITEC.028A) filed Feb. 13, 1998, now issued U.S. Pat. No. 6,099,547, issued Aug. 4, 2000, and the identically titled U.S. Provisional Patent Application Ser. No. 60/038,380, filed Feb. 13, 1997, the disclosures of which are incorporated herein by reference.

As shown in FIG. 90, the Foley catheter 1820 is inserted into the urethra 64 and advanced to the bladder neck 1826.

When the balloon 1828 of the Foley catheter is inside the bladder neck 1826, it is inflated. Alternatively, the urethra 64 may be straightened with a urethroscope or by other methods familiar to those skilled in the art.

Figure 91:
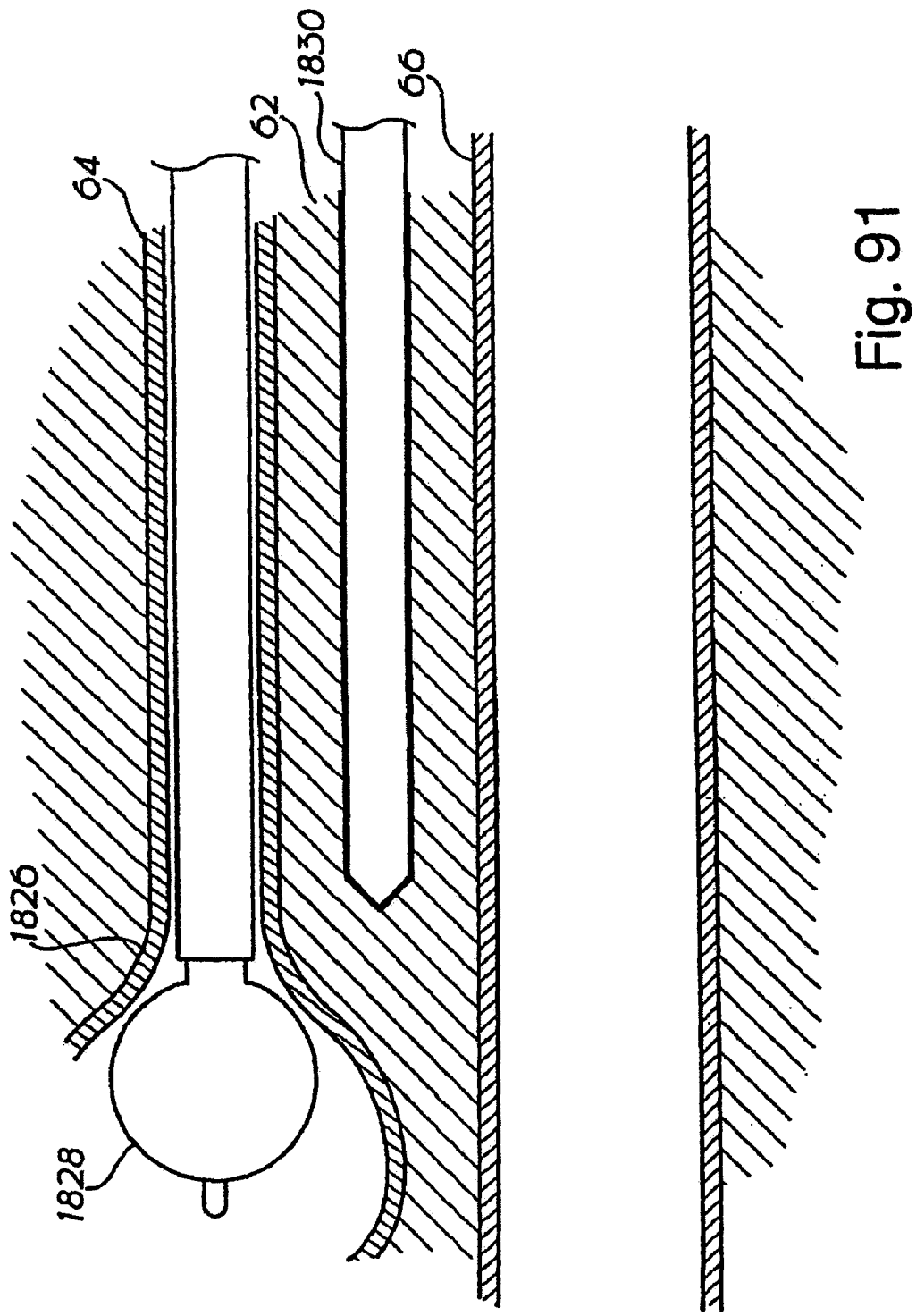
FIG. 91 shows a large bore needle being inserted into the hiatal tissue between the urethra and the upper vaginal wall.

As shown in FIG. 91, a large bore needle 1830 is inserted into the hiatal tissue 62 between the urethra 64 and the upper vaginal wall 66 at the target site 1816 indicated in FIG. 89. An appropriately sized needle may be selected by measuring the distance between the balloon 1828 of the Foley catheter 1820, which is positioned at the bladder neck 1826, and the external urethra. The needle should be slightly shorter than the measured length. For example, the needle may be approximately 0.25 inch less than the measured length.

The needle 1830 may be guided by eye or may be mechanically guided to penetrate the hiatal tissue parallel to the without penetrating the upper vaginal wall. The needle is advanced parallel to the urethra 64 below the midline of the urethra.

Figure 92:
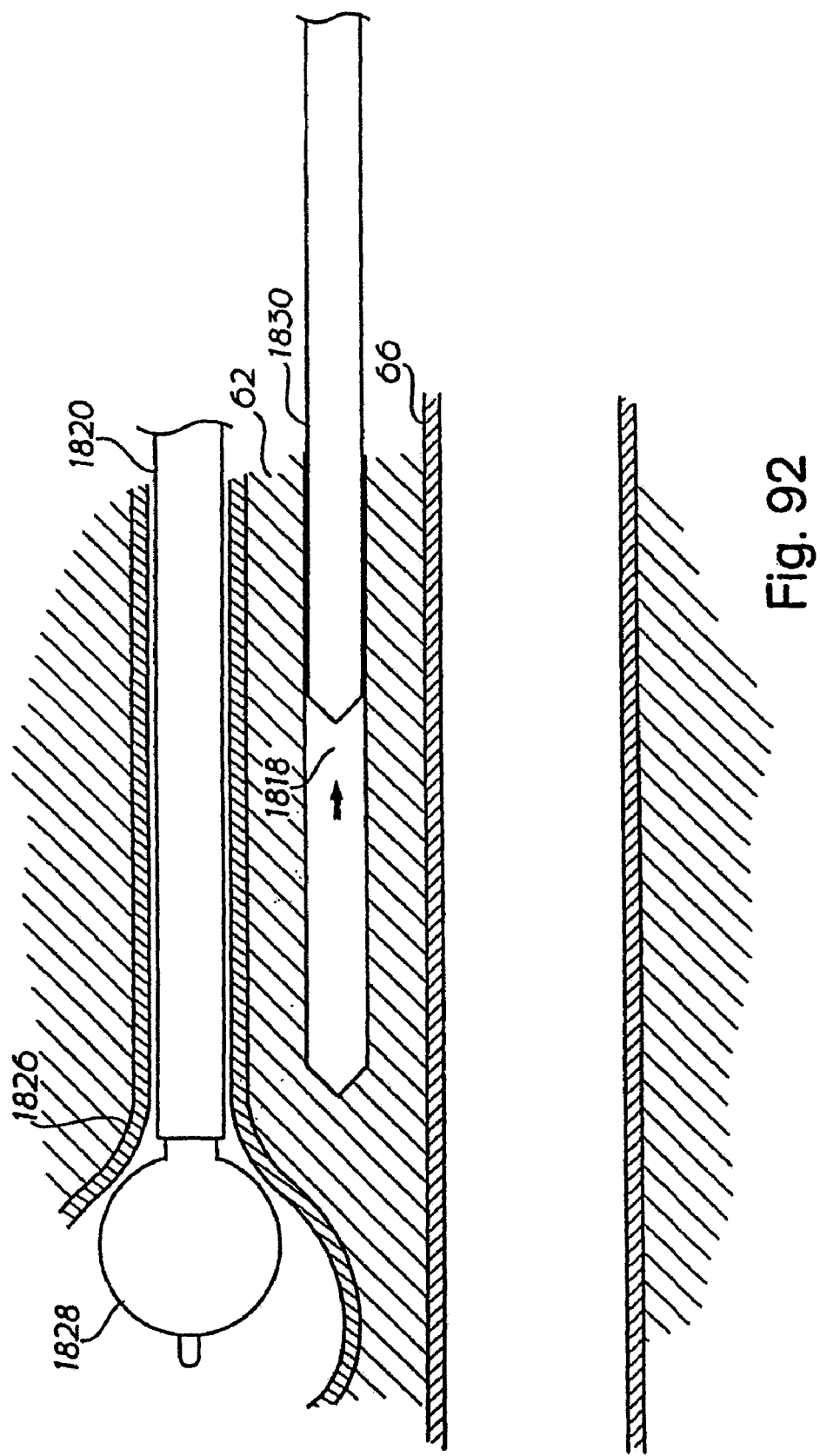
FIG. 92 shows the needle partially retracted such that the lumen created by the needle provides an access channel.

As shown in FIG. 92, the needle 1830 is partially retracted and the lumen 1818 in the hiatal tissue 62 which was created by the needle 1830 provides an access channel for the devices discussed above.

Alternatively, a bi-polar RF cutter may be used to dissect an opening in the hiatal tissue. The bi-polar cutting device comprises a pair of wires, one flexible and one rigid, for cutting a slot from the proximal portion of the hiatus to the bladder neck having a width adapted for receiving a sling therein. Preferably, the bi-polar cutting devices uses 80 Watts of power to cut and coagulate the tissue. In this embodiment, the large bore tube 1822 in which the Foley catheter is placed has a series of thermistors and associated connectors which provide temperature feedback for use in conjunction with a bi-polar RF cutter device. Such devices are described in U.S. patent application Ser. No. 09/023,533, entitled "Method and Apparatus for Minimally Invasive Pelvic Surgery" (VESITEC.028A) filed Feb. 13, 1998, now issued U.S. Pat. No. 6,099,547, issued Aug. 4, 2000, and the identically titled U.S. Provisional Patent Application Ser. No. 60/038,380, filed Feb. 13, 1997, the disclosures of which are incorporated herein by reference.

Figure 93:
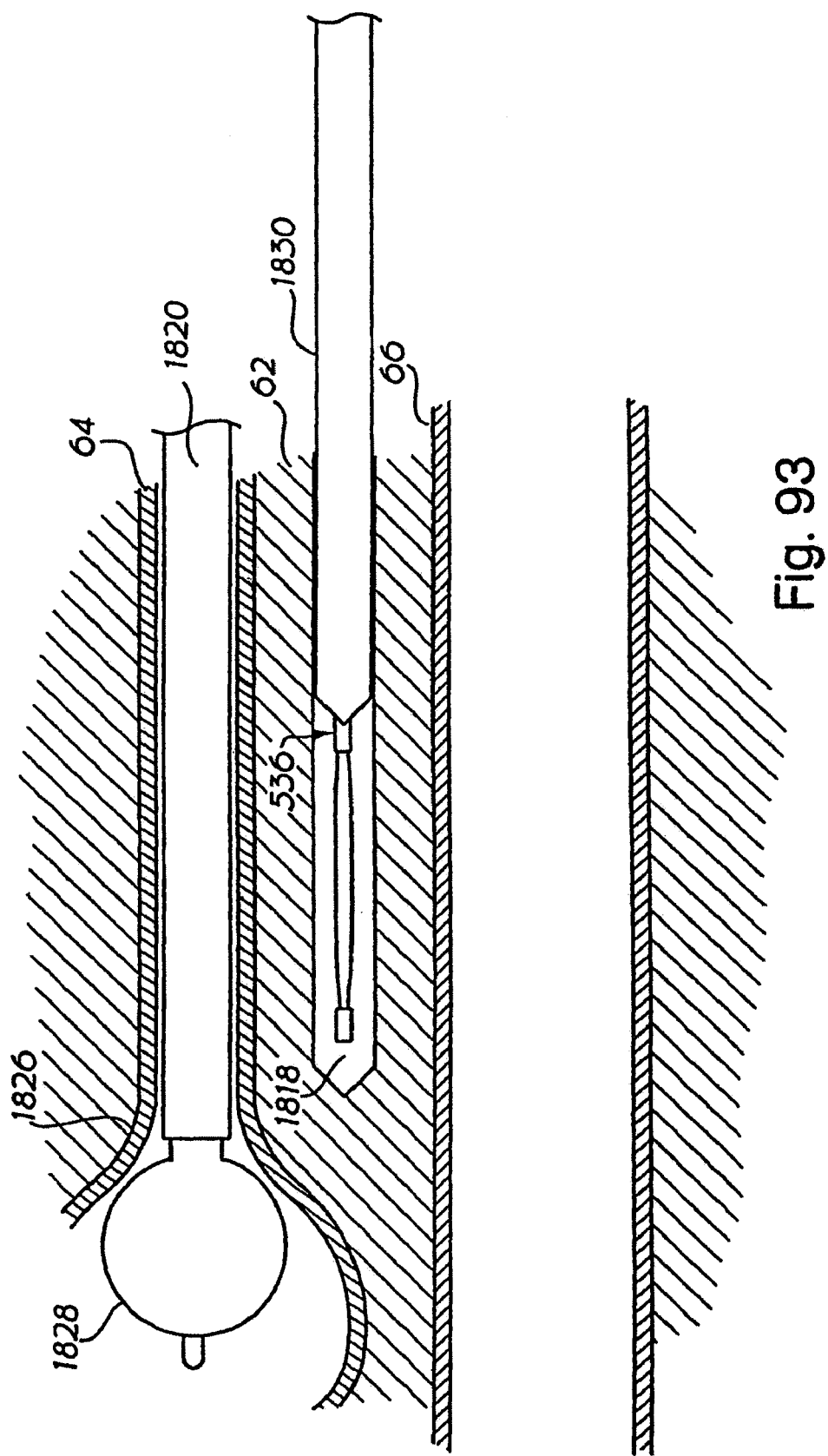
FIG. 93 shows a balloon catheter being advanced beyond the tip of the needle into the lumen created in the hiatal tissue.

A balloon catheter 536 is inserted into the bore of the needle 1830 and advanced beyond the tip of the needle 1830 into the lumen 1832 in the hiatus as shown in FIG. 93. Although FIG. 93 shows the balloon catheter 536 depicted in FIG. 26 being used, the balloon catheters 1536 and 1636 depicted in FIGS. 82-86 may also be used.

Figure 94:
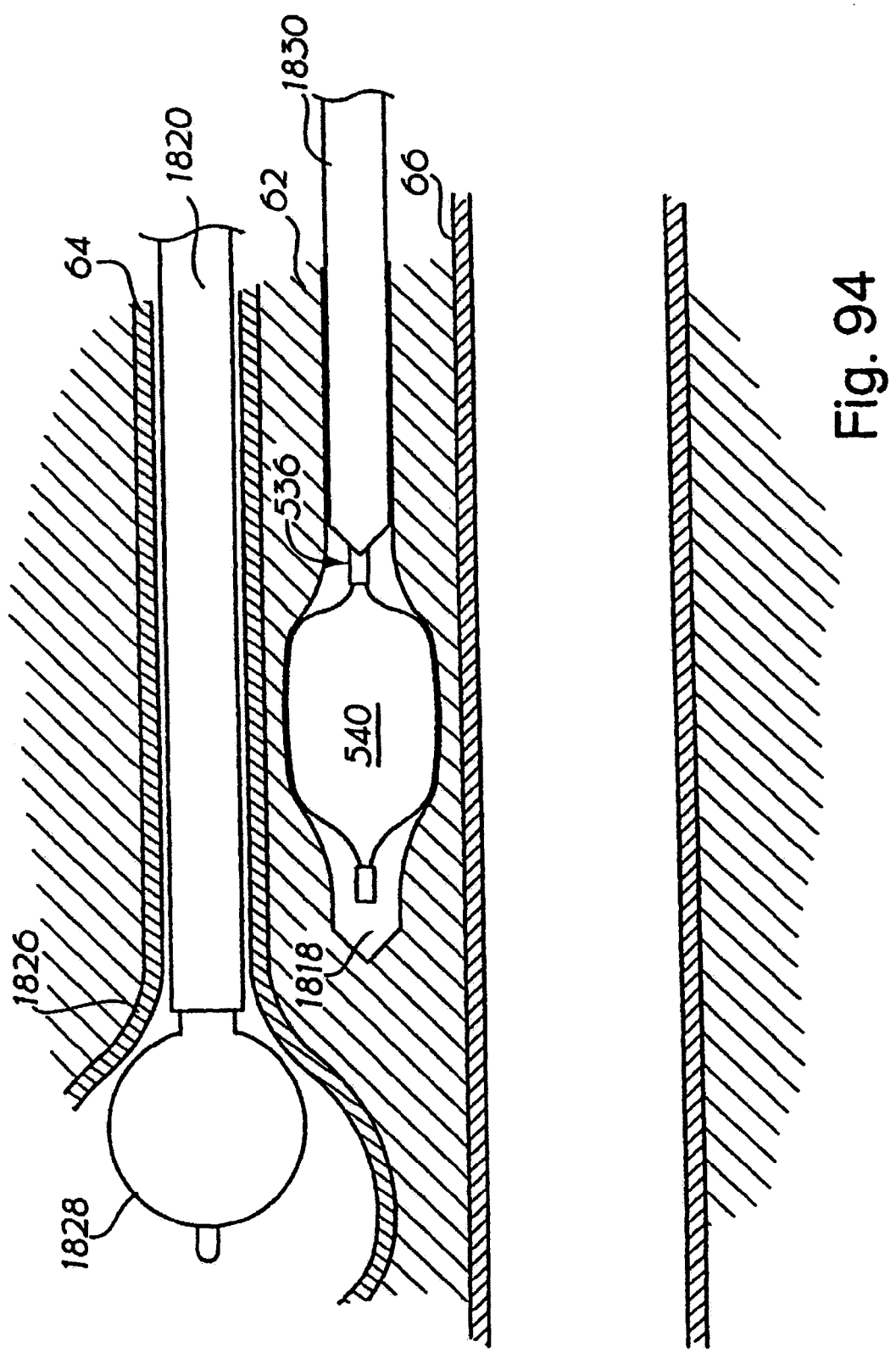
FIG. 94 shows the balloon of the balloon catheter being inflated to dilate the tissue around the lumen created in the hiatal tissue.

As shown in FIG. 94, the balloon 540 is then inflated with saline or sterile water, dilating the hiatal tissue 62 around the lumen 1818 created by the large bore needle 1830. The balloon 540 is then deflated and the balloon catheter 536 is withdrawn from the patient's body.

Figure 95:
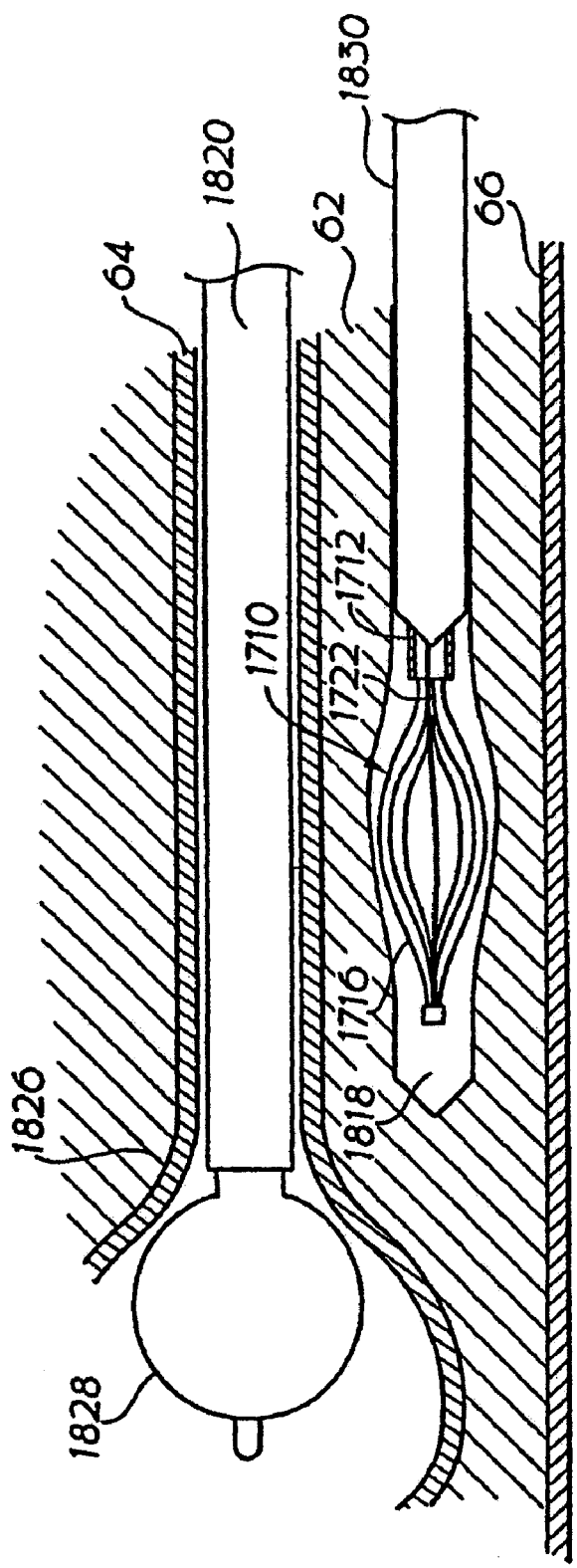
FIG. 95 shows the tissue expander being advanced beyond the tip of the needle into the lumen created in the hiatal tissue.
Figure 96:
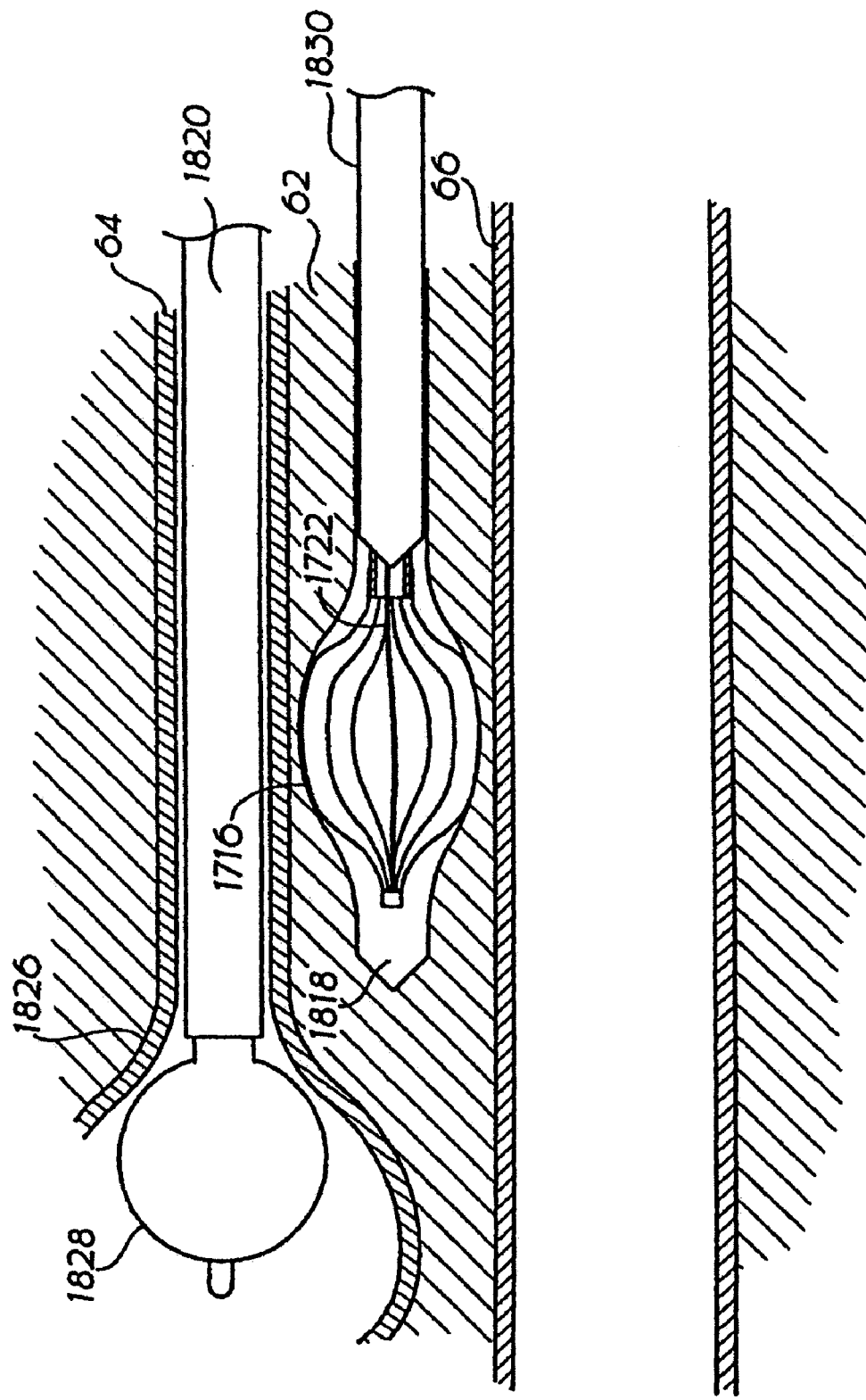
FIG. 96 shows the tissue expander in the expanded configuration within the lumen created in the hiatal tissue.

The tissue expander 1710 is inserted into the large bore of the needle 1830 and advanced beyond the tip of the needle into the lumen 1818 in the hiatal tissue 62, as shown in FIG. 95. The pull wire 1722 is then pulled towards the proximal end of the tissue expander 1710, causing the expansion basket 1716 to adopt the expanded configuration and thereby expanding the lumen 1818 in the hiatal tissue as shown in FIG. 96.

A fiberoptic scope 1832 is inserted into the tube 1712 of the tissue expander 1710 and is extended into the interior of the expansion basket 1716.

Figure 97:
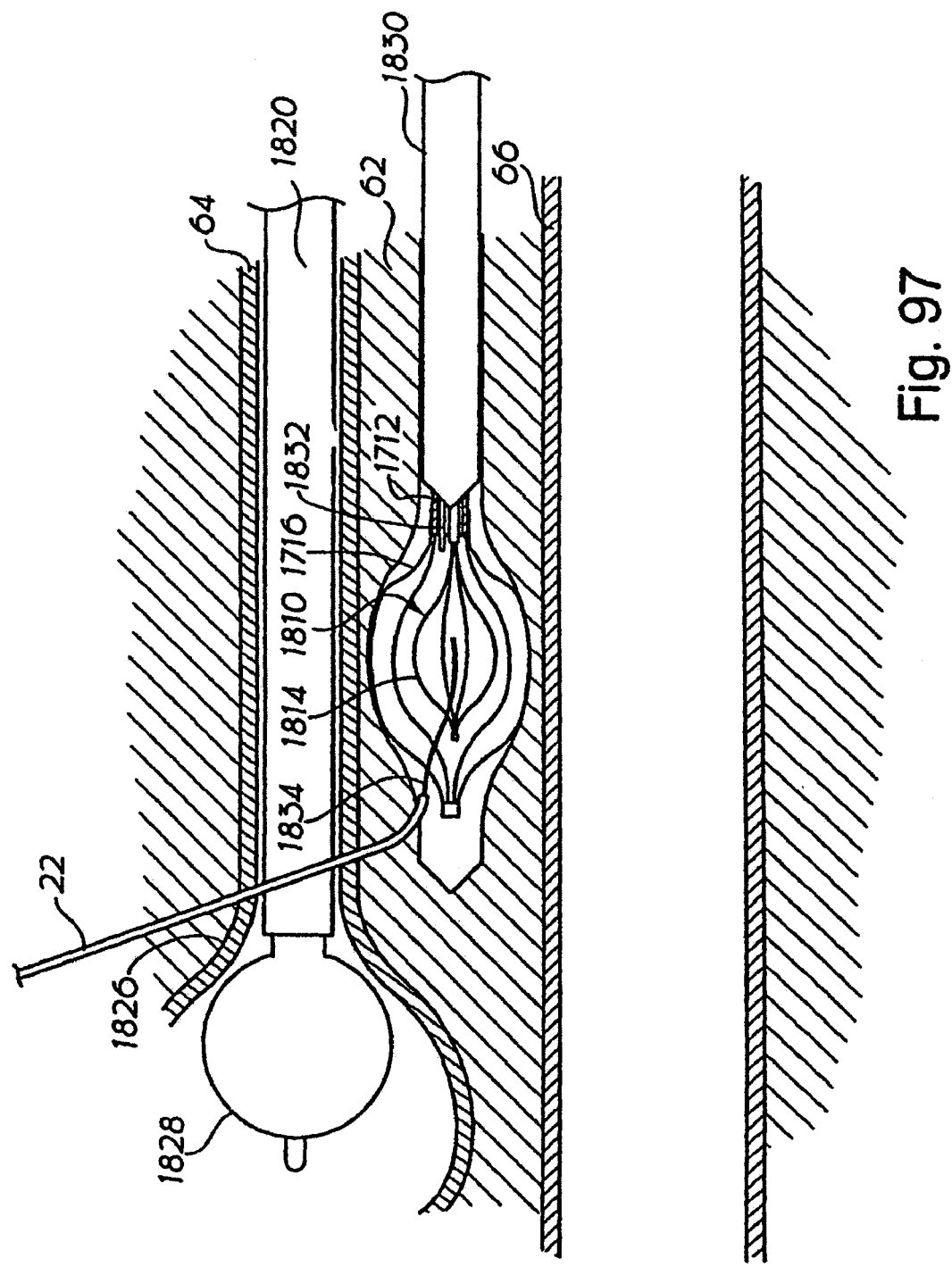
FIG. 97 shows a suture passing through the expansion basket of the tissue expander and into the self expanding basket of the grasping device.

A guide member placement device 10 such as that described above is used to advance a suture 1834 or guide member from a suprapubic incision, along the back side of the pubic bone toward the upper vaginal wall. The suture 1834 or guide member is extended into the expansion basket 1716 of the tissue expander 1710 as shown in FIG. 97. The fiber optic scope 1832 permits the physician to visualize the position of the suture 1834 or guide member in order to determine when the suture 1834 or guide member is within the expansion basket 1716.

Figure 98:
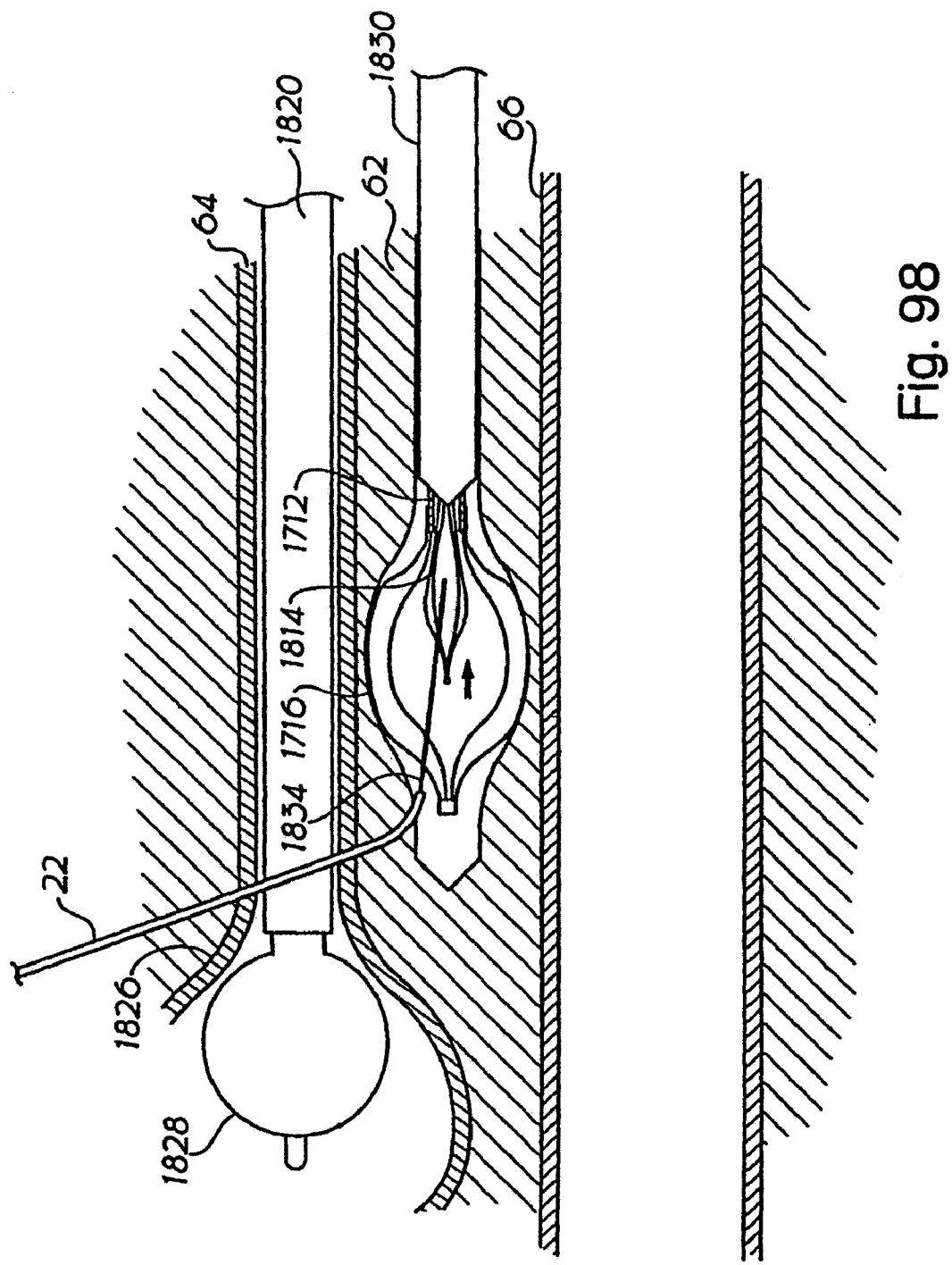
FIG. 98 shows the grasping device grasping the suture.
Figure 99:
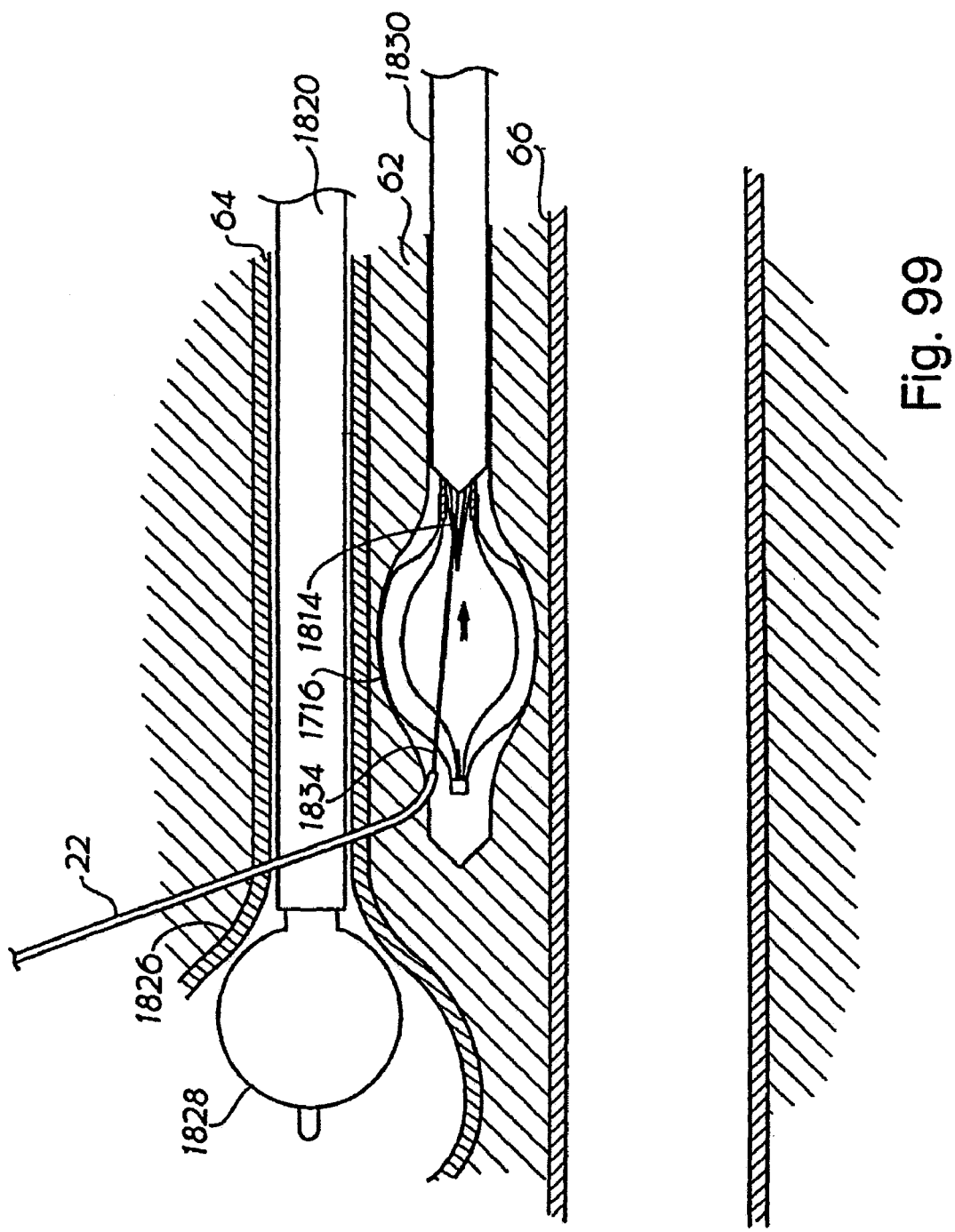
FIG. 99 shows the grasping device being withdrawn from the rigid tube and drawing the suture towards the outside of the patient's body.

A grasping device 1810 is inserted into the lumen 1714 of the tube 1712 of the tissue expander 1710. The self-expanding grasping basket 1814 of the grasping device is extended from the tube 1712, causing the self-expanding basket 1814 to expand, as shown in FIG. 97. The suture 1834 or guide member 68 is positioned inside the self-expanding basket 1814 and the self-expanding basket 1814 is pulled back into the lumen 1714 of the tube 1712, causing the self-expanding basket 1834 to collapse and grasp the suture 1834 or guide member, as shown in FIG. 98. As shown in FIG. 99, the self expanding basket 1814 is withdrawn through the tube 1712, drawing the suture toward the outside of the patient's body. The grasping device 1810 is removed from the tube 1712, pulling the suture 1834 outside the patient's body.

A second suture is advanced along the back side of the pubic bone toward the upper vaginal wall with a guide member placement device as described above. The second suture is positioned on the opposite side of the urethra from the first suture and is advanced into the expansion basket, grasped with the grasping basket, and drown outside the patient's body as described above. Following this procedure, a second suture or guide member extends from the patient's body.

The large bore needle 1830 and tissue expander 1710 are then removed from the patient's body. The ends of the two sutures are knotted together and the ends of the knotted suture extending from the suprapubic incisions are pulled to draw the knotted suture back into the body. The knot is advanced out of one of the suprapubic incisions providing an uninterrupted suture or guide member extending between the suprapubic incisions around the urethra. The suture provides a guide path from the suprapubic incisions around the urethra which may be used to introduce a sling using a sling introduction catheter as described above.

In an alternative embodiment, the large bore needle 1830 is left in place. A sling is secured to the sutures outside the body, rolled or restuffed, and then drawn through the bore of the needle and into the opening or pocket in the body tissue by pulling on the ends of the sutures extending from the suprapubic incisions.

The tension on the sling may be adjusted as described above. Bone anchors or other means may be used to secure the sutures as discussed above to support the bladder neck or stabilize the urethral floor, thereby maintaining or improving urinary continence.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. In addition, for clarity, letter references are used in some of the claims. These letter references, however, are not meant to imply any particular order for performing the method steps.

Part B

The treatment of incontinence for intrinsic sphincter deficiency (ISD) can often be corrected surgically with the placement of a sling. This sling may consist of a wide variety of well known biocompatible materials: bovine pericardium, autograft, synthetics, cadaveric tissue, collagen/synthetic blends and the like. The sling also may be placed through a variety of surgical procedures. Slings suitable for use in urethral or bladder neck stabilization or suspension procedures and methods for implanting them are disclosed in U.S. Provisional Patent Application 60/038,379, entitled "Stabilization Sling for Use in Minimally Invasive Pelvic Surgery" (VESITEC.023PR), filed Feb. 13, 1997, the disclosure of which is incorporated herein by reference. The extent of surgical intervention is a surgeon's preference, but all present surgical interventions require a vaginal incision. The presence of microorganisms is high in the vagina; in procedures utilizing slings of non-autologous material, a high rate of infection has been reported. The procedure described herein approaches sling placement in a different manner from that requiring a vaginal incision. The vaginal hiatus is approached just under the distal urethra and a cavity is dilated within the tissue parallel to the urethra and upper vaginal wall. This device and resultant pocket provide access for placement of the sling in the treatment of ISD and urethral hypermobility. The dilator also may be used in an approach from within the vagina to create a pocket in the desired location approaching the bladder neck.

Figure 100:
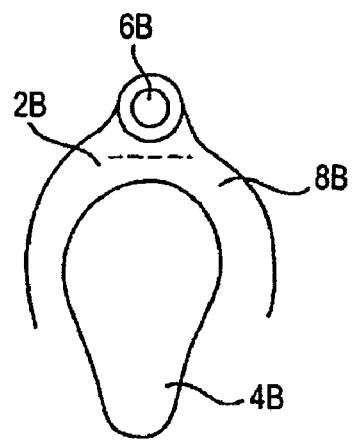
FIG. 100 shows the urethra, the vaginal wall and the vagina in transverse cross section.

Turning now to the drawings, FIG. 100 shows the urethra and the vagina 4B with the vaginal wall 8B in between. The dotted line in FIG. 100 represents an incision site in the vaginal hiatus 2B. The vaginal hiatus 2B is the external tissue between the urethra and the vagina 4B, as well as the tissue deep to that external tissue. The vaginal wall 8B is intended to refer to all interior surfaces of the vagina 4B.

The series of Figures from 101a to 101g demonstrates a sequence having to do with one aspect of the present invention, referred to herein as the dilator 10B. The dilator 10B consists of two distinct functional units, the insertion spreader 12B and the handle 18B. The insertion spreader 12B can have the appearance of a split tube, and each half of the insertion spreader 12B, or each half of the split tube, can be an elongated semi-cylindrical spreader guide 14B. The invention contemplates spreader guides 14B shaped other than semi-cylindrically, such as spreader guides 14B whose cross section when joined would describe a square, a hexagon, and the like, depending on the application for which it is used, and depending on the configuration of the card, to be discussed below.

Figure 101A:
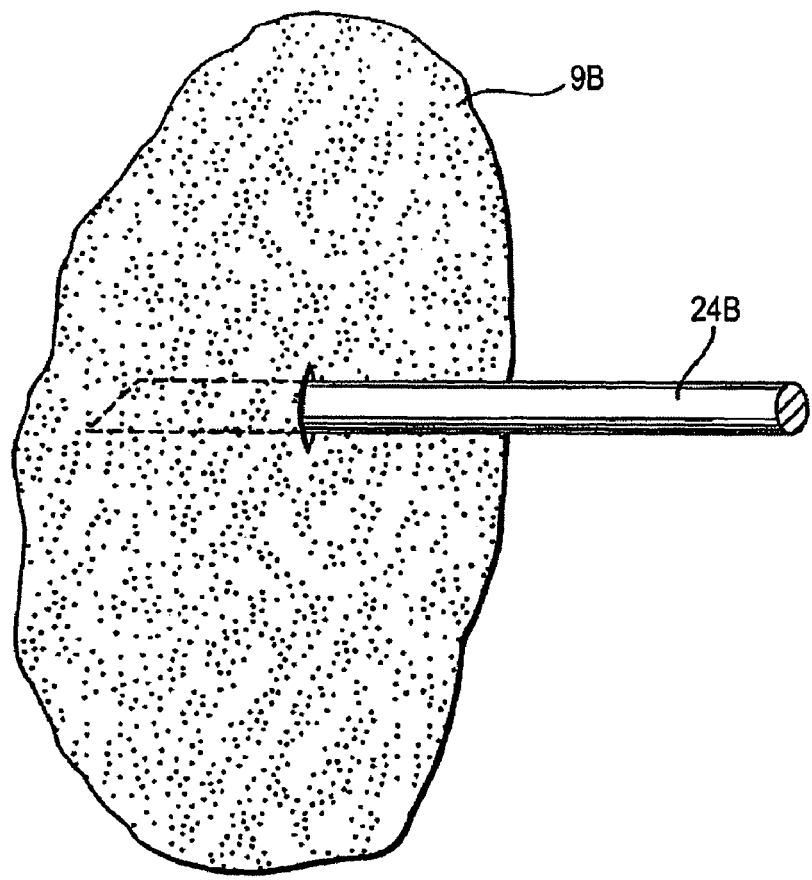
FIG. 101a represents the insertion of a needle into the vaginal hiatus.
Figure 101B:
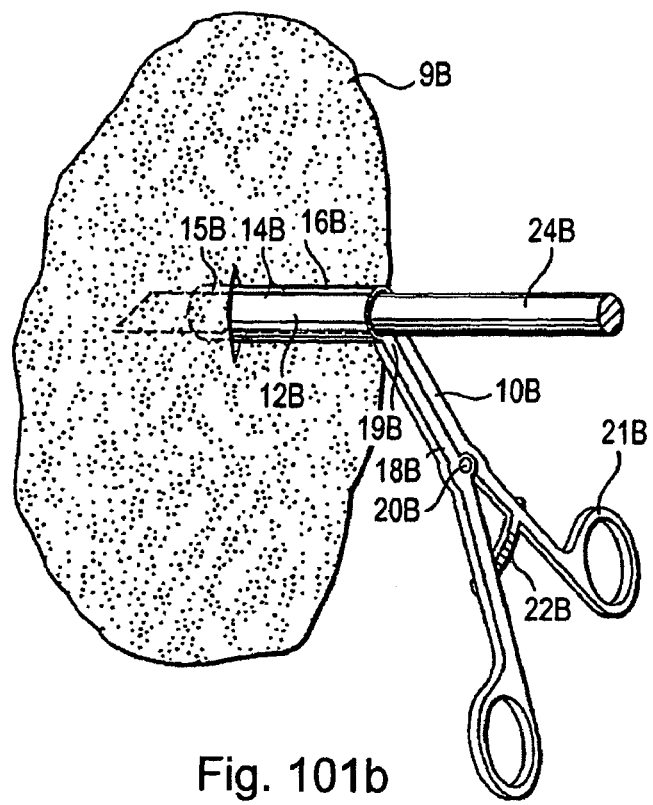
Figure 101C:
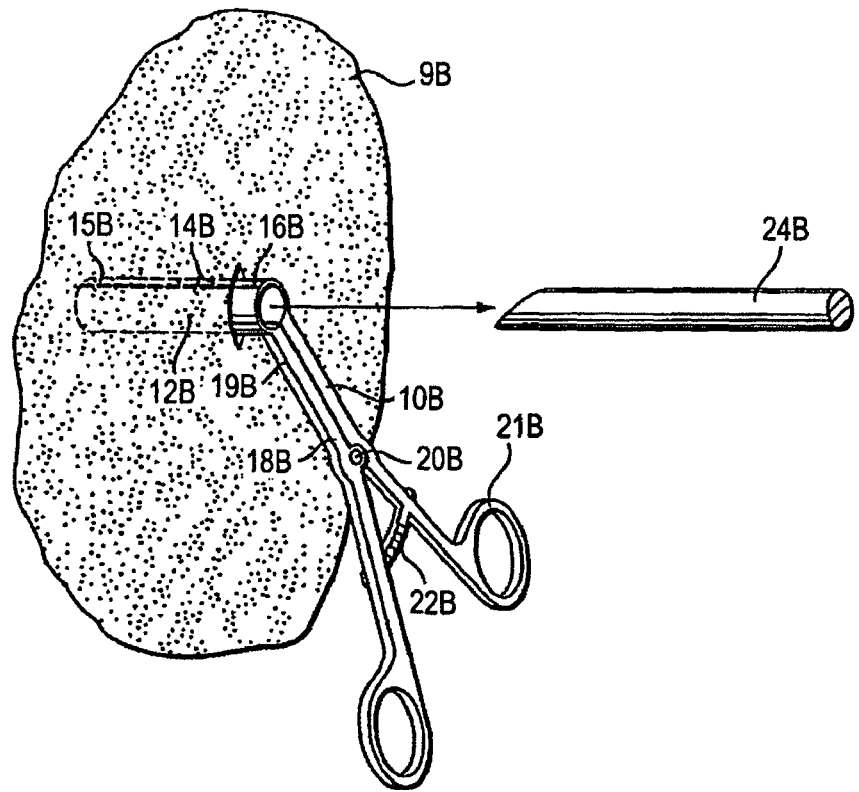
FIG. 101c depicts the withdrawal of the needle of FIG. 101a and further insertion of the dilator of FIG. 101b.
Figure 101D:
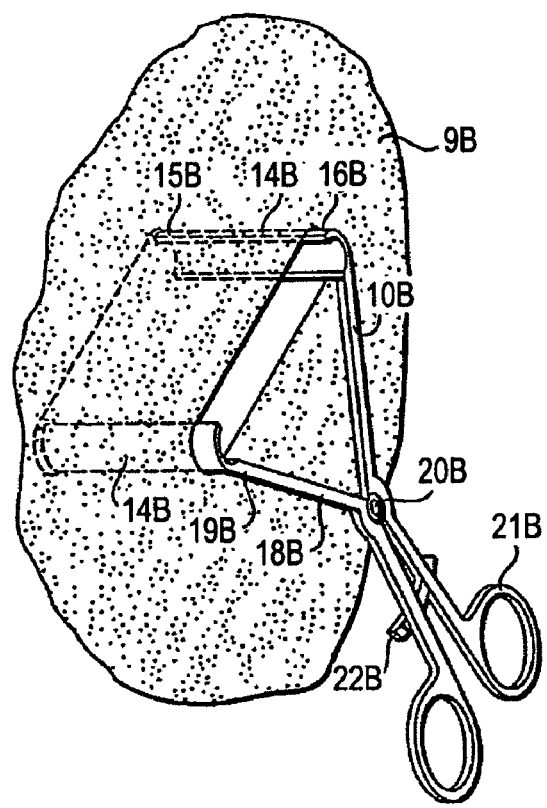
FIG. 101d represents the dilator of FIG. 101c in the open position.

The spreader 12B has an open position in which the spreader guides 14B are separated from each other, as in FIG. 101d, as well as a closed position in which the spreader guides 14B are closely aligned, substantially forming a cylinder, as in FIG. 101c. The preferred separation of the spreader guides 14B in the open position is approximately 2.5 to 4 cm.

The spreader guides 14B are substantially parallel to each other whether the spreader 12B is in the open or closed position, or is moving from one position to another. The spreader guides 14B have a distal end 15B and a proximal end 16B, the distal end 15B being for insertion into the tissue 9B, and the proximal end 16B being for attachment to the handles 18B. In a preferred embodiment of this invention, the spreader guides 14B are sharpened at the distal end 15B, to facilitate entry into a tissue 9B and passage therethrough. The distal ends 15B of the spreader guides 14B also may be shaped to cooperate with a needle 24B, which may be inserted first into the tissue 9B (see FIG. 101a) before insertion of the spreader guides 14B, to provide a path for the spreader guides 14B to follow into the tissue 9B as they are inserted over the needle 24B (FIG. 101b).

The handles 18B of the dilator 10B have first 19B and second 21B ends. The first end 19B of each handle 18B is connected to the proximal end 16B of each guide. The second end 21B of each handle 18B is adapted for a physician to grasp and manipulate the handles 18B. The handles 18B are joined at a pivot 20B and may be moved about the pivot 20B relative to one another, in such a way that movement of the handles 18B translates to displacement of the spreader guides 14B relative to one another. In a preferred embodiment of the invention, a ratcheting lock 22B is also part of the handles 18B, and provides a mechanism for the handles 18B to be locked into a particular position, thus also locking the spreader 12B in a particular position.

This aspect of the invention provides a method for creating a cavity in a tissue 9B. The needle 24B is optionally first inserted into the tissue 9B as in FIG. 101a. The spreader guides 14B of the spreader 12B are placed in a closed position and are inserted into the tissue 9B over the needle 24B (FIG. 101b) or directly into the tissue 9B. The needle 24B, is used, is then withdrawn (FIG. 101c). When the spreader guides 14B are inserted to the desired depth, the handles 18B of the dilator 10B are moved together, as shown in FIG. 101d. This causes a separation of the spreader guides 14B until the dilator 10B is in the open position. The movement of the spreader guides 14B away from each other toward the open position creates a cavity in the tissue 9B.

In a preferred embodiment of the method of this invention, the tissue 9B is the vaginal hiatus 2B. In some cases, the practice of this method may be facilitated with the additional step of performing an episiotomy on the skin of the vaginal hiatus 2B. In an alternative embodiment, this method may be practiced on a tissue 9B of the vaginal wall 8B, for example the upper vaginal wall, to create a cavity between the vagina 4B and the urethra. Also contemplated in this invention is the practice of this method in any tissue 9B wherein it may be advantageous to simultaneously create a cavity and provide guide tracks for placement of a medical device within the cavity.

An additional preferred embodiment of the method of the invention has as a first step the insertion of a needle 24B into the target tissue 9B, such as the vaginal hiatus 2B or vaginal wall 8B, as in FIG. 101a. The needle 24B may be calibrated or otherwise marked to indicate the depth of its insertion, to allow a physician to accurately determine the proximity of the tip of the needle 24B to an internal structure, such as the bladder neck 47B. In addition to a determination of the depth of penetration, the needle 24B may also provide a path for simplified insertion of the spreader 12B of the invention.

Using an embodiment of the dilator 10B wherein the distal ends 15B of the guides 14B are adapted for cooperating with a needle 24B, the spreader 12B is moved to the open position, and the spreader 12B spreader guides 14B are placed near the needle 24B, then the spreader 12B is moved to the closed position. In the closed position the spreader guides 14B, at least at their distal ends 15B, substantially conform to the shape of the needle 24B and may follow its path into the tissue 9B, as in FIG. 101b. The spreader guide 14B is then inserted to the desired depth, at which point the needle 24B may be withdrawn, as in FIG. 101c. Then, as before, the handles 18B are moved closer together, thus moving the spreader guides 14B away from each other to the open position (FIG. 101d).

The ratcheting lock 22B portion of the handles 18B holds the handles 18B together and the spreader guides 14B apart. Movement of the spreader guides 14B to the open position creates the cavity desired for insertion of a medical device, or for performing a desired surgical procedure.

As an alternative embodiment of this method, an additional step may be preformed to facilitate creation of the cavity. In this embodiment, the target tissue 9B is fluid-dissected by injecting a solution into the tissue 9B prior to advancing the insertion spreader 12B into the tissue 9B. This additional step of hydro-dissection may be preformed using a variety of physiologically suitable buffers or solutions. This additional step provides an advantage in some cases, because hydro-dissection may be tissue-selective with respect to the vaginal hiatus 2B and the urethra. That is, hydro-dissection may tend to preferentially dissect hiatal tissue without impinging upon urethral or bladder tissue. Accordingly, a first step of hydro-dissection that creates a saline bolus, may predissect the tissue without affecting the integrity of the urethra. The subsequent step of passing the insertion spreader 12B into the tissue is therefore simplified, and the movement of the spreader guides 14B into the open position is also simplified, because a substantial portion of the cavity is already created by the process of hydro-dissection.

In one method of hydro-dissection and subsequent cavity opening with use of the dilator 10B, a needle is inserted into the upper vaginal wall 8B and the saline solution is delivered into the deep tissue of the vaginal hiatus 2B. The deep tissue of the vaginal hiatus 2B is thereby dissected by the injected solution. Subsequent insertion of the spreader 12B through the external skin of the vaginal hiatus 2B provides a route of entry that is less susceptible of infection than may be the case where a tissue cavity is created entirely transvaginally. Because the interior of the vagina 4B harbors more microorganisms than the surface of the vaginal hiatus 2B, and is also much more difficult to surface sterilize, the exterior vaginal hiatus 2B may often be the preferred route of entry for creating a tissue cavity for urethral and pelvic floor reconstruction. However, certain circumstances may dictate creation of a tissue cavity transvaginally; the dilator 10B of the invention and the methods of its use are fully adaptable to creation of a cavity transvaginally. Thus, the present invention provides a surgeon with a convenient means of opening a tissue cavity and with alternative avenues of entry to the tissue cavity. Additional devices and methods for transvaginal urethral or pelvic floor reconstruction and urethral or bladder neck stabilization or suspension, suitable for use in connection with the present invention, are disclosed in U.S. patent application Ser. No. 08/744,439 entitled "Transvaginal Anchor Implantation Device," filed on Nov. 8, 1996, now issued U.S. Pat. No. 6,053,935, the disclosure of which is incorporated herein by reference.

Figure 101E:
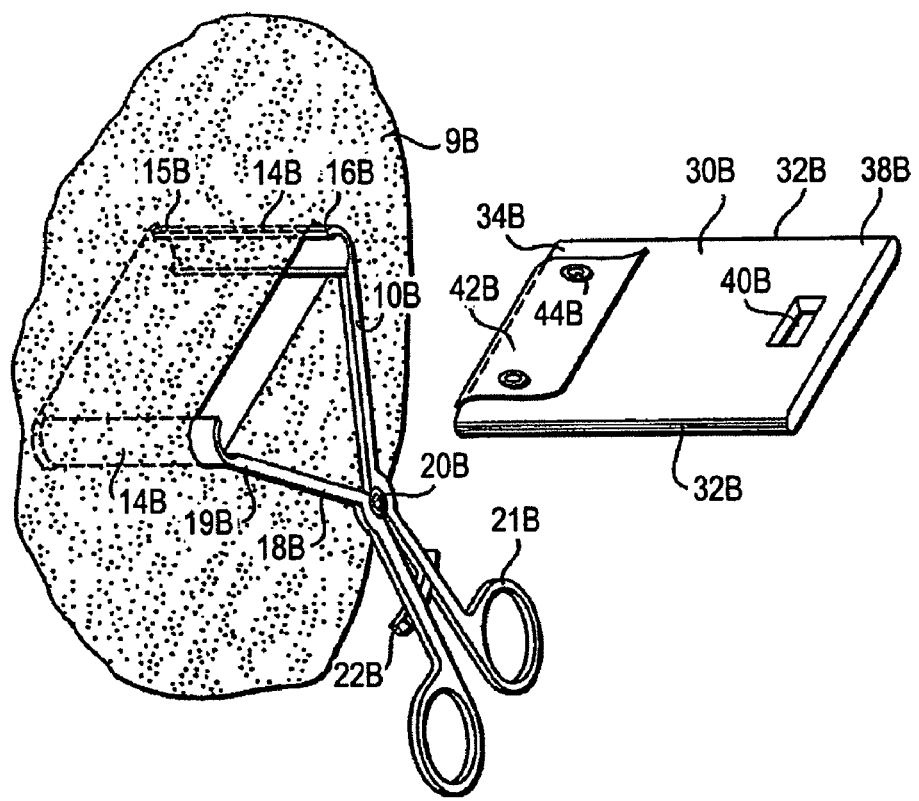
FIG. 101e illustrates the alignment of the insert card with the guides of the dilator of FIG. 101d.

Another aspect of the present invention is a card 30B for advancing a medical device into a tissue cavity as shown in FIG. 101e. The card 30B has lateral edges 32B, a distal portion 34B, and a proximal portion 38B. A part of the proximal portion 38B, the articulation opening 40B, may be adapted for articulation with additional devices that may be useful in positioning or stabilizing the card 30B in certain methods of use. The distal portion 34B of the card 30B is adapted for carrying a medical device into a tissue cavity. In one embodiment of the invention the medical device is a urethral sling 42B. The card 30B enables sling 42B manipulation without touching the sling 42B. This reduces contamination, and establishes the sling 42B position within the body and relative to other devices that may be used in positioning and securing the sling 42B. The lateral edges 32B of the insert card 30B may be specially adapted to articulate with spreader guides 14B that provide a path into the tissue cavity, such as the spreader guides 14B of dilator 10B. The distal portion 34B of the card 30B is inserted into the cavity by aligning it with the proximal ends 16B of the spreader guides 14B. Once the card 30B is thus aligned, the edges 32B of the card 30B easily slide along the semi-cylindrical spreader guides 14B into the cavity until reaching the proper depth in the cavity.

The card 30B and dilator 10B of the invention thus may be used in a method for inserting a medical device into a tissue cavity. In a preferred embodiment of this invention, the medical device is a sling 42B. Other medical devices that may be positioned with use of the card 30B include pharmaceutical implants, therapeutic devices, closures, staples and clips. In the preferred method, a urethral sling 42B is placed at the distal region of the insert card 30B. A cavity is formed in a target tissue 9B as described above. Briefly, the spreader 12B is placed in a closed position and the spreader guides 14B are positioned against the surface of the target tissue 9B. The spreader 12B is inserted into the target tissue 9B and is then moved to the open position by moving the handles 18B of the dilator 10B together. The spreader 12B is held in the open position by the ratcheting lock 22B. With the sling 42B on the card 30B and the cavity opened, the card edges 32B are aligned with the semi-cylindrical spreader guides 14B of the dilator 10B and the card 30B is inserted into the cavity until it reaches the desired depth. The card 30B is manipulated by its proximal portion 38B, and may be manipulated by means of an accessory tool contacting the card 30B at the articulation opening 40B.

There are several advantages to this method of the invention. One advantage is that the medical device can be placed without excessive contact between the device and the patient. Excessive contact between the surgeon and the device also may be avoided, which allows a reduction in handling and a reduced likelihood of contamination. This fact minimizes the risk of infection in the placement of the device. Another advantage is that the card 30B provides support for the device in subsequent steps of attaching the device in place inside the tissue cavity. A further advantage is that the spreader guides 14B provide tracks along which the card 30B may enter, minimizing difficulties and variability in the location of the sling 42B in the desired position.

This method is applicable to cavities made in the vaginal hiatus 2B as well as in the vaginal wall 8B, specifically in the upper vaginal wall. Other uses for this method, involving the placement of a medical device supported on a card 30B with the assistance of the dilator 10B of the invention, will be evident to those of skill in the art.

Figure 101F:
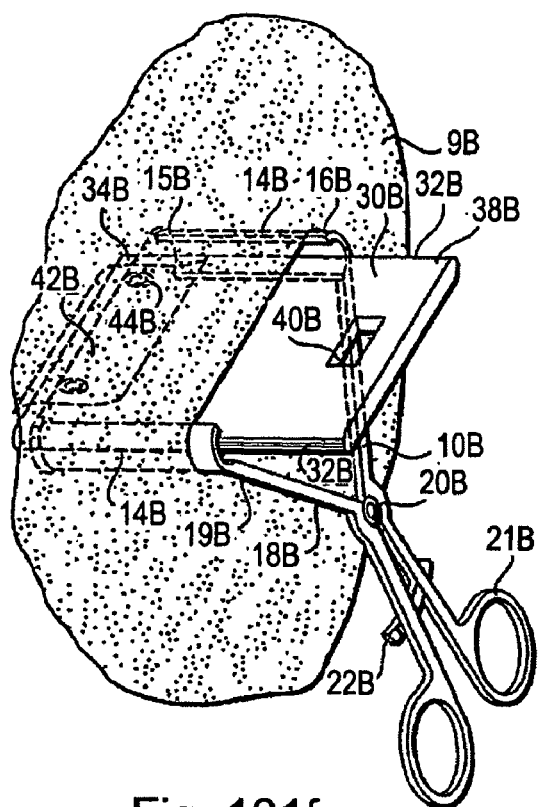
FIG. 101f shows the insertion of the insert card between the guides of the dilator of FIG. 101d.
Figure 101G:
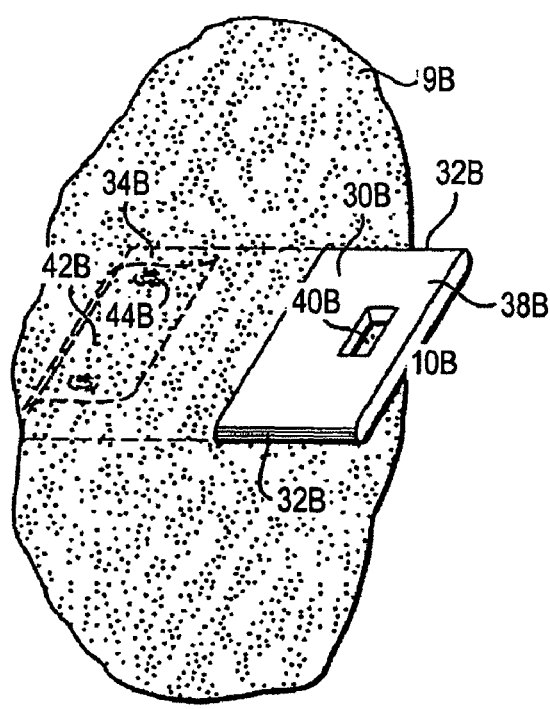
FIG. 101g shows the insert card in position in the hiatus after withdrawal of the dilator.

FIGS. 101e, 101f and 101g show the steps of the method after the cavity is created. In FIG. 101e the card 30B holding the sling 42B is aligned with the spreader guides 14B of the dilator 10B. In FIG. 101f the card 30B is inserted into the cavity by sliding the sides of the card 30B along the semicircular tracks provided by the spreader guides 14B of the dilator 10B. FIG. 101g shows the card 30B in position in the tissue cavity after removal of the dilator 10B. As can been seen in FIG. 101g the proximal portion 38B of the card 30B and the articulation opening 40B remain outside the cavity for continuing or subsequent interaction with accessory tools, such as those which are disclosed below in a discussion of other aspects of this invention.

The placement of the sling 42B or some other medical device by the method of this aspect of the invention preferably precedes the securing of such a medical device inside the tissue cavity. The invention contemplates securing the sling 42B or other medical device in several different ways. In one embodiment the sling 42B may be placed in the cavity to be sutured therein by a suture 88B entering the cavity from the upper vaginal wall 8B. In another embodiment the sling 42B may be stapled or anchored into place subsequent to its positioning with the use of the card 30B. Suturing of the sling 42B into position also may be accomplished percutaneously, or with the suture being advanced from above or through the bone. Additional devices and methods for percutaneous and hiatal approaches for urethral or pelvic floor reconstruction and urethral or bladder neck stabilization or stabilization, suitable for use in connection with the present invention, are disclosed in U.S. Provisional Patent Application No.

60/03817, entitled "Percutaneous and Hiatal Devices and Methods for use in Minimally Invasive Pelvic Surgery" (VESITEC.029PR), filed Feb. 13, 1997, the disclosure of which is incorporated herein by reference.

Preferred methods of securing the sling 42B in place may involve anchoring the sling 42B to a bone via a suture 88B and a bone anchor, or may involve attaching the sling 42B to a suture 88B which passes through a bone, such as the pubic bone. This preferred embodiment of the method of attaching the sling 42B into place after it has been delivered into a tissue cavity by the card 30B of the invention will be discussed below in connection with other aspects of the present invention. It will be evident to those of ordinary skill in that art that the method of this aspect of the invention will be applicable to the positioning of several kinds of medical devices. Such medical devices may be secured into place after their positioning by one of several known techniques.

Another aspect of the invention provides an incision guide 50B (see FIG. 104) for cutting a cavity between the urethra and the vagina 4B, in the hiatal tissue. The incision guide 50B consists of a rigid catheter 52B and a cutter 54B, and may also consist of several other accessories to enhance or vary the performance of the incision guide 50B. The rigid catheter 52B is a modified Foley-type catheter, preferably having a shaft of metal or other rigid material over the surface of the catheter.

The catheter 52B is inserted into the urethra and an integral bladder neck balloon 53B is inflated. (FIG. 102.) The rigid catheter 52B straightens the urethra and extends externally to provide a guide for attachment of devices which advance parallel to the urethra along the central hiatus plane. The balloon 53B holds the catheter 52B in place. Such devices which track along the rigid catheter 52B are used for dissecting the hiatus 2B laterally between the urethra and the upper vaginal wall 8B from the proximal urethra. A number of different methods are contemplated.

The catheter 52B is therefore insertable into the urethra and is adapted for indicating the position of the bladder neck 47B. The rigid catheter 52B functions to expand and straighten the urethra, providing a fixed reference point in the soft tissue of the urethral floor and hiatal plane. This fixed reference function also facilitates a surgeon's determination of the lateral position of the urethra by palpation, or with any of several forms of instrumentation.

Figure 103:
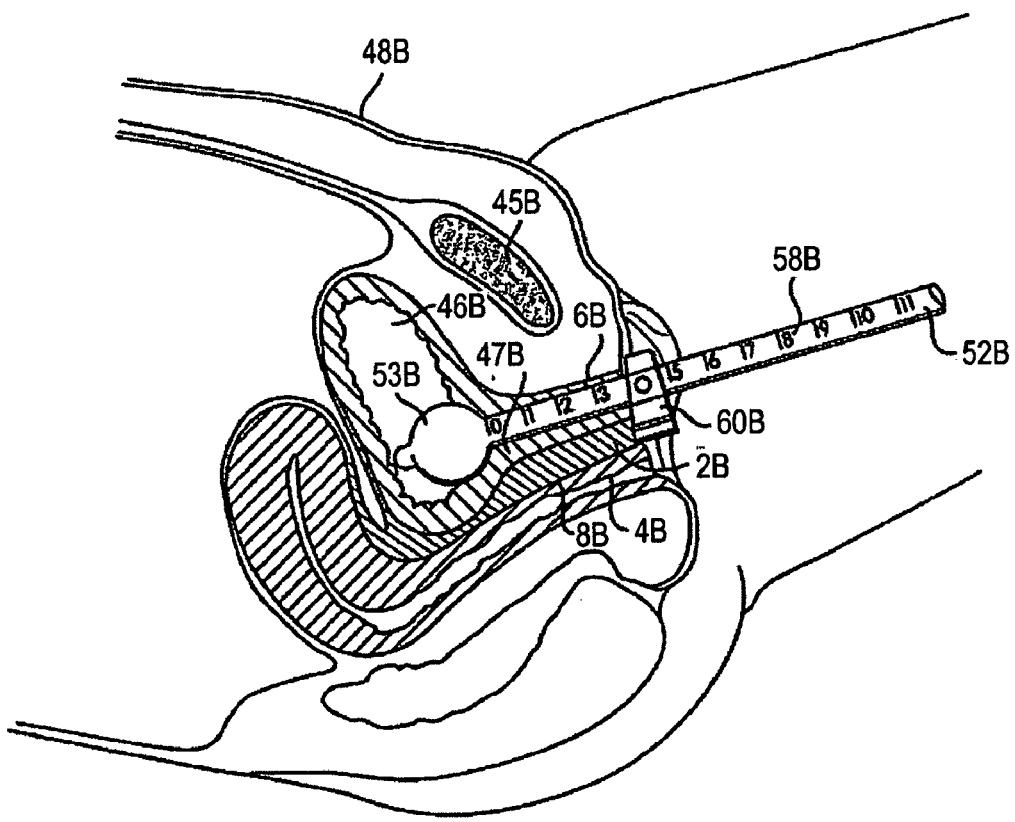
FIG. 103 is a cross section as in FIG. 102, and shows a rigid catheter with the stop attached.
Figure 104:
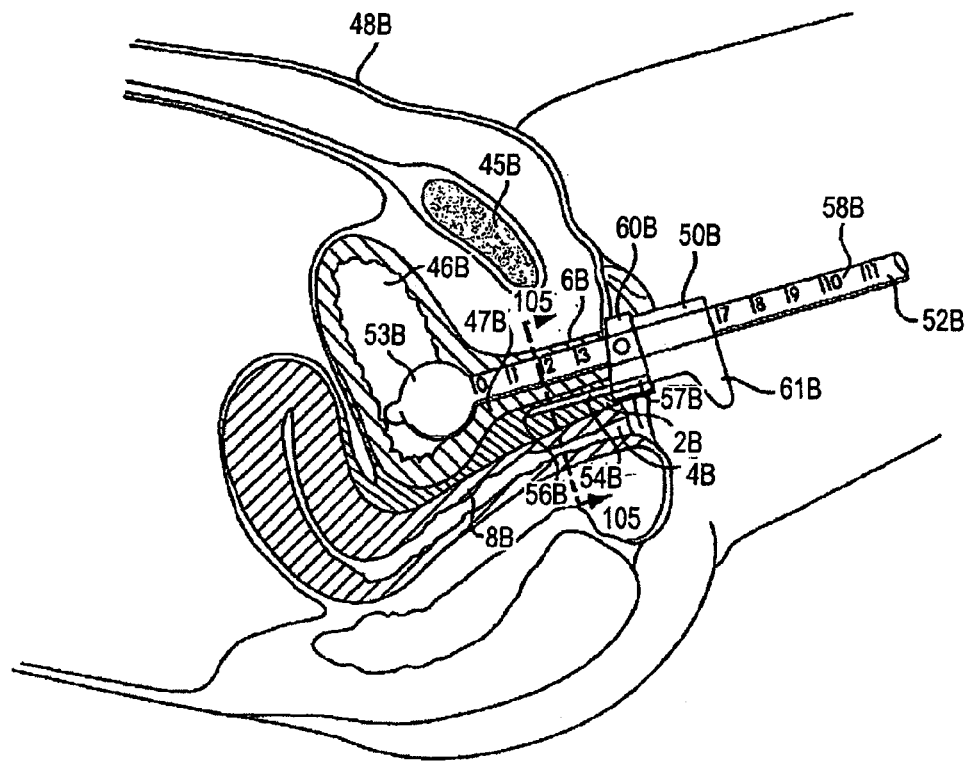
FIG. 104 is a cross section as in FIG. 102, and shows an incision guide assembly with a catheter, stop, and cutter in place.

The catheter 52B is designed to be of sufficient length to reach to the bladder 46B and also to extend outside the body of the patient. The catheter 52B will preferably have graduation marks or other indicia 58B thereon to indicate the distance from the surface of the distal urethra to the bladder neck 47B and the bladder 46B. (FIG. 103.) The catheter 52B, therefore, as it runs from the bladder neck 47B to the distal urethra and beyond, provides access for mounting and guidance of other devices, such as the cutter 54B. (FIG. 104.)

The cutter 54B is used for forming the desired cavity at a position that is a fixed distance from, and therefore parallel to, the urethra. The cutter 54B has a longitudinal axis of similar dimensions to the catheter 52B, and has a cutting end 56B and a connecting end 57B. The cutter 54B is adjustable at its connecting end 57B with the exterior portion of the rigid catheter 52B and can slide along the catheter 52B, thus providing tracking guidance for the cutter 54B. (FIG. 104.)

The manner of attachment between the cutter 54B and catheter 52B will determine the amount of offset between the cavity and the urethra. The preferred distance of offset between the cutter 54B and the catheter 52B is approximately 0.5 cm. This distance would in most patients position the cutter 54B to roughly bisect the distance between the upper vaginal wall 8B and the urethra. Because of the variability in the anatomy of patients, and the other ways in which this approach can be applied, a preferred range of offset may be from 0.25 cm to 0.75 cm. In other embodiments a useful range may be from 0.1 cm to 0.9 cm. Again, because of the variability in patient anatomy, in some cases it may be advantageous to further offset the cutter 54B from the catheter 52B by a distance of 1 cm or more.

Figure 105A:
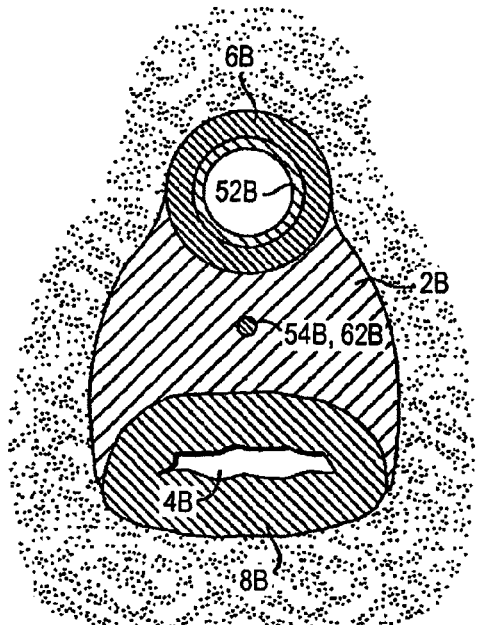
FIG. 105a is a transverse cross section taken along the line 105-105 in FIG. 104 and illustrates the hiatal region of the patient with the catheter in place and the cutter as a needle.
Figure 105B:
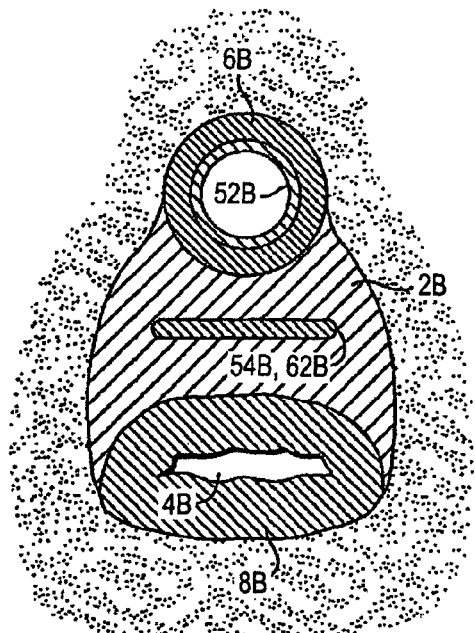
FIG. 105b is a transverse cross section as in FIG. 105a and shows the hiatal region with the catheter in place and the cutter as a blade.

The cutter 54B, being adapted to articulate with and slide along the axis of the catheter 52B, provides a means for creating a cavity in the vaginal hiatus 2B. This cavity is in a predictable and optimally safe plane between the urethra and the upper vaginal wall 8B. The desired dimensions of the cavity may vary widely depending on the anatomy of the patient and the purpose for which the cavity is made. In some cases, a preferred cutter 54B for attachment to the catheter 52B is a needle 62B. (FIG. 105a.) In other cases a preferred cutter 54B is a blade 64B. (FIG. 105b.)

A third preferred cutter 54B is a bipolar knife, providing lateral dissection of the vaginal hiatus 2B that is bloodless, by cutting and coagulating the tissue simultaneously. With use of the bipolar knife, it is preferable to equip the metal portion of the catheter 52B with thermistors along its length, to measure the heat generated by the bipolar knife and provide temperature information to the surgeon. One embodiment of the bipolar knife, also known as the bipolar cutting loop, consists of a pair of wires, one flexible and one rigid, through which a current is passed to heat the loop.

Preferred dimensions of the cavity that is created may be from 1 to 3.5 cm deep and may have a width ranging from the width of a needle 62B to approximately 3.5 cm. The most preferred width for applications in which a sling 42B is to be installed is approximately 2 to 4 cm. The preferred depth of penetration of the cutter 54B is, of course, a function of the particular anatomy of a given patient, and is to be determined by the surgeon after insertion of the rigid catheter 52B and reference to the indicia 58B thereon.

Modified embodiments of the incision guide 50B include the attachment of various other devices to further optimize the control that a surgeon may exercise over the depth and direction of penetration of the cutter 54B device. One such modification is to add one or more stops 60B to the device, as shown in FIG. 104. In one embodiment of this modification, one stop 60B is movably and lockably positioned on the catheter 52B. This stop 60B may have the form of a ring or a block, and may be locked at a particular position of the catheter 52B by means of a thumb screw or a spring snap that articulates with the indicia 58B on the catheter 52B at various positions along its length. The stop 60B slides onto the end of the end of the catheter 52B and may be locked in a certain position on the catheter 52B to prevent advancement of the cutter 54B past the position of the stop 60B. The cutter 54B may also have a block 61B intended to abut the stop 60B that is placed on the catheter 52B. Therefore the cutter 54B which slides along the catheter 52B may attach by means of a stop block 61B, or by other means of attachment that may similarly function as a stop block 61B.

This aspect of the invention provides a method for creating a cavity in the vaginal hiatus 2B. The method begins with insertion into the urethra of the rigid catheter 52B. (FIG. 102.) The preferred catheter 52B is, as discussed above, provided with indicia 58B to indicate the position of the bladder neck 47B. The catheter 52B extends from the distal urethra of the patient, providing a linear guide for the cutter 54B. According to the method, the position of the bladder neck 47B is determined. Next the cutter 54B is positioned on the catheter 52B and is advanced toward the patient along the catheter 52B until the cutter 54B contacts and penetrates the vaginal hiatus 2B. (FIG. 104.) The cutter 54B is then inserted into the vaginal hiatus 2B to a predetermined depth, thus creating a cavity in the vaginal hiatus 2B that does not extend to the bladder neck 47B.

This method allows a surgeon to make an incision into the vaginal hiatus 2B in a way that optimizes the safety, reproducibility, and reliability of the procedure. With a preferred embodiment of the incision guide 50B as discussed above, the depth of insertion may be very precisely controlled, preventing damage to the bladder neck 47B. Likewise, the displacement between the urethra and cutter 54B is maintained constant, thus assuring that creating the cavity will not compromise the urethra or the vaginal wall 8B.

The various embodiments of the incision guide 50B also provide precise control of the width of the incision. For example the incision width may be that of a needle 62B (FIG. 105a) of a selected gauge, or it may be the width of a selected blade 64B (FIG. 105b), or it may be the width determined by the dimensions and orientation of the wires in a bipolar knife. An additional benefit of the method of the invention is that, because the cutter 54B tracks along the rigid catheter 52B, and therefore tracks along the urethra itself, there is a constant lateral relationship between the dimensions of the pocket and the position of the urethra. This assures that the cavity will have the dimensions, orientation, and position to optimize placement of a device within the cavity.

The depth of incision and the distance of offset between the urethra and the cavity thus created is determined by the dimensions of the attachment block 61B between the cutter 54B and the rigid catheter 52B. (FIG. 104.) In a preferred embodiment of the invention, wherein the rigid catheter 52B has attached thereto a stop 60B, the stop 60B may be precisely positioned to prevent the advancing of the cutter 54B to a depth that would create a risk of damaging structures of the bladder 46B.

Where the rigid catheter 52B is also equipped with thermistors, providing temperature feedback for safe use of the bipolar knife, an incision may be made rapidly and bloodlessly. Because of the potential damage caused by a bipolar knife in tissue close to critical structures such as the bladder 46B and urethra, many physicians would ordinarily hesitate to make incisions with such an instrument. However, this concern is addressed through the use of the present method because the orientation of the cutter 54B and the catheter 52B provides very precise control over the offset between the cutter 54B and the catheter 52B as well as over the depth of penetration of the cutter 54B.

The incision guide 50B may be combined with the insert card 30B to provide a method for inserting a medical device into a cavity. In this method a tissue cavity is created according to the steps of the method provided immediately above, and a card 30B supporting a medical device is inserted into the cavity. The medical device may be a pharmacologically active implant, a prosthetic balloon, or a therapeutic device. In a preferred embodiment of this method, the medical device is a urethral sling 42B, as in FIG. 101e. After the cavity is created with use of the incision guide 50B, the card 30B may be inserted directly into the cavity, depending on the dimensions of the card 30B and the cavity. The medical device may be secured within the cavity by a variety of means, after which the card 30B may be withdrawn. Alternatively the card 30B may be withdrawn before the device is secured.

An additional embodiment of the method of the invention combines use of the dilator 10B of the invention together with the incision guide 50B and the card 30B. A cavity is created with use of the incision guide 50B, as explained above, and then the cavity is stabilized and further defined by insertion of the spreader 12B, which is then moved to the open position, as in FIG. 101d. With the spreader 12B in the open position, the cavity may be stretched, if necessary. The cavity is also provided with tracks along which the card 30B may easily slide to enter the cavity, as in FIGS. 101e and 101f. Thus, the invention contemplates the use of the devices of the invention alone or in combination, in order to achieve the desired result.

With reference to FIGS. 106, 107, 108 and 109 in another aspect, the present invention provides a driver 70B for driving a bone-piercing guide 84B through the pubic bone. Originally, passing a suture 88B through the pubic bone was done by drilling a hole through the generally anterior portion of the pubic bone using a drill guide attached to a stabilizer and vaginal retractor device.

A suture 88B was then passed through the drilled hole with a suture passer. The present invention does not require the use of a drill and is capable of creating small passages through the pubic bone, sufficient to allow passage of a suture 88B through the bone. The pubic bone is particularly well suited for this adaptation because it is relatively easily pierced, due to its low density.

Figure 106:
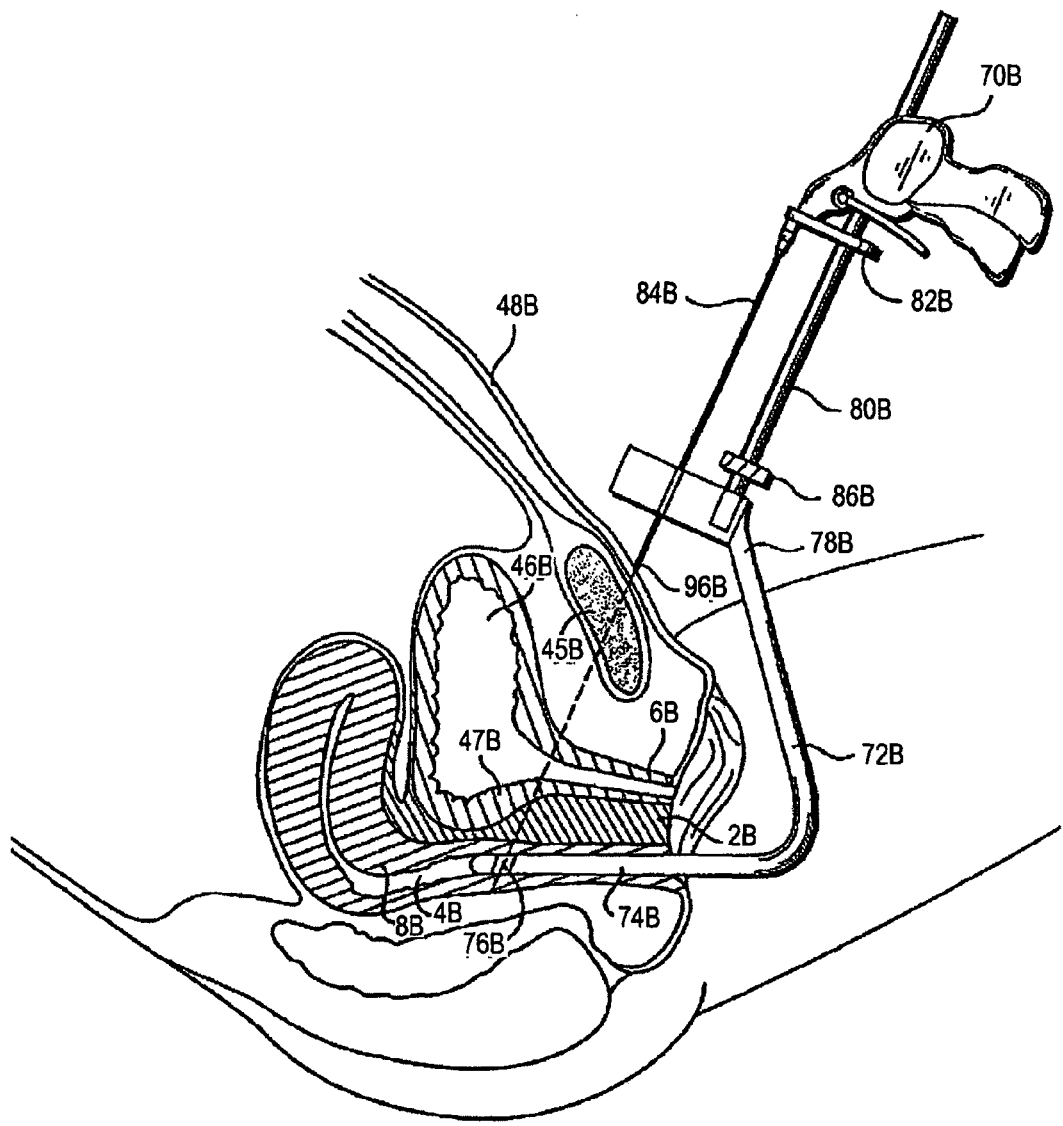
FIG. 106 is a cross section view of the pelvis as in FIG. 102 with the driver positioned above the pubic bone.

The driver 70B of the invention may be described as having four basic parts: a first jaw 72B, a slide bar 80B, a second jaw 82B, and a bone-piercing guide 84B. (FIG. 106.) The first jaw 72B has a distal end 74B and a proximal end 78B. The distal end 74B is adapted for inserting into a tissue cavity and the proximal end 78B of the first jaw 72B is attached to the slide bar 80B. The slide bar 80B connects the first or fixed jaw 72B with the second or moveable jaw 82B. The second jaw 82B slides along the slide bar 80B, with a releasable ratcheting action, toward the first jaw 72B. The bone-piercing guide 84B attaches to the second jaw 82B, and advances toward the first jaw 72B as the second jaw 82B is ratcheted along the slide bar 80B.

Figure 107:
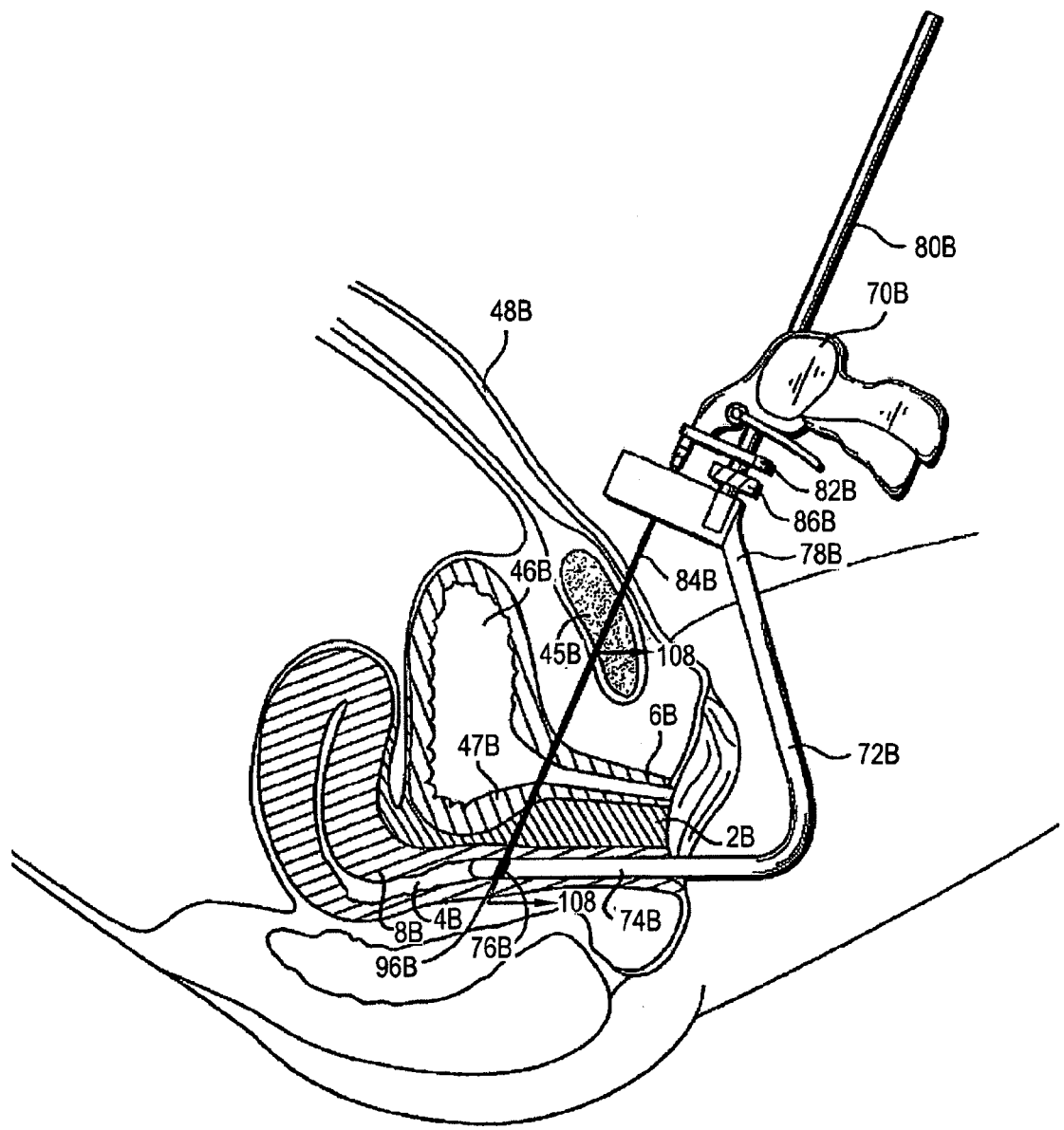

A stop 86B on the slide bar 80B prevents further closing of the jaws once the sharp end 96B of the cannula 90B exits the bone and is even with the first jaw 72B. The first jaw 72B has a slot 76B so that the sharp end 96B of the cannula 90B does not actually contact it when exiting the bone. (FIG. 107.) The driver 70B may be equipped with a double cannula jaw 82B (not shown) so that parallel passages may be created through the bone simultaneously.

It is the function of the first or fixed jaw 72B inside a tissue cavity to provide a counterpressure on the bone opposite the pressure applied by the bone-piercing guide 84B. Accordingly, the distal end 74B of the first jaw 72B may have a shape adapted to provide positions that can appress the inferior region of the pubic bone 45B lateral to the pubic symphysis without crushing the urethra 6B. Such a configuration of the distal end 74B of the first jaw 72B is shown in cross section in FIGS. 123a and b, 125a and b, and 126a; a detail view of a portion of the edge of the distal end 74B of the first jaw 72B is shown in FIG. 124. In these figures, the distal end 74B comprises a tongue 114B with a central depression 136B and elevated edges 138B. The edges 138B may have contact pins 140B adapted for piercing the tissue lying between the pubic bone 45B and the elevated edge 138B of the tongue 114B. At the elevated edge 138B there also may be a gap 144B through which a guide 84B may pass without contacting the tongue 114B. Any device with opposing jaws having one jaw adapted for insertion into a tissue cavity may preferably have a tongue configuration as described above. The choice of a desirable configuration of the distal end 74B of the first jaw 72B may be determined by one of ordinary skill in the art, taking into account anatomical considerations, the particular procedure involved, and the like.

The pubic bone is an especially important structure for piercing in surgical applications. This is true for at least two reasons: the first is that there are soft tissue structures in the proximity of the pubic bone whose dimension or displacement can result in several medical problems. The second reason is that the pubic bone is a relatively low density bone and therefore may be pierced without the application of undue force, if the force is properly oriented. The fact that the pubic bone may be pierced creates the possibility of stabilizing a soft tissue structure near the pubic bone by attaching a device or a suture to the soft tissue structure and stabilizing it by attachment to the relatively immovable pubic bone. In addition, by piercing through the bone, the suture locking and tissue securing method may be accomplished from the superior/anterior bone surface, which is much more accessible than the posterior/inferior surface. The prior need to work near or at the posterior/inferior surface of the pubic bone arose from the proximity of this surface to the structures most often sought to be stabilized. With the methods and devices of the present invention, however, passage of suture through the pubic bone combines the desired proximity to structures beneath the bone, with the convenience and simplicity of introducing and securing suture through the upper surface of the bone. Therefore the bone driver 70B of the present invention provides a device of potentially wide applicability for stabilizing structures of the pelvis, particularly in reconstruction and stabilization of the urethral and pelvic floor.

Alternative approaches to stabilizing structures of the urethral and pelvic floor or other soft structures of the pelvis by attachment to a fixed reference tissue have relied on drilling a hole into the surface of a bone and placing into the hole a bone anchor to which a suture is attached. The difference between such approaches and the present approach is that the present invention allows a much smaller opening to be made. This opening traverses the bone rather than being simply on the surface of the bone. Through this much smaller passage may be passed a suture, without the need of a bone anchor. As used herein, a bone anchor is a device that attaches a suture to the surface of a bone, wherein the suture thus attached does not pass through the bone. The present invention provides devices for connecting sutures to the bone, wherein the sutures have passed through the bone. This is the basis for the distinction, made in this specification, between "bone suture fasteners" and "bone anchors."

A preferred embodiment of the driver 70B of the present invention provides a first jaw 72B, whose distal end 74B is adapted for insertion into the vagina 4B. (FIG. 107.) An alternative embodiment provides a jaw 72B whose distal end 74B is adapted for insertion into a cavity created in the vaginal hiatus 2B as discussed above. A further embodiment may provide a first jaw 72B whose distal end 74B is adapted for insertion into a transvaginally created cavity in the hiatal plane.

As alternative embodiments to the preferred ratcheting motion of the second jaw 82B toward the first jaw 72B, the jaws also may be brought together by various other mechanical advancing means, such as a threaded bar, in combination with a thumb screw. The bone-piercing guide 84B may be hollow or solid; examples of bone-piercing guides 84B may be a needle, a cannula, or a solid rod. The guide 84B also may be a cannula with a removable obturator, so that the guide 84B behaves essentially as a solid rod while piercing the bone, but then can be converted to a hollow configuration for passing various devices along the lumen thereof. A preferred cannula size is believed to be approximately 14 gage. In a preferred embodiment the guide 84B is sharpened and relatively stiff, thus minimizing the possibility that the guide 84B will bend or skim along the surface of the bone, and increasing the tendency of the guide 84B to pierce directly into the bone along a straight line between the first jaw 72B and the second jaw 82B.

An advantage of the bone-piercing guide driver 70B is that the device does not require that a hole be drilled through the bone. The passage remains open and completely accessible until the cannula 90B is removed, whereas the drilled hole is often lost once the drill bit is removed. Also, the drill requires additional incisions on both sides of the pubic bone to expose the bone, otherwise tissue is twisted around the drill as it turns.

The driver 70B of this aspect of the invention may be used by itself or in combination with devices of other aspects of the invention. Accordingly, the driver 70B may be used in connection with the dilator 10B, for example, by creating a tissue cavity with the dilator 10B and then placing the first jaw 72B of the driver 70B in the tissue cavity created by the dilator 10B. Likewise a tissue cavity may be created by the incision guide 50B and the first jaw 72B of the driver 70B may be placed inside the cavity thus created. Furthermore, the insert card 30B, capable of introducing into a cavity a medical device, also may be used in connection with the driver 70B of the invention. In this particular combination the first jaw 72B of the driver 70B may be configured to support the card 30B or connect with the articulation opening 40B of the card 30B such that introduction of the first jaw 72B into the tissue cavity places the device in the appropriate position within the cavity. Subsequent operation of the driver 70B directly positions the bone-piercing guide 84B in the proper orientation with respect to the device supported on the card 30B. Therefore, use of the driver 70B in combination with devices of other aspects of the present invention may result in several beneficial methods for surgery on the urethral floor and other structures of the pelvis.

This method creates a path through the pubic bone, which path is useful for passing sutures 88B or medical devices through the pubic bone. There are several alternative embodiments of this method. In one embodiment the guide 84B is passed through the bone to create a path through the bone and then the guide 84B is removed, leaving the path in the bone and in the tissue. After removal of the guide 84B, medical devices such as a suture 88B, a suture passer, or a suture securing device 126B may be passed along the path through the bone that was created by the bone-piercing guide 84B. Any device capable of passing a suture through tissue may be used in accordance with the present invention, including the suture passers and methods of their use, disclosed in U.S. patent application Ser. No. 08/042,739, filed Apr. 5, 1993, entitled "Bladder Neck Suspension Procedure," now issued U.S. Pat. No. 5,611,515, the disclosure of which is incorporated herein by reference.

The driver 70B of the invention also may be used in a different orientation such that the movable jaw is adapted for insertion into a tissue cavity and for driving a device into the pubic bone from the posterior-inferior surface. As an example of a preferred embodiment, a sling 42B with pre-attached push-in bone anchors (not shown) is positioned on an insert card 30B and is placed into a tissue cavity with the assistance of the dilator 10B or the incision guide 50B of the invention, or by using both in combination. Next, the push-in anchors are oriented to face and contact the pubic bone. Finally, the movable jaw of the driver 70B is placed below the push-in anchors of the sling 42B and the fixed jaw of the driver 70B is placed against the patient's abdominal surface such that the pubic bone lies between the fixed jaw and the movable jaw. The movable jaw is then advanced toward the fixed jaw such that the push-in bone anchors are driven into the posterior-inferior surface of the pubic bone and the sling 42B is secured in place.

Other means of securing a sling 42B in place by using push-in type bone anchors are also contemplated in the invention. For example, a pivoting or otherwise manipulable tongue or insert card 30B that supports and positions the sling 42B may be forcefully angled against the pubic bone sufficient to drive into the pubic bone the push-in type anchors from the posterior-inferior surface of the bone. In another embodiment, cannulas 90B are driven through the bone, both left and right of the midline, such that a path into the pubic bone is provided for initial guidance of push-in anchors. As the cannulas 90B on either side of the midline are withdrawn from the pubic bone, the push-in anchors (not shown) are pressed upward against the bone and initially follow the path of the cannulas 90B. Thus, a guide hole is created by the cannulas 90B for the anchors. The application of additional upward pressure seats the anchors and the sling 42B is secured in place.

Figure 108A:
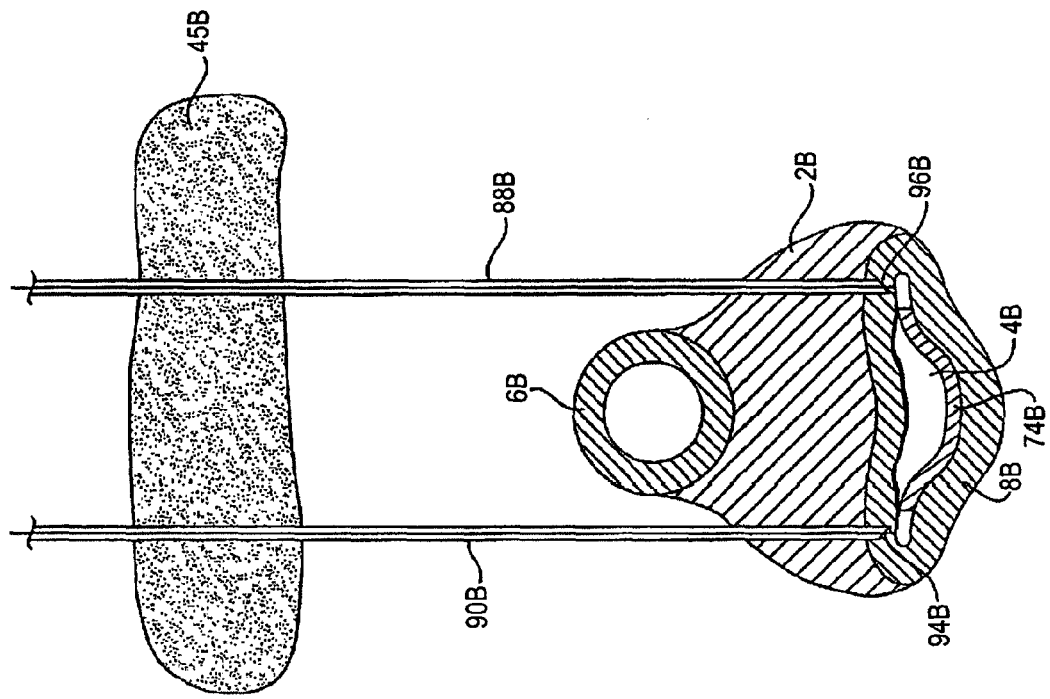
Figure 108B:
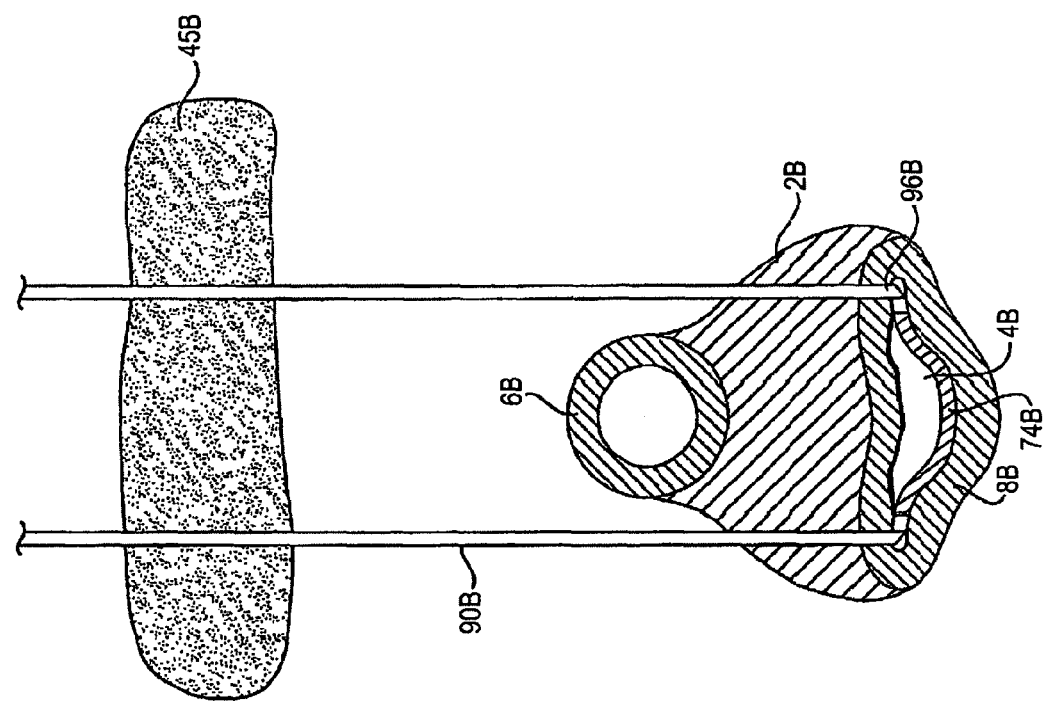

A preferred embodiment of the invention uses a cannula 90B as the bone-piercing guide 84B. (FIG. 108a.) The lumen of the cannula 90B constitutes a path through the tissue and through the pubic bone. Accordingly, the path through the lumen of the cannula 90B allows passage of sutures 88B or other devices through the bone without the difficulty of locating the path through the bone. (FIG. 108b.) In this method a cannula 90B (FIG. 108a) is attached to the driver 70B, as shown in FIG. 107, and the first jaw 72B of the driver 70B is placed inside the tissue cavity, the pubic bone is located and the driver 70B is positioned to align the pubic bone between the first jaw 72B and the second jaw 82B. The second jaw 82B is then advanced toward the first jaw 72B, pushing the cannula 90B through the pubic bone and through the soft tissue on either side of the pubic bone. Subsequently, a suture 88B is passed through the cannula 90B and into the cavity.

Depending on the internal diameter of the cannula 90B, other devices also may be passed inside the lumen. For example, devices such as a suture passer, a quick connect device, and the like, may be passed through a cannula 90B of sufficient internal diameter. In a preferred embodiment, the cannula 90B has a sharpened tip 96B, and has a relatively high degree of stiffness.

Figure 109B:
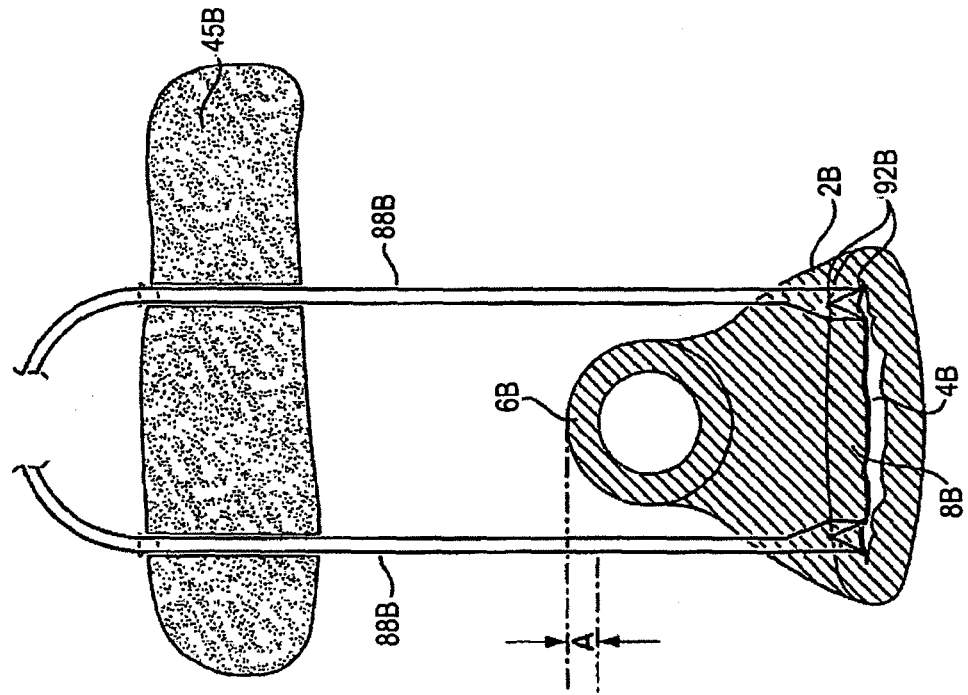
Figure 109A:
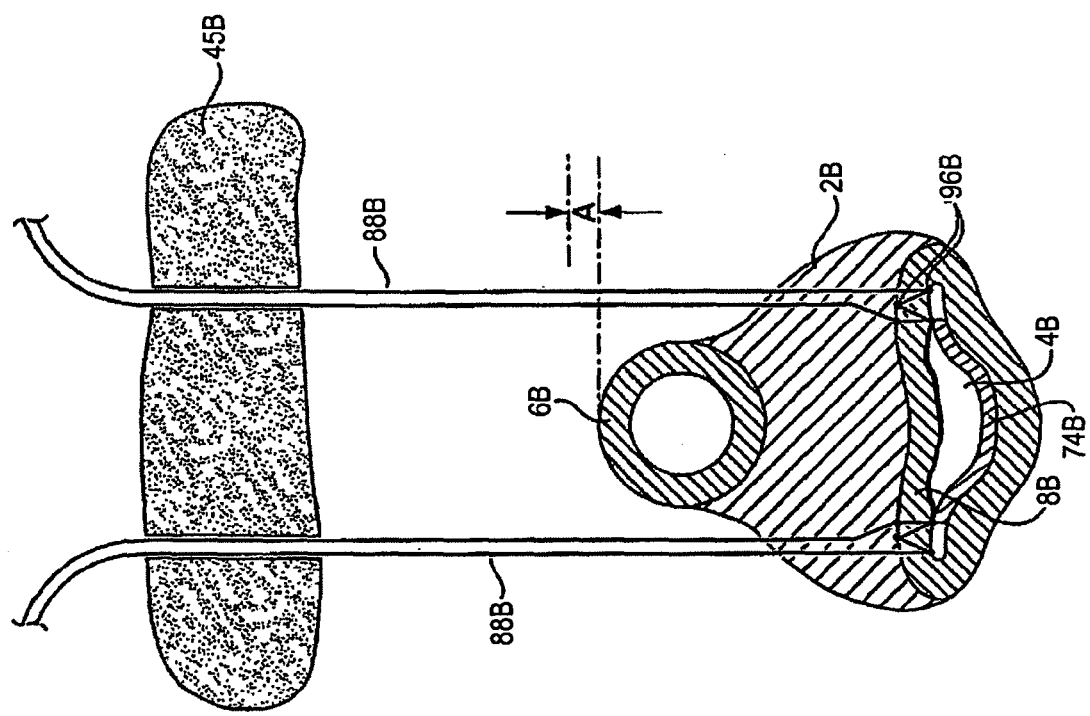

This aspect of the invention provides a method of pelvic surgery that uses the driver 70B of the invention wherein the guide 84B of the driver 70B is a cannula 90B. The first jaw 72B of the driver 70B is inserted into the tissue cavity, and the pubic bone is located. The driver 70B is positioned to align the pubic bone between the first jaw 72B of the driver 70B and the second jaw 82B of the driver 70B. The second jaw 82B is advanced toward the first jaw 72B, forcing the cannula 90B into the tissue and through the pubic bone. After the cannula 90B passes through the pubic bone it is further advanced along the same line into the cavity, approaching the first jaw 72B of the driver 70B. Alternatively, a first cannula 90B can be used to pierce the pubic bone, and a second cannula 90B may be passed within the lumen of the first cannula 90B to its final position on either side of the urethra. A suture 88B is then passed into the lumen of the cannula 90B and is advanced through the cannula 90B until it enters the tissue cavity. The end of the suture 88B that is in the tissue cavity is secured there and the second end of the suture 88B is secured to the pubic bone. The attachment thus created between the pubic bone and the tissue cavity stabilizes the tissue cavity and structures nearby. (FIG. 109b.)

There exist several alternative embodiments of the method of this aspect of the invention. In one embodiment, the cannula 90B is removed after the first end of the suture 88B passes through the cannula 90B and into the cavity. The cannula 90B is therefore withdrawn, leaving both ends of the suture 88B on opposite sides of the pubic bone prior to the attachment of either end of the suture 88B in its place. In another embodiment of this method, the suture 88B is attached within the cavity and then the cannula 90B is withdrawn, followed by the attachment of the second end of the suture 88B to the bone.

The mode of and purpose for attachment of the suture 88B within the cavity is variable, and the factors affecting the selection of the mode will be appreciated by one of ordinary skill in the art. For example, the suture 88B may be affixed in the cavity with one or more stitches 92B (FIG. 109a) to tissue therein. Alternatively, the suture 88B may be attached to a device for distribution of pressure across relatively widened area of tissue, such as suture button 94B or a sling 42B. (FIG. 108b.) The suture 88B also may be attached to a staple (not shown) within the cavity, such that the staple anchors the suture 88B, so that appropriate tension on the suture 88B elevates the tissue to which the staple is attached.

Without the use of an additional device, attaching the suture 88B to tissue within the cavity may make possible amelioration of certain incontinence conditions that arise from hypermobility of the urethra or from intrinsic sphincter deficiency. This is done simply by attaching the suture 88B to tissue and then providing an appropriate tension. This tends to elevate the tissue, which therefore elevates the urethra at that position a distance A (compare FIGS. 109a to 109b), eliminating or easing the condition causing urinary incontinence.

An alternative embodiment of this aspect of the invention uses the driver 70B to insert a cannula 90B into the tissue cavity by passing it through the pubic bone as described above. In this embodiment, however, the end of the suture 88B which is advanced through the cannula 90B and into the tissue cavity is passed through a structure 93B within the tissue cavity. It is subsequently passed back out of the cavity and secured to the pubic bone, along with the second end of the suture 88B. In this embodiment of the invention, the structure 93B through which the suture 88B may be passed include a suture button 94B or grid, a sling 42B, and a tissue mass adjacent the cavity (creating stitches 92). The cannula 90B advantageously has a sharpened end 96B and a reinforced stiffness, to facilitate its passage in a straight line through the bone and to minimize skimming along the surface of the bone. Further, for embodiments of this method, the cavity is preferably a cavity in the vaginal hiatus 2B created according to one of the other methods of this invention. The cavity also may be the vagina 4B, or a cavity in the hiatal tissue created transvaginally.

This method is advantageous particularly for the stitching of a tissue mass for stabilization of the urethra floor or other pelvic structures. (FIG. 109.) Because the suture 88B enters and then again exits the tissue cavity, it may be passed through several stitching 92B points in the tissue before it is withdrawn through the cannula 90B and out to the pubic bone. Both ends of the suture 88B may be secured to the pubic bone in a variety of ways, many of which will be explained in detail below.

This method may be advantageously practiced with the additional assistance of a suture passer device. The suture passer is advanced through the cannula 90B and into the tissue cavity upon completion of the desired number of sutured stitches 92B within the cavity, the suture 88B is grasped by the suture passer, and withdrawn through the cannula 90B to properly position it at the surface of the pubic bone for attachment. This method may be preferably used for tensioning, stabilization, or elevation of a tissue mass adjacent to the urethra or adjacent to another soft tissue structure in the pelvis that may be in need of stabilization or reorientation. The fact that the suture 88B is secured to the bone creates a stability for the target tissue mass that is desirable in many cases. It also may be desirable to use this method in securing in a tissue cavity a pharmacological implant, a prosthetic device, or a therapeutic device.

This aspect of the invention provides an additional method for pelvic surgery wherein the driver 70B is used to pass a guide 84B through the pubic bone along a first path, proceeding into the tissue cavity at a first position. A suture 88B is then passed through the cannula 90B into the cavity. The driver 70B is then used to create a second path through the pubic bone, arriving at a second location within the tissue cavity. The suture 88B which was passed along the first path through the pubic bone and into the cavity may then be passed along the second path out of the cavity and through the pubic bone at the second position. Both ends of the suture 88B may then be secured to the pubic bone. In this method, the suture 88B that passes through the cavity may preferably also be passed through a tissue mass of the cavity, a suture button 94B or a grid, or a sling 42B, prior to exiting the cavity along the second path through the pubic bone. Alternatively, by simply passing the suture 88B through the cavity and then tensioning it properly, the suture 88B may serve to elevate the tissue mass and stabilize the structures adjacent thereto.

The invention thus provides several alternatives for stabilizing structures of the urethral floor or other structures of the pelvis by securing the soft tissues to the pubic bone. The methods differ primarily in the paths along which the suture 88B is advanced. However, whether one chooses to advance the suture 88B into the cavity and anchor one end of the suture 88B therein, or to advance the suture 88B into the cavity and return it out of the cavity along one path, or to advance the suture 88B into a cavity along a first path and retract it from the cavity along a second path, all three methods may be adapted to several variations. In all of these methods, the tissue cavity may be the vagina 4B. It also may be a cavity in the hiatal tissue created, for example, either by the dilator 10B or by the incision guide 50B of the present invention as previously described. Alternatively, the cavity may be a cavity created transvaginally by opening a pocket in the hiatal tissue through the upper vaginal wall 8B.

Furthermore, in any of the methods of this aspect of the invention, a preferred embodiment would perform the method on both the right and left side of the midline of the patient, to equally distribute points of attachment on either side of the urethra. Likewise, another preferred embodiment of any of these three methods would involve the additional step of tensioning the suture 88B prior to its attachment to the pubic bone. Suture tensioning may be accomplished in a variety of ways, one of which is with the use of suture tensioning device. This type of device has a handle with which the surgeon can place the device next to the location where the suture 88B will be tied. Attached to the handle is another structure of the suture tensioner around which the suture 88B will be wrapped, and upon which the suture 88B may be tied. The external dimensions of this structure control the degree of slack that the suture 88B retains after the suture 88B is tied. Therefore, based on the linear distance between the bone and the soft tissue sought to be stabilized, as well as the amount of slack needed to achieve a particular objective for a given patient, a suture tensioner with an appropriate diameter will be selected so as to provide the proper amount of tension in the connection between the bone and the soft tissue.

The several methods of passing a suture 88B through one or more paths in the pubic bone may be particularly applied to a method for stabilizing a urethral sling 42B relative to the pubic bone. In this method a cavity is created in the vaginal hiatus 2B. The cavity may preferably be made using the dilator 10B or the incision guide 50B of the present invention, or both in combination. The dimensions of the cavity and the amount of offset from the urethra will be determined according to the size of the sling 42B that is needed, the dimensions of the patient's urethra, and the surgeon's preference. After the cavity is formed, guide 84B is driven through the pubic bone to create a path. This is done by placing the distal end 74B of the first jaw 72B of the driver 70B into the tissue cavity followed by positioning the second jaw 82B of the driver 70B, such that the pubic bone lies in a straight line between the first jaw 72B and second jaw 82B. A urethral sling 42B is placed into the cavity either before or after the cannula 90B is driven through the pubic bone and into the cavity. The sling 42B may be placed into the cavity with the aid of an insert card 30B as discussed above, or by other surgical procedures known in the art. With the cannula 90B in the cavity adjacent the sling 42B, the suture 88B is attached to the sling 42B and to the pubic bone.

This method is embodied in a technique wherein the cannula 90B is withdrawn before the suture 88B is secured on either end. The method also contemplates withdrawal of the cannula 90B after the sling 42B is secured but before the suture 88B is secured to the bone. In addition to attaching the sling 42B with sutures 88B, this method contemplates an indirect attachment of the sling 42B to sutures 88B by directly attaching the sling 42B to devices which are themselves attached to sutures 88B. An example of such an indirect attachment to a suture 88B is a securing device 126B as disclosed herein. This method may advantageously involve use of the devices of other aspects of the present invention. The tissue cavity may be made either by the dilator 10B or the incision guide 50B, or by using both together, and the sling 42B may be delivered to its proper position in the cavity with aid of the insert card 30B as discussed above. Depending on the particular manner in which the insert card 30B articulates with a driver 70B, the cooperative use of the insert card 30B may precisely position the sling 42B. This will cause the bone-piercing guide 84B to meet the sling 42B at the appropriate straight line position as is desirable in this method.

Another aspect of this invention provides a driver frame assembly 100B. The driver frame assembly 100B serves to align, support and stabilize both the patient's pelvis and the devices of the invention in procedures for reconstructing the urethral and pelvic floor or for performing other methods of pelvic surgery. The driver frame assembly 100B has an upper clamp 102B, a rigid catheter 52B, a cavity tongue 114B, a lower clamp 120B, and at least one driver 70B. The upper clamp 102B of the driver frame assembly 100B has a head portion 104B, a descending arm 106B and a base portion 108B. The head portion 104B has a compression foot 110B that is used to compress a patient's abdominal surface against the pubic bone. The compression foot 110B has stabilizing pins 112B that extend downward therefrom and that pierce the patient's skin 48B, penetrating the abdomen at a position adjacent to the superior surface of the pubic bone. The compression foot 110B may be pressed against the abdomen of the patient with, for example, a threaded screwing mechanism, a ratcheting or piston mechanism, or a linkage mechanism. The stabilizing pins 112B are designed to be of a length that makes it impossible for the pins 112B to cause damage to any abdominal or pelvic organs. At the same time the stabilizing pins 112B have dimensions making them sufficiently strong to resist the lateral forces exerted with operation of the driver 70B.

Figure 110:
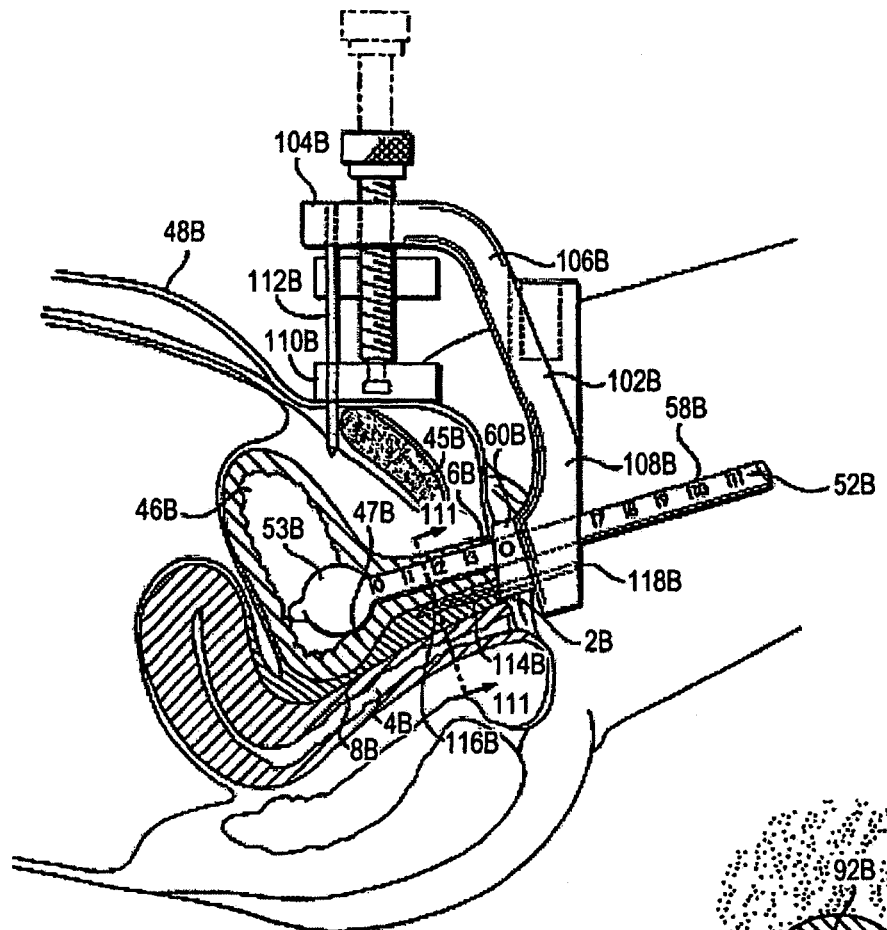

The rigid catheter 52B portion of the driver frame assembly 100B functions much as the rigid catheter 52B of the incision guide 50B, as discussed above. The catheter 52B is intended to straighten and elongate the urethra, as well as to assist in identifying the position of the urethra, the bladder 46B; and bladder neck 47B. The rigid catheter 52B is of sufficient length to extend outward beyond the distal urethra of the patient. This external extension of the rigid catheter 52B provides a structure with which the frame assembly may articulate and attach. (FIG. 110.)

Figure 111A:
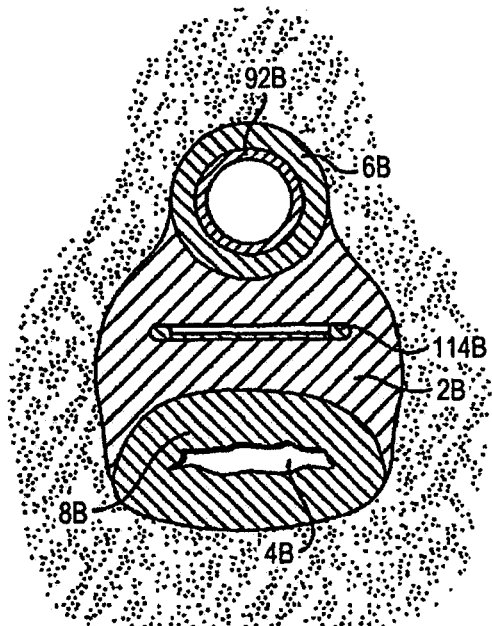
Figure 111B:
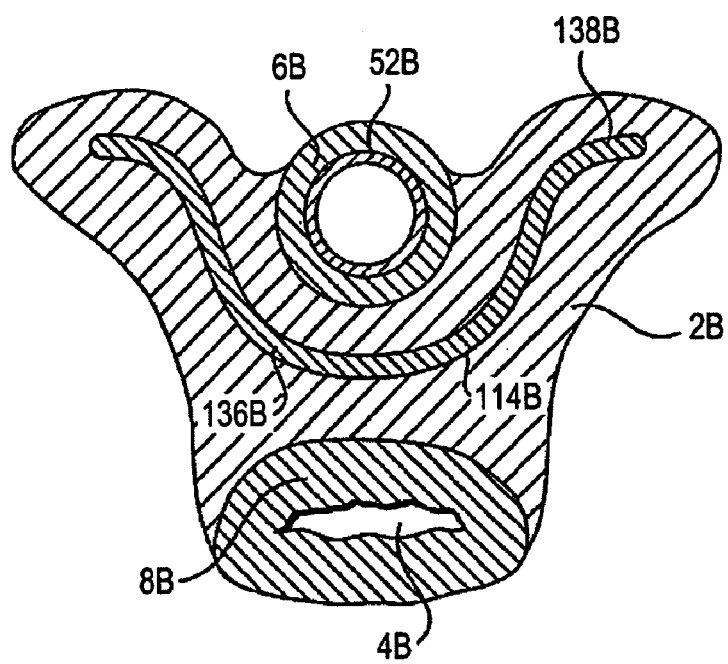

The tongue 114B portion of the driver frame assembly 100B is adapted for insertion into a tissue cavity, such as the vagina 4B or a hiatal cavity prepared prior to insertion of the tongue 114B. In a preferred embodiment, the tongue 114B has a central depression 136B and elevated edges 138B (FIG. 111b), allowing compression of the tongue 114B sides against the inferior surface of the pubic bone to counter the pressure of the compression foot 110B. Because of the shape of the tongue 114B, this type of pressure may be applied without crushing the urethra. The tongue may also have a relatively broad elevated edge 138B contact pins 140B for contacting the pubic bone. (FIGS. 123 and 124.) A flat tongue 114B does not allow the application of a strong counterpressure against the bone, because of the potential damage to the urethra. (FIG. 111a.) The tongue 114B has a first end 116B for inserting into the cavity, and a second end 118B which is adapted for articulating with the base portion 108B of the upper clamp 102B. This articulation may be, for example, by means of a threaded connector 107B that joins the tongue 114B to the base portion 108B of the upper clamp 102B.

Figure 112:
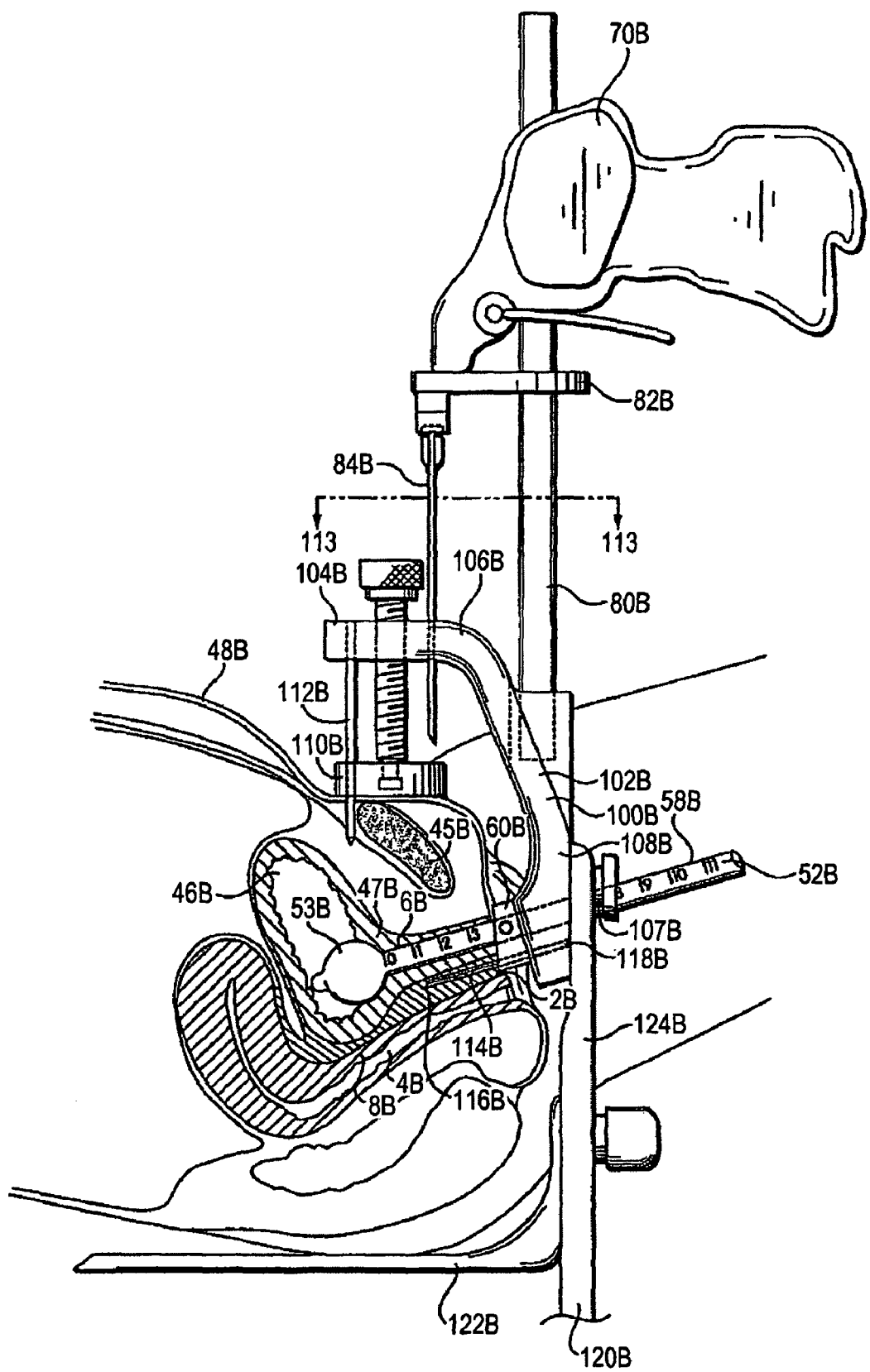

The lower clamp 120B of the driver frame assembly 100B has a buttock plate 122B for insertion beneath the patient such that the patient's weight rests on the plate to further secure the frame assembly. Attached to the buttock plate 122B is an ascending arm 124B that is adapted for articulating with the base portion 108B of the upper clamp 102B. (FIG. 112.) Thus, the upper clamp 102B attaches to the rigid catheter 52B and the cavity tongue 114B, and then the upper clamp 102B also attaches to the lower clamp 120B, which is anchored under the patient's body. The effect of these multiple attachments is to compress a patient's pelvic region to provide stability for operation of the bone-piercing guide driver 70B as well as to enhance the straight line precision of driving a guide 84B through the pubic bone.

In a preferred embodiment, an insert card 30B capable of supporting a medical device is an additional component of the driver frame assembly 100B. (FIG. 117.) In such an embodiment, the card 30B adapted to slide along the tongue 114B to reach the proper position within the cavity. The articulation opening 40B of the card 30B also may be used for attachment or positional control of the card 30B with respect to the driver frame assembly 100B.

Figure 114:
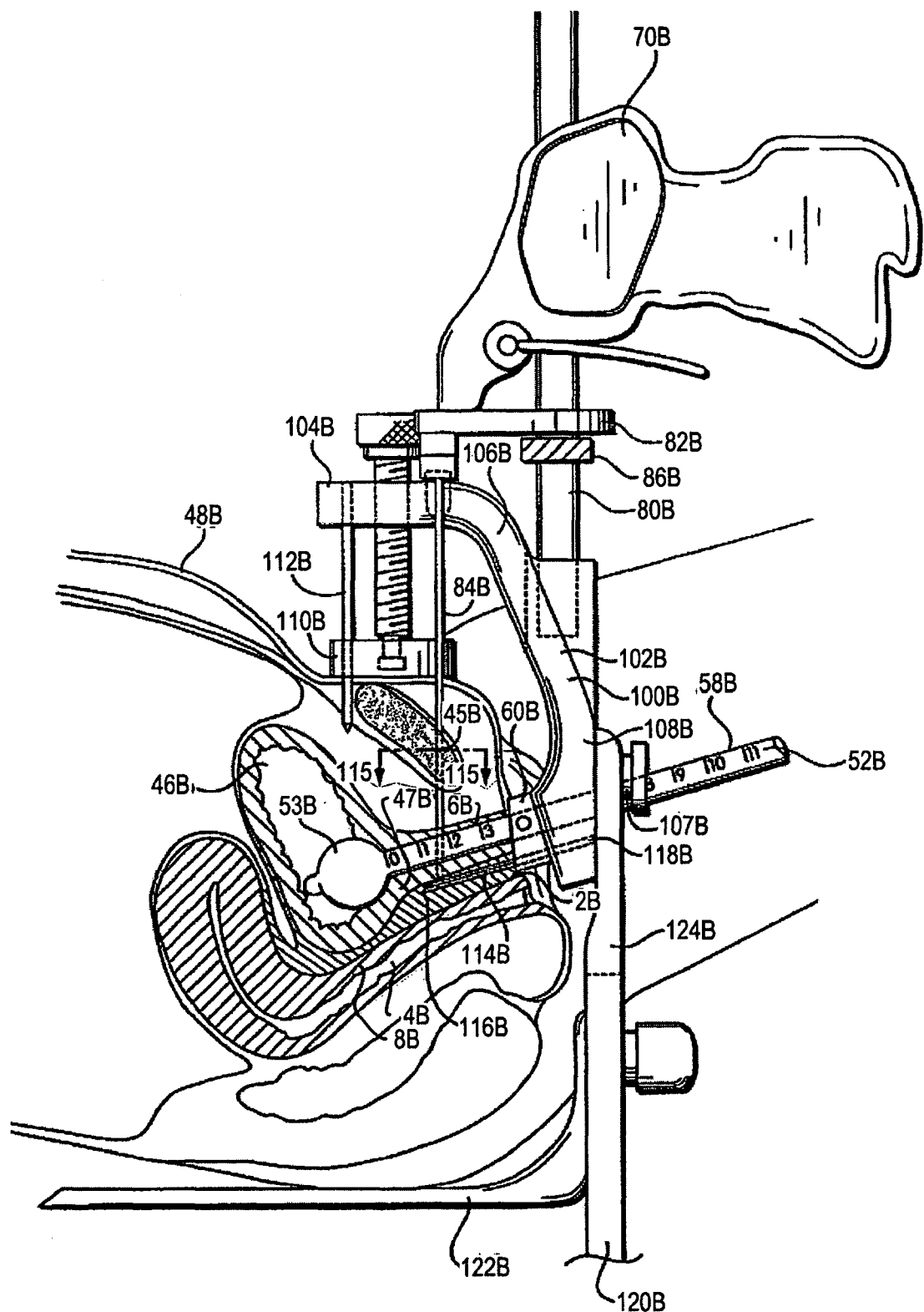

The driver 70B portion of the driver frame assembly 100B is similar to the driver 70B of a previous aspect of the invention as discussed above. The driver 70B of this aspect of the invention, however, does differ in the respect that it attaches to the driver frame assembly 100B via the slide bar 80B of the driver 70B. Accordingly, the driver 70B of this aspect of the invention has the slide bar 80B and the moveable jaw, but does not have its own immovable or first jaw 72B. However, upon attachment of the driver 70B to the driver frame assembly 100B, both the tongue 114B portion and the buttock plate 122B portion of the driver frame assembly 100B can simultaneously function as fixed jaws toward which the immovable jaw advances as it moves along the slide bar 80B. (FIG. 114.)

Figure 113:
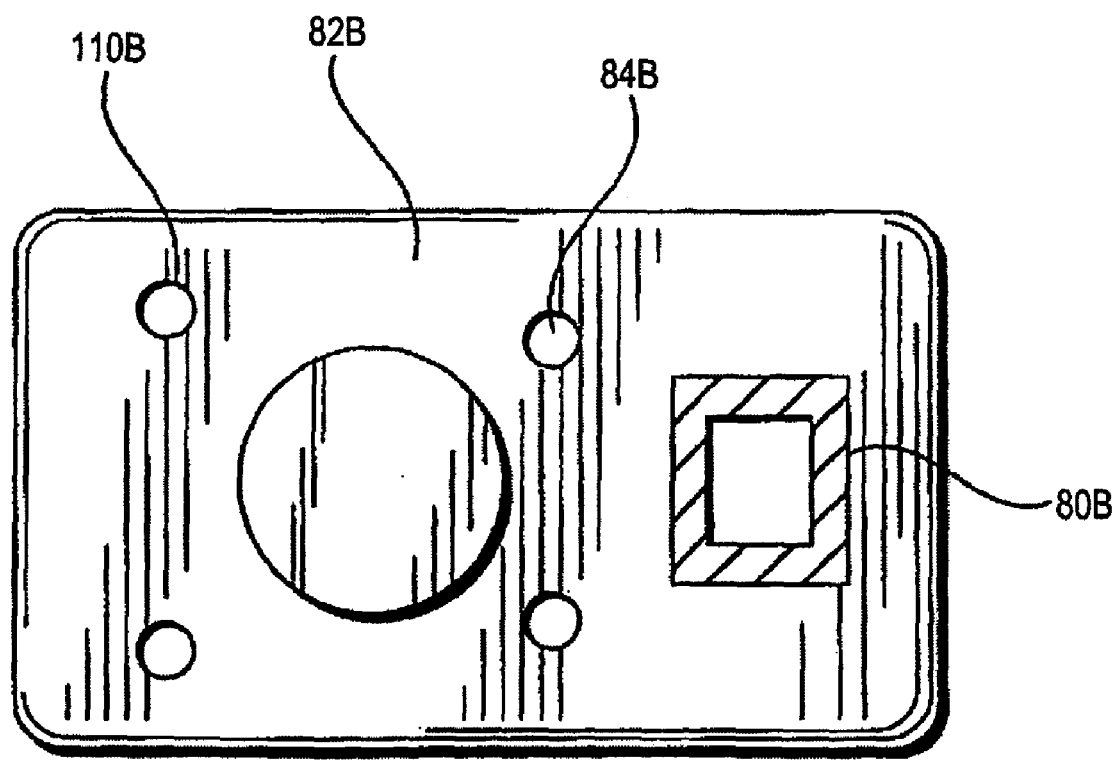

As mentioned above, the function of the first or fixed jaw is to provide counterpressure to the pressure applied to the pubic bone by the advancement of the guide 84B through the pubic bone. The preferred driver 70B portion of the driver frame assembly 100B has two positions for attachment of bone-piercing guides 84B to the second, or movable, jaw 72B. (FIG. 113.) These positions are left and right of center, being laterally spaced to provide sufficient offset from the patient's midline so as to prevent any contact of the bone-piercing guides 84B with the urethra. Thus, the driver 70B of the assembly is intended to simultaneously advance two separate bone-piercing guides 84B through the pubic bone, one left and one right of the patient's midline, as shown in FIG. 115.

Figure 111C:
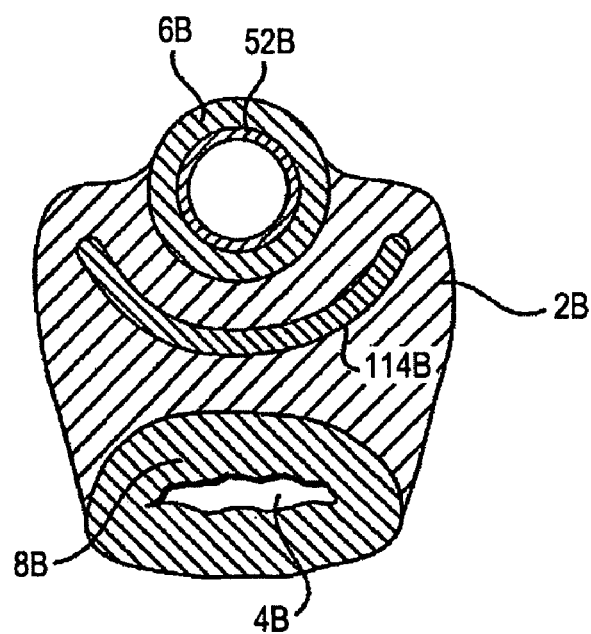

This aspect of the invention provides a method for reconstruction of the urethral and pelvic floor or for stabilizing a tissue of the pelvic region. In this method a rigid catheter 52B is placed in the urethra so that the urethra is elongated and straightened. (FIG. 110.) The catheter 52B also aids in determining the position of the bladder 46B and the bladder neck 47B. The tongue 114B of the driver frame assembly 100B is placed into the tissue cavity, and also may be attached to the rigid catheter 52B. (See FIGS. 110 and 111.) Preferably an insert card 30B holding a medical device, for example, a urethral sling 42B, is inserted into the cavity using the tongue 114B as a guide. (FIG. 117.) The upper clamp 102B is attached to the tongue 114B and to the catheter 52B, and the compression foot 110B is compressed against the patient's abdomen, after palpation to determine the proper position of the stabilizing pins 112B relative to the superior surface of the pubic bone. The compression foot 110B is tightened against the patient's abdomen to prevent slipping of the bone-piercing guide 84B, and to further immobilize the soft tissues of the pelvis. (FIG. 110). Further stabilization is achieved with attachment of the lower clamp 120B which is done by sliding the buttock plate 122B beneath the patient and firmly attaching the ascending arm 124B of the lower clamp 120B to the base portion 108B of the upper clamp 102B. (FIG. 112.)

With the driver frame assembly 100B properly installed along the patient's midline, the driver 70B portion of the driver frame assembly 100B may be mounted on the descending arm 106B of the upper clamp 102B. (FIG. 112.) Care is taken to assure that the bone-piercing guides 84B of the driver 70B are positioned such that they will enter the pubic bone. Then the second removable jaw of the driver 70B is advanced downward along the slide bar 80B and the guides 84B are advanced into the abdominal surface and through the pubic bone, emerging within the tissue cavity near the medical device supported on the card 30B. (FIG. 114.)

In a preferred example, the bone-piercing guides 84B are cannulas 90B and the medical device supported on the card 30B is a sling 42B. (FIGS. 116 and 117.) In such an embodiment, the proximity of the cannulas 90B with the sling 42B permits suturing or other attachment through the lumen on the cannula 90B to the desired location on the urethral sling 42B. (FIG. 118.) After attachment of suture 88B directly or indirectly (see FIGS. 120-122) to the sling 42B, the cannulas 90B are removed, leaving behind the suture 88B, which is then secured to the pubic bone. (FIG. 127.)

In another embodiment of this aspect of the invention, a concave insertion tongue 114B is used to provide counterpressure for driving cannulas 90B through the pubic bone 45B. The concave tongue 114B is inserted into a cavity, such as, for example, a hiatal cavity or the vagina 4B, and the compression foot 110B of the driver frame assembly 100B is placed against the patent's pubic bone 45B. (FIG. 123a.) The concave tongue has a central depression 136B and elevated edges 138B, allowing the edges 138B of the tongue 114B to provide counterpressure to the posterior/inferior surface of the pubic bone 45B, while the compression foot 110B and the cannulas 90B apply pressure to the opposite (anterior/superior) surface of the bone 45B. (FIG. 123b.)

The central depression 136B of the tongue 114B prevents the urethra 6B from being crushed upon application of counter pressure on the bone 45B by elevated edge 138B of the tongue 114B. (FIG. 123b.) The edge of the tongue may also have a gap 144B to allow the cannula 90B to pass through the plane of the elevated edge 138B without the cannula 90B impacting against the tongue 114B. The edge 138B may also have contact pins 140B of a configuration and position to pierce through soft tissue and fascia to contact the surface of the pubic bone 45B and prevent slippage of the tongue 114B. (FIG. 124.)

When pressure is applied to the opposite sides of the bone 45B, as shown in FIG. 123b, the cannulas 90B are driven through the pubic bone 45B and into the cavity. (FIG. 125a.) Suture 88B or other devices may be passed through the cannulas 90B and into the cavity. (FIG. 125b.) The suture 88B may be attached within the cavity either by stitches 92B or by attaching the suture 88B to a suture button 94B. (FIG. 125b.) After proper attachment of the suture 88B within the cavity, the pressure on both sides of the bone 45B is released, and the compression foot 110B is raised. (FIG. 126a.) The tongue 114B is removed from the cavity, and the sutures attached therein are fastened to the bone 45B with, for example, either a bone eyelet 150B or a bone suture fastener 170B. The urethra 6B is elevated by the tension that is applied to the sutures 88B in the step of fastening the sutures 88B to the bone 45B. The resulting elevation of the urethra 6B is shown as distance B in FIGS. 126a and 126b.

The advantage of the method of this aspect of the invention is that the driver frame assembly 100B, if properly installed, provides rigidity to the driver 70B to allow for highly accurate straight line passage of a bone-piercing guide 84B through the pubic bone and to a target sight within the soft tissue. Because the driver 70B is able to advance two different guides 84B through the bone at the same time, and because the contact between the guide 84B and the sling 42B is relatively precise, the entire procedure can be done very rapidly and with minimal invasion compared with other procedures used to achieve a similar objective. In addition, the method of this aspect of the invention, being minimally invasive, greatly reduces the risk of infection arising from the procedure. Also reduced is the number of incisions, resulting in a shorter recovery time for the patient and less scarring, since the external abdominal wounds are all puncture wounds, and the only incision is a relatively small incision or a knife stick in the vaginal hiatus 2B or in the upper vaginal wall 8B. In a preferred embodiment of this aspect of the invention, the sutures 88B which pass through the bone are secured to the bone after being tensioned with a suture tensioning device as discussed above.

Another aspect of the invention provides a system for attaching urethral sling 42B to a suture 88B as shown in FIG. 120-122. The system includes a urethral sling 42B and a connector 130B; the urethral sling 42B has a ring member 44B attached thereto (FIGS. 128-129) and the connector 130B is adapted to cooperate with the ring member 44B to permit unidirectional passage of the connector 130B through the ring member 44B (FIGS. 120-122, 131-134). The ring member 44B and the connector 130B further cooperate to prevent retrograde movement of the connector 130B through the ring member 44B.

The invention contemplates several embodiments both of the ring member 44B and of the connector 130B. The ring member 44B may be as simple as a hole in an appropriate part of the sling 42B, suited for passage therethrough by a connector 130B. (FIG. 132-134.) The ring member 44B also may be a more elaborate structure, such as a reinforced ring with flanges 142B protruding into the central opening 128B of the ring member 44B. (FIGS. 128, 129, 131.)

In a preferred embodiment, the connector 130B has a conical tip 131B attached to a cylindrical portion 133B behind the tip 131B to which a suture 88B may attach. This embodiment is referred to as the arrowhead connector 132B. (FIG. 131.) The cylindrical portion 133B behind the tip 131B has a smaller circumference than the widest part of the conical tip 131B, such that there is a substantially flat shoulder 129B behind the tip 131B. Accordingly, the arrowhead connector 132B is adapted for cooperating with the reinforced ring member 44B having flanges 142B that protrude into the central opening 128B. As the tip 131B penetrates the central opening 128B, the flanges 142B move aside, allowing passage of the tip 131B. However, once the entire conical portion of the tip 131B has passed through the central opening 128B, the flanges 142B return to their initial orientation around the central opening 128B and rest against the shoulder 129B, resisting retrograde movement of the connector 130B through the ring member 44B. (FIGS. 121, 122, 129, 131.) Since the cylindrical portion 133B behind the shoulder 129B of the arrowhead connector 132B has a means for connecting to a suture 88B, the passage of the connector 130B through the ring member 44B creates a connection between the suture 88B and the sling 42B. (FIG. 131.) By this method of connecting suture 88B to sling 42B, there is no need for stitching or tying knots to the sling 42B, which greatly simplifies and accelerates the securing procedure.

Another preferred embodiment of the securing device 126B has a connector 130B with two perpendicular cylindrical members 135B, 137B wherein the members 135B, 137B are substantially flexibly attached one to the other at a flexible joint 139B. (FIG. 133.) The rear cylinder 135B has a means of attaching to a suture 88B, while the leading cylinder 137B is adapted for passage through the ring member 44B. As this embodiment of the connector 130B, referred to herein as the T connector 134B, is inserted into a cannula 90B for advancement toward the sling 42B, the perpendicularity between the two cylindrical members 135B, 137B is distorted, and the leading cylinder 137B assumes a position that is more closely parallel, rather than perpendicular, to the rearward cylinder 135B. (FIG. 134.) However, after the T connector 134B has passed through the cannula 90B and the leading cylinder 137B of the T connector 134B has also passed through the ring member 44B of the sling 42B, the angular relationship between the two cylindrical members 135B, 137B reverts to perpendicular. (FIG. 132.) In this conformation, the connector 130B may not pass back through the ring member 44B, and a secure connection between the suture 88B and the sling 42B is therefore established.

This aspect of the invention provides a method for simple, minimally invasive placement and securing of a sling 42B in a tissue cavity. A tissue cavity, such as a cavity in the hiatal tissue, is created by use of, for example, the dilator 10B or the incision guide 50B of the invention. Alternatively an existing tissue cavity, such as the vagina 4B, may be selected for placement of the sling 42B. In addition, a tissue cavity in the hiatal tissue may be created by inserting a dilator 10B or an incision guide 50B through the upper vaginal wall 8B. A sling 42B is then placed into the cavity in its desired location. This step is preferably performed with the use of the insert card 30B of the invention, wherein the insert card 30B carries and supports the sling 42B in its appropriate position within the cavity until it secured there. (FIG. 117.)

A cannula 90B is driven through the pubic bone using, for example, either the driver 70B of the invention or the driver frame assembly 100B of the invention. (FIG. 117.) The cannula 90B is then further driven through tissue until it approaches and aligns with the sling 42B, (FIG. 118.) which is equipped with ring members 44B. A connector 130B attached to the suture 88B is then inserted into the lumen of the cannula 90B and advanced therethrough until it contacts with and passes through the ring member 44B of the sling 42B. (FIGS. 119, 120, 121.) At this point, the suture 88B is tested for the integrity of the connection between the connector 130B and the ring member 44B, and the cannula 90B is withdrawn from the pubic bone. The suture 88B may then be appropriately tensioned and secured to the pubic bone (FIG. 127) as will be discussed below. Also contemplated as embodiments of this aspect of the invention are similar connections between other kinds of medical devices and suture 88B via, for example, arrowhead connector 132B or T connector 134B passing through a cannula 90B which has been driven through the pubic bone.

As a further embodiment of the present invention, the securing devices 126B of the invention may be used to secure a urethral sling 42B or other medical device after such a device has been positioned in a tissue cavity that was created transvaginally. For example, a cavity may be opened in the upper vaginal wall 8B by hydrodissection, or by means of the spreader 12B of the invention, or by blunt dissection. A medical device such as a urethral sling 42B may then be placed into the cavity, wherein the medical device has one or more ring members 44B capable of permitting unidirectional passage of a connector 130B of the securing device 126B. The appropriate connector 130B is then passed through the corresponding ring member 44B, and the device is secured in place in the transvaginally created tissue pocket. (See FIG. 122.)

This invention is further characterized by a bone eyelet 150B for securing suture 88B to a bone. The bone eyelet 150B consists of a sleeve 152B and at least one crosspiece 160B. (FIG. 130.) The sleeve 152B has an outer surface 154B that is adapted for inserting into and contacting with a bone, and also has an inner surface 156B such that the sleeve 152B is a substantially hollow structure with openings at either end. (FIG. 131.) The crosspiece 160B is attached to the inner surface 156B of the sleeve 152B, and creates a plurality of channels within the sleeve 152B.

Several alternative embodiments of the bone eyelet 150B are contemplated in the present invention. In one preferred embodiment, the crosspiece 160B is a single rod 164B. (FIG. 132.) In another preferred embodiment, the crosspiece 160B is a plane 162B. (FIG. 131.) In both of these embodiments, the presence of the single crosspiece 160B produces two channels 168B through which a suture 88B may pass. In another embodiment, the crosspiece 160B is created by crimping or piercing the sleeve 152B. In this embodiment, the thus-distorted portion of the sleeve 152B becomes the crosspiece 160B, as shown in FIG. 131. In other embodiments, multiple crosspieces 160B may be present in the sleeve 152B, to produce more than two channels 168B through which a suture 88B may pass. In another embodiment, the sleeve 152B includes a perpendicular flange rim 158B. This flange rim 158B suspends the sleeve 152B at the surface of the bone and prevents it from sliding into the hole in the bone. (FIGS. 130-132.)

This aspect of the invention provides a method for securing a suture 88B to a bone. In this method, a suture 88B is passed through a bone in which a path for suture 88B has been created, for example, by driving a bone-piercing guide 84B according to this invention. Where two ends of a suture 88B both extend past the surface of the bone, each end may be advanced through one of the channels 168B among the plurality of channels 168B provided in the bone eyelet 150B. The suture 88B ends may then be tied together and will be prevented from sliding into the bone by the action of the crosspiece 160B of the bone eyelet 150B. (See FIGS. 131, 132.)

Another embodiment of this method includes a step of tensioning the suture 88B during the tying step to achieve a desired elevation of the structures to which the suture 88B is attached. For example, this method may be employed in connection with a securing device 126B discussed above to greatly accelerate and simplify the steps in securing a tissue mass or a urethral sling 42B in a tissue cavity. (FIGS. 131, 132.) Accordingly, the bone eyelet 150B may be used in connection with the driver 70B aspect of the this invention, as well as the driver frame assembly 100B aspect of the invention. It may further be adapted for use with other means of advancing a suture 88B through a pubic bone.

A further aspect of the present invention provides a bone suture fastener 170B for quick and simplified connection of a suture 88B to a bone. (FIGS. 135-137.) The suture fastener 170B consists of a sleeve 172B having an opening 174B at each end, and a sleeve plug 178B. The sleeve 172B is provided with a friction surface 180B for contacting the sleeve plug 178B and for preventing disengagement of the plug 178B from the sleeve 172B. Different embodiments of the bone suture fastener 170B have a sleeve 172B that is substantially conical or cylindrical and a sleeve plug 178B that is likewise substantially conical or cylindrical. In one embodiment the friction surface 180B is a plurality of friction flanges 184B partially occluding one opening 174B of the suture fastener sleeve 172B. (FIGS. 135, 136a.) These flanges 184B flex is one direction to allow insertion of the sleeve plug 178B into the sleeve 172B and then prevent release of the sleeve plug 178B from the sleeve 172B. In another embodiment, the friction surface 180B is threaded 182B and the sleeve 172B is substantially cylindrical. (FIG. 137.) The sleeve plug 178B is likewise threaded 182B and is adapted for frictionally contacting the threads 182B of the suture fastener sleeve 172B. An additional embodiment, the sleeve plug 178B may have a series of distortable angled rings 179B along its length, wherein the circumference of the top of each ring 179B is smaller than the circumference of the bottom of the same ring 179B. The suture 88B may be tied directly to the sleeve plug 178B. In this embodiment, the friction surface 180B of the sleeve 172B has a rim 183B adapted to allow unidirectional passage of the sleeve plug 178B and to prevent retrograde passage thereof, resulting in a one-way zipper-lock action. This embodiment allows a surgeon to adjust the tension on the suture 88B simply by pulling the sleeve plug 178B through the sleeve 172B to the desired position. (FIG. 136b.) In any of these embodiments, a flange rim 186B may extend around the circumference of one end of the sleeve 172B to prevent sinking of the bone suture fastener 170B past the surface of the bone. (FIG. 137.)

This aspect of the invention provides a method for quick and simple securing of a suture 88B that has passed through a bone. According to the method, one or multiple ends of a suture 88B may be passed through the sleeve 172B of the suture fastener 170B and the suture fastener 170B may be advanced along the suture 88B until it contacts the bone through which the suture 88B passes. (FIG. 135.) The sleeve 172B is secured in the bone near the bone surface either by a friction surface 180B on the outside of the sleeve 172B, or by a flange rim 186B extending around the circumference of one end of the sleeve 172B. With the sleeve 172B in place, and the suture 88B passing therethrough, the suture 88B may be tensioned to approximately the desired tension and the sleeve plug 178B partially inserted into the opening 174B of the sleeve 172B at the surface of the bone. Any desired tensioning or release of tension in the suture 88B is done prior to final seating of the sleeve plug 178B in the sleeve 172B against the friction surface 180B. (FIGS. 136a and 137.) When the sleeve plug 178B is appropriately seated against the friction surface 180B, the suture 88B is secured in place at the surface of the bone, and excess suture 88B is cut off by the surgeon.

Another embodiment of this aspect of the invention contemplates the use of the bone suture fastener 170B to secure a suture 88B that is connected to a device or a stitch 92B in a transvaginally created tissue cavity. For example, a tissue cavity is dissected between the urethra and the upper vaginal wall 8B by hydrodissection, blunt instrument dissection, or by the spreader 12B of the invention. Subsequently, a sling 42B or other medical device may be placed in the cavity, or a suture 88B may be passed through a tissue mass to elevate or stabilize the tissue mass (compare FIG. 126a to FIG. 126b and note distance of elevation B, see also FIGS. 108, 109, 125).

In cases where the suture 88B is passed through the tissue and follows a path through the pubic bone, the end of the suture 88B that protrudes from the pubic bone may be anchored thereto by means of the bone suture fastener 170B of this aspect of the invention. (FIG. 127.)

This method of the invention may be practiced in cooperation with several other methods and devices of the present invention. In any aspect of the invention in which a suture 88B is passed through a bone, the suture 88B may be advantageously secured to the bone in this manner. Thus, the quick connect bone suture fastening may be used in coordination with the quick connect securing devices 126B used to connect a sling 42B or other internally placed medical device with a suture 88B. They also may be used to secure the ends of a suture 88B that has been passed through a tissue mass by stitching 92B. They also may be used in connection with the bone-piercing guide driver 70B or with the driver frame assembly 100B of the invention.

Accordingly, the several aspects of the present invention cooperate to achieve the desired effect of providing a variety of surgical options for and solutions to problems associated with stress urinary incontinence and related dysfunctions or deformations of the urethral or pelvic floor. Also contemplated within the overall scope of the present invention are other applications for securing a soft target tissue to a relatively fixed reference tissue, such as the pubic bone. It is understood that the examples of embodiments and methods provided herein are merely representative of the invention, and are not taken to limit the invention beyond the express limitations of the following claims.

What is claimed is:

1. A guide member placement device for inserting a guide member in a body tissue, comprising:
   a handle;
   a shaft attached to said handle and having a proximal end, a distal end, and a lumen extending therethrough, said lumen adapted for receiving a guide member; and
   an engaging member at said distal end of said shaft adapted to engage another guide member placement device.

2. The guide member placement device of claim 1, wherein the engaging member comprises a male connector configured to be releasably couple to a female connector on the second guide member device.

3. The guide member placement device of claim 1, wherein the shaft includes a straight proximal section, a bent intermediate section and a distal section, the distal section being oriented at an angle of approximately 90 degrees relative to the proximal section.

4. The guide member placement device of claim 1, further comprising a guide member removably positioned in the lumen of the shaft.

5. The guide member placement device of claim 4, wherein the guide member comprises a guidewire.

6. The guide member placement device of claim 4, wherein the guide member comprises a suture.

7. The guide member placement device of claim 1, further comprising an axially-movable blunt dissection tip positioned near the distal end of the shaft.

8. The guide member placement device of claim 7, wherein the blunt dissection tip is positioned on a blunt dissector disposed within the lumen of the shaft, the blunt dissection tip being extendable from and retractable into the shaft.

9. The guide member placement device of claim 8, wherein the blunt dissector is biased toward a retracted position.

10. The guide member placement device of claim 8, wherein the blunt dissector comprises a narrow portion including a lumen, the narrow portion being connected to a body portion located within the handle.

11. The guide member placement device of claim 8, wherein a body portion of the blunt dissector comprises a recessed portion and a spring, the recess portion being adapted for receiving the spring which biases the blunt dissector toward the retracted position.

12. The guide member placement device of claim 8, further comprising a rotatable cam adapted to place an axial distal force upon a body portion of the blunt dissector to thereby place blunt dissector tip in the extended position.

13. The guide member placement device of claim 10, wherein a body portion of the blunt dissector comprises a lumen which is in fluid communication with a lumen disposed in the narrow portion of the blunt dissector.

14. The guide member placement device of claim 8, wherein a body portion of the blunt dissector has an axial range of motion from about 2 mm to about 10 mm.

15. The guide member placement device of claim 1, wherein the shaft and the handle are oriented along a common longitudinal axis.

16. The guide member placement device of claim 1, wherein at least part of the exterior surface of the handle is textured to produce a high-friction gripping surface.

17. The guide member placement device of claim 1, wherein the distal end of the shaft is oriented at an angle of approximately 90 degrees relative to the handle.

* * * * *